United States Patent
Rudd et al.

(10) Patent No.: US 9,328,138 B2
(45) Date of Patent: May 3, 2016

(54) HCV NS3 PROTEASE INHIBITORS

(71) Applicants: Merck Sharp & Dohme Corp., Rahway, NJ (US); MSD Italia S.R.L., Rome (IT); Merck Canada Inc., Kirkland (CA)

(72) Inventors: Michael T. Rudd, Collegeville, PA (US); John McCauley, Maple Glen, PA (US); Nigel Liverton, Harleysville, PA (US); Christiane Grisé-Bard, Dollard-des-Ormeaux (CA); Marie-Christine Brochu, St-Laurent (CA); Sylvie Charron, Laval (CA); Virender Aulakh, Whitehorse (CA); Benoit Bachand, Montreal (CA); Patrick Beaulieu, Laval (CA); Helmi Zaghdane, Pincourt (CA); Yongxin Han, Shanghai (CN); Marco Ferrara, San Donato Milanese (IT); Steven Harper, Fanwood, NJ (US); Vincenzo Summa, Rome (IT); Samuel Chackalamannil, Califon, NJ (US); Srikanth Venkatraman, Edison, NJ (US); Unmesh Shah, Watchung, NJ (US); Francisco Velazquez, Clinton, NJ (US)

(73) Assignees: MSD Italia S.R.L., Rome (IT); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/358,050

(22) PCT Filed: Nov. 9, 2012

(86) PCT No.: PCT/US2012/064270
§ 371 (c)(1),
(2) Date: May 14, 2014

(87) PCT Pub. No.: WO2013/074386
PCT Pub. Date: May 23, 2013

(65) Prior Publication Data
US 2014/0296136 A1    Oct. 2, 2014

Related U.S. Application Data

(60) Provisional application No. 61/560,042, filed on Nov. 15, 2011.

(51) Int. Cl.
| | | |
|---|---|---|
| *A61K 38/06* | (2006.01) | |
| *C07K 5/08* | (2006.01) | |
| *C07K 5/078* | (2006.01) | |
| *C07K 5/083* | (2006.01) | |
| *C07K 5/087* | (2006.01) | |
| *A61K 38/21* | (2006.01) | |
| *C07K 5/097* | (2006.01) | |

(Continued)

(52) U.S. Cl.
CPC .............. *C07K 5/08* (2013.01); *A61K 31/4745* (2013.01); *A61K 31/5377* (2013.01); *A61K 31/675* (2013.01); *A61K 31/7056* (2013.01); *A61K 38/005* (2013.01); *A61K 38/06* (2013.01); *A61K 38/21* (2013.01); *C07K 5/0804* (2013.01); *C07K 5/0808* (2013.01); *C07K 5/0812* (2013.01); *C07K 5/0821* (2013.01); *A61K 38/12* (2013.01)

(58) Field of Classification Search
None
See application file for complete search history.

(56) References Cited

U.S. PATENT DOCUMENTS

| | | | |
|---|---|---|---|
| 2,794,806 A | 6/1957 | Elam et al. | |
| 3,480,613 A | 11/1969 | Walton | |

(Continued)

FOREIGN PATENT DOCUMENTS

| | | |
|---|---|---|
| GB | 2337262 | 11/1999 |
| WO | WO9741211 A1 | 11/1997 |

(Continued)

OTHER PUBLICATIONS

Allison et al, Immunosuppressive and other anti-rheumatic activities of mycophenolate mofetil, Agents Action, 1993, 165-188, 44 (Suppl).

(Continued)

*Primary Examiner* — Jeffrey E Russel
(74) *Attorney, Agent, or Firm* — Alysia A. Finnegan; Anna L. Cocuzzo

(57) ABSTRACT

The present invention relates to macrocyclic compounds of formula (I) that are useful as inhibitors of the hepatitis C virus (HCV) NS3 protease, their synthesis, and their use for treating or preventing HCV infections.

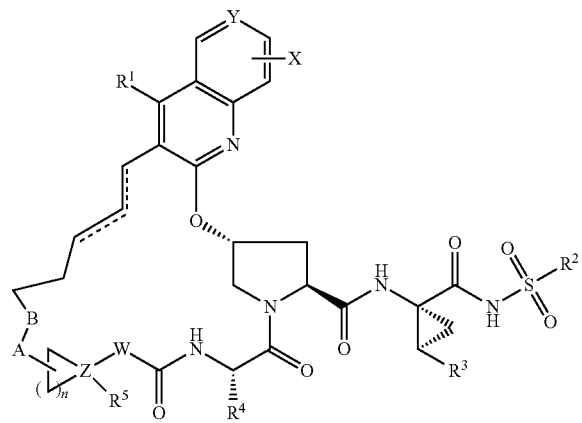

17 Claims, No Drawings

(51) Int. Cl.
*A61K 31/4745* (2006.01)
*A61K 31/5377* (2006.01)
*A61K 31/675* (2006.01)
*A61K 31/7056* (2006.01)
*A61K 38/00* (2006.01)
*A61K 38/12* (2006.01)

(56) References Cited

U.S. PATENT DOCUMENTS

| | | | |
|---|---|---|---|
| 5,059,609 A * | 10/1991 | Eggler | C07C 43/253 514/217.05 |
| 6,323,180 B1 | 11/2001 | Llinas-Brunet et al. | |
| 6,777,392 B2 | 8/2004 | Maurya et al. | |
| 6,995,174 B2 | 2/2006 | Wang et al. | |
| 7,135,462 B2 | 11/2006 | Scola et al. | |
| 7,781,454 B2 | 8/2010 | Anthony et al. | |
| 7,879,797 B2 | 2/2011 | Holloway et al. | |
| 2002/0019363 A1 | 2/2002 | Ismaili et al. | |
| 2003/0236216 A1 | 12/2003 | Devos et al. | |
| 2004/0006007 A1 | 1/2004 | Gosselin et al. | |
| 2004/0029776 A1 | 2/2004 | Warne et al. | |
| 2004/0063658 A1 | 4/2004 | Roberts et al. | |
| 2004/0067901 A1 | 4/2004 | Bhat et al. | |
| 2004/0229818 A1 | 11/2004 | Llinas-Brunet | |
| 2005/0020503 A1 | 1/2005 | Llinas-Brunet et al. | |
| 2005/0038240 A1 | 2/2005 | Connolly et al. | |
| 2010/0093779 A1 | 4/2010 | Liverton et al. | |
| 2010/0286185 A1 | 11/2010 | Liverton et al. | |
| 2012/0121624 A1 | 5/2012 | Liverton et al. | |

FOREIGN PATENT DOCUMENTS

| | | |
|---|---|---|
| WO | WO9822496 A2 | 5/1998 |
| WO | WO9846630 A1 | 10/1998 |
| WO | WO9907733 A2 | 2/1999 |
| WO | WO9907734 A2 | 2/1999 |
| WO | WO9943691 A1 | 9/1999 |
| WO | WO9938888 A2 | 10/1999 |
| WO | WO9950230 A1 | 10/1999 |
| WO | WO9964442 A1 | 12/1999 |
| WO | WO0009543 A2 | 2/2000 |
| WO | WO0025780 A1 | 5/2000 |
| WO | WO0059929 A1 | 10/2000 |
| WO | WO0100622 A1 | 1/2001 |
| WO | WO0147883 A1 | 7/2001 |
| WO | WO0160379 A1 | 8/2001 |
| WO | WO0168663 A1 | 9/2001 |
| WO | WO0177091 A2 | 10/2001 |
| WO | WO0179246 A2 | 10/2001 |
| WO | WO0190121 A2 | 11/2001 |
| WO | WO0192282 A2 | 12/2001 |
| WO | WO0204425 A2 | 1/2002 |
| WO | WO0206246 A1 | 1/2002 |
| WO | WO0218404 A2 | 3/2002 |
| WO | WO0220497 A1 | 3/2002 |
| WO | WO0232920 A2 | 4/2002 |
| WO | WO0248116 A2 | 6/2002 |
| WO | WO0248165 A2 | 6/2002 |
| WO | WO0248172 A2 | 6/2002 |
| WO | WO02051425 A1 | 7/2002 |
| WO | WO02057287 A2 | 7/2002 |
| WO | WO02057425 A2 | 7/2002 |
| WO | WO02100415 A2 | 12/2002 |
| WO | WO03026589 A2 | 4/2003 |
| WO | WO03026675 A1 | 4/2003 |
| WO | WO03029226 A1 | 4/2003 |
| WO | WO03068244 A1 | 8/2003 |
| WO | WO03093290 A2 | 11/2003 |
| WO | WO04000858 A2 | 12/2003 |
| WO | WO2004002422 A2 | 1/2004 |
| WO | WO2004002999 A2 | 1/2004 |
| WO | WO2004003000 A2 | 1/2004 |
| WO | WO2004003138 A2 | 1/2004 |
| WO | WO2004007512 A2 | 1/2004 |
| WO | WO2004011478 A2 | 2/2004 |
| WO | WO2004013300 A2 | 2/2004 |
| WO | WO2004028481 A2 | 4/2004 |
| WO | WO2005003147 A2 | 1/2005 |
| WO | WO2005016927 A1 | 2/2005 |
| WO | WO2006021341 A1 | 3/2006 |
| WO | WO2008051514 | 5/2008 |
| WO | WO2008057208 A2 | 5/2008 |
| WO | WO2008057209 A1 | 5/2008 |
| WO | WO2009055331 A1 | 4/2009 |
| WO | WO2009061699 A1 | 5/2009 |
| WO | WO2009101917 A1 | 8/2009 |
| WO | WO2009108507 A1 | 9/2009 |
| WO | WO2009134624 A1 | 11/2009 |
| WO | WO2010011566 A1 | 1/2010 |
| WO | WO2010045266 A1 | 4/2010 |
| WO | WO2011014487 | 2/2011 |
| WO | WO2011036576 A1 | 3/2011 |
| WO | WO 2012040040 A1 * | 3/2012 |

OTHER PUBLICATIONS

Bartenschlager, Candidate targets for Hepatitis C Virus-specific antiviral therapy, Intervirology, 1997, 378-393, 40.
Crabb, Hard-won advances spark excitement about Hepatitis C, Science, 2001, 506-507, 294.
Dymock et al., Novel approaches to the treatment of hepatitis C virus infection, Antiviral Chem. & Chemotherapy, 2000, 79-96, 11.
Dymock, Emerging therapies for hepatitis C virus infection, Emerging Drugs, 2001, 13-42, 6.
Harry-O'Kuru, A short, flexible route toward 2'-C-branched ribonucleosides, J. Org. Chem., 1997, 1754-1759, 62.
Kirschbaum, Amantadine, Analytical Profiles of Drug Substances, 1983, 1-36, 12.
Lauer et al, Hepatitis C Virus Infection, N. Engl. J. Med., 2001, 41-52, 345.
Moradpour et al., Current and evolving therapies for hepatitis C, Euro. J. Gastroenterol. Hepatol., 1999, 1189-1202, 11.
Rosen et al, Hepatitis C virus: current understanding and prospects for future therapies, Molecular Medicine Today, 1999, 393-399, 5.
Wang et al, Self-curable system of an aqueous-based polyurethane dispersion via a ring-opening reaction of azetidine end groups, J. Applied Polymer Science, 2006, 4383-4393, 102.
Wolfe, A concise synthesis of 2'-C-methylribonucleosides, Tet. Lett., 1995, 7611-14, 36.
Zink et al, Synthesis and aqueous chemistry of a-acetoxy-N-nitrosomorpholine: Reactive intermediates and products, J. Org. Chem., 2006, 202-209, 71.

* cited by examiner

HCV NS3 PROTEASE INHIBITORS

CROSS-REFERENCE TO RELATED APPLICATIONS

This application is a §371 National Stage Application of PCT/US2012/64270, international filing date of Nov. 9, 2012, which claims the benefit of U.S. Provisional Application Ser. No. 61/560,042, filed Nov. 15, 2011.

FIELD OF THE INVENTION

The present invention relates to macrocyclic compounds that are useful as inhibitors of the hepatitis C virus (HCV) NS3 protease, the synthesis of such compounds, and the use of such compounds for treating HCV infection and/or reducing the likelihood or severity of symptoms of HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 3.9 million infected people in the United States alone, according to the U.S. Center for Disease Control, roughly five times the number of people infected with the human immunodeficiency virus (HIV). According to the World Health Organization, there are more than 170 million infected individuals worldwide, with at least 3 to 4 million people being infected each year. Once infected, about 20% of people clear the virus, but about 80% of those infected harbor HCV the rest of their lives. Ten to 20% of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The current state of the art in the treatment of HCV infection has been discussed in the following references: Dymock et al., 2000, *Antiviral Chem. & Chemotherapy* 11:79-96; Rosen et al., 1999, *Molec. Med. Today* 5:393-399; Moradpour et al., 1999, *Euro. J. Gastroenterol. Hepatol.* 11:1189-1202; Bartenschlager, 1997, *Intervirology* 40(5-6): 378-393; Lauer et al., 2001, *N. Engl. J. Med.* 345:41-52; Dymock, 2001, *Emerging Drugs* 6:13-42; and Crabb, 2001, *Science* 294:506-507.

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein. Because it is responsible for an intramolecular cleavage at the NS3/4A site and for downstream intermolecular processing at the NS4A/4B, NS4B/5A and NS5A/5B junctions, the NS3 protease is considered a prime drug target. Previous research has identified classes of peptides, such as hexapeptides as well as tripeptides discussed in U.S. Patent Application Publications Nos. US2005/0020503, US2004/0229818, and US2004/00229776, showing degrees of activity in inhibiting the NS3 protease. Additional HSV NS3 protease inhibitors have been described in International Patent Application Publication Nos. WO2008/057208 and WO2008/057209. The aim of the present invention is to provide further compounds which exhibit activity against the HCV NS3 protease.

SUMMARY OF THE INVENTION

The present invention relates to novel macrocyclic compounds of formula (I) and/or pharmaceutically acceptable salts or hydrates thereof. These compounds are useful in the inhibition of HCV (hepatitis C virus) NS3 (non-structural 3) protease, the prevention or treatment of one or more of the symptoms of HCV infection, either as compounds or their pharmaceutically acceptable salts or hydrates (when appropriate), or as pharmaceutical composition ingredients. As pharmaceutical composition ingredients, these compounds, salts and hydrates may be the primary active therapeutic agent, and, when appropriate, may be combined with other therapeutic agents including but not limited to other HCV antivirals, anti-infectives, immunomodulators, antibiotics or vaccines. More particularly, the present invention relates to a compound of formula (I) and/or a pharmaceutically acceptable salt thereof:

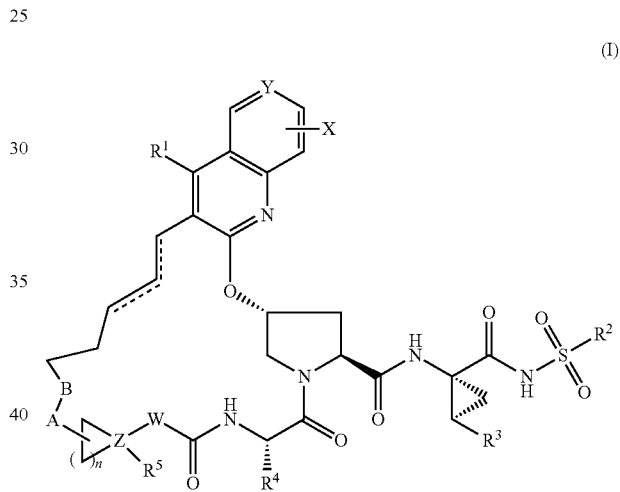

(I)

wherein:
Y is CH or N;
$R^1$ is:
—OH,
—$OC_{1-6}$alkyl,
—$OC_{1-6}$alkyl-$het_1$,
—$OC_{1-6}$alkyl-OH,
—$OC_{1-6}$alkyl-$NR^aR^b$,
—O-$het_1$,
—$OC_{1-6}$alkyl$CO_2$H,
—$OC_{1-6}$alkylC(=O)-$het_1$,
—O($CH_2)_{1-6}$OC(=O)$CH_2NR^aR^b$,
—$OC_{1-6}$alkyl-$C_{1-6}$alkoxy,
—$OC_{1-6}$alkyl-$C_{1-6}$alkoxy-$C_{1-6}$alkoxy,
—OC(O)$C_{1-6}$alkyl,
—OC(O)$NR^aR^b$,
—$OC_{1-6}$alkyl-S-$het_1$,
—$OC_{1-6}$alkyl-phosphate,
a phosphate group,
—$(CH_2)_{1-6}$-$het_1$,
pyridinyl, or
thiazolyl;
wherein said alkyl is optionally substituted with 1 or 2 fluoro substituents,
said phosphate group is optionally substituted with 1, 2 or 3 $C_{1-6}$alkyl;
said het₁ is:
a) aryl selected from phenyl or naphthyl optionally substituted with 1 or 2 substituents selected from —OH, C1-6alkyl, or halo;
b) heteroaryl selected from 5- and 6-membered aromatic rings having 1, 2 or 3 heteroatoms independently selected from N, O and S, wherein said heteroaryl is attached through a ring atom selected from C or N and optionally substituted with 1 or 2 substituents independently selected from $C_{1-6}$alkyl and —OH; or
c) heterocycle selected from 4-7 membered monocyclic or 6-10 membered polycyclic bridged, linearly fused or spirocyclic saturated or unsaturated non-aromatic rings having 1, 2, 3 or 4 heteroatoms independently selected from N, O and S, wherein said heterocycle is attached through a ring atom selected from C or N and optionally substituted with 1 or 2 substituents independently selected from $C_{1-6}$alkyl, oxo, —$(CH_2)_mF$, Boc,
—$(CH_2)_mCF_3$,
$(CH_2)_mOCF_3$, —OH, —$NR^aR^b$, —$C_{1-6}$alkoxy, —$(CH_2)_mSO_2CH_3$, aryl, —$C_{1-6}$alkoxy-$C_{1-6}$ alkyl, —$C_{1-6}$alkyl-$C_{1-6}$alkoxy optionally substituted with $CF_3$, cyano, C(=O)$NH_2$, $C_{3-6}$ cycloalkyl, —$C_{1-6}$alkyl-$C_{3-6}$cycloalkyl, —$COOC_{1-6}$alkyl, —$C_{1-6}$ alkyl-$SO_2C_{1-6}$ alkyl, and benzimidazolyl wherein the benzimidazolyl is optionally substituted with F;
$R^a$ and $R^b$ are independently selected from H; $C_{1-6}$ alkyl; t-Boc; aryl; $C_{3-6}$cycloalkyl optionally substituted with 1 or 2 fluoro substituents; $C_{1-6}$alkoxy-$C_{1-6}$alkyl; tetrahydropyranyl; $C_{1-6}$alkyl-OH; $C_{1-6}$alkyl-aryl; $C_{1-6}$ alkyl-C(OH)-aryl; $C_{1-6}$alkyl-imidazolyl optionally substituted with methyl, $C_{1-6}$alkyl-benzimidazolyl optionally substituted with methyl; $C_{1-6}$alkyl-pyrazolyl; $C_{1-6}$alkyl-dihydrotriazole optionally substituted with oxo; or $C_{1-6}$alkyl-pyrrolidinyl optionally substituted with oxo; wherein
m is 0 or 1 to 4;
said aryl is phenyl, naphthalenyl, tetrahydronaphthalenyl, or 7-10 membered fused bicyclic ring structure wherein at least one of the rings is aromatic and is optionally substituted with 2 —OH; said tetrahydropyranyl is optionally substituted with 1 oxo;
$R^2$ is $C_{1-6}$alkyl, $C_{2-6}$alkenyl, $C_3$-$C_6$cycloalkyl or $NR^cR^d$; wherein
the $C_{3-6}$cycloalkyl is optionally substituted with $C_{1-6}$alkyl optionally substituted with OH, morpholinyl, $C_{1-6}$alkoxy, $C_{1-6}$alkoxy-$C_{1-6}$alkoxy, $C_{1-6}$alkoxyphenyl, or $C_{1-6}$alkenyl;
$R^c$ and $R^d$ are independently H or $C_{1-6}$alkyl, or may be taken together, with the N to which they are attached, to form a 4-7-membered monocyclic ring;
$R^3$ is $C_{1-6}$alkyl, $C_{2-6}$alkenyl, $C_3$-$C_6$cycloalkyl, $CF_2$ or $CF_3$;
$R^4$ is $C_{1-8}$ alkyl, $C_{3-8}$ cycloalkyl, $C_{1-8}$ alkyl-$C_{3-8}$ cycloalkyl, adamantyl, dihydroindenyl, or a 4-8 membered heterocycloalkyl having 1 or 2 heteroatoms selected from N, O, or S, wherein $R^4$ is optionally substituted with one or two substituents independently selected from ($C_1$-$C_6$)alkyl, halo, and —O($C_1$-$C_6$)alkyl; or
$R^3$ and $R^4$ together form heptene;
Z is C or N;
$R^5$ is H or $C_{1-6}$alkyl; or $R^5$ is absent when Z is N;

W is a bond, O or NR;
R is H or $C_{1-6}$alkyl;
X is absent or is halo, $CF_3$, —$OCHF_2$, —$OCH_2F$, —$OCD_2F$, —$OCDF_2$, $C_1$-$C_6$alkyl, $C_{1-6}$alkoxy, aryl, heteroaryl, or —$O(CH_2)_{1-6}NR^aR^b$;
A is absent, O or N;
B is $(CH_2)_m$; and
n is 1-4.

The present invention also includes pharmaceutical compositions containing a compound of the present invention and methods of preparing such pharmaceutical compositions. The present invention further includes methods of treating or reducing the likelihood or severity of one or more symptoms of HCV infection.

Other embodiments, aspects and features of the present invention are either further described in or will be apparent from the ensuing description, examples and appended claims.

DETAILED DESCRIPTION OF THE INVENTION

The present invention relates to compounds of Formula (I) and pharmaceutically acceptable salts thereof, as defined above and a first embodiment of the invention. Different embodiments further describing Formula (I) variables are described below.

In a second embodiment of the invention, the present invention relates to compounds, or a pharmaceutically acceptable salt thereof, having a formula of

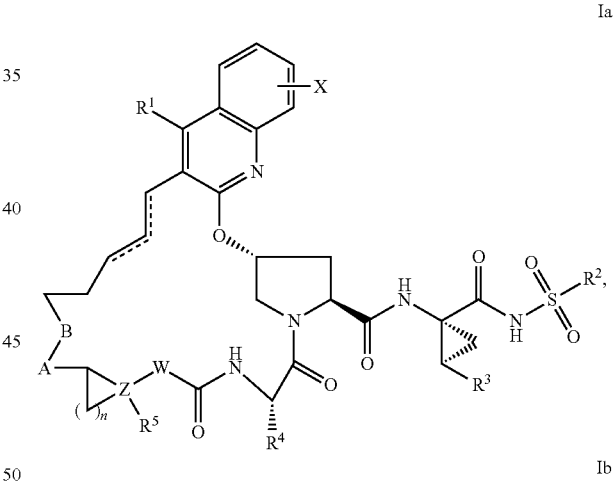

Ia

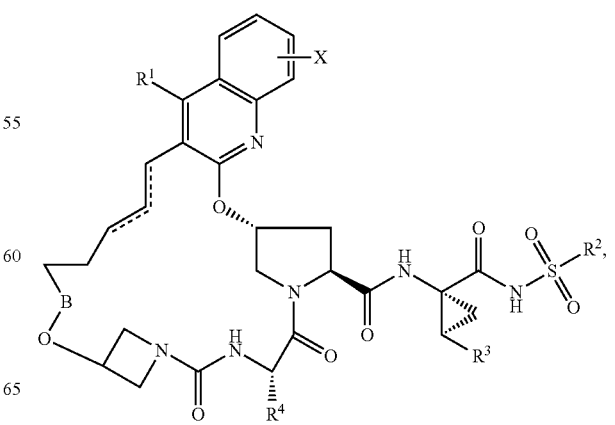

Ib

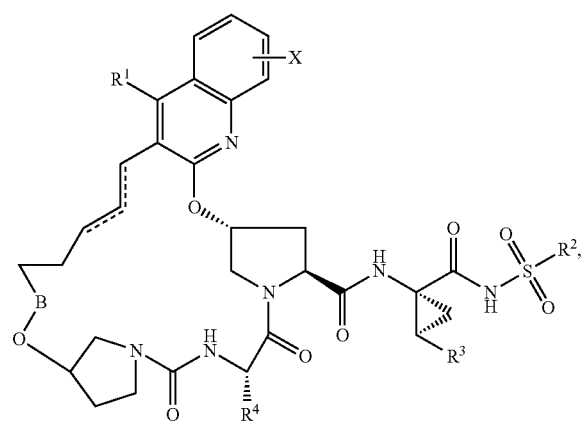

Ic

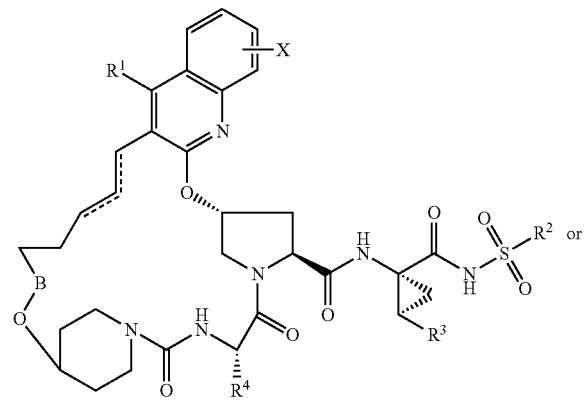

Id

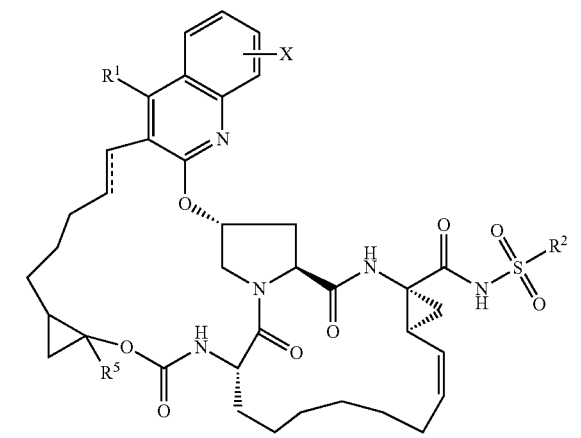

Ie and pharmaceutically acceptable salts thereof, where all variables as provided for in the first embodiment.

In a third embodiment of the invention, the present invention relates to compounds of Formula (I), (Ia), (Ib), (Ic), (Id) or (Ie) and pharmaceutically acceptable salts thereof, wherein Z is C and the other variables are as provided for in the first or second embodiments.

In a fourth embodiment of the invention, the present invention relates to compounds of Formula

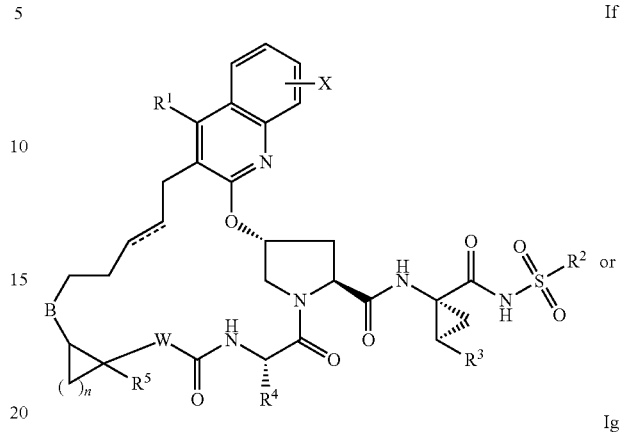

If

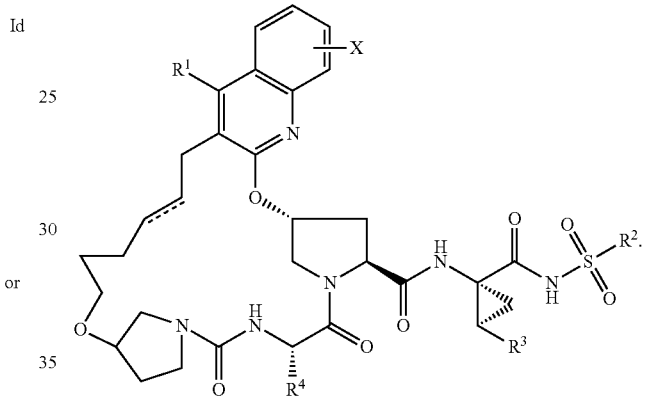

Ig and pharmaceutically acceptable salts thereof, wherein the variables are as provided for in the first embodiment.

In a fifth embodiment of the invention, the present invention relates to a compound having the formula of

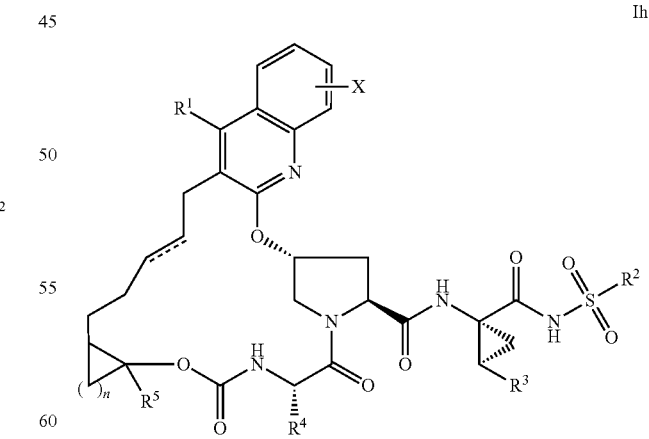

Ih and pharmaceutically acceptable salts thereof, wherein the variables are as provided for in the first embodiment.

In a sixth embodiment of the invention, the present invention relates to compounds of Formula (I), (Ia), (Ib), (Ic), (Id), (Ie), (If), (Ig) and (Ih) and pharmaceutically acceptable salts thereof, wherein $R^5$ is H or $CH_3$ wherein the other variables are as provided for in the first embodiment In a seventh embodiment of the invention, the present invention relates to compounds of Formula (I), (Ia), (Ib), (Ic), (Id), (Ie), (If), (Ig) and (Ih) and pharmaceutically acceptable salts thereof, wherein $R^3$ is ethyl, ethylene, or cyclopropyl and the other variables are as provided for in the first or sixth embodiments. In one aspect of this embodiment, $R^3$ is ethylene.

In a eighth embodiment of the invention, the present invention relates to compounds of Formula (I), (Ia), (Ib), (Ic), (Id), (Ie), (If), (Ig) and (Ih) and pharmaceutically acceptable salts thereof, wherein $R^4$ is propyl, t-butyl, cyclopentyl, cyclohexyl optionally substituted with 1 or 2 F, cyclohexylmethyl, methylcyclohexyl, methylcyclopentyl, dihydroindenyl, or tetrahydro-2H-pyranyl, and the other variables are as provided for in any of the first, sixth or seventh embodiments. In one aspect of this embodiment, $R^4$ is t-butyl, cyclopentyl, or cyclohexyl, 1-methylcyclohexyl, propan-2-yl, 2,3-dihydroindenyl, tetrahydro-2H-pyranyl, or cyclohexylmethyl. In another aspect of this embodiment, $R^4$ is t-butyl, cyclopentyl, or cyclohexyl, 1-methylcyclohexyl, 2,3-dihydroindenyl, or tetrahydro-2H-pyranyl.

In a ninth embodiment of the invention, the present invention relates to compounds of Formula (I), (Ia), (Ib), (Ic), (Id), (Ie), (If), (Ig) and (Ih) and pharmaceutically acceptable salts thereof, wherein n is 1 or 3, and the other variables are as provided for in any of the first or sixth to eighth embodiments.

In a tenth embodiment of the invention, the present invention relates to compounds of Formula (I), (Ia), (Ib), (Ic), (Id), (Ie), (If), (Ig) and (Ih) and pharmaceutically acceptable salts thereof, wherein $R^2$ is cyclopropyl, $N(CH_3)_2$, or azetidinyl, wherein the cyclopropyl is optionally substituted with methyl, $CH(CH_3)_2$, $C(CH_3)=CH_2$; $C(CH_3)_2OH$, $CH_2CH_2$-morpholinyl, $CH_2OCH_3$, $CH_2OCH_2CH_2OCH_3$, or $CH_2OCH_2$-phenyl, and the other variables are as provided for in any of the first or sixth through ninth embodiments. In one aspect of this embodiment, $R^2$ is cyclopropyl, $N(CH_3)_2$, (methyl)cyclopropyl, (methoxymethyl)cyclopropyl, [(benzyloxy)methyl]cyclopropyl, 1-(prop-1-en-2-yl)cyclopropyl, or 1-[2-(morpholin-4-yl)ethyl]cyclopropyl. In another aspect of this embodiment, $R^2$ is cyclopropyl, $N(CH_3)_2$, (methyl)cyclopropyl, or 1-(methoxymethyl)cyclopropyl.

In an eleventh embodiment of the invention, the present invention relates to compounds of Formula (I), (Ia), (Ib), (Ic), (Id), (Ie), (If), (Ig) and (Ih) and pharmaceutically acceptable salts thereof, wherein $R^1$ is —OH; —O—$C_{1-6}$alkyl; —OC(O)$C_{1-6}$alkyl; —O$C_{1-6}$alkyl-$het_1$; —O$C_{1-6}$alkyl-$C_{1-6}$alkoxy; —O$C_{1-6}$alkyl-$C_{1-6}$alkoxy-$C_{1-6}$alkoxy; —OCH$_2$C(=O)-$het_1$; —O(CH$_2$)$_{1-6}$ OC(=O)CH$_2$NR$^a$R$^b$; —OC(O)NR$^a$R$^b$; —O$C_{1-6}$alkyl-phosphate; —O$C_{1-6}$alkyl-S-$het_1$; —O-$het_1$; —O—$C_{1-6}$alkyl-OH optionally substituted with 1 or 2 fluoro substituents; or —O$C_{1-6}$alkyl-NR$^a$R$^b$ wherein R$^a$ and R$^b$ are independently
H,
$C_{1-6}$ alkyl,
t-Boc,
$C_{3-6}$cycloalkyl optionally substituted with 1 or 2 fluoro substituents,
$C_{1-6}$ alkyl-$C_{1-6}$alkoxy,
$C_{1-6}$alkyl-OH, phenyl,
$C_{1-6}$alkyl-phenyl,
tetrahydropyranyl,
$C_{1-6}$alkyl-C(OH)-phenyl,
naphthalenyl,
$C_{1-6}$alkyl-naphthalenyl,
$C_{1-6}$alkyl-dihydrooxopyrrolidinyl,
$C_{1-6}$alkyl-benzimidazolyl optionally substituted with methyl,
$C_{1-6}$alkyl-pyrazolyl,
$C_{1-6}$alkyl-triazole optionally substituted with oxo, or
$C_{1-6}$alkyl-imidazolyl optionally substituted with methyl, and the other variables are as provided for in any of the first or sixth through tenth embodiments. In one aspect of this embodiment, $het_1$ is phenyl; oxazepanyl; oxooxazolidinyl; pyridinyl; pyrazolyl; pyrrolyl; tetrahydropyranyl, triazolyl optionally substituted with $C_{1-6}$alkyl; dioxolanyl; oxoimidazolidinyl; morpholinyl optionally substituted with dimethyl or ethyl; pyrrolidinyl optionally substituted with 1 or 2 substituents independently selected from oxo, Boc, $C_{1-6}$alkyl, OH, C(O)NH$_2$, dimethylamino, and methylsulfonyl; piperidinyl optionally substituted with 1 or 2 substituents independently selected from $C_{1-6}$alkyl, $C_{1-6}$alkoxy, $C_{1-6}$alkoxy-$C_{1-6}$alkyl optionally substituted with CF$_3$, cyclopropyl-$C_{1-6}$alkyl, cyclopropyl, —(CH$_2$)$_m$F, OH, —$C_{1-6}$alkyl-SO$_2$$C_{1-6}$alkyl, —(CH2)$_m$CF$_3$, —COO$C_{1-6}$alkyl, Boc, and benzimidazol; imidizolyl; thiazolyl optionally substituted with methyl; azabicycloheptyl; azaspiroheptyl; azaspirononyl; oxaazabiocycloheptyl; oxaazaspiroheptyl optionally substituted with methoxyethyl; azetidinyl optionally substituted with 1 or 2 substituents independently selected from $C_{1-6}$alkyl, $C_{1-6}$alkoxy, cyano, fluoro, OH, phenyl and Boc; dioxidothiomorpholinyl; piperazinyl optionally substituted with 1 or 2 substituents independently selected from $C_{1-6}$alkyl, $C_{1-6}$alkylcyclopropyl, CF$_3$, methylsulfonyl, Boc, and oxo; azabicyclooctyl substituted with $C_{1-6}$alkyl, $C_{1-6}$alkoxy-$C_{1-6}$alkyl, —COO$C_{1-6}$alkyl, or —(CH$_2$)$_m$CF$_3$; oxaazabicyclononyl optionally substituted with Boc, $C_{1-6}$alkyl, —COO$C_{1-6}$alkyl, $C_{1-6}$alkoxy-$C_{1-6}$alkyl or cyclopropyl$C_{1-6}$alkyl; or azabicyclooctanyl optionally substituted with $C_{1-6}$alkyl. In one aspect of the invention, $R^1$ is —OH; —OC(O)CH$_3$; methoxy; ethoxy; 2-(tert-butylamino)ethoxy; 3-aminopropoxy; 2-methoxyethoxy; 3-methoxypropoxy; 3-(2-methoxyethoxy)propoxy; 3-(2-azabicyclo[2.2.1]hept-2-yl)propoxy; 2-(2-azaspiro[3.3]hept-2-yl)ethoxy; 3-(2-azaspiro[3.3]hept-2-yl)propoxy; 3-(2-azaspiro[4.4]non-2-yl)propoxy; azetidin-3-yloxy; 2-(azetidin-1-yl)ethoxy; 3-(azetidin-1-yl)propoxy; 3-{[2-(1H-benzimidazol-2-yl)ethyl](ethyl)amino}propoxy; 3-[benzyl(2-hydroxyethyl)amino]propoxy; 3-[bis(2-methoxyethyl)amino]propoxy; 3-[(2R)-2-carbamoylpyrrolidin-1-yl]propoxy; 3-(3-cyanoazetidin-1-yl)propoxy; 3-(cyclobutylamino)propoxy; 3-(cyclopentylamino)propoxy; 2-(cyclopropylamino)ethoxy; [1-(cyclopropylmethyl)piperidin-4-yl]oxy; (1-cyclopropylpiperidin-4-yl)oxy; 3-(cyclopropylamino)propoxy; [1-(cyclopropylmethyl)azetidin-3-yl]oxy; 3-(3,3-difluoroazetidin-1-yl)propoxy; 2,2,-difluoro-3-hydroxypropoxy; 3-{[2-(3,4-dihydroxyphenyl)-2-hydroxyethyl](propan-2-yl)amino}propoxy; 2-(dimethylamino)ethoxy; 3-(dimethylamino)propoxy; 2-(2,2-dimethylmorpholin-4-yl)ethoxy; (1,4-dimethylpiperazin-2-yl)methoxy; 3-(dimethylamino)pyrrolidin-1-yl; 2-(1,3-dioxalan-2-yl)ethoxy; 2-(1,1-dioxidothiomorpholin-4-yl)ethoxy; 3-(1,1-dioxidothiomorpholin-4-yl)propoxy; 2-(2,5-dioxopyrrolidin-1-yl)ethoxy; (4-ethylmorpholin-2-yl)methoxy; 1-ethylpiperidin-3-yl)methoxy; (1-ethylpiperidin-4-yl)methoxy; (1-ethylpiperidin-4-yl)oxy; 3-(3-fluoroazetidin-1-yl)propoxy; 3-[2-(5-fluoro-1H-benzimidazol-2-yl)piperidin-1-yl]propoxy; 3-(3-fluoropiperidin-1-yl)propoxy; 2-(3-hydroxyazetidin-1-yl)ethoxy; 4-hydroxybutoxy; 2-hydroxyethoxy; 3-hydroxy-3-methylbutoxy; 2-(4-hydroxy-4-methylpiperidin-1-yl)ethoxy; 3-(3-hydroxy-3-methylpyrrolidin-1-yl)propoxy; 3-(3-hydroxy-3-phenylazetidin-1-yl)propoxy; 3-[(1-hydroxy-1-phenylpropan-2-yl)(methyl)amino]propoxy; 3-hydroxypropoxy; 3-[(3R)-3-hydroxy pyrrolidin-1-yl]propoxy; 2-(1H-imidazol-1-yl)ethoxy; 3-[(1H-imidazol-2-ylmethyl)(methyl)amino]propoxy; 3-(1H-imidazol-1-yl)propoxy; 3-(3-methoxy azetidin-1-yl)propoxy; [(1R,4R,5R)-2-(2-methoxyethyl)-2-azabicyclo[2.2.1]hept-5-yl]oxy; 1-(2-methoxyethyl)piperidin-4-yl]methoxy; [1-(2-methoxyethyl)piperidin-4-yl]oxy; 3-(4-methoxypiperidin-1-yl)propoxy; 3-[(1-methoxypropan-2-yl)amino]propoxy; 3-(methylamino)propoxy; (1-methylazetidin-3-yl)methoxy; 3-{methyl[(5-methyl-1H-benzimidazol-2-yl)methyl]amino}propoxy; 3-{methyl[(5-methyl 1H-imidazol-2-yl)methyl]amino}propoxy; 3-{methyl[(5-oxo-4,5-dihydro-1H-1,2,4-triazol-3-yl)methyl]amino}propoxy; 3-(4-methyl-3-oxopiperazin-1-yl)propoxy; 3-{methyl[(5-oxopyrrolidin-2-yl)methyl]amino}propoxy; 3-(4-methylpiperazin-1-yl)propoxy; (1-methylpiperidin-2-yl)oxy; (1-methylpiperidin-4-yl)oxy; 3-[methyl(1H-pyrazol-5-ylmethyl)amino]propoxy; (1-methylpyrrolidin-3-yl)methoxy; 3-[4-(methylsulfonyl)piperazin-1-yl]propoxy; 3-[3-(methyl sulfonyl)pyrrolidin-1-yl]propoxy; 3-[(4-methyl-4H-1,2,4-triazol-3-yl)sulfanyl]propoxy; (2R)-morpholin-2-ylmethoxy; 2-(morpholin-4-yl)ethoxy; 3-(morpholin-4-yl)propoxy; 4-(morpholin-4-yl)butoxy; 3-{[2-(naphthalen-1-yl)ethyl]amino}propoxy; 3-[(1S,4S)-2-oxa-5-azabicyclo[2.2.1] hept-5-yl]propoxy; 3-(2-oxa-6-azaspiro[3.3]hept-6-yl)propoxy; 3-(1,4-oxazepan-4-yl)propoxy; 3-(2-oxoimidazolidin-1-yl-propoxy; (2-oxo-1,3-oxazolidin-3-yl)ethoxy; 2-oxo-2-(pyrrolidin-1-yl)ethoxy; 2-(2-oxopyrrolidin-1-yl)ethoxy; 3-{[2-(2-oxopyrrolidin-1-yl)ethyl]amino}propoxy; 3-(2-oxopyrrolidin-1-yl)propoxy; 3-[(4-phenylbutyl)amino]propoxy; 2-(piperidin-1-yl)ethoxy; 3-(piperidin-1-yl)propoxy; 3-(propan-2-ylamino) propoxy; 2-(1H-pyrazol-1-yl)ethoxy; 2-(pyridin-2-yl)ethoxy; 2-(pyridin-3-yl)ethoxy; 2-(pyridine-4-yl)ethoxy; 2-(1H-pyrrol-1-yl)ethoxy; 3-(1H-pyrrol-1-yl)propoxy; 2-(pyrrolidin-1-yl)ethoxy; 3-(pyrrolidin-1-yl)propoxy; 3-(1,2,3,4-tetrahydronaphthalen-1-ylamino)propoxy; 3-(tetrahydro-2H-pyran-4-ylamino)propoxy; 3-(4H-1,2,4-triazol-4-yl)propoxy; 3-[3-(trifluoromethyl)piperazin-1-yl]propoxy; —O(CH$_2$)$_3$OC(=O)CH$_2$N(CH$_3$)$_2$; —O(CH$_2$)$_3$NHBoc; —OC(=O)NHCH(CH$_3$)$_2$; —O(CH$_2$)$_3$OP(=O)(OH)$_2$; [1-(tert-butoxycarbonyl)pyrrolidin-4-yl]methoxy, [1-(2,2,2-trifluoroethyl)piperidin-4-yl]oxy; [1-(tert-butoxycarbonyl)piperidin-4-yl]oxy; 3-[(3,3-difluorocyclobutyl)amino]propoxy; pyridin-2-yl; pyridine-3-yl; pyridine-4-yl; 1,3-thiazol-2-yl; (morpholin-4-yl)methoxy; tetrahydro-2H-pyran-4-yloxy; [7-(tert-butoxycarbonyl)-3-oxa-7-azabicyclo[3.3.1]non-9-yl] oxy; [7-(cyclopropylmethyl)-3-oxa-7-azabicyclo[3.3.1]non-9-yl]oxy; [7-(2-methoxyethyl)-3-oxa-7-azabicyclo[3.3.1] non-9-yl]oxy; 3-oxa-7-azabicyclo[3.3.1]non-9-yl}oxy; (7-ethyl-3-oxa-7-azabicyclo[3.3.1]non-9-yl)oxy; {1-[2-(trifluoromethoxy)ethyl]piperidin-4-yl}oxy; (8-methyl-8-azabicyclo[3.2.1]oct-3-yl)oxy; [1-(tert-butoxycarbonyl)piperazin-4-yl]propoxy; (4-methylpiperazin-1-yl)methoxy; piperidin-4-yloxy; {1-[2-(methylsulfonyl)ethyl]piperidin-4-yl}oxy; [(2-fluoroethyl)piperidin-4-yl]oxy; [8-(tert-butoxycarbonyl)-8-azabicyclo[3.2.1]oct-3-yl]oxy; (8-azabicyclo[3.2.1]oct-3-yl)oxy; [8-(2,2,2-trifluoroethyl)-8-azabicyclo[3.2.1]oct-3-yl]oxy; [8-(2-methoxyethyl)-8-azabicyclo[3.2.1]oct-3-yl]oxy; (8-ethyl-8-azabicyclo[3.2.1]oct-3-yl)oxy; [9-(tert-butoxycarbonyl)-3-oxa-9-azabicyclo[3.3.1] non-7-yl]oxy; 3-oxa-9-azabicyclo[3.3.1]non-7-yloxy; [9-(2-methoxyethyl)-3-oxa-9-azabicyclo[3.3.1]non-7-yl]oxy; [9-ethyl)-3-oxa-9-azabicyclo[3.3.1]non-7-yl]oxy; [1-(tert-butoxycarbonyl)-3-fluoro-piperidin-4-yl]oxy; (3-fluoropiperidin-4-yl)oxy; and (3-fluoro-1-methylpiperidin-4-yl)oxy.

In a twelfth embodiment of the invention, the present invention relates to compounds of Formula (I), (Ia), (Ib), (Ic), (Id), (Ie), (If), (Ig) and (Ih) and pharmaceutically 5 acceptable salts thereof, wherein X is absent or selected from —Br, —Cl, —F, methoxy, methyl, propanyl and CF3, and the other variables are as provided for in any of the first or sixth through eleventh embodiments.

In a thirteenth embodiment of the invention, the compound of the invention is selected from the exemplary species depicted in Examples 1 through 306 shown below (or a pharmaceutically acceptable salt thereof).

In a fourteenth embodiment of the invention, the compound of the invention is one of the following compounds:

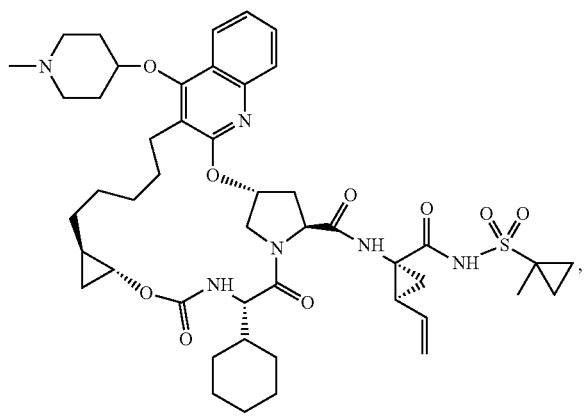

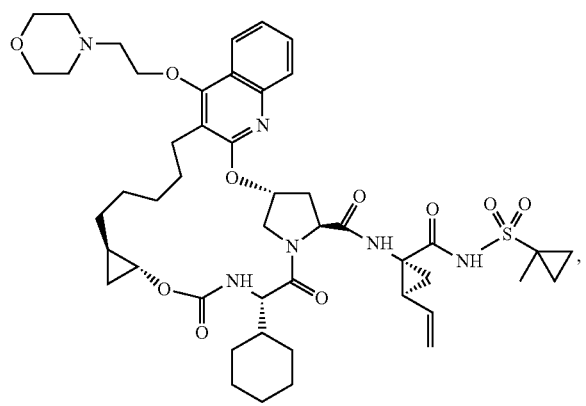

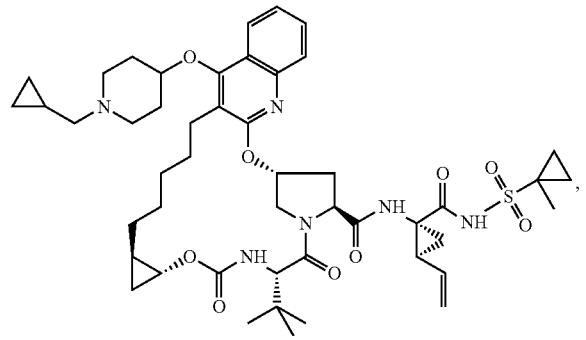

11
-continued
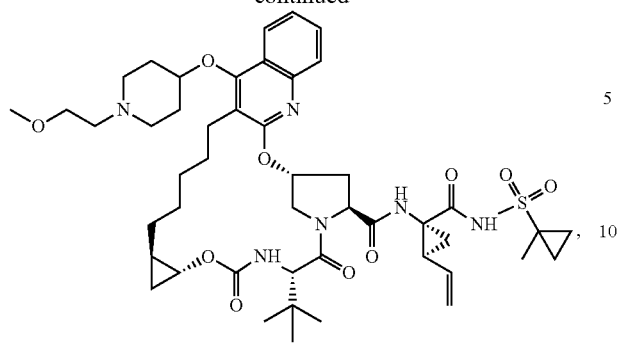
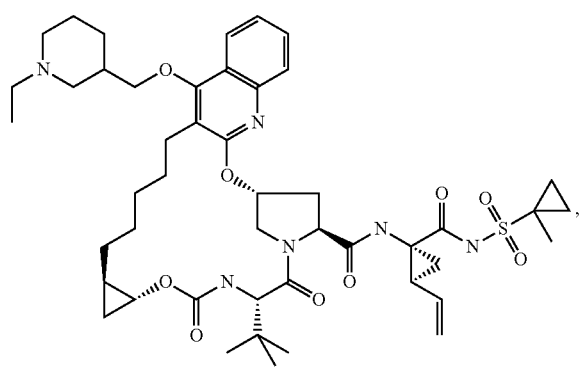
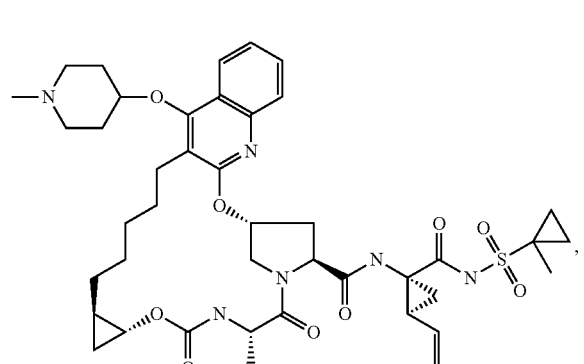
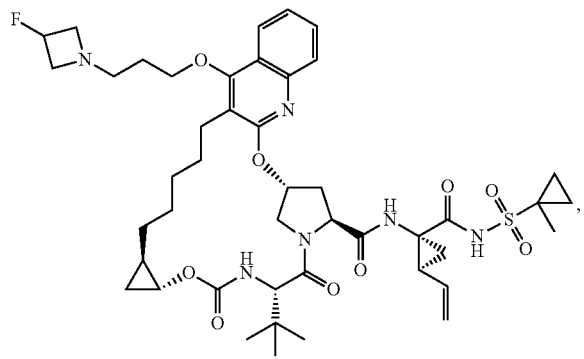
12
-continued
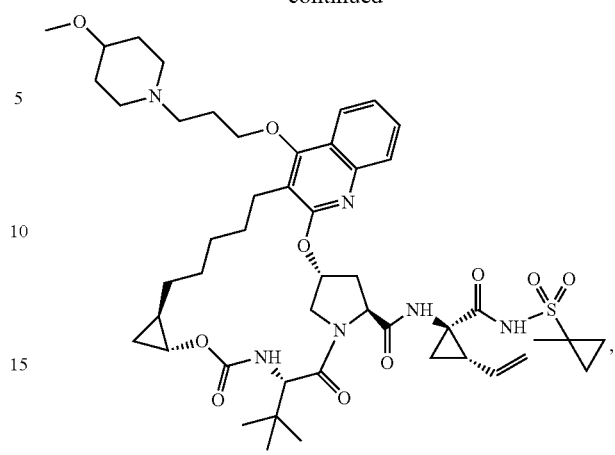
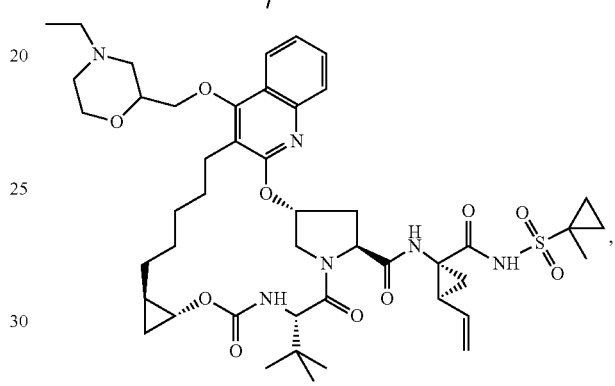
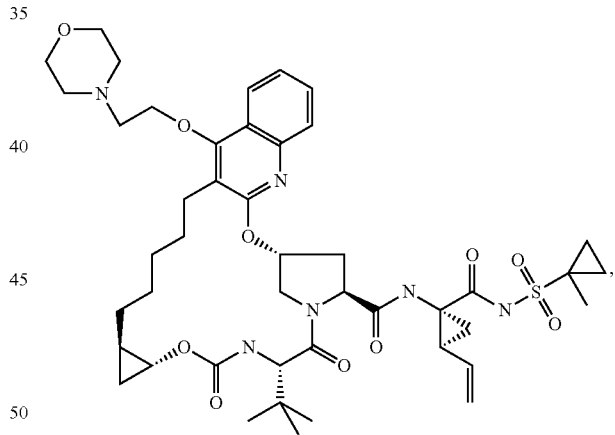
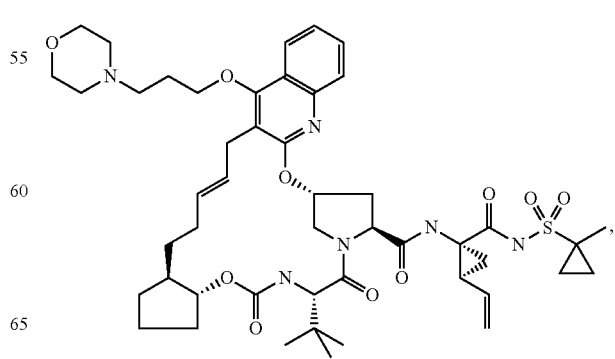

13
-continued
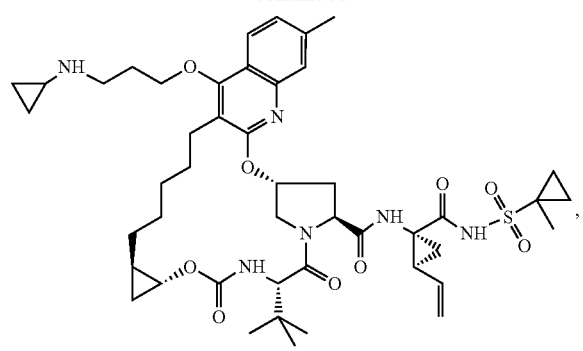
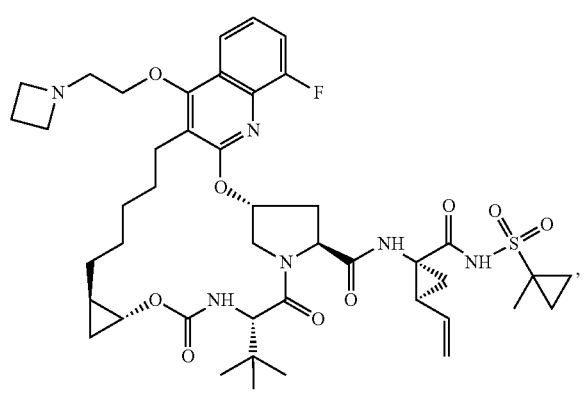
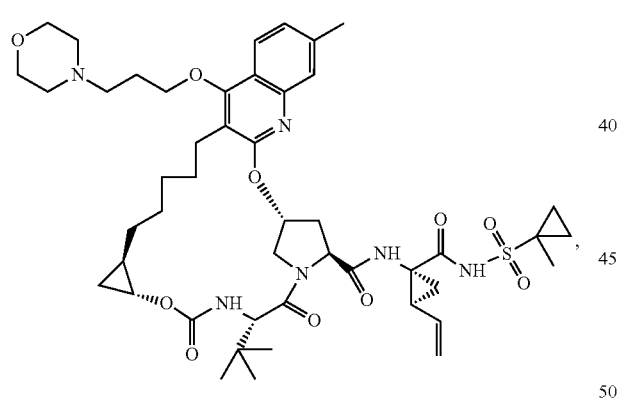
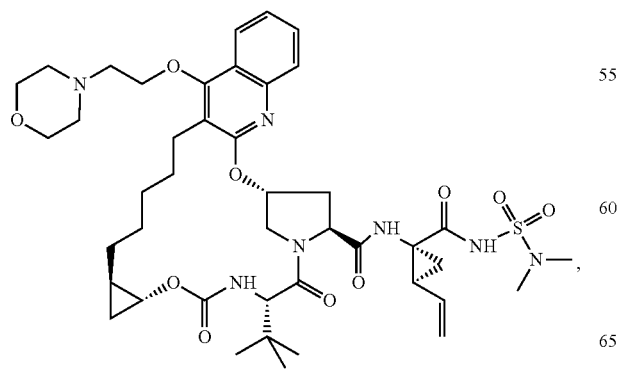
14
-continued
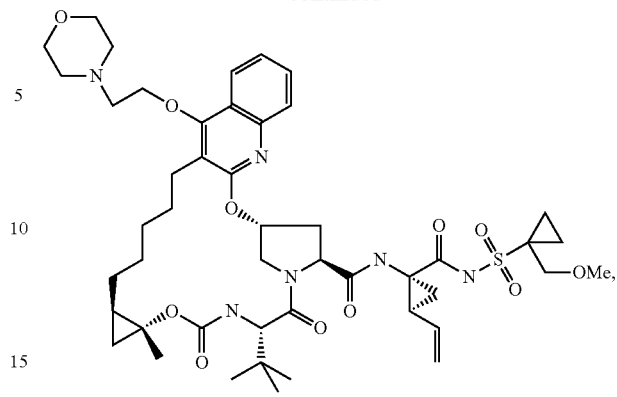
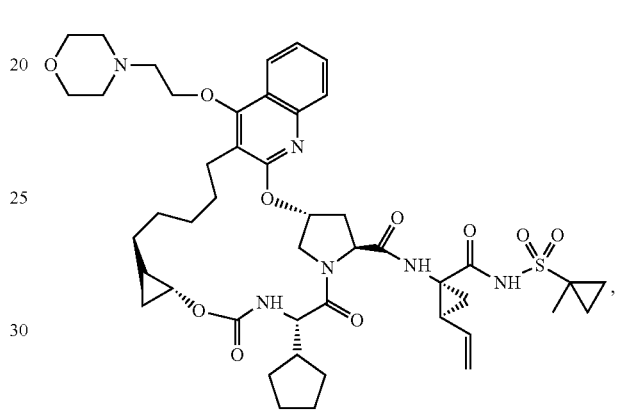
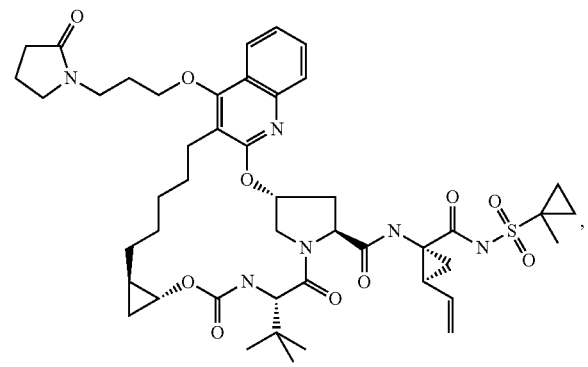
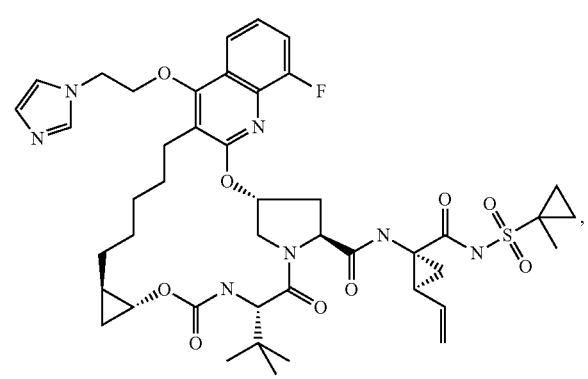

-continued
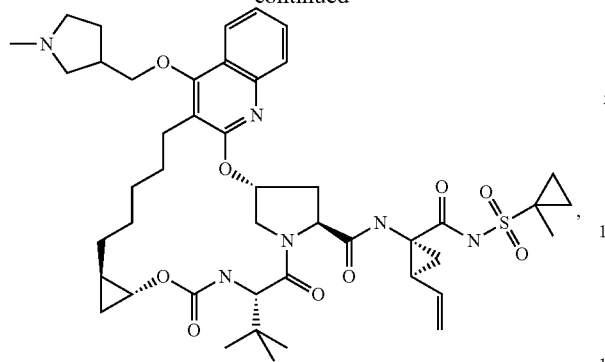
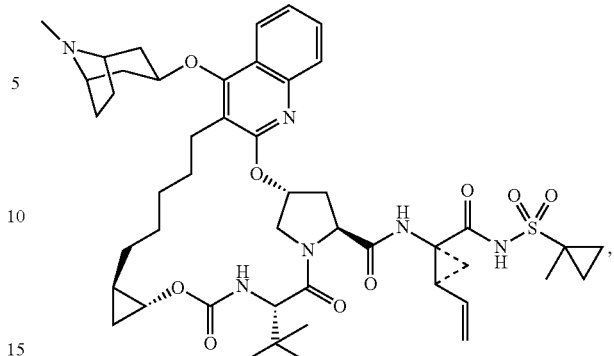
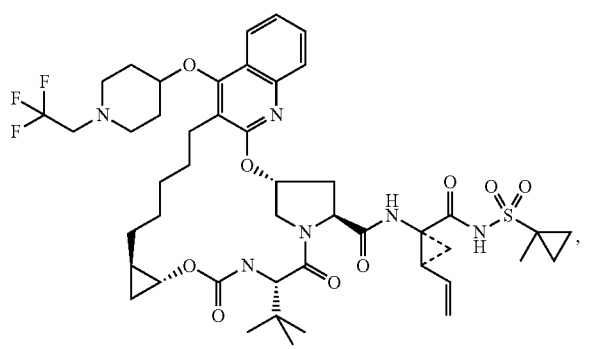
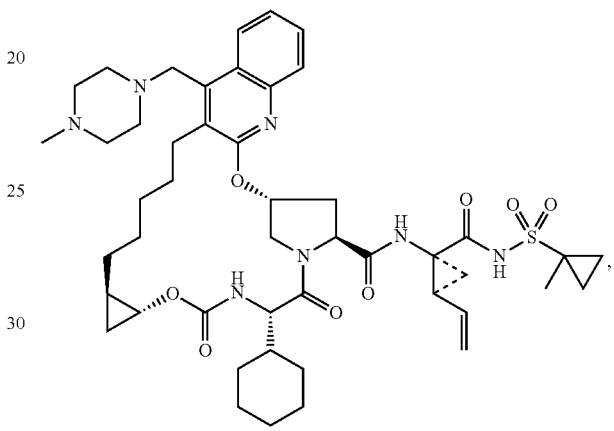
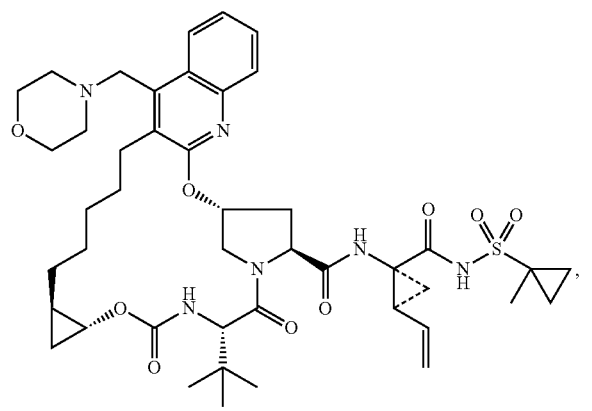
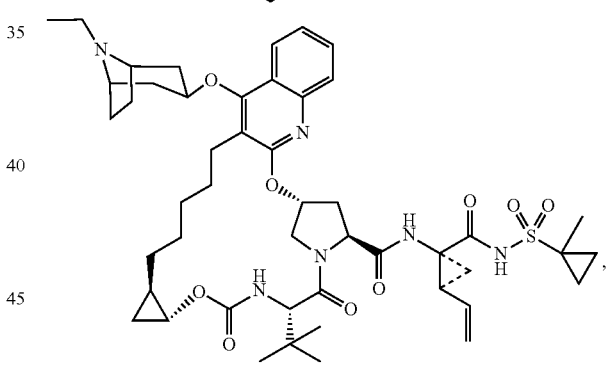
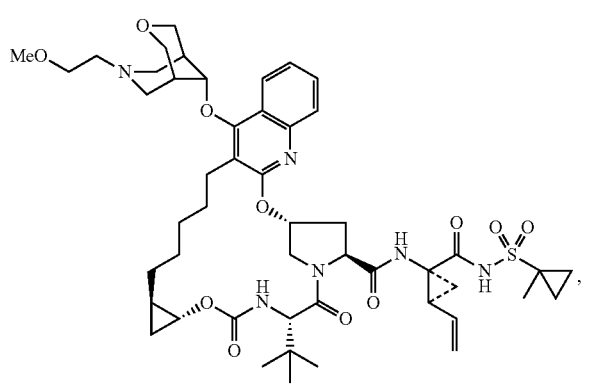
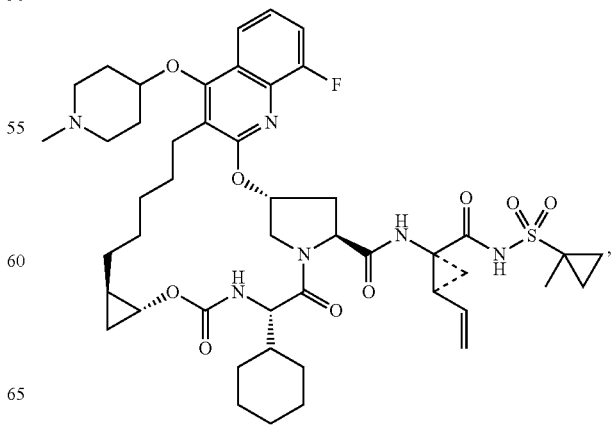

-continued

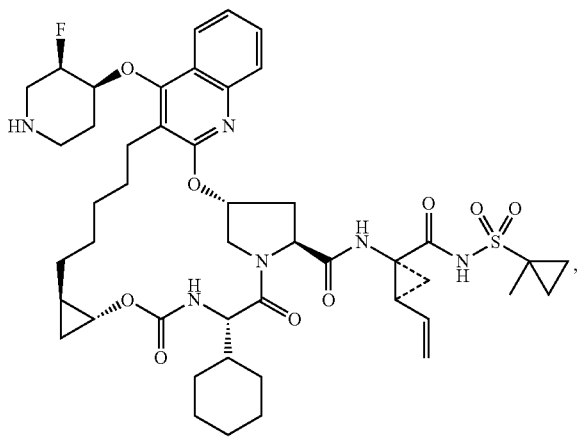

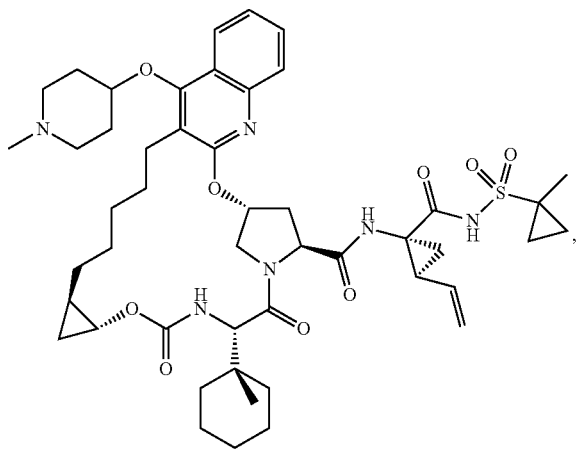

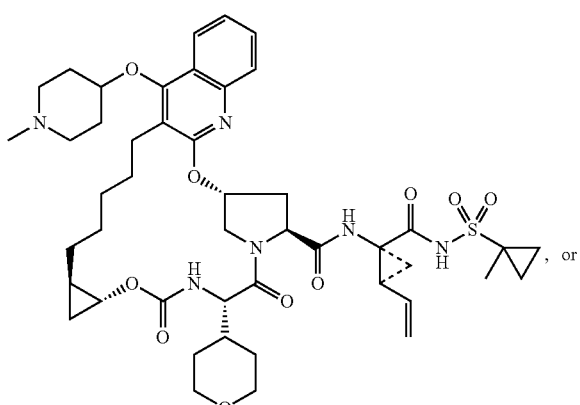

-continued

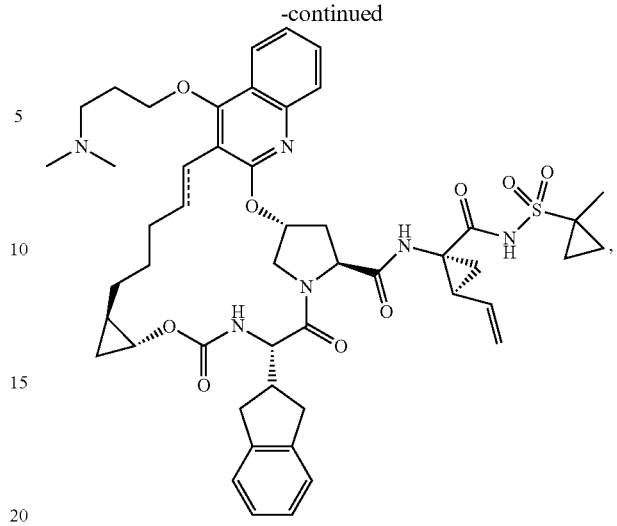

or a pharmaceutically acceptable salt of any of the above.

In a fifteenth embodiment of the invention, the compound of the invention is one of the following compounds:

(1aR,5S,11Z,12aS,13aR,16S,19R,27E,31aR)—N-[(1-methylcyclopropyl)sulfonyl]-3,15,33-trioxo-26-[2-(piperidin-1-yl)ethoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,27E,31aR)—N-[(1-methylcyclopropyl)sulfonyl]-26-[2-(morpholin-4-yl)ethoxy]-3,15,33-trioxo-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,27E,31aR)—N-[(1-methylcyclopropyl)sulfonyl]-26-[3-(morpholin-4-yl)propoxy]-3,15,33-trioxo-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,27E,31aR)—N-[(1-methylcyclopropyl)sulfonyl]-3,15,33-trioxo-26-[2-(pyrrolidin-1-yl)ethoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(141)-carboxamide;

(1aR,5S,11Z,12aS,13aR,16S,19R,27E,31aR)-26-methoxy-N-[(1-methylcyclopropyl)sulfonyl]-3,15,33-trioxo-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,31aR)—N-[(1-methylcyclopropyl)sulfonyl]-26-[2-(morpholin-4-yl)ethoxy]-3,15,33-trioxo-1,1a,3,4,5,6,7,8,9,10,12a,13,15,16,18,19,27,28,29,30,31,31a-docosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,27E,31aR)—N-[(1-methylcyclopropyl)sulfonyl]-3,15,33-trioxo-26-[3-(piperidin-1-yl)propoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,27E,31aR)—N-[(1-methylcyclopropyl)sulfonyl]-3,15,33-trioxo-26-[3-(pyrrolidin-1-yl)propoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide; or (1aR,5S,11Z,12aS,13aR,16S,19R,27E,31aR)—N-[(1-methylcyclopropyl)sulfonyl]-26-[3-(4-methylpiperazin-1-yl)propoxy]-3,15,33-trioxo-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide, or a pharmaceutically acceptable salt of any of the above.

Other embodiments of the present invention include the following:

(a) A pharmaceutical composition comprising an effective amount of a compound of formula (I), in any of the described embodiments, and a pharmaceutically acceptable carrier.

(b) The pharmaceutical composition of (a), further comprising a second therapeutic agent selected from the group consisting of HCV antiviral agents, immunomodulators, and anti-infective agents. In one aspect of the invention, the second therapeutic agent is ribavirin.

(c) The pharmaceutical composition of (b), wherein the HCV antiviral agent is an antiviral selected from the group consisting of HCV protease inhibitors and HCV NS5B polymerase inhibitors.

(d) A pharmaceutical combination which is (i) a compound of formula (I) and (ii) a second therapeutic agent selected from the group consisting of WV antiviral agents, immunomodulators, and anti-infective agents; wherein the compound of formula (I) and the second therapeutic agent are each employed in an amount that renders the combination effective for inhibiting HCV NS3 protease, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV NS3 protease in a subject in need thereof which comprises administering to the subject an effective amount of a compound of formula (I).

(g) A method of treating HCV infection and/or reducing the likelihood or severity of symptoms of HCV infection in a subject in need thereof which comprises administering to the subject an effective amount of a compound of formula (I).

(h) The method of (g), wherein the compound of formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV NS3 protease in a subject in need thereof which comprises administering to the subject the pharmaceutical composition of (a), (b), or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b), or (c) or the combination of (d) or (e).

In the embodiments of the compounds provided above, it is to be understood that each embodiment may be combined with one or more other embodiments, to the extent that such a combination provides a stable compound and is consistent with the description of the embodiments. It is further to be understood that the embodiments of compositions and methods provided as (a) through (k) above are understood to include all embodiments of the compounds, including such embodiments as result from combinations of embodiments.

The present invention also includes a compound of the present invention for use (i) in, (ii) as a medicament for, or (iii) in the preparation of a medicament for: (a) inhibiting HCV NS3 protease, or (b) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators. In one aspect of the invention, the second therapeutic agent is ribavirin.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

As used herein, all ranges are inclusive, and all sub-ranges are included within such ranges, although not necessarily explicitly set forth. In addition, the term "or," as used herein, denotes alternatives that may, where appropriate, be combined; that is, the term "or" includes each listed alternative separately as well as their combination.

As used herein, ══ represents a bond where the dotted line is an optional bond. When the optional bond is present, the bond (in its entirety) is a double bond. When the optional bond is absent, the bond (it its entirety) is a single bond. Each such ----- bond is independently a single bond or a double bond. Thus, when two such ----- bonds are adjacent to each other, it can represent two single bonds, two double bonds, a single bond adjacent to a double bond, or a double bond adjacent to a single bond.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl. Alkyl groups may be substituted as indicated.

The term "halogenated" refers to a group or molecule in which a hydrogen atom has been replaced by a halogen. Similarly, the term "haloalkyl" refers to a halogenated alkyl group. The term "halogen" (or "halo") refers to atoms of fluorine, chlorine, bromine and iodine (alternatively referred to as fluoro, chloro, bromo, and iodo).

The term "alkoxy" refers to an "alkyl-O—" group. Alkoxy groups may be substituted as indicated.

The term "alkylene" refers to any linear or branched chain alkylene group (or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—. Alkylene groups may be substituted as indicated.

The term "cycloalkyl" refers to any monocyclic or bicyclic ring structure of an alkane or alkene having a number of carbon atoms in the specified range. Thus, for example, "$C_{3-8}$ cycloalkyl" (or "$C_3$-$C_8$ cycloalkyl") includes cyclopropyl, cyclobutyl, cyclopentyl, cyclohexyl, cycloheptyl, and cyclooctyl. The term "cycloalkoxy" refers to a "cycloalkyl-O—" group. Cycloalkyl groups may be substituted as indicated.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. Carbocycle groups may be substituted as indicated, for example with $C_{1-6}$ alkyl, $C_{1-6}$ alkenyl, $C_{1-6}$ alkynyl, aryl, halogen, —$NH_2$ or —OH. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which both rings are saturated is a saturated bicyclic ring system. Saturated carbocyclic rings are also referred to as cycloalkyl rings, e.g., cyclopropyl, cyclobutyl, etc. A fused bicyclic carbocycle in which one or both rings are unsaturated is an unsaturated bicyclic ring system. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include

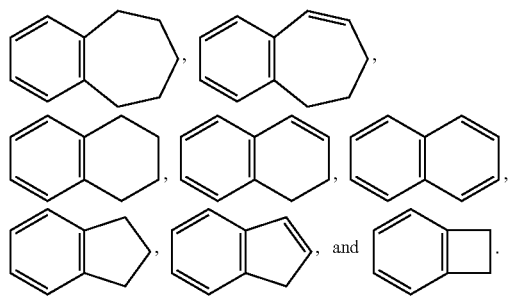

Depicted ring systems include, where appropriate, an indication of the variable to which a particular ring atom is attached. For example, the indole structure

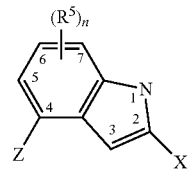

shows ring atom 2 is directly attached to variable X and ring atom 4 is directly attached to variable Z. Variable $R^5$ is shown as a floating variable which can be attached to any ring atom, provided that such attachment results in formation of a stable ring.

The term "aryl" refers to aromatic mono- and poly-carbocyclic ring systems, also referred to as "arenes," wherein the individual carbocyclic rings in the polyring systems are fused or attached to each other via a single bond. Suitable aryl groups include phenyl, naphthyl, and biphenylenyl. Aryl groups may be substituted as indicated.

Unless indicated otherwise, the term "heterocycle" (and variations thereof such as "heterocyclic" or "heterocyclyl") broadly refers to (i) a stable 4- to 8-membered, saturated or unsaturated monocyclic ring, (ii) a stable 7- to 12-membered bicyclic ring system, or (iii) a stable 11- to 15-membered tricyclic ring system, wherein each ring in (ii) and (iii) is independent of, or fused to, the other ring or rings and each ring is saturated or unsaturated, and the monocyclic ring, bicyclic ring system or tricyclic ring system contains one or more heteroatoms (e.g., from 1 to 6 heteroatoms, or from 1 to 4 heteroatoms) independently selected from N, O and S and a balance of carbon atoms (the monocyclic ring typically contains at least one carbon atom and the bicyclic and tricyclic ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Heterocycle groups may be substituted as indicated, and unless otherwise specified, the substituents may be attached to any atom in the ring, whether a heteroatom or a carbon atom, provided that a stable chemical structure results.

Saturated heterocyclics form a subset of the heterocycles. Unless expressly stated to the contrary, the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring, a stable 7- to 12-membered bicyclic ring system, or a stable 11- to 15-membered tricyclic ring system, which consists of carbon atoms and one or more heteroatoms independently selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl). Saturated heterocyclics include 4-8 membered heterocycloalkyls having 1 to 2 heteroatoms selected from N, O, and S.

Unsaturated heterocyclics form another subset of the heterocycles. Unless expressly stated to the contrary, the term "unsaturated heterocyclic" generally refers to a heterocycle as defined above in which the entire ring system (whether mono- or poly-cyclic) is not saturated, i.e., such rings are either unsaturated or partially unsaturated. Unless expressly stated to the contrary, the term "heteroaromatic ring" refers a stable 5- or 6-membered monocyclic aromatic ring, a stable 7- to 12-membered bicyclic ring system, or a stable 11- to 15-membered tricyclic ring system, which consists of carbon atoms and one or more heteroatoms selected from N, O and S. In the case of substituted heteroaromatic rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

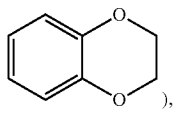

), imidazo (2,1-b)(1,3)thiazole, (i.e.,

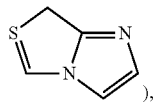

), and benzo-1,3-dioxolyl (i.e.,

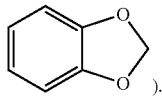

).

In certain contexts herein,

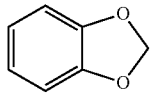

is alternatively referred to as phenyl having as a substituent methylenedioxy attached to two adjacent carbon atoms.

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

When any variable (e.g., $R^7$ and $R^{10}$) occurs more than one time in any constituent or in formula (I) or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers. For the purposes of the present invention a reference to a compound of formula (I) is a reference to the compound per se, or to any one of its tautomers per se, or to mixtures of two or more tautomers.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The compounds of the present inventions are useful in the inhibition of HCV protease (e.g., HCV NS3 protease) and the treatment of HCV infection and/or reduction of the likelihood or severity of symptoms of HCV infection. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus, the compounds of this invention may be commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt (or hydrate) and other agents.

As used herein, the term "prodrug" is intended to encompass an inactive drug form or compound that is converted into an active drug form or compound by the action of enzymes, chemicals or metabolic processes in the body of an individual to whom it is administered.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HCV NS3 protease and treating HCV infection and/or reducing the likelihood or severity of symptoms of HCV infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, $18^{th}$ edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention also relates to a method of inhibiting HCV NS3 protease, inhibiting HCV replication, treating HCV infection and/or reducing the likelihood or severity of symptoms of HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, R7025 (an enhanced interferon (Roche)), interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), pegylated interferon-α2a (Pegasys™), interferon-α2b (such as Intron-A interferon available from Schering Corp., Kenilworth, N.J.), pegylated interferon-α2b (PegIntron™), a recombinant consensus interferon (such as interferon alphacon-1), albuferon (interferon-α bound to human serum albumin (Human Genome Sciences), and a purified interferon-α product. Amgen's recombinant consensus interferon has the brand name Infergen®. Levovirin is the L-enantiomer of ribavirin which has shown immunomodulatory activity similar to ribavirin. Viramidine represents an analog of ribavirin disclosed in International Patent Application Publication No. WO 01/60379. In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in International Patent Application Publication Nos. WO 98/22496, WO 98/46630, WO 99/07733, WO 99/07734, WO 99/38888, WO 99/50230, WO 99/64442, WO 00/09543, WO 00/59929, WO 02/48116 and WO 02/48172, British Patent No. GB 2 337 262, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in International Patent Application Publication Nos. WO 97/41211 and WO 01/00622; another IMPDH inhibitor, such as that disclosed in International Patent Application Publication No. WO 00/25780; or mycophenolate mofetil. See Allison et al., 1993, *Agents Action* 44 (Suppl.):165.

For the treatment of HCV infection, the compounds of the present invention may also be administered in combination with the antiviral agent amantadine (1-aminoadamantane). For a comprehensive description of this agent, see Kirschbaum, 1983, *Anal. Profiles Drug Subs.* 12:1-36.

For the treatment of HCV infection, the compounds of the present invention may also be administered in combination with the antiviral agent polymerase inhibitor R7128 (Roche).

The compounds of the present invention may also be combined for the treatment of HCV infection with antiviral 2'-C-branched ribonucleosides disclosed in Harry-O'Kuru et al., 1997, *J. Org. Chem.* 62:1754-59; Wolfe et al., 1995, *Tet. Lett.* 36:7611-14; U.S. Pat. No. 3,480,613; and International Patent Application Publication Nos. WO 01/90121, WO 01/92282, WO 02/32920, WO 04/002999, WO 04/003000 and WO 04/002422. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in International Patent Application Publication Nos. WO 02/51425, WO 01/79246, WO 02/32920, WO 02/48165, WO05/003147 (including R1656, (2'R)-2'-deoxy-2'-fluoro-2'-C-methylcytidine), WO 01/68663, WO 99/43691, WO 02/18404, WO06/021341, WO 02/100415, WO 03/026589, WO 03/026675, WO 03/093290, WO 04/011478, WO 04/013300 and WO 04/028481, and U.S. Patent Application Publication Nos. US2005/0038240 (including 4'-azido nucleosides such as R1626, 4'-azidocytidine), US2002/0019363, US2003/0236216, US2004/0006007 and US2004/0063658.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in International Patent Application Publication Nos. WO 02/057287, WO 02/057425, WO 03/068244, WO 04/000858, WO 04/003138 and WO 04/007512; U.S. Pat. No. 6,777,392 and U.S. Patent Application Publication No. US2004/0067901. Other such HCV polymerase inhibitors include, but are not limited to, valopicitabine (NM-283; Idenix) and 2'-F-2'-beta-methylcytidine (see also International Patent Application Publication No. WO 05/003147).

In one embodiment, nucleoside HCV NS5B polymerase inhibitors that are used in combination with the present HCV NS3 protease inhibitors are selected from the following compounds: 4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4 (3H)-one; 4-amino-7-(2-C-ethyl-β-D-ribofuranosyl)-7H-pyrrolo[2,3-d]pyrimidine; 4-amino-7-(2-C,2-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4 (3H)-one; 2-amino-5-methyl-7-(2-C, 2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl- β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-(3-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as HCV-796 (Viropharma Inc.) and those disclosed in International Patent Application Publication Nos. WO 01/77091; WO 01/47883; WO 02/04425; WO 02/06246; WO 02/20497; and WO 05/016927 (in particular JTK003).

In one embodiment, non-nucleoside HCV NS5B polymerase inhibitors that are used in combination with the present HCV NS3 protease inhibitors are selected from the following compounds: 14-cyclohexyl-6-[2-(dimethylamino) ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5] benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis (trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5] benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5] benzodiazocine-11-carboxylic acid; 14-cyclohexyl-6-[2-(diethylamino)ethyl]-7-oxo-5,6,7,8-tetrahydroindolo[2,1-a][2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

The HCV NS3 protease inhibitory activity of the present compounds may be tested using assays known in the art. One such assay is HCV NS3 protease time-resolved fluorescence (TRF) assay as described below and in International Patent Application Publication No. WO2006/102087. Other examples of such assays are described in e.g., International Patent Application Publication No. WO2005/046712. The assay is performed in a final volume of 100 μl in assay buffer containing 50 mM HEPES, pH 7.5, 150 mM NaCl, 15% glycerol, 0.15% Triton X-100, 10 mM DTT, and 0.1% PEG 8000. NS3 protease is pre-incubated with various concentrations of inhibitors in DMSO for 30 minutes. The reaction is initiated by adding the TRF peptide substrate (final concentration 100 nM). NS3 mediated hydrolysis of the substrate is quenched after 1 hour at room temperature with 100 μl of 500 mM MES, pH 5.5. Product fluorescence is detected using either a VICTOR V2 or FUSION fluorophotometer (Perkin Elmer Life and Analytical Sciences) with excitation at 340 nm and emission at 615 nm with a 400 μs delay. Testing concentrations of different enzyme forms are selected to result in a signal to background ratio (S/B) of 10-30. $IC_{50}$ values are derived using a standard four-parameter fit to the data. $K_i$ values are derived from $IC_{50}$ values using the following formula, $$IC_{50} = K_i(1+[S]/K_m),\qquad \text{Eqn (1)},$$

where [S] is the concentration of substrate peptide in the reaction and $K_M$ is the Michaelis constant. See Gallinari et al., 1999, *Biochem.* 38:5620-32; Gallinari et al., 1998, *J. Virol.* 72:6758-69; Taliani et al., 1996, *Anal. Biochem.* 240:60-67.

The present invention also includes processes for making compounds of formula (I). The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Olefin metathesis catalysts include the following Ruthenium based species: Miller et al., 1996, *J. Am. Chem. Soc.* 118:9606; Kingsbury et al., 1999, *1 Am. Chem. Soc.* 121:791; Scholl et al., 1999, *Org. Lett.* 1:953; U.S. Patent Application Publication US2002/0107138; Furstner et al., 1999, *J. Org. Chem.* 64:8275. The utility of these catalysts in ring closing metathesis is well known in the literature (e.g. Trnka et al., 2001, *Acc. Chem. Res.* 34:18).

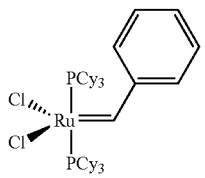

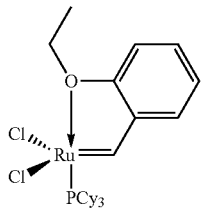

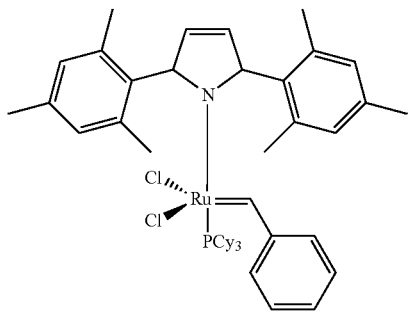

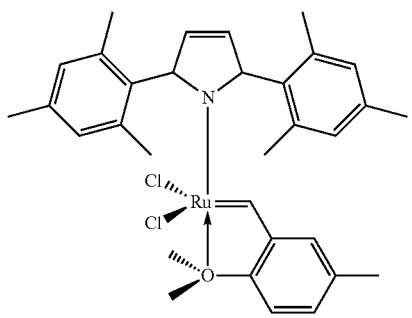

(Zhan catalyst 1A,
Zannan Pharma Ltd.)

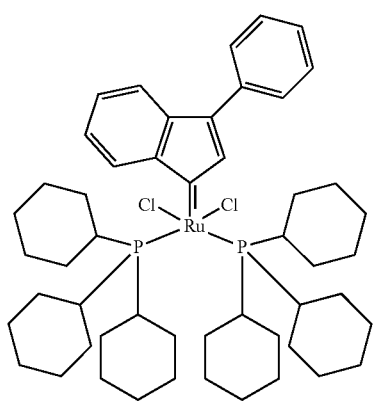

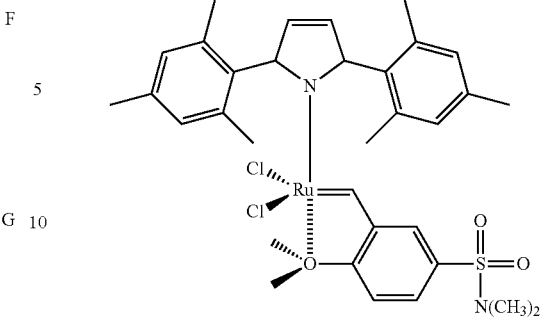

Zhan ruthenium metathesis catalyst RC-303
(Zhan catalyst 1B, RC-303,
Zannan Pharma Ltd.)

The following reaction schemes and examples serve only to illustrate the invention and its practice. The examples are not to be construed as limitations on the scope or spirit of the invention.

LIST OF ABBREVIATIONS

ACN Acetonitrile
Aq. Aqueous
ACN Acetonitrile
Bn Benzyl
BOC (also Boc) t-Butyloxycarbonyl
BuLi Butyl lithium
$CDCl_3$ Deuterio-trichloromethane
DBU 1,8-Diazabicyclo[5.4.0]undec-7-ene
DCM Dichloromethane
DIPEA Diisopropylethylamine
DMA Dimethylacetamide
DMAP 4-Dimethylamine pyridine
DMF Dimethylformamide
DMSO Dimethyl sulfoxide
ES Electronspray ionization
$Et_2O$ Diethyl ether
EtOAc Ethyl acetate
HCl Hydrochloric acid
HATU O-(7-Azabenzotriazol-1-yl)-N,N,N',N'-tetramethyluronium hexafluorophosphate
HF-TEA Hydrogen fluoride triethylamine
HPLC High performance liquid chromatography
HRMS High resolution mass spectrometry
Int. Intermediate
KHMDS Potassium hexamethyldisilazane
$KHSO_4$ Potassium bisulfate
LiOH Lithium hydroxide
LCMS High performance liquid chromatography mass spectrometry
LRMS Low resolution mass spectrometry
MeOH Methanol
MES 2-(N-morpholino)ethanesulfonic acid
NaOH Sodium hydroxide
$NaHCO_3$ Sodium hydrogen carbonate (sodium bicarbonate)
$Na_2CO_3$ Sodium carbonate
NMM N-methylmorpholine
Pd/C Palladium on carbon
$Pd(Ph_3P)_4$ Tetrakis(triphenylphosphine)palladium(0)
$PPh_3$ Triphenylphosphine
Rh/C Rhodium on carbon
TBS tert-Butyldimethylsilyl
TEA Triethylamine TFA Trifluoroacetic acid
THF Tetrahydrofuran
TLC Thin Layer Chromatography
Tosyl p-Toluenesulfonyl
General Methods For Intermediates A, various salt forms have been used for the coupling reaction. These include but are not limited to tosylate and TFA salts.

For the final products, they have been isolated either in their free form or a salt derivative (TFA$^-$, MeS(O)$_2$O$^-$, K$^+$, Na$^+$, etc.).

General Methods

Scheme 1
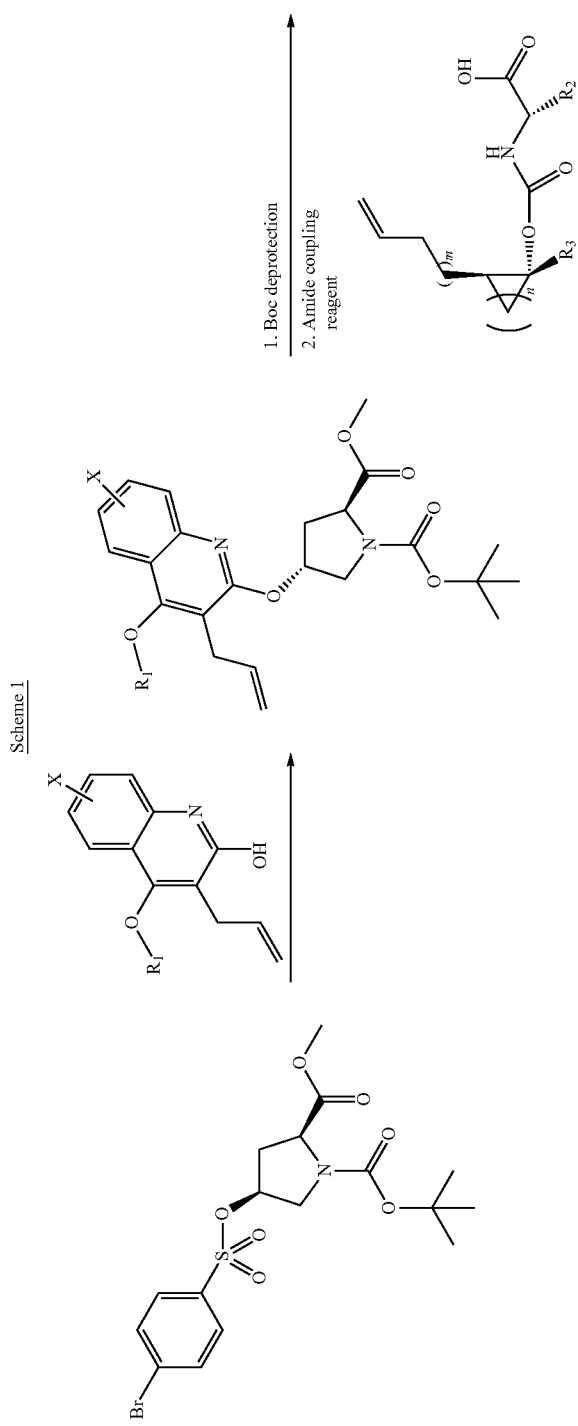

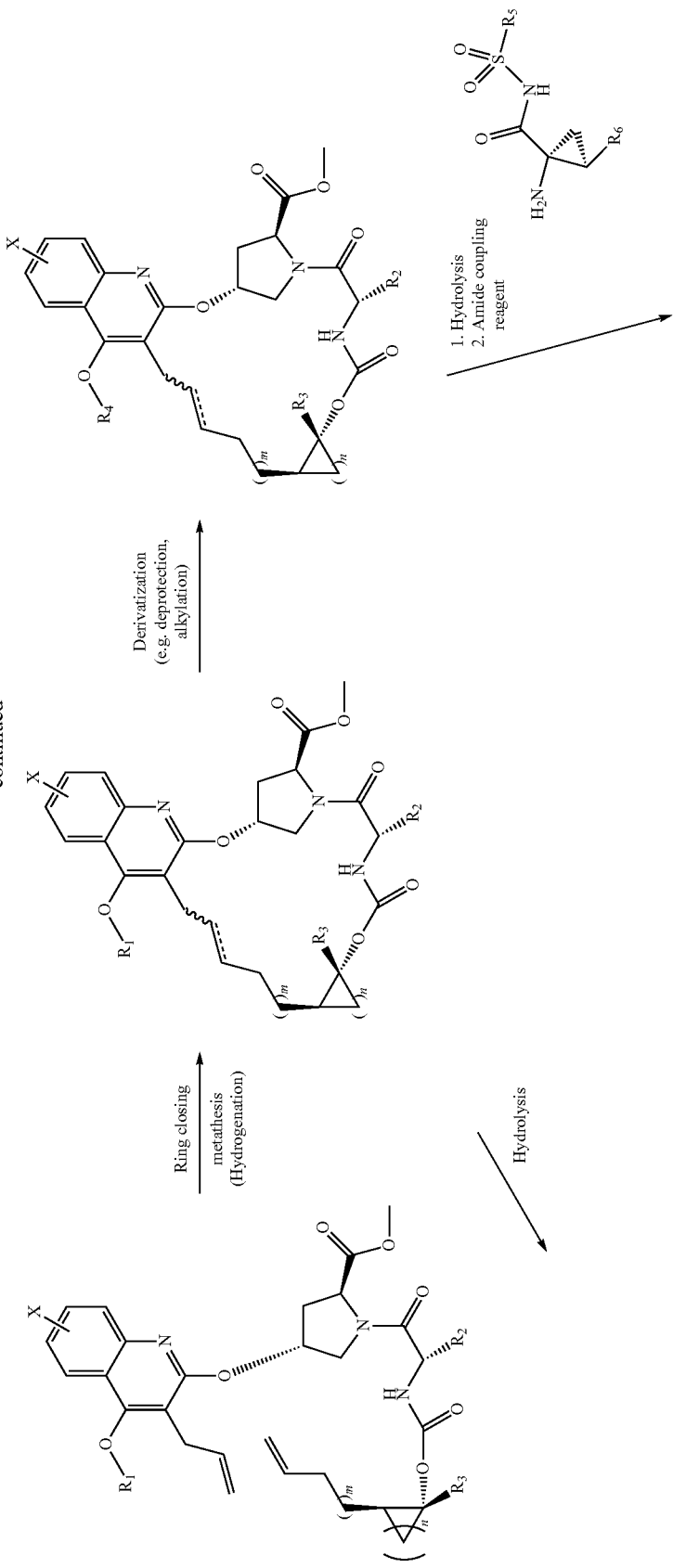

-continued
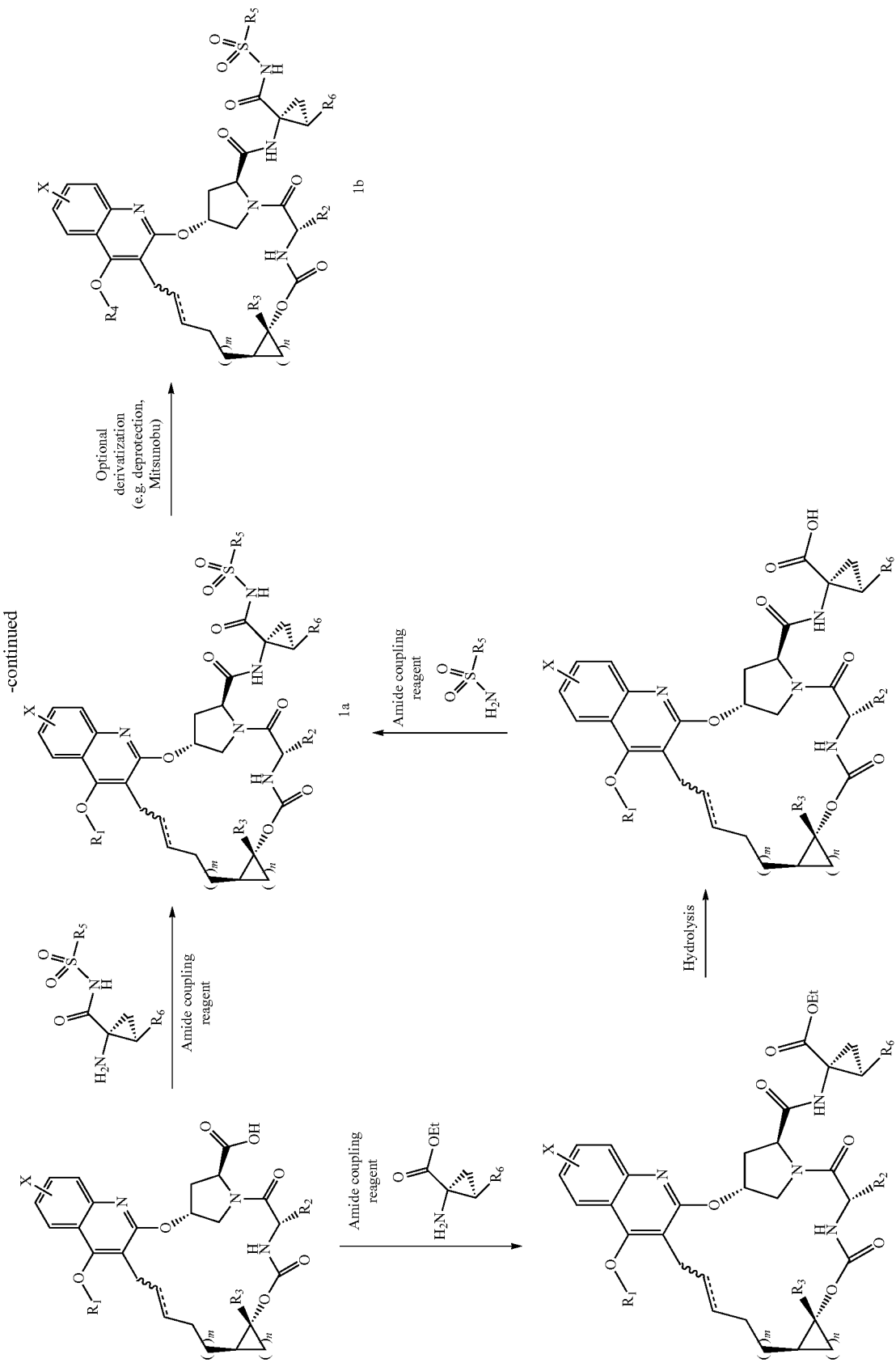

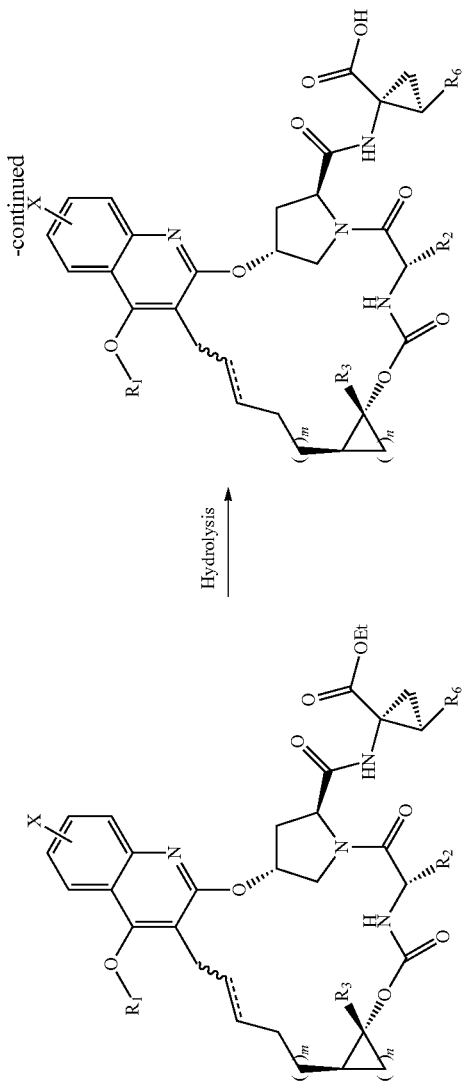

Scheme 2
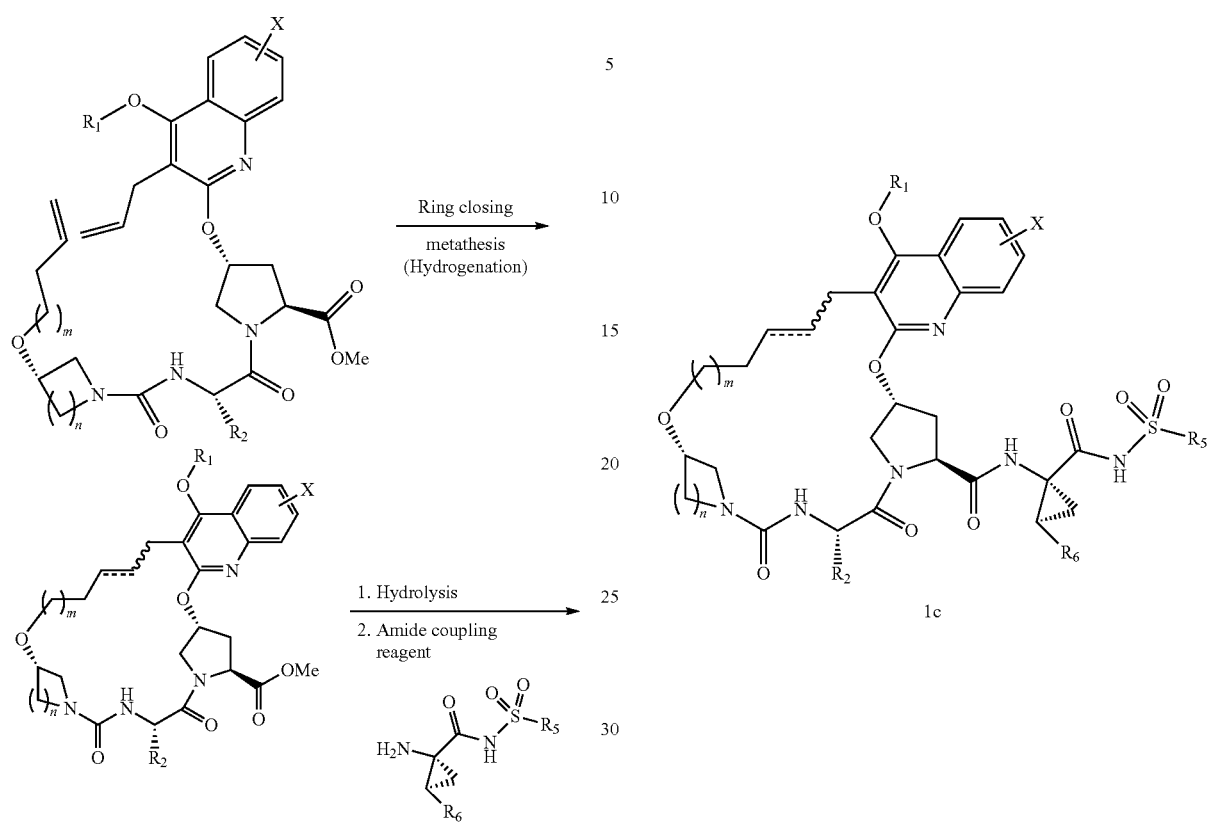

Scheme 3
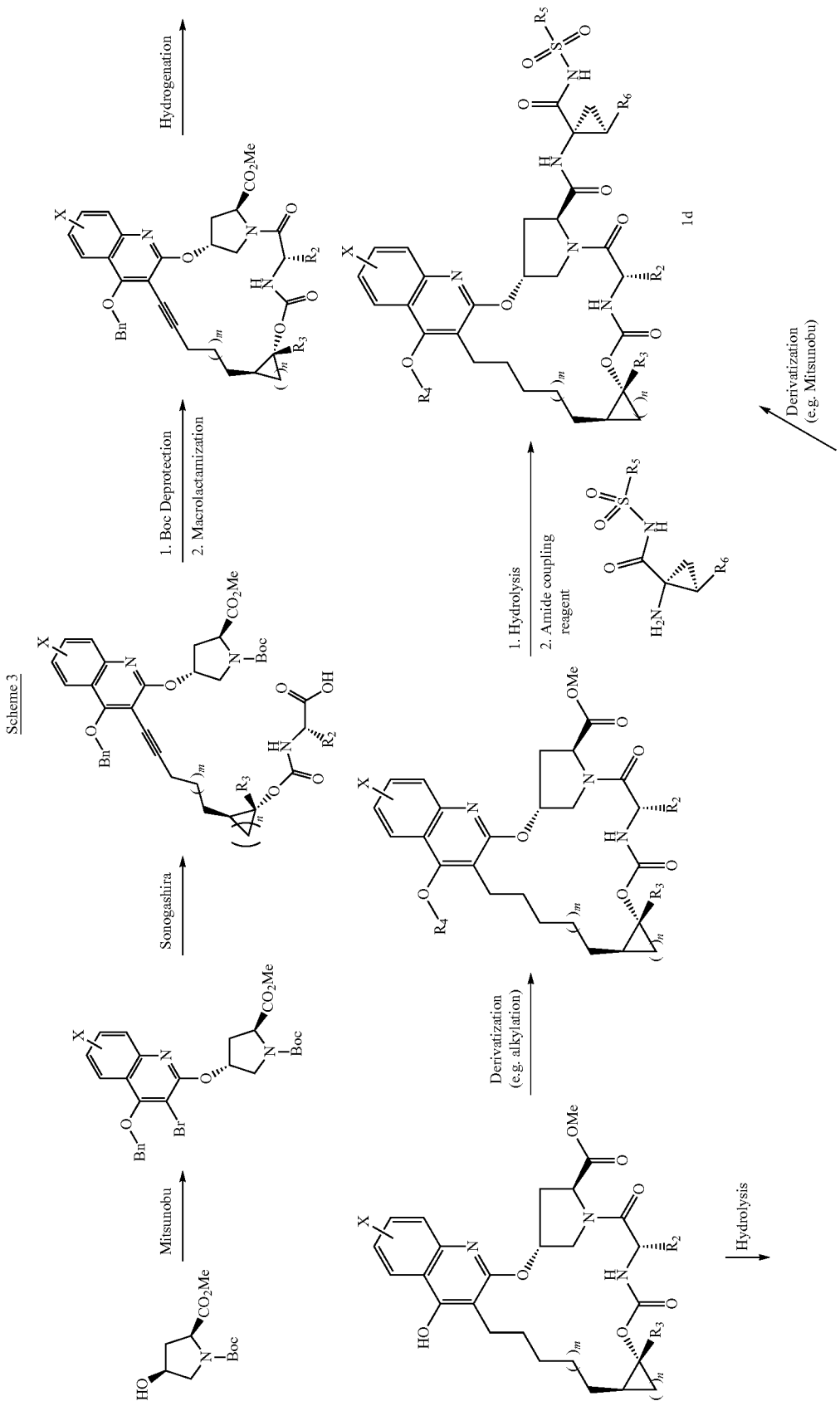

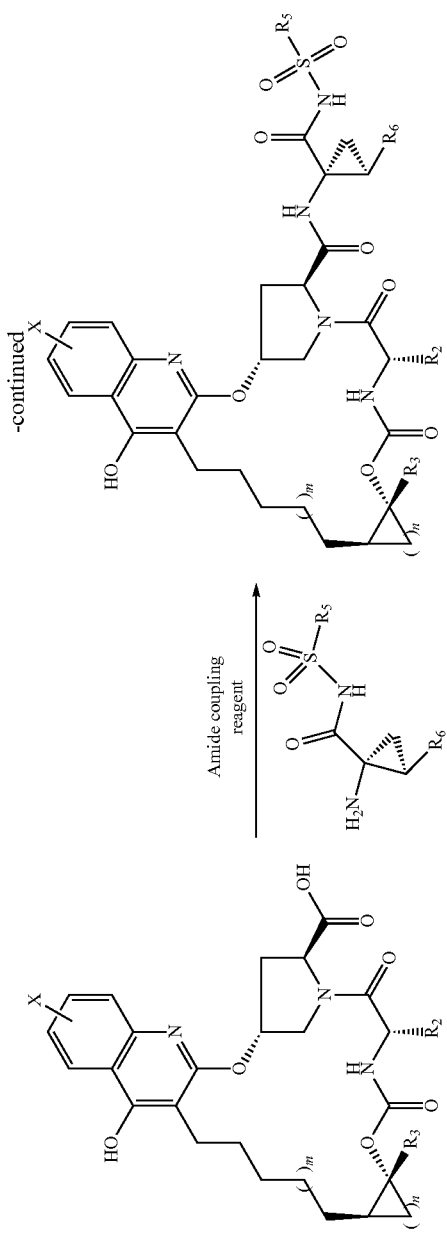

Scheme 4
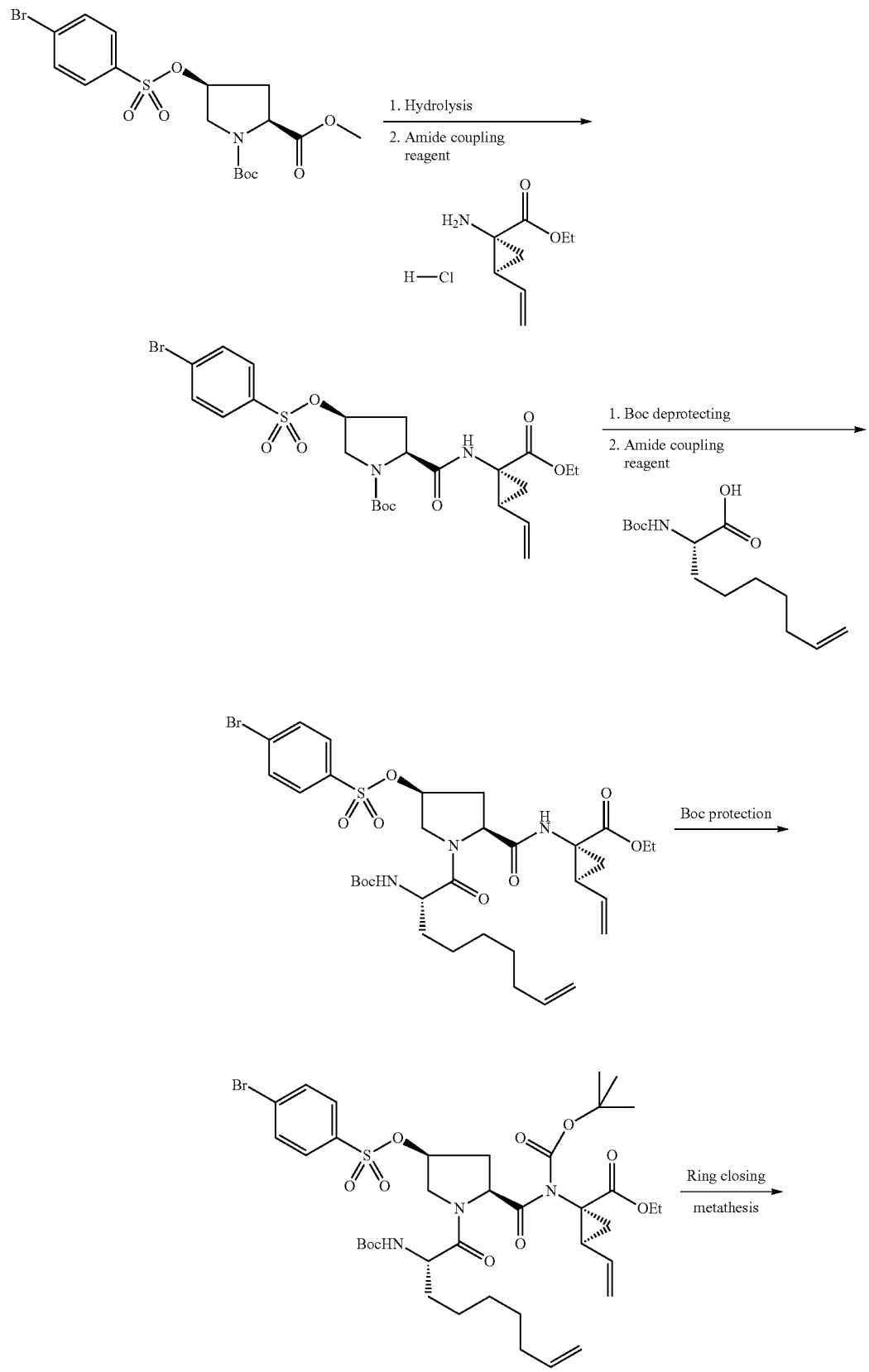

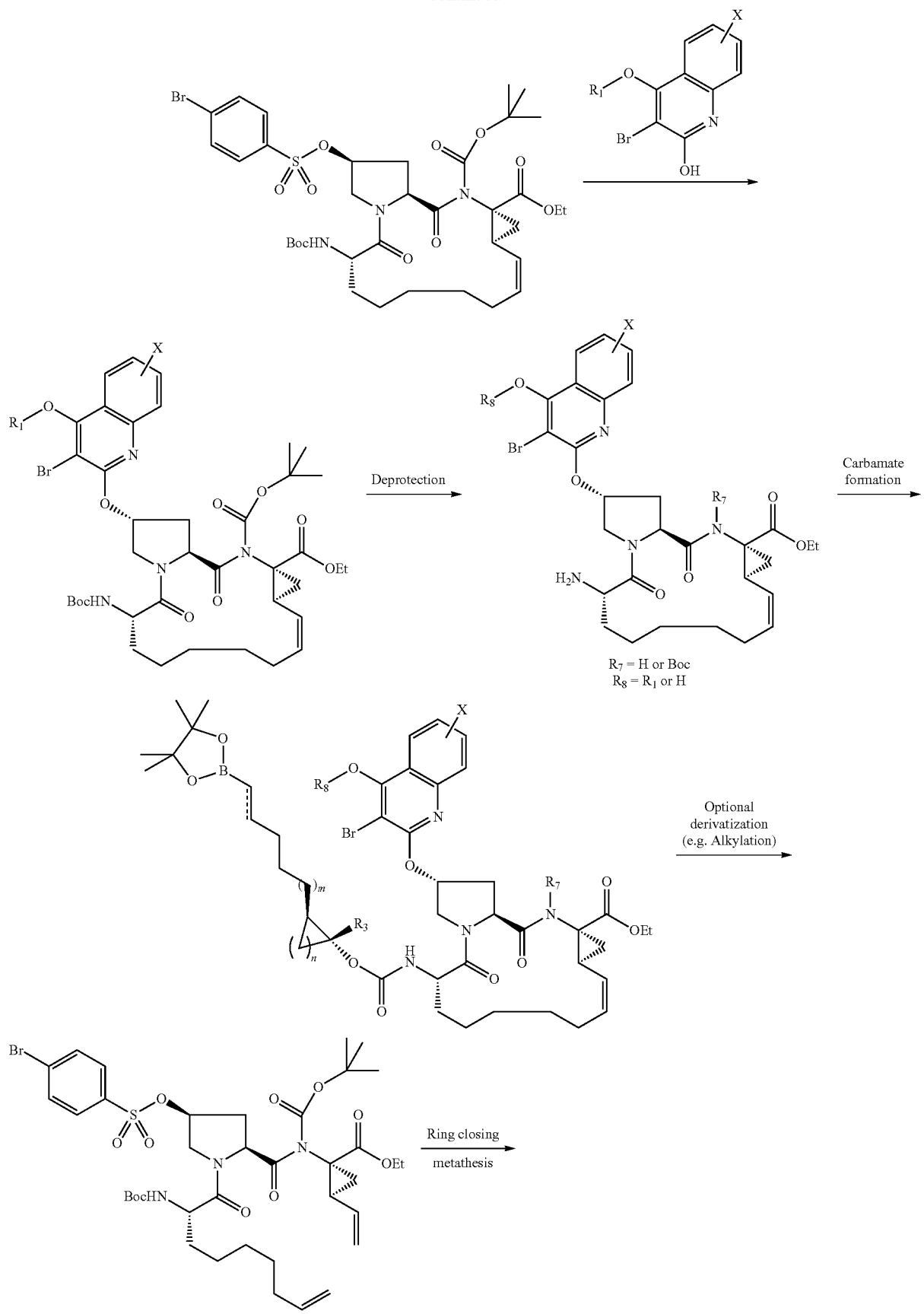

-continued
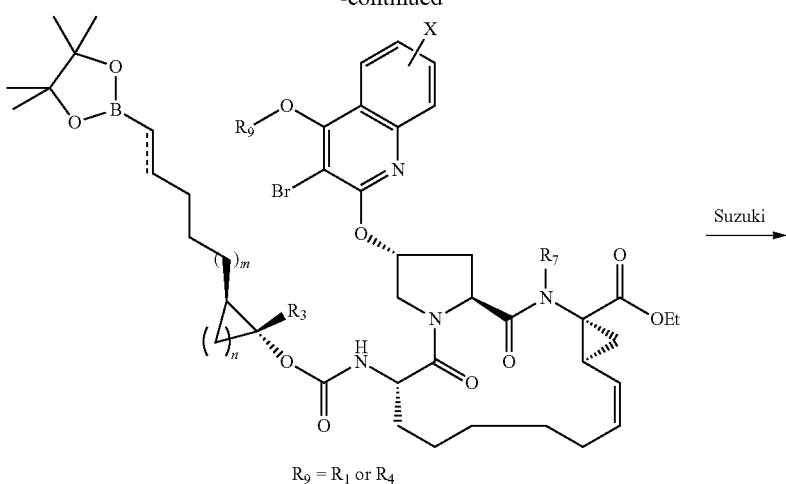
R$_9$ = R$_1$ or R$_4$
Suzuki →
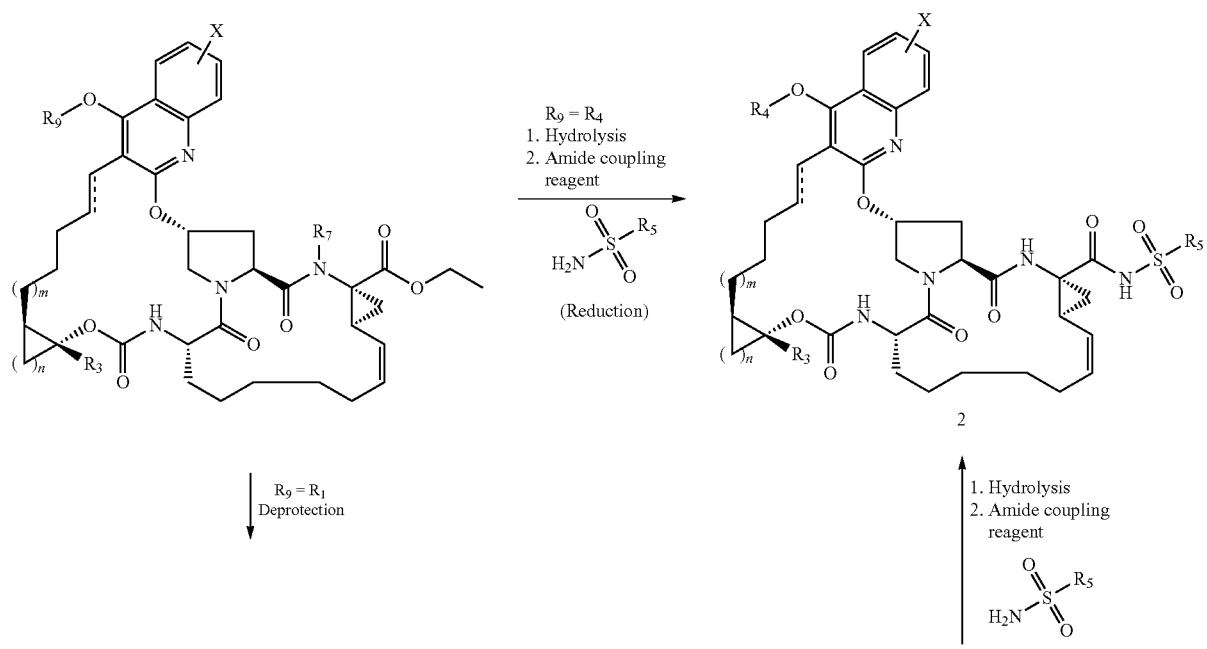
R$_9$ = R$_4$
1. Hydrolysis
2. Amide coupling reagent
R$_9$ = R$_1$
Deprotection ↓
1. Hydrolysis
2. Amide coupling reagent
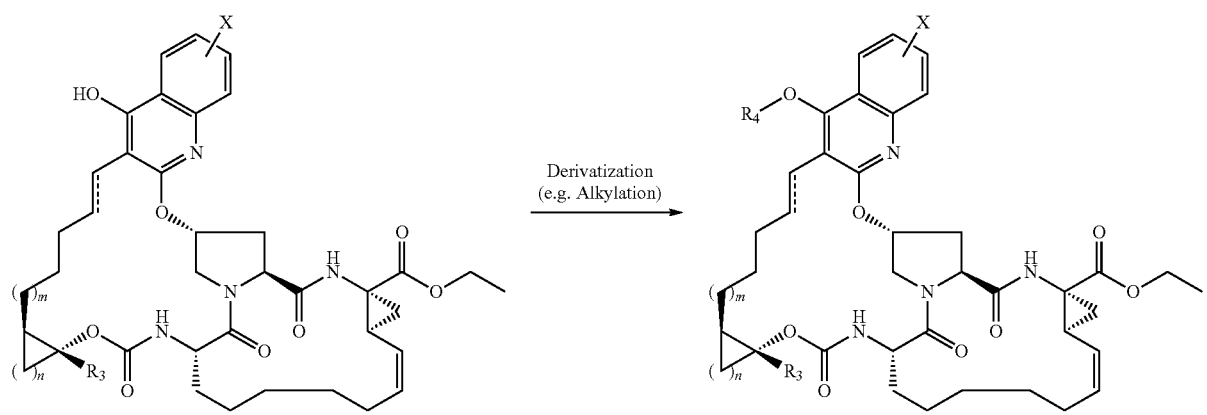
Derivatization (e.g. Alkylation) →

Synthesis of Intermediates

Intermediates A

| Intermediate | Structure | Name | Literature reference |
|---|---|---|---|
| A1 | 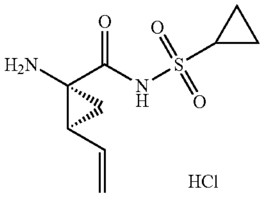 | (1R,2S)-1-amino-N-(cyclopropylsulfonyl)-2-ethenylcyclopropanecarboxamide hydrochloride | U.S. Pat. No. 6,995,174 |
| A2 | 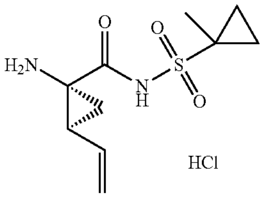 [SMILES: C=C[C@@H]1C[C@]1(N)C(=O)NS(=O)(=O)C1(C)CC1 ; Cl] | (1R,2S)-1-amino-2-ethenyl-N-[(1-methylcyclopropyl)sulfonyl]cyclopropanecarboxamide hydrochloride | U.S. Pat. No. 7,135,462 |
| A3 | 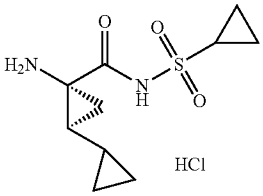 [SMILES: N[C@]1(C(=O)NS(=O)(=O)C2CC2)C[C@H]1C1CC1 ; Cl] | (1S,2R)-2-amino-N-(cyclopropylsulfonyl)-1,1'-bi(cyclopropyl)-2-carboxamide hydrochloride | WO 2010045266 |
| A4 | 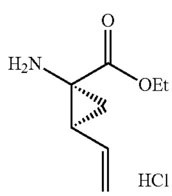 | ethyl (1R,2S)-1-amino-2-ethenylcyclopropanecarboxylate hydrochloride | U.S. Pat. No. 6,323,180 |
| A5 | 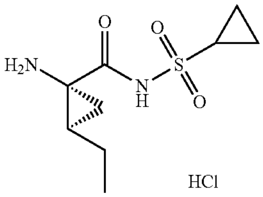 | (1R,2R)-1-amino-N-(cyclopropylsulfonyl)-2-ethylcyclopropanecarboxamide hydrochloride | WO 2009108507 |

Intermediate A6: (1R,2S)-1-amino-2-ethenyl-N-{[1-(methoxymethyl)cyclopropyl]sulfonyl}cyclopropanecarboxamide trifluoroacetate

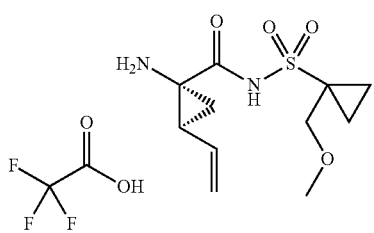 [SMILES: O=C(O)C(F)(F)F ; C=C[C@@H]1C[C@]1(N)C(=O)NS(=O)(=O)C1(COC)CC1]

Step 1: tert-butyl [(1R,2S)-2-ethenyl-1-({[1-(methoxymethyl)cyclopropyl]sulfonyl}carbamoyl)cyclopropyl]carbamate

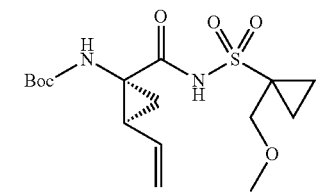 [SMILES: C=C[C@@H]1C[C@]1(NC(=O)OC(C)(C)C)C(=O)NS(=O)(=O)C1(COC)CC1]

A solution of (1R,2S)-1-[(tert-butoxycarbonyl)amino]-2-ethenylcyclopropanecarboxylic acid (132 mg) in THF (3 mL)

was added 1,1'-carbonyldiimidazole (283 mg). The mixture was stirred 4 hours at reflux. The mixture was cooled to room temperature and a solution of 1-(methoxymethyl)cyclopropanesulfonamide (125 mg; Li et al., 2006, Synlett 5:725) and DBU (0.438 mL) in THF (3 mL) was added via cannula. The mixture was stirred for 40 hours at room temperature. The reaction was quenched with 1N HCl and the mixture was extracted twice with ethyl acetate. The combined organic layers were washed with brine, dried over anhydrous magnesium sulfate, filtered and concentrated under reduced pressure. The resulting residue was purified by flash chromatography (ISCO) to give the desired product (120 mg). $^1$H NMR (400 MHz, CDCl$_3$): 5.71-5.62 (m, 1H), 5.29 (d, 1H), 5.16 (d, 1H), 3.36 (s, 2H), 2.15 (dt, 1H), 1.89 (dd, 1H), 1.75-1.68 (m, 2H), 1.49 (s, 9H), 1.34-1.30 (m, 1H), 1.08-1.03 (m, 2H).

Step 2: (1R,2S)-1-amino-2-ethenyl-N-{[1-(methoxymethyl)cyclopropyl]sulfonyl}cyclopropanecarboxamide trifluoroacetate

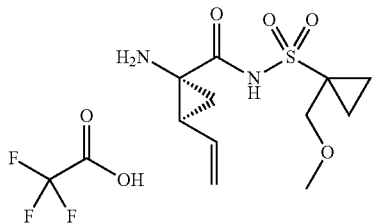 [SMILES: O=C(O)C(F)(F)F ; C=C[C@@H]1C[C@]1(N)C(=O)NS(=O)(=O)C1(COC)CC1]

To a 0° C. solution of the product of Step 1 (120 mg) in DCM (1 mL) at 0° C. was added TFA (1 mL). The mixture was slowly warmed to room temperature and stirred for 3 hours. The solvent was removed in vacuo and the crude product was used in the next step. $^1$H NMR (400 MHz, CDCl$_3$): δ (ppm) 5.82 (ddd, 1H), 5.44 (d, 1H), 5.43 (d, 1H), 3.67 (d, 1H), 3.63 (d, 1H), 3.35 (s, 3H), 2.64 (dt, 1H), 1.92 (dd, 1H), 1.83 (dd, 1H), 1.76-1.70 (m, 1H), 1.67-1.60 (m, 1H), 1.14-1.02 (m, 2H).

Intermediate A7: (1R,2S)-1-amino-2-ethenyl-N-{[1-(prop-1-en-2-yl)cyclopropyl]sulfonyl}cyclopropanecarboxamide hydrochloride

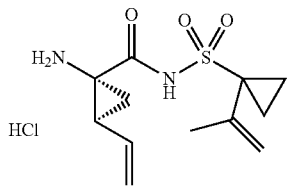 [SMILES: Cl ; C=C[C@@H]1C[C@]1(N)C(=O)NS(=O)(=O)C1(C(=C)C)CC1]

Step 1: tert-butyl [(1R,2S)-2-ethenyl-1-({[1-(prop-1-en-2-yl)cyclopropyl]sulfonyl}carbamoyl)cyclopropyl]carbamate

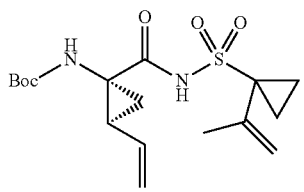 [SMILES: C=C[C@@H]1C[C@]1(NC(=O)OC(C)(C)C)C(=O)NS(=O)(=O)C1(C(=C)C)CC1]

The title compound was prepared using the same method as described for Intermediate A6, Step 1 using 1-(prop-1-en-2-yl)cyclopropanesulfonamide. $^1$H NMR (500 MHz, CDCl$_3$): δ (ppm) 5.66-5.59 (m, 1H), 5.30 (d, 1H), 5.24 (s, 1H), 5.22 (s, 1H), 5.16 (d, 1H), 5.16 (s, 1H), 2.14 (dt, 1H), 1.96 (s, 3H), 1.90-1.80 (m, 3H), 1.48 (s, 9H), 1.33-1.30 (m, 1H), 1.12-1.08 (s, 2H).

Step 2: (1R,2S)-1-amino-2-ethenyl-N-{[1-(prop-1-en-2-yl)cyclopropyl]sulfonyl}cyclopropanecarboxamide hydrochloride

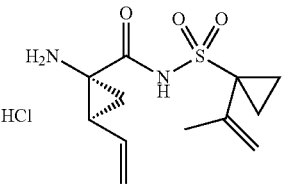 [SMILES: Cl ; C=C[C@@H]1C[C@]1(N)C(=O)NS(=O)(=O)C1(C(=C)C)CC1]

The product of step 1 (136 mg) was dissolved in a solution of HCl in dioxane (1.5 mL). The mixture was stirred for 3 hours at room temperature. The solvent was removed in vacuo and the crude product was used in the next step. $^1$H NMR (400 MHz, CDCl$_3$): δ (ppm) 5.69-5.62 (m, 1H), 5.41 (d, 1H), 5.26 (d, 1H), 5.23 (s, 1H), 5.21 (s, 1H), 2.77-2.72 (m, 1H), 2.02-1.98 (m, 1H), 1.95 (s, 3H), 1.93-1.84 (m, 2H), 1.74-1.69 (m, 1H), 1.17-1.06 (m, 2H).

Intermediate A8: (1R,2S)-1-amino-N-({1-[(benzyloxy)methyl]cyclopropyl}sulfonyl)-2-ethenylcyclopropanecarboxamide hydrochloride Step 1: tert-butyl {(1R,2S)-1-[({1-[(benzyloxy)methyl]cyclopropyl}sulfonyl)carbamoyl]-2-ethenylcyclopropyl}carbamate

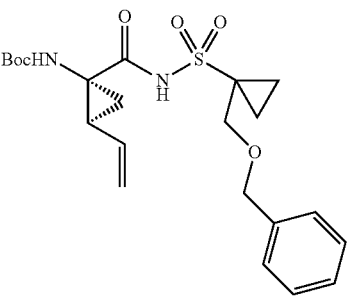 [SMILES: C=C[C@@H]1C[C@]1(NC(=O)OC(C)(C)C)C(=O)NS(=O)(=O)C1(COCc2ccccc2)CC1]

The title compound was prepared using the same method as described for Intermediate A6, Step 1 using 1-[(benzyloxy)methyl]cyclopropanesulfonamide. See International Patent Publication No. WO 09/061699. $^1$H NMR (500 MHz, CDCl$_3$): δ (ppm) 7.40-7.33 (m, 5H), 5.67-5.57 (m, 1H), 5.25 (d, 1H), 5.12 (d, 1H), 4.55 (d, 1H), 4.50 (d, 1H), 3.85 (d, 1H), 3.77 (d, 1H), 1.96 (br s, 1H), 1.80 (dd, 1H), 1.74-1.72 (m, 2H), 1.46 (s, 9H), 1.12 (dd, 1H), 1.08-1.01 (m, 2H).

Step 2: (1R,2S)-1-amino-N-({1-[(benzyloxy)methyl]cyclopropyl}sulfonyl)-2-ethenylcyclopropanecarboxamide hydrochloride

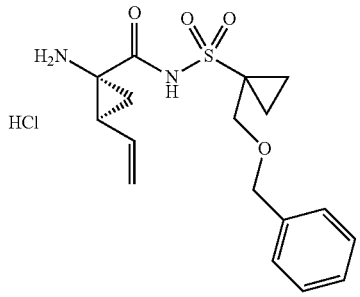 [SMILES: Cl ; C=C[C@@H]1C[C@]1(N)C(=O)NS(=O)(=O)C1(COCc2ccccc2)CC1]

The title compound was prepared using the same method as described for Intermediate A7, Step 2. The crude product was used without further purification.

Intermediate A9: (1R,2S)-1-amino-2-ethenyl-N-({1-[(2-methoxyethoxy)methyl]cyclopropyl}sulfonyl)cyclopropanecarboxamide hydrochloride

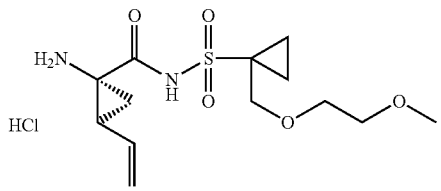

Step 1: tert-butyl ({1-[(2-methoxyethoxy)methyl]cyclopropyl}sulfonyl)carbamate

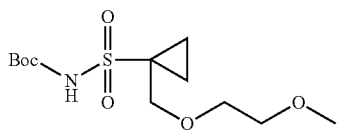 [SMILES: COCCOCC1(S(=O)(=O)NC(=O)OC(C)(C)C)CC1]

BuLi 2.5 M in hexanes (7.53 ml) was added dropwise to the solution of tert-butyl (cyclopropylsulfonyl)carbamate (1.81 g) in THF (40 ml) at −78° C. This solution was stirred at −78° C. for 1 hour then 2-methoxyethoxymethyl chloride (1.85 ml) was added dropwise. The reaction was allowed to warm to room temperature and was stirred for 3 days. The solvent was evaporated under reduced pressure and the residue was diluted with ethyl acetate. At this point, HCl (1 M) was added and the mixture was extracted with ethyl acetate (3×). The combined organic layers were washed with brine, dried over magnesium sulfate, filtered and the solvent was evaporated under reduced pressure. The residue was purified by flash chromatography (ISCO, 0 to 100% ethyl acetate in hexanes) to give the desired product (0.630 g) as a clear oil. LRMS (ES+) m/z 332.2 (M+Na)⁺.

Step 2: 1-[(2-methoxyethoxy)methyl]cyclopropanesulfonamide

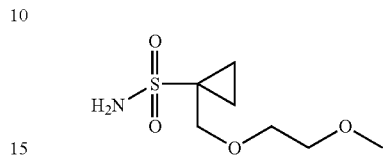

TFA (5 ml) was added to the solution of the product of Step 1 (0.63 g) in dichloromethane (5 ml) at 0° C. The reaction was allowed to warm to room temperature and was stirred for 1.5 hour. The solvent was removed under reduced pressure to give the desired product (0.426 g) as a light brown oil. $^1$H NMR (400 MHz, CDCl$_3$): δ (ppm) 6.80-6.21 (m, 2H), 3.75 (s, 2H), 3.66-3.64 (m, 2H), 3.56-3.53 (m, 2H), 3.36 (s, 3H), 1.42-1.39 (m, 2H), 0.91-0.89 (m, 2H)

Step 3: tert-butyl {(1R,2S)-2-ethenyl-1-[({1-[(2-methoxyethoxy)methyl]cyclopropyl}sulfonyl)carbamoyl]cyclopropyl}carbamate

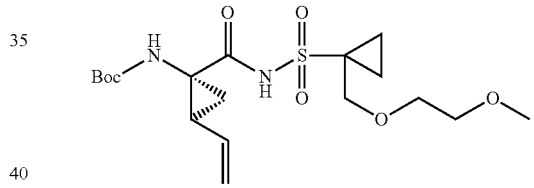

The title compound was prepared using the same method as described for Intermediate A6, Step 1. LRMS (ES+) m/z 441.2 (M+Na)⁺.

Step 4: (1R,2S)-1-amino-2-ethenyl-N-({1-[(2-methoxyethoxy)methyl]cyclopropyl}sulfonyl)cyclopropanecarboxamide hydrochloride

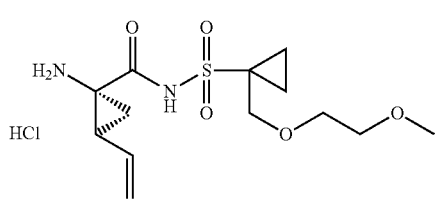

The title compound was prepared using the same method as described for Intermediate A7, Step 2. LRMS (ES+) m/z 341.2 (M+Na)⁺.

Intermediate A10: (1R,2S)-1-amino-2-ethenyl-N-({1-[2-(morpholin-4-yl)ethyl]cyclopropyl}sulfonyl)cyclopropanecarboxamide dihydrochloride Step 1: tert-butyl {(1R,2S)-2-ethenyl-1-[({1-[2-(morpholin-4-yl)ethyl]cyclopropyl}sulfonyl)carbamoyl]cyclopropyl}carbamate

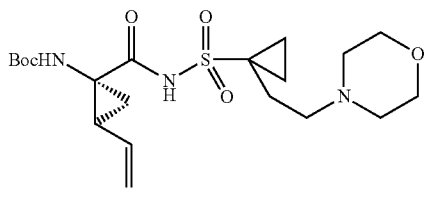

The title compound was prepared using the same method as described for Intermediate A9, Steps 1-3 with 4-(2-bromoethyl)morpholine. LRMS (ES+) m/z 444.4 (M+H)$^+$.

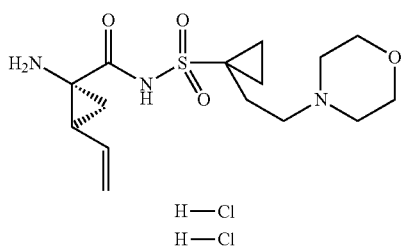

The title compound was prepared using the same method as described for Intermediate A7, Step 2. The crude product was used directly in the next step.

Intermediate A11: 3-(4H-1,2,4-triazol-4-yl)propyl 4-methylbenzenesulfonate

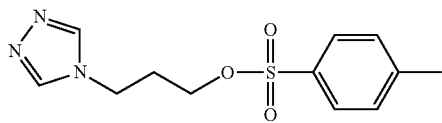 [SMILES: Cc1ccc(S(=O)(=O)OCCCn2cnnc2)cc1]

To a solution of 3-(4H-1,2,4-triazol-4-yl)propan-1-ol (100 mg) in pyridine (2.62 mL) under nitrogen at 0° C. was added Tosyl-Cl (165 mg). The reaction was stirred for 18 hours. Pyridine was removed in vacuo and the remaining oil and solids were dissolved in ethyl acetate and washed several times with an aqueous solution of KHSO$_4$. The combined aqueous layers were back extracted with ethyl acetate. The combined organics were dried over magnesium sulfate, filtered and concentrated to provide a clear oil. Since the product was still in the aqueous layer, the pH of the aqueous phases was adjusted to 10 using 4.0 N NaOH. The mixture was extracted (3×) with ethyl acetate. The combined organics were dried over magnesium sulfate, filtered and concentrated. Purification of the reaction mixture by flash chromatography (ISCO, 0 to 50% ethyl acetate in hexanes) provided the desired product (50 mg). LRMS (ES+) m/z 282.2 (M+H)$^+$.

Intermediate A12: 3-(3,3-difluoropiperidin-1-yl)propan-1-ol

Step 1: 1-(3-{[tert-butyl(dimethyl)silyl]oxy}propyl)-3,3-difluoropiperidine

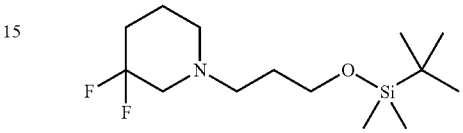

To a solution of 3,3-difluoropiperidine hydrochloride (518 mg) in DMF (15 mL) was added cesium carbonate (3.21 g) and (3-bromopropoxy)-tert-butyldimethylsilane (0.838 mL). The resulting reaction mixture was heated to 50° C. for 1.5 hours before cooling back to room temperature. Water and ethyl acetate were added to the reaction mixture. The mixture was extracted with ethyl acetate (2×). The combined organics were washed with water (2×), brine, dried over magnesium sulfate, filtered and concentrated. Purification by flash chromatography (ISCO, 0 to 40% ethyl acetate in hexanes with 1% triethylamine) gave the desired product (612 mg). $^1$H NMR (400 MHz, CDCl$_3$): δ (ppm) 4.20 (t, 1H), 3.71-3.64 (m, 2H), 3.46 (t, 1H), 2.62 (t, 1H), 2.50-2.47 (m, 1H), 2.44-2.42 (m, 1H), 2.05-1.98 (m, 1H), 1.91-1.82 (m, 2H), 1.77-1.67 (m, 4H), 0.89 (d, 9H), 0.05 (s, 3H), 0.04 (s, 3H).

Step 2: 3-(3,3-difluoropiperidin-1-yl)propan-1-ol

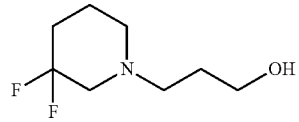 [SMILES: OCCCN1CCCC(F)(F)C1]

To a solution of the product of Step 1 (612 mg) in THF (20 mL) was added HF-TEA (13.58 mL) at room temperature. The solution was heated to 50° C. for 45 minutes. The reaction mixture was concentrated to remove THF and then diluted with ethyl acetate (100 mL) and water was added (100 mL). To that mixture was added Na$_2$CO$_3$ (14.4 g) portion wise at 0° C. When the quench was complete, the layers were separated. The organic layer was washed with 10% Na$_2$CO$_3$, water and brine. The aqueous layer was re-extracted with ethyl acetate (2×). The combined organics were dried over magnesium sulfate, filtered and concentrated. The crude product (350 mg) was used directly in the next step. HRMS (ES+) m/z 180.1202 (M+H)+.

Intermediate A13: 1-(2-hydroxypropan-2-yl)cyclopropanesulfonamide

Step 1: benzyl(cyclopropylsulfonyl)carbamate

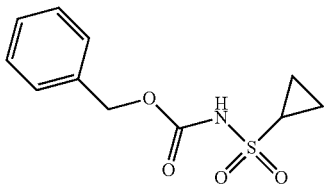 [SMILES: O=C(NS(=O)(=O)C1CC1)OCc1ccccc1]

To a solution of cyclopropanesulfonamide (6.51 g, triethylamine (40 mL) and DMAP (0.656 g) in DCM (150 mL) was slowly added benzyl chloroformate (12 mL). The mixture was stirred at room temperature for 18 hours. The mixture was washed with 1 N HCl. The aqueous layer (pH 1) was extracted with EtOAc (×2). The combined organics were washed with brine, dried over anhydrous MgSO$_4$ and concentrated. The resulting residue was purified by flash chromatography (ISCO, 0-10% methanol in dichloromethane) to afford the desired product (7.8 g). $^1$H NMR (400 MHz, CDCl$_3$): δ (ppm) 7.56-7.44 (m, 1H), 7.38 (s, 5H), 5.22 (s, 2H), 2.92-2.84 (m, 1H), 1.40-1.35 (m, 2H), 1.12-1.06 (m, 2H).

Step 2: benzyl {[1-(2-hydroxypropan-2-yl)cyclopropyl]sulfonyl}carbamate

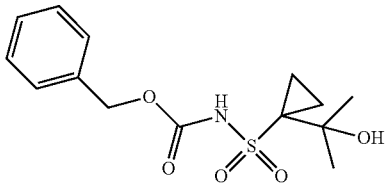 [SMILES: CC(C)(O)C1(S(=O)(=O)NC(=O)OCc2ccccc2)CC1]

The title compound was prepared using the same method as described for Intermediate A9, Step 1 using acetone. $^1$H NMR (400 MHz, CDCl$_3$): δ (ppm) 8.03-7.83 (m, 1H), 7.36 (s, 5H), 5.18 (s, 2H), 1.72-1.68 (m, 2H), 1.36 (s, 6H), 1.10-1.06 (m, 2H).

Step 3: 1-(2-hydroxypropan-2-yl)cyclopropanesulfonamide

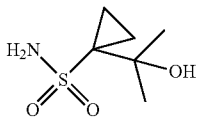

To a solution of the product of Step 2 (995 mg) in methanol (30 mL) under nitrogen was added Pd/C (169 mg). The flask was purged with hydrogen and stirred for 3 hours. Celite was added to the reaction mixture and it was filtered through a pad of Celite. The solvent was removed in vacuo. The resulting residue was purified by flash chromatography (ISCO, 0 to 10% methanol in dichloromethane) to afford the desired product (391 mg). $^1$H NMR (400 MHz, CDCl$_3$): δ (ppm) 4.88 (br s, 2H), 2.58 (s, 1H), 1.44-1.41 (m, 2H), 1.41 (s, 6H), 1.06-1.03 (m, 2H).

Intermediate A14: 1-{[({(1R,2R)-2-[(4E)-5-(4,4,5,5-tetramethyl-1,3,2-dioxaborolan-2-yl)pent-4-en-1-yl]cyclopropyl}oxy)carbonyl]oxy}pyrrolidine-2,5-dione

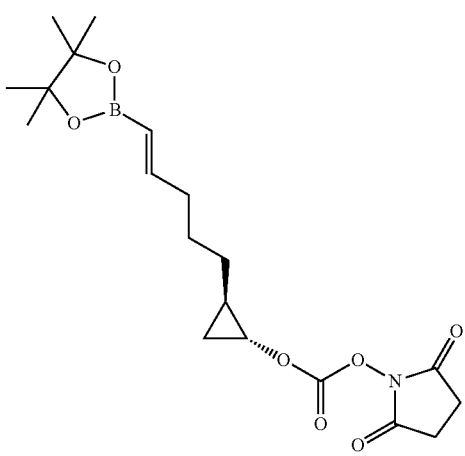 [SMILES: CC1(C)OB(/C=C/CCC[C@@H]2C[C@H]2OC(=O)ON2C(=O)CCC2=O)OC1(C)C]

Step 1: 1-[({[(1R,2R)-2-(pent-4-yn-1-yl)cyclopropyl]oxy}carbonyl)oxy]pyrrolidine-2,5-dione

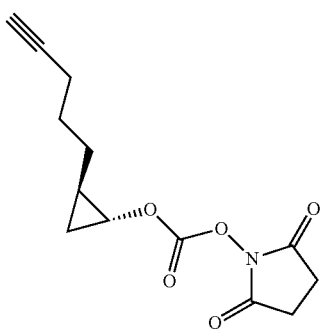 [SMILES: C#CCCC[C@@H]1C[C@H]1OC(=O)ON1C(=O)CCC1=O]

To a solution of (1R,2R)-2-(pent-4-en-1-yl)cyclopropanol (see International Patent Application Publication No. WO 08/057209) (17.1 g) in acetonitrile (193 mL) was added N,N'-disuccinimidyl carbonate (49.3 g) then triethylamine (53.7 mL) The mixture was heated to 40° C. for 18 hours. The reaction mixture was cooled to room temperature and the solids were removed by filtration. The solvent was removed in vacuo. The residue was purified by flash chromatography (ISCO, 10 to 70% ethyl acetate in hexanes) to give the desired product (18 g). $^1$H NMR (500 MHz, CDCl$_3$): δ (ppm) 4.06-4.03 (m, 1H), 2.87 (s, 4H), 2.28-2.25 (m, 2H), 1.98-1.97 (m, 1H), 1.72-1.63 (m, 2H), 1.44-1.39 (m, 2H), 1.30-1.25 (m, 1H), 1.12-1.08 (m, 1H), 0.72-0.68 (m, 1H).

Step 2: 1-{[({(1R,2R)-2-[(4E)-5-(4,4,5,5-tetramethyl-1,3,2-dioxaborolan-2-yl)pent-4-en-1-yl]cyclopropyl}oxy)carbonyl]oxy}pyrrolidine-2,5-dione

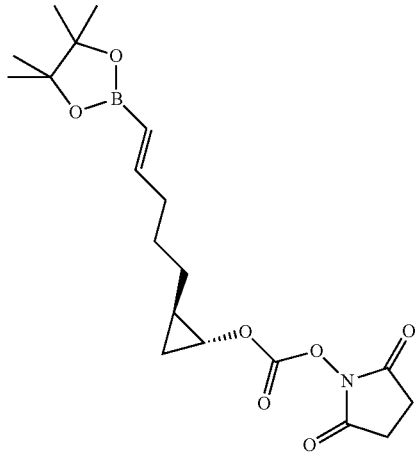 [SMILES: CC1(C)OB(/C=C/CCC[C@@H]2C[C@H]2OC(=O)ON2C(=O)CCC2=O)OC1(C)C]

Cyclohexene (1.09 mL) was added to a 10 M dimethyl sulfide solution of borane (0.58 mL). Upon addition, a white solid had formed and 3 mL of degassed heptane was added to suspend it. The mixture was stirred for 5 minutes at room temperature. At this point, alkyne from Step 1 (15.5 g) in THF (55 mL) was added dropwise to the reaction mixture. After complete addition, the mixture was warmed to 40° C. for 20 minutes. Pinacolborane (8.48 mL) was added slowly to reaction mixture and the heating was continued for 2 hours at 40° C. The reaction mixture was cooled to room temperature and quenched with brine (100 mL). The mixture was extracted with ethyl acetate (3×). The combined organics were dried over magnesium sulfate, filtered and concentrated to provide the desired compound. $^1$H NMR (500 MHz, CDCl$_3$): δ (ppm) 6.66-6.58 (m, 1H), 5.45 (d, 1H), 4.02-3.99 (m, 1H), 2.87 (s, 4H), 2.22-2.17 (m, 2H), 1.61-1.54 (m, 3H), 1.32-1.23 (m, 2H), 1.29 (s, 12H), 1.09-1.05 (m, 1H), 0.68-0.63 (m, 1H).

Intermediate A15: 1-{[({(1R,2R)-2-[5-(4,4,5,5-tetramethyl-1,3,2-dioxaborolan-2-yl)pentyl]cyclopropyl}oxy)carbonyl]oxy}pyrrolidine-2,5-dione

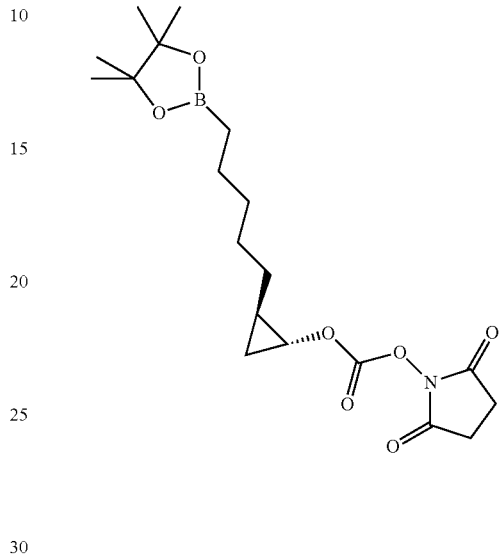

To a degassed suspension of Pd/C (812 mg) in ethyl acetate (51 mL) was added vinyl boronate (intermediate A14, 10 g). After degassing, the mixture was purged and re-filled with hydrogen (balloon, 1 atm). The reaction mixture was stirred at room temperature for 2 hours. The atmosphere was carefully exchanged for nitrogen and the mixture was filtered over celite (rinsing with ethyl acetate). The solvent was removed in vacuo. The residue was purified by flash chromatography (ISCO, 0 to 50% ethyl acetate in hexanes) to give the desired product (7 g). $^1$H NMR (500 MHz, CDCl$_3$): δ (ppm) 4.03-4.00 (m, 1H), 2.87 (s, 4H), 1.46-1.39 (m, 4H), 1.35-1.24 (m, 5H), 1.26 (s, 12H), 1.07-1.03 (m, 1H), 0.81-0.77 (m, 2H), 0.67-0.63 (m, 1H).

Synthesis of Intermediates B

| Intermediate | Structure | Name | Literature reference |
|---|---|---|---|
| B1 | 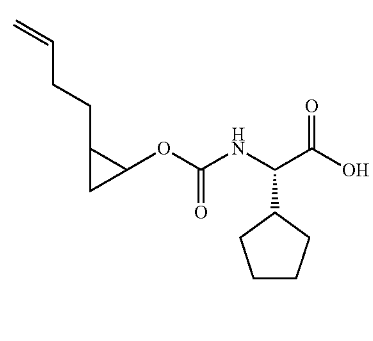 [SMILES: C=CCCC1CC1OC(=O)N[C@H](C(=O)O)C1CCCC1] | (2S)-[({[2-(but-3-en-1-yl)cyclopropyl]oxy}carbonyl)amino](cyclopentyl)ethanoic acid | WO2009/134624 |

-continued

| Intermediate | Structure | Name | Literature reference |
|---|---|---|---|
| B2 | 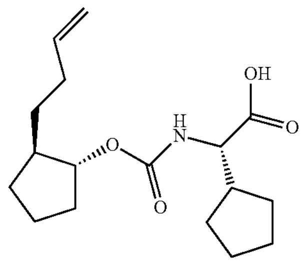 [SMILES: C=CCC[C@@H]1CCC[C@H]1OC(=O)N[C@H](C(=O)O)C1CCCC1] | (2S)-[({[(1R,2S)-2-(but-3-en-1-yl)cyclopentyl]oxy}carbonyl)amino](cyclopentyl)ethanoic acid | WO2009/134624 |
| B3 | 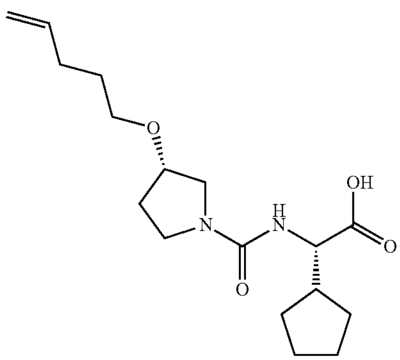 [SMILES: C=CCCCO[C@H]1CCN(C(=O)N[C@H](C(=O)O)C2CCCC2)C1] | (2S)-cyclopentyl({[(3S)-3-(pent-4-en-1-yloxy)pyrrolidin-1-yl]carbonyl}amino)ethanoic acid | WO2009/108507 |
| B4 | 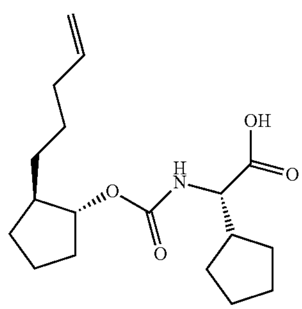 [SMILES: C=CCCC[C@@H]1CCC[C@H]1OC(=O)N[C@H](C(=O)O)C1CCCC1] | (2S)-cyclopentyl[({[(1R,2R)-2-(pent-4-en-1-yl)cyclopentyl]oxy}carbonyl)amino]ethanoic acid | WO2009/134624 |
| B5 | 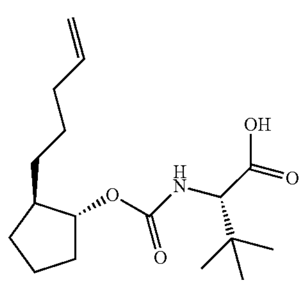 [SMILES: C=CCCC[C@@H]1CCC[C@H]1OC(=O)N[C@H](C(=O)O)C(C)(C)C] | 3-methyl-N-({[(1R,2R)-2-(pent-4-en-1-yl)cyclopentyl]oxy}carbonyl)-L-valine | WO2008/057209 |

Intermediate B6: N-({[(1R,2S)-2-(but-3-en-1-yl)cyclopentyl]oxy}carbonyl)-3-methyl-L-valine

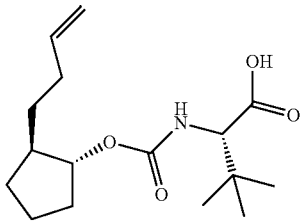 [SMILES: C=CCC[C@@H]1CCC[C@H]1OC(=O)N[C@H](C(=O)O)C(C)(C)C]

To a stirred solution of (1R,2S)-2-(but-3-en-1-yl)cyclopentanol (see International Patent Application Publication No. WO2009/134624) (2.1 g) and DIPEA (5.3 mL) in anhydrous 1,4-dioxane (51 ml), at 10° C. and under nitrogen, was added a solution of triphosgene (1.5 g) in dioxane (51 ml). This reaction was stirred at 22° C. for 1.5 hour and 3-methyl-L-valine (2 g) and NaOH (1M, 30.5 mL) were added, then stirred at 70° C. for 15 hours. At 22° C., the reaction solution was acidified to pH 3 with 1 N HCl and extracted with (3×100 ml) ether. The combined organic layer were washed with water (100 ml), brine (70 ml), dried over Na$_2$SO$_4$, filtered and concentrated. The residue was purified by flash chromatography (silica gel, eluting with 10 to 100% EtOAc in hexane) to give the desired product (3.26 g). LRMS (ES+) M/Z (M+Na)$^+$ 320.1.

Intermediate B7: (2S)-[({[(1R,2S)-2-(but-3-en-1-yl)-1-methylcyclopentyl]oxy}carbonyl)amino](cyclopentyl)ethanoic acid and (2S)-[({[(1S,2R)-2-(but-3-en-1-yl)-1-methylcyclopentyl]oxy}carbonyl)amino](cyclopentyl)ethanoic acid

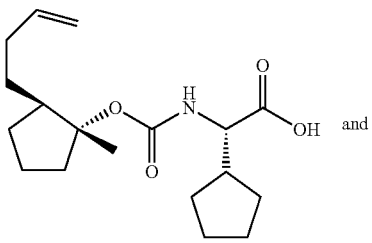 and

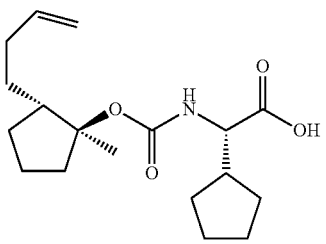

Step 1: (±)-(1R,2S)-2-(but-3-en-1-yl)-1-methylcyclopentanol

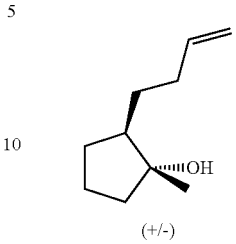

(+/-)

To a 0° C. solution of butenyl magnesium chloride (45.6 mL, 0.5 M) was added copper(I) chloride (0.113 g) followed by methylcyclopropane oxide (1.12 g) in diethyl ether (5 ml). The reaction mixture was warmed to room temperature and stirred for 20 hours. The mixture was cooled back to 0° C. before pouring into a saturated solution of ammonium chloride (at 0° C.). The mixture was extracted with ethyl acetate (3×). The combined organic fractions were dried over magnesium sulfate, filtered and concentrated carefully. The residue was purified by flash chromatography (ISCO, 0 to 30% ethyl acetate in hexanes) to give the desired product (1.3 g). $^1$H NMR (400 MHz, CDCl$_3$): δ (ppm) 5.86-5.79 (m, 1H), 5.05-4.99 (m, 1H), 4.97-4.93 (m, 1H), 2.20-2.09 (m, 1H), 2.02-1.92 (m, 2H), 1.73-1.50 (m, 7H), 1.31-1.10 (m, 5H).

Step 2: methyl (2S)-[({[(1R,2S)-2-(but-3-en-1-yl)-1-methylcyclopentyl]oxy}carbonyl)amino](cyclopentyl)ethanoate and methyl (2S)-[({[(1S,2R)-2-(but-3-en-1-yl)-1-methylcyclopentyl]oxy}carbonyl)amino](cyclopentyl)ethanoate

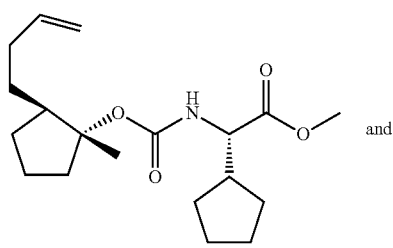 and

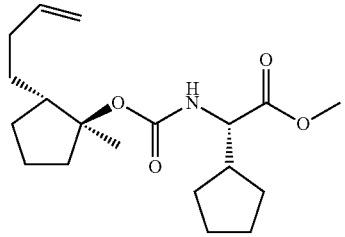

DMAP (0.59 g) was added to a stirred mixture of the product of Step 1 (0.75 g) and methyl (2S)-cyclopentyl(isocyanato)ethanoate (1.34 g) (See International Patent Application Publication No.: WO08/057209) in toluene (24 ml). DIPEA (3.40 mL) was then added and the mixture was stirred at 100° C. for 22 hours. Since the reaction wasn't complete, methyl (2S)-cyclopentyl(isocyanato)ethanoate (0.6 g), DIPEA (1.5 mL) and DMAP (0.3 g) were added and the mixture was stirred at 100° C. for 8 hours. The reaction mixture was worked up with ethyl acetate and 5% KHSO$_4$.

Step 3: (2S)-[({[(1R,2S)-2-(but-3-en-1-yl)-1-methyl-cyclopentyl]oxy}carbonyl)amino](cyclopentyl)ethanoic acid and (2S)-[({[(1S,2R)-2-(but-3-en-1-yl)-1-methylcyclopentyl]oxy}carbonyl)amino](cyclopentyl)ethanoic acid

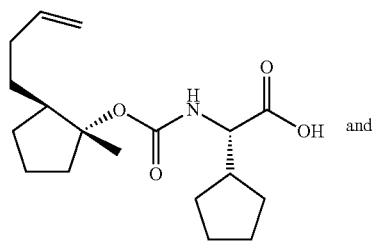

and

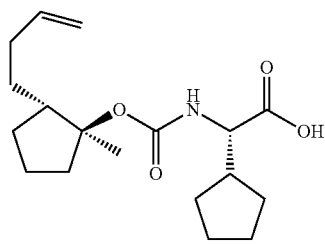

To a solution of the product of Step 2 (1.17 g) in THF (10 mL), methanol (1 ml), and water (2 ml) was added LiOH (0.415 g). After 1 hour 45 min, the reaction was done. The pH was adjusted (13 mL 1N HCl, then 5% KHSO$_4$ until pH 3), and then extracted with Et$_2$O and then EtOAc. The combined organic layers were dried over magnesium sulfate and the solvent was removed in vacuo to yield 1.2 g of the desired product. HRMS (ES+) M/Z (M+Na)$^+$ 346.1988.

Intermediate B8: (2S)-[({[(1R,2R)-2-(but-3-en-1-yl)-1-methylcyclopropyl]oxy}carbonyl)amino](cyclopentyl)ethanoic acid and (2S)-[({[(1S,2S)-2-(but-3-en-1-yl)-1-methylcyclopropyl]oxy}carbonyl)amino](cyclopentyl)ethanoic acid

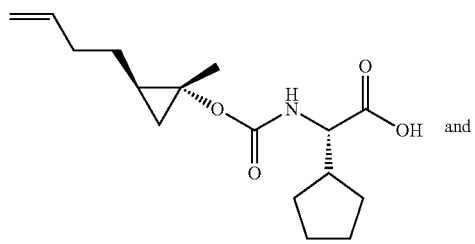

and

-continued

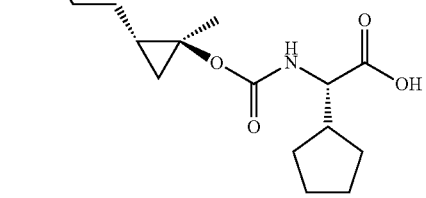

Step 1: (±)-(1R,2R)-2-(but-3-en-1-yl)-1-methylcyclopropanol

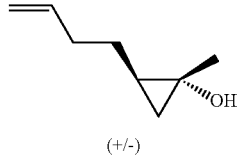

(+/-)

In a dry sure seal, ethyl acetate (2 mL) was added to THF (204 mL) followed by 1,5-hexadiene (7.28 ml) and chlorotitanium triisopropoxide (20.43 ml). At this point, cyclohexylmagnesium chloride (46.0 mL) was added via a syringe pump over 1 hour. The mixture was stirred 1 hour.

It was then slowly poured into ice water and ether. The mixture was extracted with ether (3×). The combined organic layers were washed with brine, dried over magnesium sulfate and the solvent was removed in vacuo. The residue was purified by flash chromatography on silica gel (0 to 40% diethyl ether in hexanes) to give the desired product (1.4 g). $^1$H NMR (400 MHz, CDCl$_3$): δ (ppm) 5.88-5.79 (m, 1H), 5.05-5.00 (m, 1H), 4.98-4.94 (m, 1H), 2.17-2.12 (m, 2H), 1.79 (s, 1H), 1.46-1.39 (m, 2H), 1.32-1.15 (m, 3H), 1.04-0.96 (m, 1H), 0.90-0.84 (m, 1H), 0.10-0.07 (m, 1H).

Step 2: methyl (2S)-[({[(1R,2R)-2-(but-3-en-1-yl)-1-methylcyclopropyl]oxy}carbonyl)amino](cyclopentyl)ethanoate and methyl (2S)-[({[(1S,2S)-2-(but-3-en-1-yl)-1-methylcyclopropyl]oxy}carbonyl)amino](cyclopentyl)ethanoate

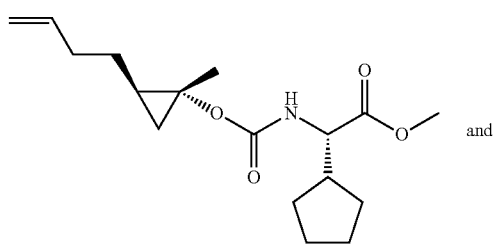

and

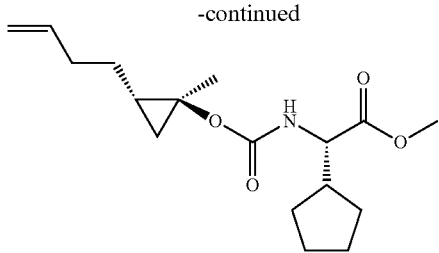

The title compound was prepared using the same method as described for Intermediate B6, Step 2. LRMS (ES+) M/Z (M+H)+ 310.4.

Step 3: (2S)-[({[(1R,2R)-2-(but-3-en-1-yl)-1-methyl-cyclopropyl]oxy}carbonyl)amino](cyclopentyl)ethanoic acid and (2S)-[({[(1S,2S)-2-(but-3-en-1-yl)-1-methylcyclopropyl]oxy}carbonyl)amino](cyclopentyl)ethanoic acid

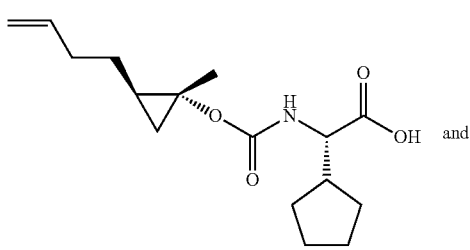

The title compound was prepared using the same method as described for Intermediate B7, Step 3. LRMS (ES+) M/Z (M+K)+ 334.1417.

Intermediate B9: N-({[(1R,2R)-2-(but-3-en-1-yl)-1-methylcyclopropyl]oxy}carbonyl)-3-methyl-L-valine and N-({[(1S,2S)-2-(but-3-en-1-yl)-1-methylcyclopropyl]oxy}carbonyl)-3-methyl-L-valine

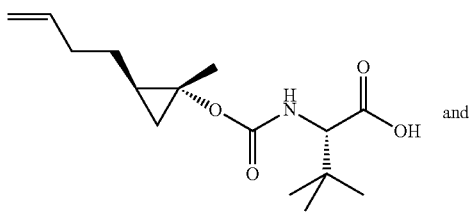

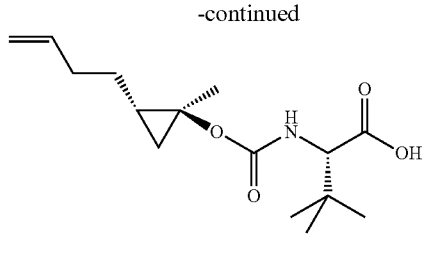

The title compound was prepared using the same method as described for Intermediate B8, Steps 1 to 3 using methyl 3-methyl-N-(oxomethylidene)-L-valinate (See International Patent Application Publication No. WO 10/11566). LRMS of ester (ES+) M/Z (M+K)+ 336.1573.

Intermediate B10: 3-methyl-N-({[(1R,2R)-2-(pent-4-yn-1-yl)cyclopropyl]oxy}carbonyl)-L-valine-N-benzyl-1-phenylmethanamine (1:1)

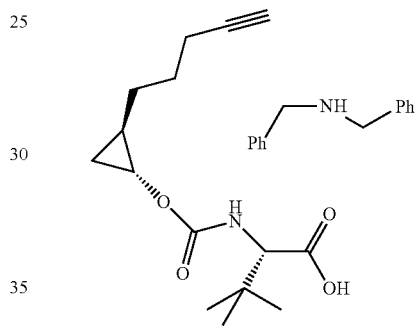

The title compound was synthesized in a manner similar to the synthesis of the corresponding terminal alkene-bearing intermediate described in WO2008/057209.

Intermediate B11: (2S)-cyclohexyl[({[(1R,2R)-2-(pent-4-yn-1-yl)cyclopropyl]oxy}carbonyl)amino] ethanoic acid

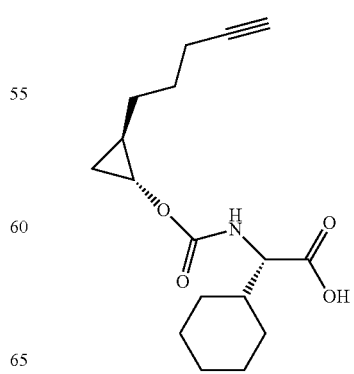

Step 1: 1-[({[(1R,2R)-2-(pent-4-yn-1-yl)cyclopropyl]oxy}carbonyl)oxy]pyrrolidine-2,5-dione

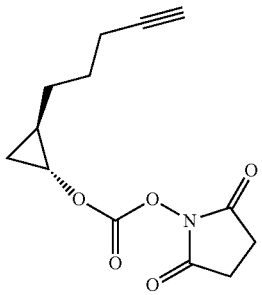 [SMILES: C#CCCC[C@@H]1C[C@H]1OC(=O)ON1C(=O)CCC1=O]

To a solution of (1R,2R)-2-(pent-4-en-1-yl)cyclopropanol (See International Patent Application Publication No. WO08/057209) (2.13 g; 70% wt) in acetonitrile (20 ml) was added pyridine (1.5 ml), followed by N,N'-disuccinimidyl carbonate (3.74 g) and a crystal of DMAP. The mixture was stirred at 40° C. overnight. After cooling to room temperature, the reaction mixture was diluted with ether and washed with HCl 1N, water and brine and dried over sodium sulfate. The organic layer was filtered and concentrated to provide the desired product (2.88 g) as an oil. $^1$H NMR (500 MHz, CDCl$_3$): δ (ppm) 4.06-4.03 (m, 1H), 2.87 (s, 4H), 2.28-2.25 (m, 2H), 1.98-1.97 (m, 1H), 1.72-1.65 (m, 2H), 1.46-1.40 (m, 2H), 1.31-1.24 (m, 1H), 1.12-1.08 (m, 1H), 0.72-0.68 (m, 1H).

Step 2: (2S)-cyclopentyl[({[(1R,2R)-2-(pent-4-yn-1-yl)cyclopropyl]oxy}carbonyl)amino]ethanoic acid

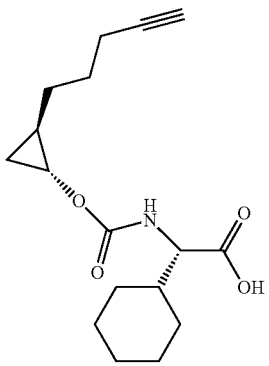 [SMILES: C#CCCC[C@@H]1C[C@H]1OC(=O)N[C@H](C(=O)O)C1CCCCC1]

To a solution of the product of Step 1 (457 mg) in acetonitrile (6 ml) was added (2S)-amino(cyclohexyl)ethanoic acid (352 mg) followed by triethylamine (0.720 ml) and water (6.00 ml). The mixture was stirred at room temperature for 18 hours. The mixture was diluted with ethyl acetate and washed with HCl 1N, water and brine. The organic layer was dried over sodium sulfate, filtered and concentrated. This provided the desired product (510 mg) as an oil. LRMS (ES+) M/Z (M+H)$^+$ 308.2.

Intermediate B12: (2S)-cyclopentyl[({[(1R,2R)-2-(pent-4-yn-1-yl)cyclopropyl]oxy}carbonyl)amino]ethanoic acid

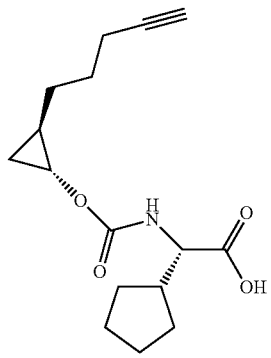 [SMILES: C#CCCC[C@@H]1C[C@H]1OC(=O)N[C@H](C(=O)O)C1CCCC1]

Steps 1-2: methyl (2S)-cyclopentyl[({[(1R,2R)-2-(pent-4-yn-1-yl)cyclopropyl]oxy}carbonyl)amino]ethanoate The title compound was prepared using the same method as described for Intermediate B10, Steps 1 to 2 using methyl (2S)-amino(cyclopentyl)ethanoate. $^1$H NMR (500 MHz, CDCl$_3$): δ (ppm) 5.14-5.09 (m, 1H), 4.33-4.29 (m, 1H), 3.74 (s, 3H), 2.25-2.20 (m, 2H), 1.94-1.93 (m, 1H), 1.74-1.49 (m, 9H), 1.44-1.27 (m, 4H), 1.23-1.20 (m, 1H), 1.02-0.97 (m, 1H), 0.85-0.78 (m, 1H), 0.56-0.49 (m, 1H).

Step 3: (2S)-cyclopentyl[({[(1R,2R)-2-(pent-4-yn-1-yl)cyclopropyl]oxy}carbonyl)amino]ethanoic acid

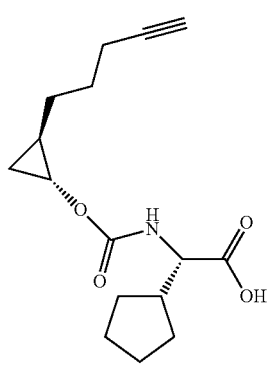 [SMILES: C#CCCC[C@@H]1C[C@H]1OC(=O)N[C@H](C(=O)O)C1CCCC1]

The title compound was prepared using the same method as described for Intermediate B7, Step 3. LRMS (ES+) M/Z (M+H)$^+$ 294.1.

Intermediates B13-B15

Using the same method as described for either Intermediate B11 (amino acid) or Intermediate B12 (amino ester), the following intermediates were synthesized:

| Intermediate | Reagent | Structure | Name | LRMS |
|---|---|---|---|---|
| B13 | 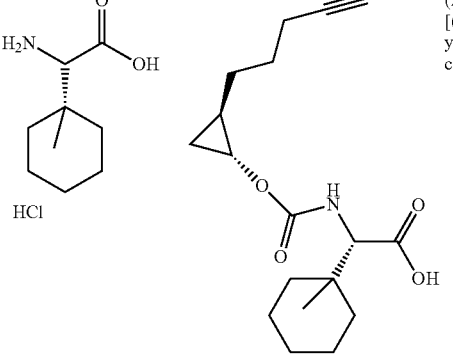 | 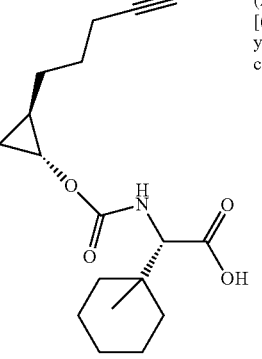 | (2S)-(1-methylcyclohexyl)[({[(1R,2R)-2-(pent-4-yn-1-yl)cyclopropyl]oxy}carbonyl)amino]ethanoic acid | 322.1 |
| B14 | 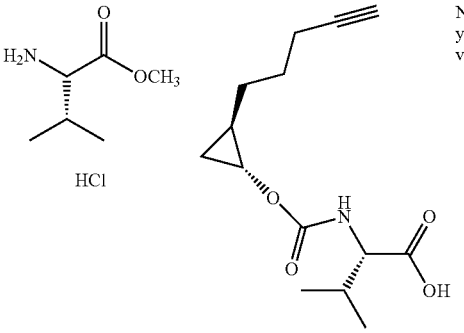 | 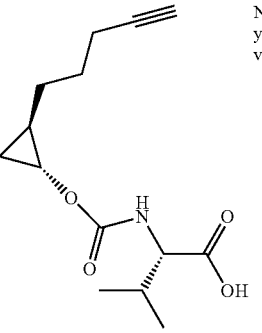 | N-({[(1R,2R)-2-(pent-4-yn-1-yl)cyclopropyl]oxy}carbonyl)-L-valine | NMR* |
| B15 | 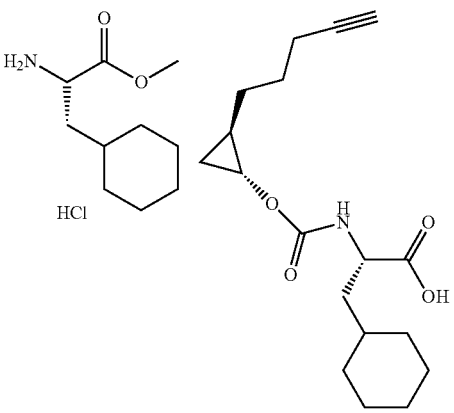 | 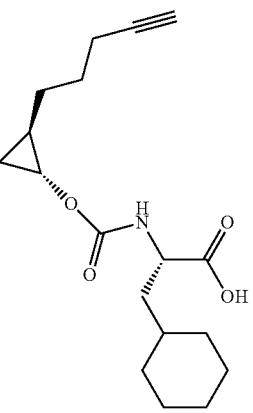 [SMILES: C#CCCC[C@@H]1C[C@H]1OC(=O)N[C@@H](CC1CCCCC1)C(=O)O] | 3-cyclohexyl-N-({[(1R,2R)-2-(pent-4-yn-1-yl)cyclopropyl]oxy}carbonyl)-L-alanine | 322.1 |

*B14 NMR characterization: $^1$H NMR (400 MHz, CDCl$_3$): δ (ppm) 5.16-5.11 (m, 1H), 4.40-4.33 (m, 1H), 3.82-3.79 (m, 1H), 2.29-2.23 (m, 3H), 1.97-1.95 (m, 1H), 1.72-1.61 (m, 2H), 1.46-1.31 (m, 2H), 1.07-0.93 (m, 8H), 0.89-0.83 (m, 1H), 0.60-0.52 (m, 1H).

Intermediate B16: 15-tert-butyl 14a-ethyl(2S,6S, 12Z,13aS,14aR,16aS)-2-{[(4-bromophenyl)sulfonyl] oxy}-6-[(tert-butoxycarbonyl)amino]-5,16-dioxo-2, 3,6,7,8,9,10,11,13a,14,16,16a-dodecahydrocyclopropa[e]pyrrolo[1,2-a][1,4] diazacyclopentadecine-14a,15(1H,5H)-dicarboxylate

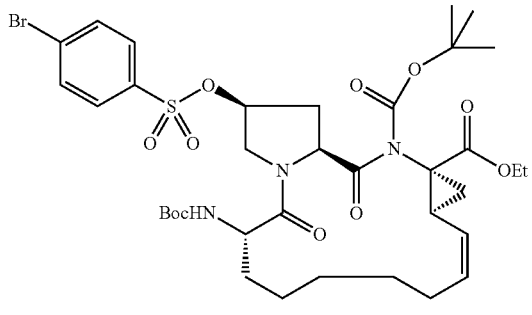 [SMILES: CCOC(=O)[C@@]12C[C@H]1/C=C\CCCCC[C@H](NC(=O)OC(C)(C)C)C(=O)N1C[C@@H](OS(=O)(=O)c3ccc(Br)cc3)C[C@H]1C(=O)N2C(=O)OC(C)(C)C]

Step 1 (4S)-4-{[(4-bromophenyl)sulfonyl]oxy}-1-(tert-butoxycarbonyl)-L-proline

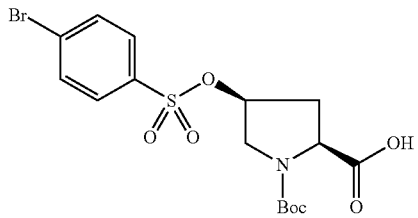 [SMILES: CC(C)(C)OC(=O)N1C[C@@H](OS(=O)(=O)c2ccc(Br)cc2)C[C@H]1C(=O)O]

LiOH (1M in water, 250 ml) was added to the solution of 1-tert-butyl 2-methyl(2S,4S)-4-{[(4-bromophenyl)sulfonyl] oxy}pyrrolidine-1,2-dicarboxylate (56.37 g) in THF (250 ml). The mixture was stirred at room temperature for 5 hours. The solution was acidified to pH=1 with HCl 1N and extracted with ethyl acetate (3×). The combined organic fractions were washed with brine, dried over magnesium sulfate, filtered and concentrated. The desired acid was obtained as a white solid (53.4 g). LRMS (ES+) m/z 471.9 (M+Na)$^+$.

Step 2: tert-butyl (2S,4S)-4-{[(4-bromophenyl)sulfonyl]oxy}-2-{[(1R,2S)-2-ethenyl-1-(ethoxycarbonyl) cyclopropyl]carbamoyl}pyrrolidine-1-carboxylate

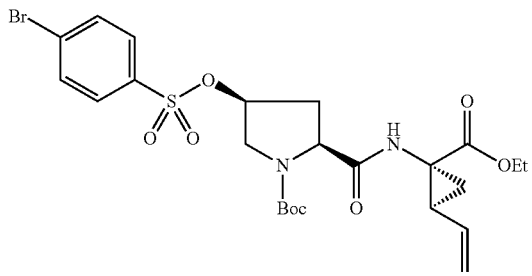 [SMILES: C=C[C@@H]1C[C@]1(NC(=O)[C@@H]1C[C@H](OS(=O)(=O)c2ccc(Br)cc2)CN1C(=O)OC(C)(C)C)C(=O)OCC]

HATU (49.6 g) was added to the solution of the acid from Step 1 (53.4 g), (1R,2S)-cyclopropanecarboxylic acid, 1-amino-2-ethenyl-, ethyl ester, hydrochloride (Intermediate A4, 34.1 g) and DIPEA (62.2 ml) in DMF (475 ml). The solution was stirred at room temperature until disappearance of the starting material. HCl 1 N and water were added and the mixture was extracted with ether (3×). The combined organic fractions were washed with brine, dried over magnesium sulfate, filtered and concentrated. The residue was purified on a pad of silica gel (hexanes: ethyl acetate 100:0 to 40:60). The residue was further purified by flash chromatography (ISCO, 0 to 100% ethyl acetate in hexanes) to give the desired product (40 g) as a white solid. LRMS (ES+) m/z 609.0 (M+Na)$^+$.

Step 3: ethyl (1R,2S)-1-{[(4S)-4-{[(4-bromophenyl) sulfonyl]oxy}-L-prolyl]amino}-2-ethenylcyclopropanecarboxylate

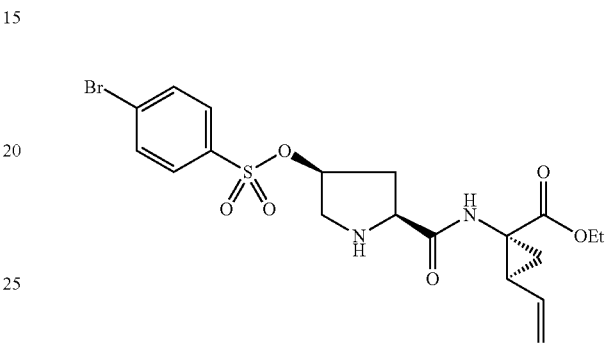

HCl (4M in dioxane, 300 ml) was added to the product of Step 2 (40 g) and the solution was stirred at room temperature for 30 min. The solvent was evaporated under reduced pressure. The residue was dissolved in ethyl acetate and a saturated sodium bicarbonate solution was added. The phases were separated. The precipitated solid was filtrated from the organic layer to give the desired product (33.8 g) as a white solid. LRMS (ES+) m/z 487.0 (M+H)$^+$.

Step 4: ethyl (1R,2S)-1-{[(4S)-4-{[(4-bromophenyl) sulfonyl]oxy}-1-{(2S)-2-[(tert-butoxycarbonyl) amino]non-8-enoyl}-L-prolyl]amino}-2-ethenylcyclopropanecarboxylate

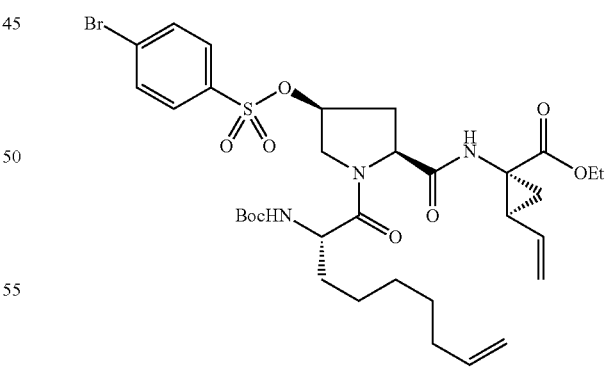

HATU (27.3 g) was added to the solution of (2S)-2-[(tert-butoxycarbonyl)amino]non-8-enoic acid (19.5 g) in DMF (100 ml) and the solution was stirred 15 minutes. The reaction mixture was cooled to 0° C. Then, the amine from Step 3 (31.8 g) in DMF (200 ml) (cooled to 0° C.) was added followed by DIPEA (11.40 ml). The solution was stirred at 0° C. for 1 hour. Hydrochloric acid (1M) was added and the mixture was extracted with diethyl ether (3×). The combined organic fractions were washed with brine, dried over magnesium sulfate, filtered and concentrated. The residue was purified by flash chromatography (ISCO, 0 to 100% ethyl acetate in hexanes) to give the desired product (40.2 g) as a white foam. LRMS (ES+) m/z 762.2 (M+Na)+.

Step 5: ethyl (1R,2S)-1-{[(4S)-4-{[(4-bromophenyl) sulfonyl]oxy}-1-{(2S)-2-[(tert-butoxycarbonyl) amino]non-8-enoyl}-L-prolyl](tert-butoxycarbonyl) amino}-2-ethenylcyclopropanecarboxylate

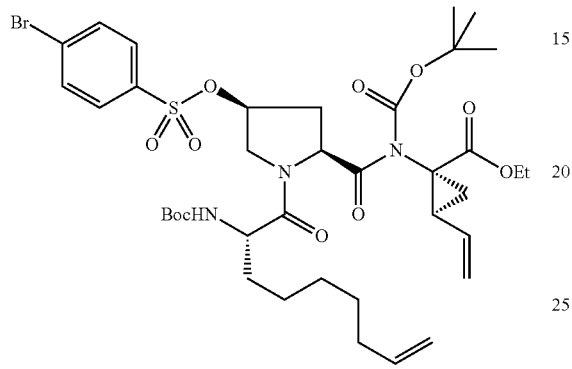

Di-tert-butyl dicarbonate (17.54 ml) was added at 0° C. to the solution of the product of Step 4 (37.3 g) and DMAP (1.85 g) in ethyl acetate (504 ml). The solution was stirred at room temperature for 4 hours. At this point, another 2.5 g of di-tert-butyl dicarbonate was added and the solution was stirred at room temperature for 2 hours. The reaction was quenched with water and the mixture was extracted with ethyl acetate (3x). The combined organic fractions were dried over magnesium sulfate, filtered and concentrated. The residue was purified by flash chromatograph (ISCO, 0 to 40% ethyl acetate in hexanes) to give the desired product (35.8 g) as a white foam. LRMS (ES+) m/z 862.2 (M+Na)+.

Step 6: 15-tert-butyl 14a-ethyl(2S,6S,12Z,13aS, 14aR,16aS)-2-{[(4-bromophenyl)sulfonyl]oxy}-6-[(tert-butoxycarbonyl)amino]-5,16-dioxo-2,3,6,7,8,9, 10,11,13a,14,16,16a-dodecahydro cyclopropa[e] pyrrolo[1,2-a][1,4]diazacyclopentadecine-14a,15 (1H,5H)-dicarboxylate

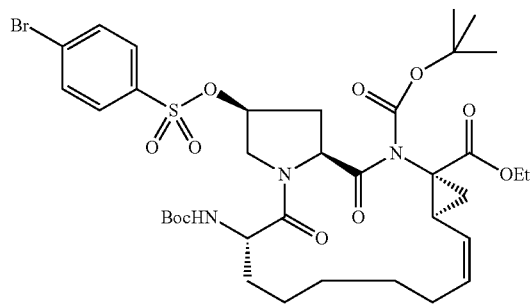 [SMILES: CCOC(=O)[C@@]12C[C@H]1/C=C\CCCCC[C@H](NC(=O)OC(C)(C)C)C(=O)N1C[C@@H](OS(=O)(=O)c3ccc(Br)cc3)C[C@H]1C(=O)N2C(=O)OC(C)(C)C]

The stirred solution of di-ene from Step 5 (15 g) in dichloroethane (1784 ml) was bubbled with nitrogen for 1 hour. 1,4 benzoquinone (0.19 g) and Zhan catalyst 1B (1.31 g) were added and the solution was purged with nitrogen. The solution was then stirred at 75° C. for 2 hours under a nitrogen flow. The reaction mixture was cooled to room temperature and ethyl vinyl ether (1.71 ml) was added to quench the catalyst. At this point, the solvent was evaporated under reduced pressure. The residue was purified by flash chromatography (ISCO, 0 to 40% ethyl acetate in hexanes) to give the desired product (12.3 g) as a white solid. LRMS (ES+) m/z 834.2 (M+Na)+.

Synthesis of Intermediates C

Intermediate C1: 4-methoxy-3-(prop-2-en-1-yl) quinolin-2-ol

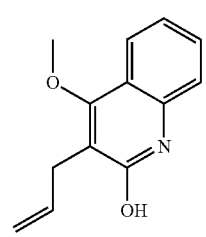 [SMILES: C=CCc1c(O)nc2ccccc2c1OC]

Step 1: 3-(prop-2-en-1-yl)quinoline-2,4-diol

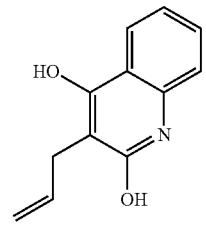

To a degassed solution of 2,4-dihydroxyquinoline (10.0 g) in DMF (100 ml) was added triethylamine (9.51 ml), Pd(Ph3P)4 (2.151 g), followed by allyl acetate (7.43 ml). The mixture was allowed to stir at 60° C. under nitrogen for 18 hours. The reaction mixture was cooled to room temperature and quenched into water (600 mL). The pH was adjusted to 12 using a saturated sodium carbonate solution. Dichloromethane was added and the layers were cut. The aqueous layer was extracted with dichloromethane once more. Then, the aqueous layer was cooled with ice and the pH was slowly adjusted to 2.5 with 12N HCl to give a pink solid. The solids were filtered and washed with water to give 11.5 g (92% yield). LRMS (ES+) M/Z (M+H)+ 202.0.

Step 2: 4-methoxy-3-(prop-2-en-1-yl)quinolin-2-ol

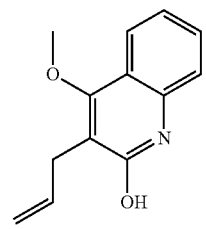 [SMILES: C=CCc1c(O)nc2ccccc2c1OC]

Dimethyl sulfate (0.237 ml) was added to a mixture of 3-(prop-2-en-1-yl)quinoline-2,4-diol (1.0 g) and potassium carbonate (1.37 g) in acetone (100 ml) and the mixture was stirred at room temperature for 3 hours then warmed to 40° C. for 30 minutes. The reaction mixture was cooled and the solids were removed by filtration. The filtrate was concentrated in vacuo. Purification by flash chromatography (ISCO, 4-10% acetone/DCM) gave the desired product (0.70 g). LRMS (ES+) M/Z (M+H)+ 216.0.

Intermediate C2: 4-ethoxy-3-(prop-2-en-1-yl)quinolin-2-ol

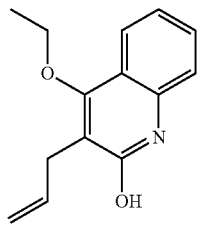 [SMILES: C=CCc1c(O)nc2ccccc2c1OCC]

The title compound was prepared using the same method as described for Intermediate C1 using diethyl sulfate. LRMS (ES+) m/z 230.1 (M+H)+.

Intermediate C3: 4-(benzyloxy)-3-(prop-2-en-1-yl)quinolin-2-ol

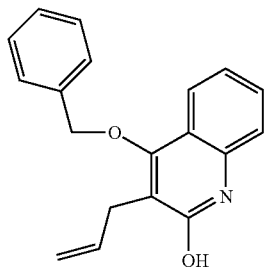 [SMILES: C=CCc1c(O)nc2ccccc2c1OCc1ccccc1]

To a mixture of 3-(prop-2-en-1-yl)quinoline-2,4-diol (4.0 g), triphenylphosphine (6.78 g) and benzyl alcohol (2.27 ml) in THF (240 ml) at 0° C. was added dropwise a THF (12 mL) solution of diisopropylazodicarboxylate (5.02 ml). Upon completion of addition, the mixture was allowed to stir at room temperature for 60 minutes. The reaction mixture was concentrated in vacuo to give a thick oil. Oil dissolved in DCM (20 mL) and solids started to precipitate. The solids were filtered and washed with DCM (10 mL). This provided 2.0 g of the desired product. Purification of the mother liquors using flash chromatography (ISCO, 1-8% acetone/DCM) gave an oil that was a mixture of products. This oil was dissolved in 15 mL of diethyl ether and seeded with the desired product. The mixture was stirred overnight and crystallization occurred. The solids were filtered and washed with ether to provide the desired product (1.06 g) as a white solid for a total of 3.06 g of product. LRMS (ES+) M/Z (M+H)+ 292.1.

Intermediate C4: 4-(benzyloxy)-6-bromo-3-(prop-2-en-1-yl)quinolin-2(1H)-one

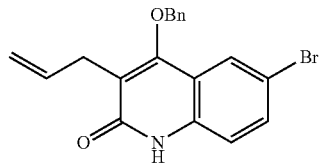 [SMILES: C=CCc1c(OCc2ccccc2)c2cc(Br)ccc2[nH]c1=O]

Step 1: ethyl 3-[(4-bromophenyl)amino]-3-oxopropanoate

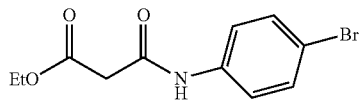 [SMILES: O=C(O)CC(=O)Nc1ccc(Br)cc1]

4-Bromoaniline (10.0 g) was dissolved in benzene (70 mL) and cooled to 0° C. A solution of ethyl malonyl chloride in benzene (70 mL) was added over 15 minutes. The reaction was allowed to warm to room temperature and was stirred for 1 hour. The reaction mixture was diluted with an aqueous saturated sodium carbonate solution (50 mL) and stirred for 1 hour. The reaction was complete by LCMS. The reaction mixture was diluted with water and the layers were separated. The aqueous layer was re-extracted with diethyl ether. The combined organics were washed with brine, dried over sodium sulfate and concentrated to give 18 g of a cake that was used directly in the next step.

Step 2: 3-[(4-bromophenyl)amino]-3-oxopropanoic acid

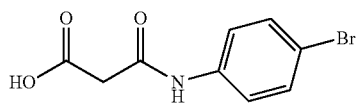

The product of Step 1 (16.63 g) was dissolved in THF (150 mL) and 2N NaOH (145 mL) was added over 15 minutes. The reaction was stirred for 24 hours. The reaction mixture was concentrated to remove the THF. Diethyl ether (20 mL) was added and the layers were separated. The aqueous layer was acidified to pH=2.2 with 1N HCl which resulted in the precipitation of solids. Ethyl acetate was added until the solids were dissolved and the layers were separated. The organic extract was dried with sodium sulfate, filtered and concentrated to give 14.7 g of a cake.

Step 3: 6-bromo-4-hydroxyquinolin-2(1H)-one

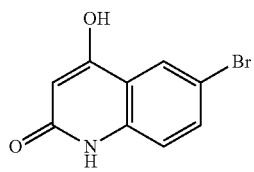 [SMILES: O=c1cc(O)c2cc(Br)ccc2[nH]1]

The product of Step 2 (14.7 g) was added to polyphosphoric acid (55.3 mL) and mixture was heated to 140° C. for 3 hrs. The reaction mixture was cooled slightly and poured into 3N HCl (168 mL). The pH was adjusted to 4 with 3N NaOH and resulting solid was filtered after cooling the reaction mixture to 10° C. The cake was washed with water and then slurried in 400 mL of 50% isopropanol/water for 18 hours. The solids were filtered, air dried to give a pasty solid which was dried in vacuo at 90° C. for 4 hours, ground in mortar/pestle and re-dried at 90° C. for another 18 hours to give 15 g of the desired product.

Step 4: 6-bromo-4-hydroxy-3-(prop-2-en-1-yl)quinolin-2(1H)-one

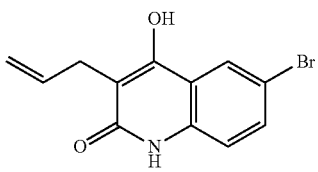 [SMILES: C=CCc1c(O)c2cc(Br)ccc2[nH]c1=O]

The title compound was prepared using the same method as described for Intermediate C1, Step 1 using the product of step 3. LRMS (ES+) m/z 280.0 (M+H)+.

Step 5: 4-(benzyloxy)-6-bromo-3-(prop-2-en-1-yl)quinolin-2(1H)-one

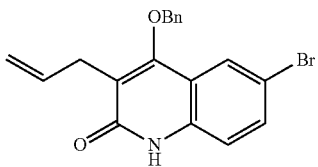 [SMILES: C=CCc1c(OCc2ccccc2)c2cc(Br)ccc2[nH]c1=O]

The title compound was prepared using the same method as Intermediate C3, using the product of step 4. LRMS (ES+) m/z 371.9 (M+H)+.

Intermediate C5: 7-chloro-4-methoxy-3-(prop-2-en-1-yl)quinolin-2-ol (A) and 5-chloro-4-methoxy-3-(prop-2-en-1-yl)quinolin-2-ol (B)

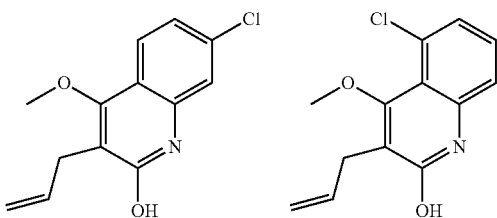 [SMILES: C=CCc1c(O)nc2cc(Cl)ccc2c1OC ; C=CCc1c(O)nc2cccc(Cl)c2c1OC]

Step 1: N,N'-bis(3-chlorophenyl)propanediamide

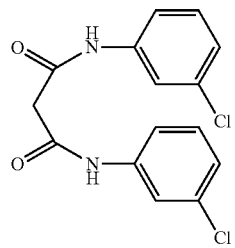 [SMILES: O=C(CC(=O)Nc1cccc(Cl)c1)Nc1cccc(Cl)c1]

3-chloroaniline (5.01 g) and diethyl malonate (2.51 ml) were combined in a flask and heated to 220° C. utilizing a short path condenser with nitrogen bleed over the reaction to remove reaction ethanol. The reaction was stirred for 18 hours and then cooled to room temperature. The solid that had formed in the flask was broken up in diethyl ether 30 mL to give free flowing orange solid upon filtration and washing with ether (3.75 g). LRMS (ES+) m/z (M+H)+ 322.9.

Step 2: 7-chloroquinoline-2,4-diol and 5-chloroquinoline-2,4-diol

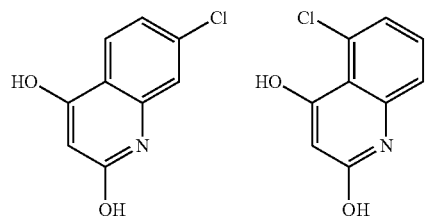 [SMILES: Oc1cc(O)c2ccc(Cl)cc2n1 ; Oc1cc(O)c2c(Cl)cccc2n1]

To the product of Step 1 (3.75 g) in a flask was added a solution of methanesulfonic acid (8 ml) containing phosphorus pentoxide (0.8 g) and the mixture was warmed to 170° C. for 1 hour. The reaction was cooled and poured into 50 g of ice. The mixture was allowed to stir then it was diluted with water and solids were filtered. The solid was dissolved with 0.5N sodium hydroxide and washed with toluene (2×). The pH was adjusted to 3 with concentrated HCl to give solids which were filtered and washed with water to give 2.1 g of an orange solid. The material was clean but it was a 1:1 mixture of regioisomers. LRMS (ES+) m/z (M+H)+ 196.1.

Step 3: 7-chloro-3-(prop-2-en-1-yl)quinoline-2,4-diol and 5-chloro-3-(prop-2-en-1-yl)quinoline-2,4-diol

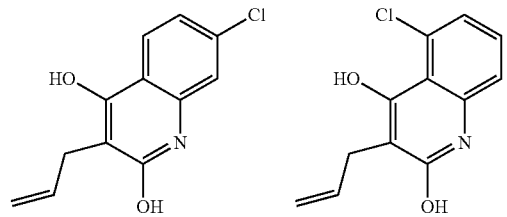 [SMILES: C=CCc1c(O)nc2cc(Cl)ccc2c1O ; C=CCc1c(O)nc2cccc(Cl)c2c1O]

The title compound was prepared using the same method as described for Intermediate C1, Step 1 using the product of step 2. LRMS (ES+) m/z 236.1 (M+H)+.

Step 4: 7-chloro-4-methoxy-3-(prop-2-en-1-yl) quinolin-2-ol (A) and 5-chloro-4-methoxy-3-(prop-2-en-1-yl)quinolin-2-ol (B)

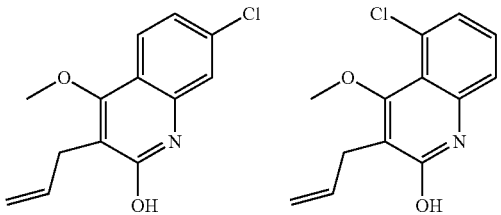 [SMILES: C=CCc1c(O)nc2cc(Cl)ccc2c1OC ; C=CCc1c(O)nc2cccc(Cl)c2c1OC]

The title compound was prepared using the same method as described for Intermediate C1, Step 2 using the product of step 3. The separation of isomers was done by flash chromatography (15-60% ethyl acetate/hexanes) to provide product A (570 mg) and B (350 mg). (A) LRMS (ES+) m/z 250.0 (M+H)$^+$. (B) LRMS (ES+) m/z 250.0 (M+H)$^+$.

Intermediate C6: 4-(benzyloxy)-3-bromoquinolin-2(1H)-one

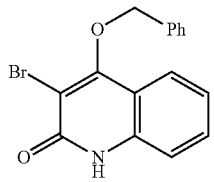 [SMILES: O=c1[nH]c2ccccc2c(OCc2ccccc2)c1Br]

Step 1: 3-bromo-4-hydroxyquinolin-2(1H)-one

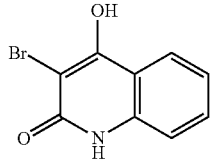 [SMILES: O=c1[nH]c2ccccc2c(O)c1Br]

N-bromosuccinimide (2.21 g) was added to the solution of 2,4-dihydroxyquinoline (2 g) in DCM (50 ml). The mixture was stirred at room temperature for 3 days. The mixture was filtrated and the solid was triturated with isopropanol. After filtration, toluene was added to the solid and the solvent was evaporated under reduced pressure to give the desired product (1.92 g) as a beige solid. LRMS (ES+) m/z 240.1 (M+H)$^+$.

Step 2: 4-(benzyloxy)-3-bromoquinolin-2(1H)-one

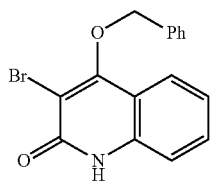 [SMILES: O=c1[nH]c2ccccc2c(OCc2ccccc2)c1Br]

To a 0° C. solution of PPh$_3$ (1.64 g) in THF (42 mL) was added diisopropylazodicarboxylate (1.21 mL) dropwise. The mixture was stirred at 0° C. for 15 minutes before the addition of benzyl alcohol (0.52 mL) followed by quinoline alcohol from Step 1 (1.0 g). The mixture was stirred 15 minutes at 0° C. then 5 hours at room temperature. A suspension had formed at that point. The solid was filtered and washed with cold isopropanol to afford the desired product (0.78 g). LRMS (ES+) m/z 352.1 (M+Na)$^+$.

Intermediate C7: 4-(benzyloxy)-3-bromo-8-fluoro-quinolin-2(1H)-one

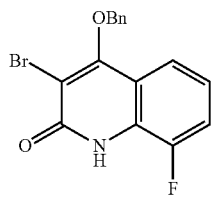 [SMILES: O=c1[nH]c2c(F)cccc2c(OCc2ccccc2)c1Br]

Step 1: ethyl 3-[(2-fluorophenyl)amino]-3-oxopropanoate

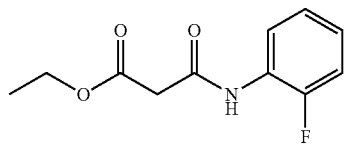 [SMILES: CCOC(=O)CC(=O)Nc1ccccc1F]

To a solution of 2-fluoroaniline (8.67 ml) in ethyl acetate (266 ml) was added water (200 ml) and sodium bicarbonate (15.12 g). Ethyl malonyl chloride (13.82 ml) was added and the solution was stirred at room temperature for 1 hour. The two layers were separated and the organic phase was washed with a saturated aqueous solution of sodium bicarbonate, water and brine, dried over sodium sulfate and evaporated to provide a brownish oil. The crude reaction mixture was used directly in the next step. LRMS (ES+) m/z 226.1 (M+H)$^+$.

Step 2: 8-fluoro-4-hydroxyquinolin-2(1H)-one

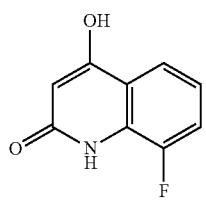 [SMILES: O=c1cc(O)c2cccc(F)c2[nH]1]

A solution of the product from step 1 (20.27 g) in DCM (100 ml) was added to polyphosphoric acid (43.7 ml). Dichloromethane was distilled from the reaction mixture by increasing the temperature slowly and then the brownish gummy solution was stirred at 120° C. for 3 hours and then left at room temperature for 16 hours. The reaction mixture was quenched by adding ice cooled water and the product was filtered. The filter cake was stirred with 500 mL of water and filtered to give the desired product (9.38 g) as a colorless solid. LRMS (ES+) m/z 180.1 (M+H)$^+$.

Step 3: 3-bromo-8-fluoro-4-hydroxyquinolin-2(1H)-one

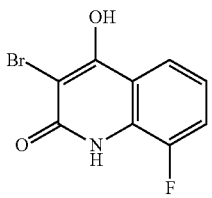 [SMILES: O=c1[nH]c2c(F)cccc2c(O)c1Br]

The title compound was prepared using the same method as described for Intermediate C6, Step 1 using the product of step 2. LRMS (ES+) m/z 257.95 (M+H)⁺.

Step 4: 4-(benzyloxy)-3-bromo-8-fluoroquinolin-2(1H)-one

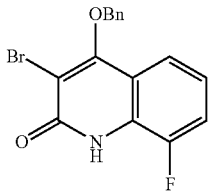

The title compound was prepared using the same method as described for Intermediate C6, Step 2 using the product of step 3. LRMS (ES+) m/z 370.15 (M+Na)⁺.

Intermediate C8: 4-(benzyloxy)-3-bromo-8-methoxyquinolin-2(1H)-one

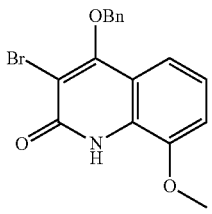 [SMILES: COc1cccc2c(OCc3ccccc3)c(Br)c(=O)[nH]c12]

The title compound was prepared using the same method as described for Intermediate C7 starting with o-anisidine. LRMS (ES+) m/z 382.1 (M+Na)⁺.

Intermediate C9: 4-(benzyloxy)-3-bromo-7-(propan-2-yl)quinolin-2(1H)-one

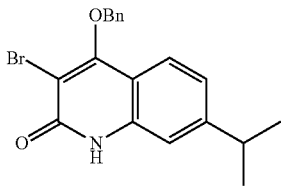 [SMILES: CC(C)c1ccc2c(OCc3ccccc3)c(Br)c(=O)[nH]c2c1]

The title compound was prepared using the same method as described for Intermediate C7 starting with 3-(propan-2-yl)aniline. LRMS (ES+) m/z 372.1 (M+Na)⁺.

Intermediate C10: 4-(benzyloxy)-3-bromo-7-(trifluoromethyl)quinolin-2(1H)-one

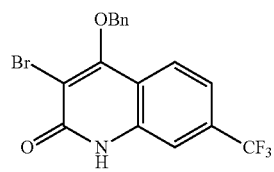 [SMILES: O=c1[nH]c2cc(C(F)(F)F)ccc2c(OCc2ccccc2)c1Br]

Step 1: methyl 2-amino-4-(trifluoromethyl)benzoate

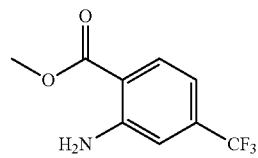

To a solution of 2-amino-4-(trifluoromethyl)benzoic acid (5 g) in THF (85 ml) was added diazomethane (48.7 ml) in ether until completion of the reaction. Nitrogen was bubbled into the reaction mixture for 15 minutes to remove the excess of diazomethane and the solvent was removed under reduced pressure to provide a light brown solid (5.34 g). The compound was used in the next without purification. LRMS (ES+) m/z 220.1 (M+H)⁺.

Step 2: methyl 2-(acetylamino)-4-(trifluoromethyl)benzoate

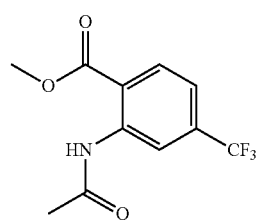 [SMILES: COC(=O)c1ccc(C(F)(F)F)cc1NC(C)=O]

To a solution of the product from Step 1 (5.34 g) in dioxane (25 ml) was added acetic anhydride (6 ml) and pyridine (4 ml). After 60 hours of stirring at 80° C., the solution was concentrated under reduced pressure and the residue was dissolved into ethyl acetate. The organic layer was washed with 2M sodium carbonate, 10% aqueous HCl, water and brine, dried over sodium sulfate and evaporated. The product was purified by flash chromatography (ISCO, 5%-20% ethyl acetate in hexanes) to provide a beige solid (5.27 g). LRMS (ES+) m/z 262.0 (M+H)⁺.

Step 3: 4-hydroxy-7-(trifluoromethyl)quinolin-2(1H)-one

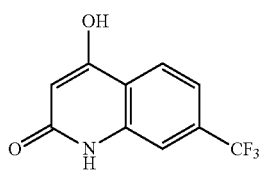 [SMILES: O=c1cc(O)c2ccc(C(F)(F)F)cc2[nH]1]

To a solution of the product of step 2 (3.0 g) in THF (60 ml) was added 0.5 M KHMDS in toluene (108 ml) dropwise at −78° C. After the addition was completed, the mixture was kept at −78° C. for 40 minutes, then it was allowed to warm up slowly at room temperature. The mixture was quenched with $H_2O$ and the product was extracted twice with water. The combined aqueous layers were washed with ethyl acetate twice and then acidified with 6N HCl. The solid was filtered and the filter cake was washed with water and dried by vacuum aspiration to get a beige solid which was triturated into ethyl acetate to get a white solid (1.7 g). LRMS (ES+) m/z 230.05 (M+H)+.

Step 4: 3-bromo-4-hydroxy-7-(trifluoromethyl)quinolin-2(1H)-one

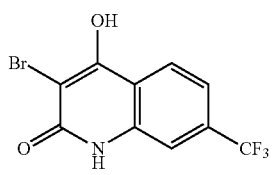

The title compound was prepared using the same method as described for Intermediate C6, Step 1 using the product of step 3. LRMS (ES+) m/z 308.2 (M+H)+.

Step 5: 4-(benzyloxy)-3-bromo-7-(trifluoromethyl)quinolin-2(1H)-one

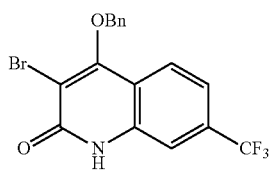

The title compound was prepared using the same method as described for Intermediate C6, Step 2 using the product of step 4. LRMS (ES+) m/z 420.2 (M+Na)+.

Intermediate C11: 4-(benzyloxy)-3-bromo-7-methylquinolin-2(1H)-one

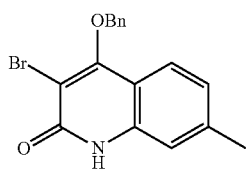 [SMILES: Cc1ccc2c(OCc3ccccc3)c(Br)c(=O)[nH]c2c1]

The title compound was prepared using the same method as described for Intermediate C10 starting from 2-amino-4-methylbenzoic acid. LRMS (ES+) m/z 344.05 (M+H)+.

Intermediate C12: 4-(benzyloxy)-3-bromo-7-fluoro-quinolin-2(1H)-one

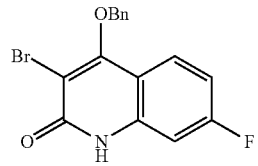 [SMILES: O=c1[nH]c2cc(F)ccc2c(OCc2ccccc2)c1Br]

The title compound was prepared using the same method as described for Intermediate C10 starting from 2-amino-4-fluorobenzoic acid. LRMS (ES+) m/z 348.0 (M+H)+.

Intermediate C13: 3-bromo-4-[(4-methoxybenzyl)oxy]quinolin-2(1H)-one

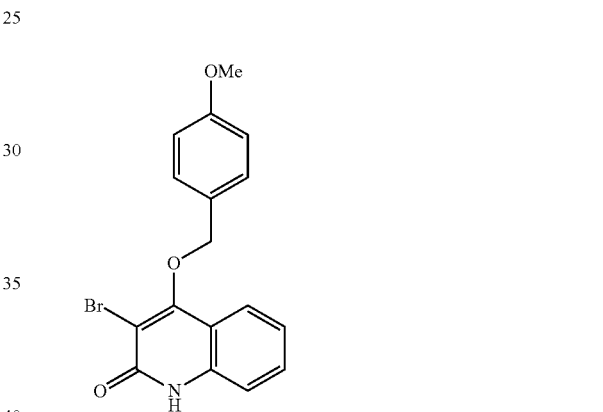

The title compound was prepared using the same method as described for Intermediate C6 using (4-methoxyphenyl)methanol. LCMS (ES+) m/z 382.0 (M+Na)+.

Intermediate D1: (S)-2-amino-2-(1-methylcyclohexyl)acetic acid hydrochloride

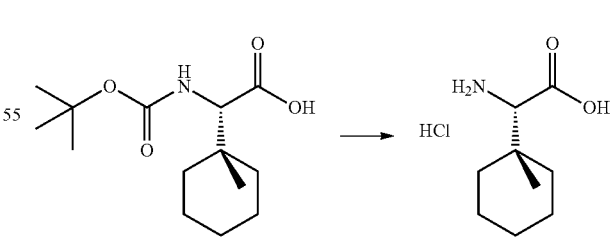

A round-bottom flask was charged with (S)-2-(tert-butoxycarbonylamino)-2-(1-methylcyclohexyl)acetic acid (synthesized according to procedures described in *Tetrahedron Lett.* 2007, 48(36):6343-6347) (10 g, 36.9 mmol) and 4M hydrochloric acid (40 ml, 160 mmol) in dioxane. The mixture was stirred for 1 hour and then concentrated to dryness in rotavap to give intermediate D1 (7.6 g, 36.6 mmol, 99% yield) as a white powder. No further purification was carried out.

Intermediate D2: (2S,4R)-1-tert-butyl 2-methyl 4-((4-(benzyloxy)-3-bromoquinolin-2-yl)oxy)pyrrolidine-1,2-dicarboxylate

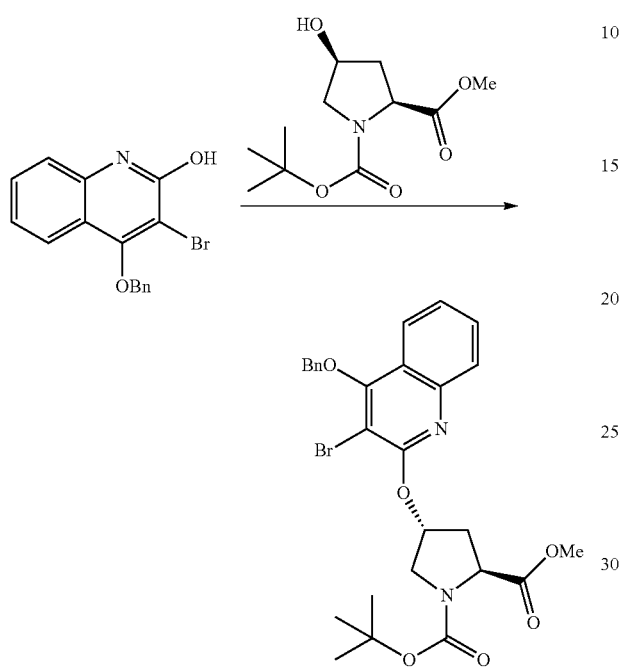

A round-bottom flask was charged with triphenylphosphine (3.61 g, 13.77 mmol), L-cis-Boc-4-hydroxyproline methyl ester (BaChem) (3.25 g, 13.26 mmol) and 4-(benzyloxy)-3-bromoquinolin-2-ol (3.37 g, 10.2 mmol). Dry THF (68.0 ml) was added under anhydrous conditions and the resulting slurry was stirred at 0° C. Diisopropyl azodicarboxylate (2.67 ml, 13.77 mmol) was added dropwise and the slurry was stirred for 10 min. The cooling bath was removed and the mixture was stirred for 2 hour (reaction mixture became homogeneous after approximately 30 min). The mixture was diluted with ethyl acetate (500 mL) and washed with aq. 1M HCl (100 mL), aq saturated sodium bicarbonate (2×100 mL) and brine (100 mL), dried over magnesium sulfate, filtered and concentrated in rotavap. The residue was purified on RediSep® (330 g; Teledyne Isco, Inc., Lincoln, Nebr.) silica gel column (gradient: 0 to 50% ethyl acetate in hexanes) to give intermediate D2 (5.42 g, 9.72 mmol, 95% yield) as a colorless foam.

Intermediate D3: 2,5-dioxopyrrolidin-1-yl((1R,2R)-2-(pent-4-yn-1-yl)cyclopropyl)carbonate A solution of (1R,2R)-2-(pent-4-ynyl)cyclopropanol (8.5 g, 68.4 mmol) in dry acetonitrile (68.4 ml) was treated with pyridine (6.64 ml, 82 mmol) and N,N'-disuccinimidyl carbonate (17.53 g, 68.4 mmol). The slurry was stirred for 10 min at room temp and then heated at 40° C. overnight. The mixture was diluted with ethyl acetate (1.2 L) and washed with water (200 mL), aq 1M HCl (200 mL), aq. saturated sodium bicarbonate (200 mL), and brine (200 mL), dried over magnesium sulfate, filtered and concentrated in rotavap to give intermediate D3 (14.56 g, 54.9 mmol, 80% yield) as a slightly yellow gum. No further purification was carried out.

Intermediate D4: (1R,2S)-1-amino-N-((1-methylcyclopropyl)sulfonyl)-2-vinylcyclopropanecarboxamide hydrochloride Step 1: (1R,2S)-1-((tert-butoxycarbonyl)amino)-2-vinylcyclopropanecarboxylic acid

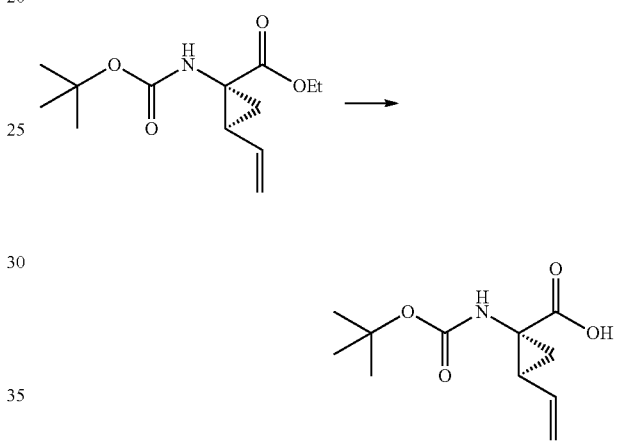

A round-bottom flask was charged with (1R,2S)-ethyl 1-((tert-butoxycarbonyl)amino)-2-vinylcyclopropanecarboxylate (4 g, 15.67 mmol) and lithium hydroxide monohydrate (2.63 g, 62.7 mmol). Methanol (52.2 ml), THF (52.2 ml) and water (52.2 ml) were added. The mixture was heated (oil bath at 45° C.) overnight. The reaction mixture was concentrated to half-its volume in rotavap and the pH of the mixture was adjusted to pH=2-3 with aq 1M HCl. The mixture was extracted with dichloromethane (3×150 mL). The combined organic extracts were washed with brine (50 mL), dried over magnesium sulfate, filtered and concentrated in rotavap to give the title compound (3.5 g, 15.40 mmol, 98% yield) as a white powder. No further purification was carried out.

Step 2: tert-butyl ((1R,2S)-1-(((1-methylcyclopropyl)sulfonyl)carbamoyl)-2-vinylcyclopropyl)carbamate

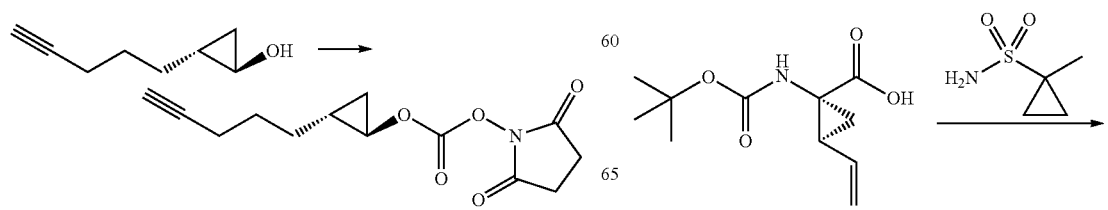

-continued

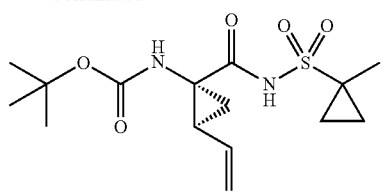

A round-bottom flask was charged with the carboxylic acid product of step 1 (2 g, 8.80 mmol) and 1,1'-carbonyldiimidazole (2.141 g, 13.20 mmol). Dry THF (44.0 ml) was added under anhydrous conditions and the mixture was heated (oil bath at 85° C.) for 2 hours with exclusion of moisture. The mixture was cooled to room temp and a solution of 1-methylcyclopropane-1-sulfonamide (2.379 g, 17.60 mmol) in dry THF (10 mL) was added followed by 1,8-diazabicyclo[5.4.0]undec-7-ene (2.63 ml, 17.60 mmol). The mixture was heated (oil bath at 75° C.) overnight. The reaction mixture was treated with aq 1M HCl (20 mL) and water (50 mL). The product was extracted into ethyl acetate (400 mL) Upon separation, the organic layer was washed with aq 1M HCl/water (1:2, 80 mL), and brine (80 mL), dried over magnesium sulfate, filtered and concentrated in rotavap. The residue was purified on a gold cap RediSep® (120 g) silica gel column (gradient: 0 to 25% ethyl acetate in dichloromethane) to give the title compound (2.25 g, 6.53 mmol, 74.2% yield) as a white powder.

Step 3: (1R,2S)-1-amino-N-((1-methylcyclopropyl)sulfonyl)-2-vinylcyclopropanecarboxamide hydrochloride

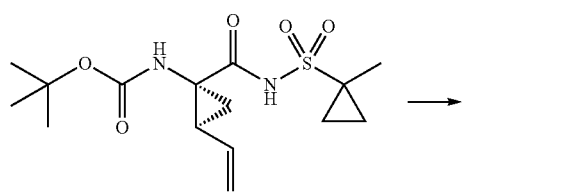

The N-Boc protected amine product of step 2 (2.25 g, 6.53 mmol) was dissolved in 4M hydrochloric acid (20 ml, 80 mmol) in dioxane and stirred for 30 minutes. TLC showed complete reaction. The reaction mixture was concentrated to dryness to afford Intermediate D4 (1.85 g, 6.59 mmol, 101% yield) as a white powder. No further purification was carried out.

Intermediate D5: (S)-2-amino-2-(2,3-dihydro-1H-inden-2-yl)acetic acid hydrochloride

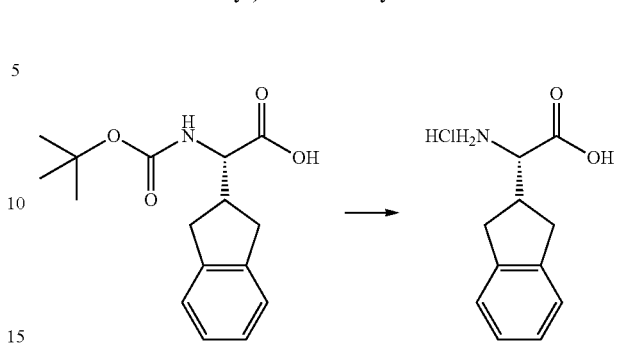

Boc-L-indanylglycine (Chem-Impex International Inc., Wood Dale, Ill.) (4.2 g, 14.42 mmol) was treated with 4M hydrochloric acid (80 ml, 320 mmol) in dioxane at room temperature. The resulting slurry was stirred for 2 hours. TLC showed complete reaction and the mixture was concentrated to dryness in rotavap. The residue was dried under vacuum to give the product D5 (3.3 g, 101%) as a white powder.

NS3 Protease Enzymatic Activity

The HCV NS3 protease inhibitory activity was measured using the protease time-resolved fluorescence (TRF) assay as described below and in International Patent Application Publication No. WO 2006/102087. The assay was performed with HCV genotype 1b (BK) NS3 modified enzyme with a R155K mutation and genotype 3a (3A-1).

The assay was performed in a final volume of 50 µl in assay buffer containing 50 mM HEPES, pH 7.5, 150 mM NaCl, 15% glycerol, 0.15% TRITON X-100, 10 mM DTT, and 0.1% PEG 8000. NS3 and NS4A protease is pre-incubated with various concentrations of inhibitors in DMSO for 10 minutes. The reaction was initiated by adding the TRF peptide substrate (final concentration 25 nM) and NS3 mediated hydrolysis of the substrate proceeds for 6 hours at room temperature. Product fluorescence is detected using an Envision plate reader (Perkin Elmer) with excitation at 340 nm and emission at 615 nm with a 400 µs delay. Testing concentrations of the enzymes were selected to result in a signal to background ratio (S/B) of 5-20. $IC_{50}$ values are derived using a standard four-parameter fit to the data.

Alternatively, the Ki values can be obtained using the following protocol: The assay is performed in a final volume of 100 µl in assay buffer containing 50 mM HEPES, pH 7.5, 150 mM NaCl, 15% glycerol, 0.15% TRITON X-100, 10 mM DTT, and 0.1% PEG 8000. NS3 and NS4A protease is pre-incubated with various concentrations of inhibitors in DMSO for 30 minutes. The reaction is initiated by adding the TRF peptide substrate (final concentration 100 nM). NS3 mediated hydrolysis of the substrate is quenched after 1 hour at room temperature with 100 µl of 500 mM MES, pH 5.5. Product fluorescence is detected using either a VICTOR V2 or FUSION fluorophotometer (Perkin Elmer Life and Analytical Sciences) with excitation at 340 nm and emission at 615 nm with a 400 µs delay. Testing concentrations of the enzymes are selected to result in a signal to background ratio (S/B) of 8-30. $IC_{50}$ values are derived using a standard four-parameter fit to the data. $K_i$ values are derived from $IC_{50}$ values using the following formula, $$IC_{50} = K_i(1+[S]/K_M), \quad \text{Eqn (1),}$$

where [S] is the concentration of substrate peptide in the reaction and $K_M$ is the Michaelis constant. See Gallinari et al., 1999, *Biochem.* 38:5620-32; Gallinari et al., 1998, *J. Virol.* 72:6758-69; and Taliani et al., 1996, *Anal. Biochem.* 240:60-67. ND means not determined.

| Example | Ki 1b R155K (nM) | Ki 3a (nM) | Example | Ki 1b R155K (nM) | Ki 3a (nM) |
|---|---|---|---|---|---|
| 1 | 0.25 | 6.1 | 156 | 0.079 | 0.84 |
| 2 | 2.7 | 31 | 157 | 0.049 | 0.76 |
| 3 | 1.4 | 35 | 158 | 0.19 | 2.6 |
| 4 | 0.11 | 3.4 | 159 | 0.050 | 0.53 |
| 5 | 0.59 | 17 | 160 | 0.053 | 0.44 |
| 6 | 0.10 | 1.3 | 161 | 0.31 | 2.8 |
| 7 | 0.76 | 17 | 162 | 0.18 | 1.7 |
| 8 | 1.6 | 51 | 103 | 0.13 | 1.1 |
| 9 | 0.14 | 2.9 | 164 | 0.096 | 1.2 |
| 10 | 0.19 | 11 | 165 | 0.24 | 2.8 |
| 11 | 0.26 | 11 | 166 | 0.11 | 2.2 |
| 12 | 3.3 | 340 | 167 | 1.3 | 41 |
| 13 | 0.93 | 15 | 168 | 0.078 | 1.3 |
| 14 | 0.81 | 28 | 169 | 0.042 | 0.75 |
| 15 | 0.81 | 36 | 170 | 1.1 | 21 |
| 16 | 1.1 | 70 | 171 | 0.099 | 2.0 |
| 17 | <0.016 | 0.45 | 172 | 1.1 | 14 |
| 18 | 0.79 | 12 | 173 | 0.34 | 9.5 |
| 19 | 0.091 | 0.70 | 174 | 0.057 | 1.1 |
| 20 | 0.55 | 22 | 175 | 0.091 | 0.89 |
| 21 | 0.51 | 9.6 | 176 | 0.10 | 1.3 |
| 22 | 0.33 | 9.3 | 177 | 0.14 | 1.1 |
| 23 | 0.11 | 0.64 | 178 | 0.14 | 3.6 |
| 24 | 0.39 | 9.1 | 179 | 0.034 | 0.58 |
| 25 | 5.2 | 88 | 180 | 0.037 | 0.58 |
| 26 | 0.33 | 13 | 181 | 0.065 | 0.78 |
| 27 | 2.5 | 59 | 182 | 0.064 | 0.61 |
| 28 | 0.70 | 35 | 183 | 0.070 | 0.95 |
| 29 | 0.12 | 1.4 | 184 | 0.057 | 1.1 |
| 30 | 1.3 | 4.9 | 185 | 0.032 | 0.36 |
| 31 | 4.1 | 23 | 186 | 0.078 | 1.9 |
| 32 | 0.54 | 9.2 | 187 | 0.24 | 6.1 |
| 33 | 0.32 | 22 | 188 | 0.033 | 0.85 |
| 34 | 0.10 | 1.8 | 189 | 0.081 | 3.4 |
| 35 | 0.15 | 2.0 | 190 | 0.074 | 1.5 |
| 36 | 0.15 | 3.2 | 191 | 0.16 | 1.5 |
| 37 | 0.16 | 6.0 | 192 | 0.10 | 0.71 |
| 38 | 1.2 | 94 | 193 | 0.16 | 1.5 |
| 39 | 0.13 | 3.5 | 194 | 0.032 | 0.38 |
| 40 | 1.3 | 27 | 195 | 0.049 | 0.66 |
| 41 | 6.6 | 73 | 196 | 0.10 | 0.85 |
| 42 | 0.073 | 1.5 | 197 | 0.027 | 0.31 |
| 43 | 0.28 | 9.9 | 198 | 0.050 | 0.77 |
| 44 | 0.25 | 7.9 | 199 | 0.057 | 0.74 |
| 45 | 0.10 | 0.50 | 200 | 0.074 | 0.96 |
| 46 | 0.15 | 4.0 | 201 | 0.079 | 1.3 |
| 47 | 0.12 | 2.9 | 202 | 0.050 | 0.95 |
| 48 | 0.12 | 0.76 | 203 | 0.13 | 4.9 |
| 49 | 0.16 | 1.5 | 204 | 0.15 | 2.4 |
| 50 | 0.23 | 6.6 | 205 | 0.19 | 1.9 |
| 51 | 0.21 | 1.9 | 206 | 0.20 | 2.6 |
| 52 | 1.1 | 10 | 207 | 0.11 | 1.3 |
| 53 | 0.11 | 0.55 | 208 | 0.11 | 1.0 |
| 54 | 0.02 | 0.45 | 209 | 0.056 | 0.55 |
| 55 | 0.22 | 3.9 | 210 | 0.046 | 0.29 |
| 56 | 0.09 | 0.95 | 211 | 0.033 | 0.30 |
| 57 | 0.11 | 2.3 | 212 | 0.22 | 1.9 |
| 58 | 0.10 | 0.57 | 213 | 0.36 | 3.8 |
| 59 | 0.11 | 0.45 | 214 | 0.021 | 1.2 |
| 60 | 0.61 | 12 | 215 | 1.7 | 55 |
| 61 | 0.70 | 20 | 216 | 0.24 | 6.4 |
| 62 | 1.6 | 85 | 217 | 0.27 | 7.1 |
| 63 | 0.35 | 7.2 | 218 | 0.035 | 2.6 |
| 64 | 0.43 | 5.5 | 219 | 0.12 | 1.9 |
| 65 | 0.56 | 16 | 220 | 0.29 | 3.9 |
| 66 | 0.077 | 25 | 221 | 0.050 | 1.4 |
| 67 | 0.081 | 6.6 | 222 | 0.045 | 0.44 |
| 68 | 0.16 | 1.6 | 223 | 0.055 | 1.2 |
| 69 | <0.016 | 1.8 | 224 | 0.061 | 0.67 |
| 70 | 0.066 | 0.59 | 225 | 0.079 | 0.60 |
| 71 | <0.016 | 0.42 | 226 | 0.11 | 1.6 |
| 72 | <0.016 | 1.1 | 227 | 0.095 | 0.36 |
| 73 | 0.14 | 2.5 | 228 | 0.11 | 0.47 |
| 74 | 0.10 | 1.3 | 229 | 0.034 | 0.25 |
| 75 | 0.28 | 2.3 | 230 | 0.065 | 0.38 |
| 76 | 0.09 | 0.71 | 231 | 0.13 | 1.8 |
| 77 | 0.09 | 0.72 | 232 | 0.020, 0.040 | 0.275 |
| 78 | 0.08 | 0.54 | 233 | 0.015, 0.080 | 4.2 |
| 79 | 0.06 | 1.8 | 234 | 0.08, 1.38 | 29.12 |
| 80 | 0.20 | 2.4 | 235 | 0.53, 4.36 | 203.15 |
| 81 | 0.29 | 4.6 | 236 | 0.33, 5.44 | 109.95 |
| 82 | 0.18 | 2.5 | 237 | 0.013, 0.098 | 0.80 |
| 83 | 1.1 | 23 | 238 | 0.031, 0.047 | 0.90 |
| 84 | 0.24 | 7.2 | 239 | 0.016, 0.064 | 0.278 |
| 85 | 0.11 | 0.56 | 240 | 0.019, 0.28 | 2.904 |
| 86 | 0.23 | 4.4 | 241 | 0.021, 0.162 | 2.787 |
| 87 | 0.24 | 3.2 | 242 | 0.013, 0.072 | 0.935 |
| 88 | 0.34 | 4.4 | 243 | 0.033, 0.275 | 3.305 |
| 89 | 0.07 | 0.32 | 244 | 1.589, 1.653 | 296.200 |
| 90 | 0.15 | 1.6 | 245 | 0.546, 1.414 | 128.100 |
| 91 | 0.16 | 1.0 | 246 | 1.016, 1.136 | 211.500 |
| 92 | 1.6 | 19 | 247 | ND | ND |
| 93 | 0.26 | 2.8 | 248 | 0.100, 0.348 | 40.220 |
| 94 | 0.093 | 0.59 | 249 | 0.026, 0.500 | 7.550 |
| 95 | 0.18 | 1.0 | 250 | 0.024, 0.160 | 4.450 |
| 96 | 0.15 | 0.78 | 251 | 0.015, 0.051 | 1.150 |
| 97 | 0.08 | 073 | 252 | 0.009, 0.022 | 0.088 |
| 98 | 0.18 | 2.9 | 253 | 0.026, 0.265 | 11.000 |
| 99 | 0.28 | 2.8 | 254 | 0.116, 2.304 | 47.531 |
| 100 | 0.24 | 2.0 | 255 | 0.120, 2.206 | 59.112 |
| 101 | 0.090 | 0.96 | 256 | 0.021, 0.122 | 5.450 |
| 102 | 0.21 | 3.2 | 257 | 0.032, 0.230 | 3.900 |
| 103 | 0.77 | 8.5 | 258 | 0.012, 0.079 | 2.750 |
| 104 | 1.3 | 26 | 259 | 0.030, 0.350 | 7.400 |
| 105 | 0.43 | 14 | 260 | 0.019, 0.093 | 2.400 |
| 106 | 0.78 | 17 | 261 | 0.026, 0.155 | 3.450 |
| 107 | 0.74 | 23 | 262 | 0.018, 0.120 | 1.200 |
| 108 | 0.93 | 23 | 263 | 0.006, 0.011 | 0.041 |
| 109 | 4.1 | 122 | 264 | 0.037, 1.400 | 7.700 |
| 110 | 14 | 488 | 265 | 0.016, 0.110 | 1.150 |
| 111 | 11 | 272 | 266 | 0.020, 0.044 | 7.500 |
| 112 | 24 | 620 | 267 | 0.114, 4.600 | 56.000 |
| 113 | 0.090 | 1.6 | 268 | 0.012, 0.034 | 0.200 |
| 114 | 0.051 | 0.25 | | | |
| 115 | 0.057 | 0.25 | 270 | 0.021, 0.180 | 1.400 |
| 116 | 0.17 | 1.6 | 271 | 0.023, 0.215 | 5.200 |
| 117 | 0.080 | 0.93 | 272 | 0.015, 0.128 | 2.120 |
| 118 | 0.066 | 0.89 | 273 | 0.100, 1.850 | 68.000 |
| 119 | 0.12 | 3.2 | 274 | 0.015, 0.015 | 0.094 |
| 120 | 0.062 | 1.1 | 275 | 0.110, 1.150 | 16.000 |
| 121 | 0.38 | 12 | 276 | 0.013, 0.019 | 0.140 |
| 122 | 0.33 | 8.8 | 277 | 0.008, 0.013 | 0.078 |
| 123 | 0.49 | 6.1 | 278 | 0.860, 20.000 | 740.000 |
| 124 | 0.79 | 10 | 279 | 0.012, 0.145 | 2.600 |
| 125 | 4.1 | 114 | 280 | 0.024, 0.280 | 4.650 |
| 126 | 0.40 | 7.7 | 281 | 0.016, 0.125 | 1.245 |
| 127 | 0.11 | 2.1 | 282 | 0.140, 5.300 | 140.000 |
| 128 | 0.41 | 13 | 283 | 0.014, 0.022 | 0.108 |
| 129 | 0.51 | 8.7 | 284 | 0.023, 0.053 | 0.280 |
| 130 | 2.2 | 18 | 285 | 0.042, 0.104 | 0.410 |
| 131 | 0.11 | 1.3 | 286 | 0.022, 0.094 | 0.515 |
| 132 | 0.39 | 6.8 | 287 | 0.092, 2.550 | 58.000 |
| 133 | 0.11 | 1.0 | 288 | 0.018, 0.050 | 0.224 |
| 134 | 0.56 | 6.1 | 289 | 0.030, 0.197 | 3.275 |
| 135 | 0.20 | 1.8 | 290 | 0.012, 0.125 | 1.144 |
| 136 | 0.58 | 5.1 | 291 | 0.010, 0.085 | 0.774 |
| 137 | 0.14 | 1.2 | 292 | 0.120, 0.733 | 49.400 |
| 138 | 0.63 | 7.0 | 293 | 0.029, 0.138 | 1.300 |

-continued

| Example | Ki 1b R155K (nM) | Ki 3a (nM) | Example | Ki 1b R155K (nM) | Ki 3a (nM) |
|---|---|---|---|---|---|
| 139 | 0.10 | 0.38 | 294 | 0.015, 0.046 | 2.270 |
| 140 | 0.26 | 3.0 | 295 | 0.082 | 1.070 |
| 141 | 0.066 | 0.33 | 296 | 0.27 | 6.0 |
| 142 | 0.70 | 15 | 297 | 0.27 | 4.3 |
| 143 | 0.059 | 0.64 | 298 | 0.49 | 4.0 |
| 144 | 0.61 | 6.2 | 299 | 0.19 | 3.8 |
| 145 | 0.079 | 1.2 | 300 | 0.23 | 7.1 |
| 146 | 0.054 | 0.68 | 301 | 0.35 | 5.9 |
| 147 | 0.26 | 2.2 | 302 | 0.16 | 2.0 |
| 148 | 0.065 | 0.74 | 303 | 0.28 | 3.6 |
| 149 | 0.041 | 0.74 | 304 | 0.078 | 1.2 |
| 150 | 0.12 | 1.3 | 305 | 0.066 | 2.0 |
| 151 | 0.074 | 0.62 | 306 | 0.083 | 0.72 |
| 152 | 0.25 | 1.5 | | | |
| 153 | 0.059 | 0.61 | | | |
| 154 | 0.11 | 1.5 | | | |
| 155 | 0.11 | 1.4 | | | |

Example 1

(3aR,7S,10S,12R,21E,24aS)-7-cyclopentyl-N-{(1R,2S)-1-[(cyclopropylsulfonyl)carbamoyl]-2-ethenyl-cyclopropyl}-19-ethoxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

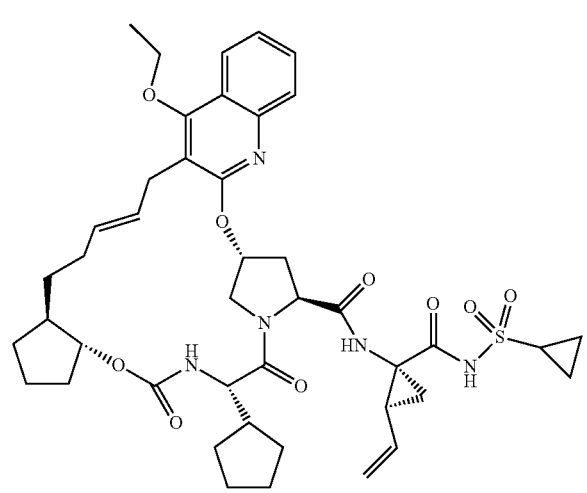 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OCC)O2)C(=O)NS(=O)(=O)C1CC1]

Step 1: 1-tert-butyl 2-methyl(2S,4R)-4-{[4-ethoxy-3-(prop-2-en-1-yl)quinolin-2-yl]oxy}pyrrolidine-1,2-dicarboxylate

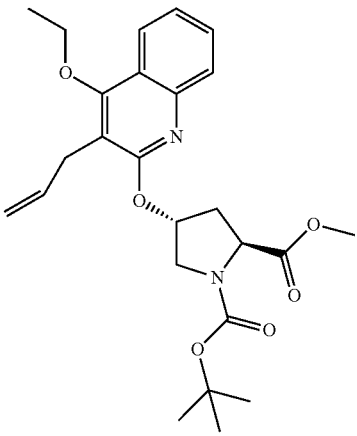 [SMILES: C=CCc1c(O[C@@H]2C[C@@H](C(=O)OC)N(C(=O)OC(C)(C)C)C2)nc2ccccc2c1OCC]

To a mixture of 1-tert-butyl 2-methyl(2S,4S)-4-{[(4-bromophenyl)sulfonyl]oxy}pyrrolidine-1,2-dicarboxylate (1337 mg) and Intermediate C2 (600 mg) in N-methyl-2-pyrrolidinone (12 ml) was added cesium carbonate (2558 mg) and the mixture was stirred at 60° C. for 1 hour. The reaction was not complete and additional brosylate (250 mg) and cesium carbonate (450 mg) were added. The mixture was stirred at 60° C. for 1 more hour. The reaction mixture was then cooled before quenching into water (150 mL) and aqueous KHSO₄ (pH=3.5). The product was extracted into ethyl acetate (150 mL). The organic layer was washed with aq. NaHCO₃ and brine, dried over sodium sulfate, filtered and concentrated. The material was dissolved in ACN and purified by reverse phase HPLC. After extractive workup (aq. NaHCO₃) with ethyl acetate, the desired product was obtained (1.0 g). LRMS (ES+) M/Z (M+H)⁺ 457.0.

Step 2: methyl (4R)-4-{[4-ethoxy-3-(prop-2-en-1-yl)quinolin-2-yl]oxy}-L-prolinate To a 0° C. solution of the product of Step 1 (500 mg) in dichloromethane (10 ml) was added TFA (10 ml) and the mixture was stirred at room temperature for 1 hour. The reaction mixture was concentrated in vacuo. The residue was dissolved in dichloromethane and the organic was washed with aq. NaHCO₃ then brine, dried over sodium sulfate, filtered and concentrated to give the desired product (0.39 g). LRMS (ES+) M/Z (M+H)⁺ 357.0.

Step 3: methyl (4R)-1-{(2S)-2-[({[(1R,2S)-2-(but-3-en-1-yl)cyclopentyl]oxy}carbonyl)amino]-2-cyclopentylacetyl}-4-{[4-ethoxy-3-(prop-2-en-1-yl)quinolin-2-yl]oxy}-L-prolinate

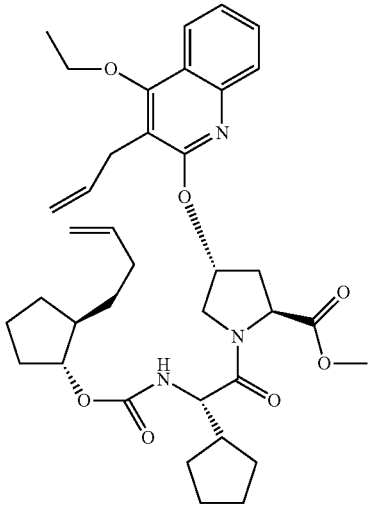 [SMILES: C=CCC[C@@H]1CCC[C@H]1OC(=O)N[C@H](C(=O)N1C[C@H](Oc2nc3ccccc3c(OCC)c2CC=C)C[C@H]1C(=O)OC)C1CCCC1]

The product of Step 2 (390 mg), DMAP (66.8 mg), DIPEA (0.573 ml) and Intermediate B2 (406 mg) were combined in DMF (10 mL) and stirred 5 minutes before adding HATU (541 mg). The reaction was stirred for 1 hour before quenching with aq. KHSO₄ and water (60 mL). The product was extracted into ethyl acetate (70 mL) The organic layer was washed with 10% aq. NaHCO₃ then brine. The aqueous extracts were re-extracted with ethyl acetate. The combined organics were dried over sodium sulfate, filtered and concentrated. Purification by flash chromatography (ISCO, 10-50% ethyl acetate/hexanes) gave the desired product as a foam (0.662 g). LRMS (ES+) M/Z (M+H)$^+$ 648.2.

Step 4: methyl (3aR,7S,10S,12R,21Z,24aS)-7-cyclopentyl-19-ethoxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxylate (A) and methyl (3aR,7S,10S,12R,21E,24aS)-7-cyclopentyl-19-ethoxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxylate (B)

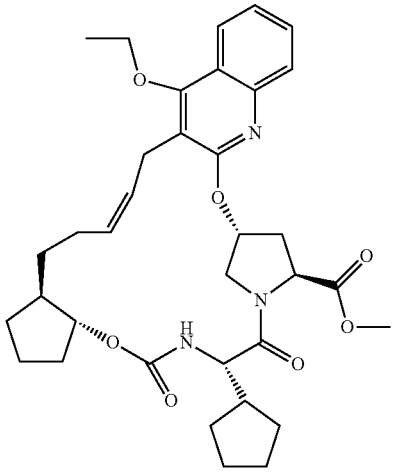

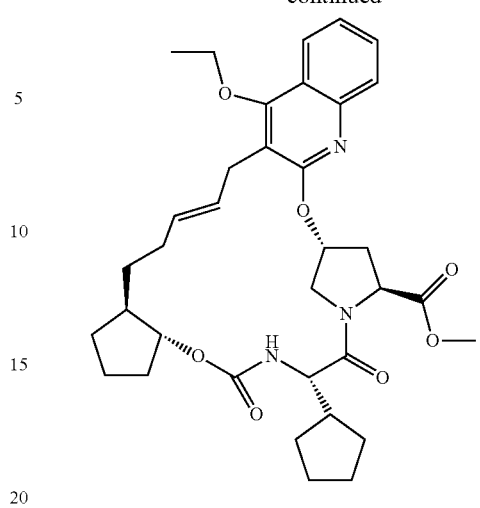

To degassed solution of the product of Step 3 (660 mg) in dichloroethane (150 ml) was added p-benzoquinone (44.1 mg) followed by Zhan 1B (150 mg). The mixture was stirred at room temperature for 4 hours. The reaction mixture was concentrated in vacuo. Purification by flash chromatography (ISCO, 1-8% acetone/DCM) provided 60 mg of a hi-RF product (cis, A) and 440 mg of a low-RF product (trans,B). LRMS (ES+) M/Z (M+H)$^+$ 620.1.

Step 5: (3aR,7S,10S,12R,21E,24aS)-7-cyclopentyl-19-ethoxy-5,8-dioxo-1,2,3,3a,5,6,7,8,11,12,20,23,24,24a-tetradecahydro-10H-9,12-methanocyclopenta[18,19][7,10,3,6]dioxadiazacyclononadecino[11,12-b]quinoline-10-carboxylic acid

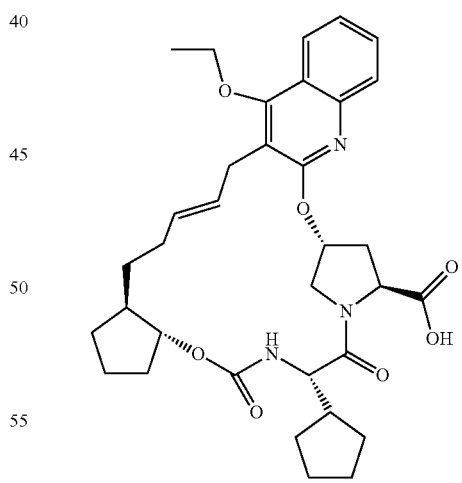

To a solution of the ester from Step 4 (100 mg) in THF (4 ml) was added 1 M NaOH (1.291 ml) and the mixture was stirred 18 hours at room temperature. The reaction mixture was diluted with 1N HCl (1.35 mL) and 10% aq. KHSO₄. The product was extracted into ethyl acetate. The combined organics were dried over sodium sulfate, filtered and concentrated to give the desired acid as a foam (98 mg). LRMS (ES+) M/Z (M+H)$^+$ 606.1.

Step 6: (3aR,7S,10S,12R,21E,24aS)-7-cyclopentyl-N-{(1R,2S)-1-[(cyclopropylsulfonyl)carbamoyl]-2-ethenylcyclopropyl}-19-ethoxy-5,8-dioxo-1,2,3,3a,5,6,7,8,11,12,20,23,24,24a-tetradecahydro-10H-9,12-methanocyclopenta[18,19][7,10,3,6]dioxadiazacyclononadecino[11,12-b]quinoline-10-carboxamide

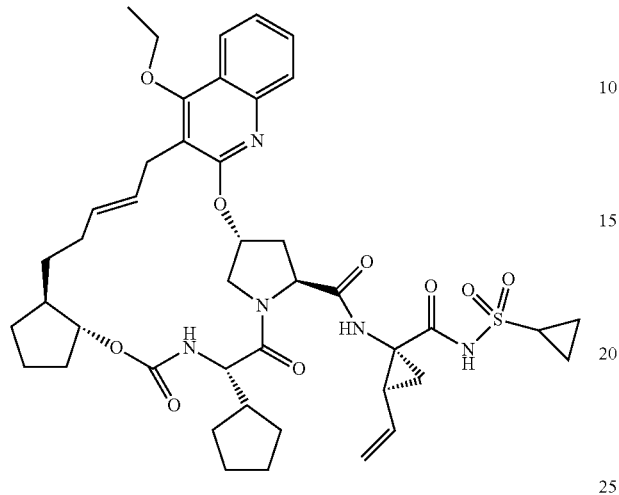

The acid from Step 5 (0.040 g), DMAP (4.03 mg), DIPEA (0.035 ml) and Intermediate A1 (0.040 g) were combined in DMF (2 mL) and stirred 5 minutes before adding HATU (33 mg). The reaction was stirred for 2 hours. The reaction mixture was purified by reverse phase HPLC to provide the desired product as a foam (40 mg). LRMS (ES+) M/Z (M+H)+ 818.2.

Examples 2-16

By following the procedures outlined in Example 1 and using the appropriate A, B and C intermediates and indicated reaction schemes (depicted below the structure as Int. and Rx., respectively), the following compounds were prepared.

| Ex | Structure | Name | LRMS or HRMS (M + H)+ |
|---|---|---|---|
| 2 | 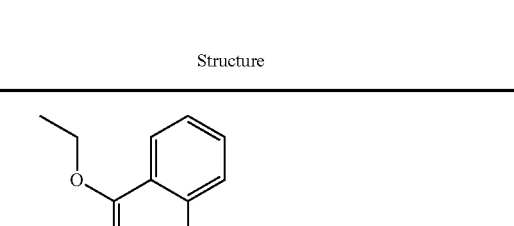<br>Int. A5, B2, C2 | (3aR,7S,10S,12R,21E,24aS)-7-cyclopentyl-N-{(1R,2R)-1-[(cyclopropylsulfonyl)carbamoyl]-2-ethylcyclopropyl}-19-ethoxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 820.3 |

| Ex | Structure | Name | LRMS or HRMS (M + H)+ |
|---|---|---|---|
| 3 | 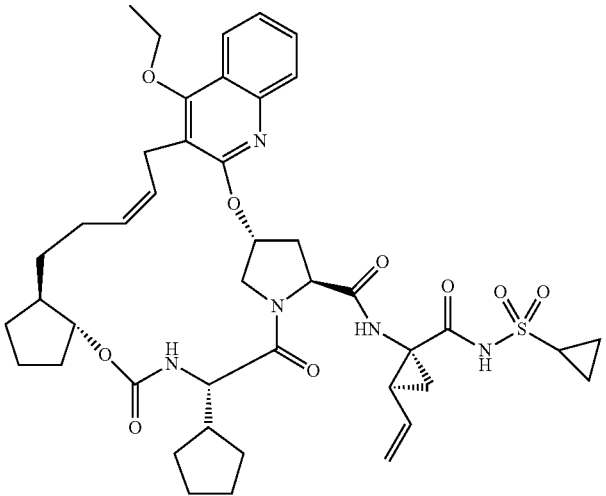 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C\Cc1c(nc3ccccc3c1OCC)O2)C(=O)NS(=O)(=O)C1CC1]<br>Int. A1, B2, C2 | (3aR,7S,10S,12R,21Z,24aS)-7-cyclopentyl-N-{(1R,2S)-1-[(cyclopropylsulfonyl)carbamoyl]-2-ethenylcyclopropyl}-19-ethoxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 818.2 |
| 4 | 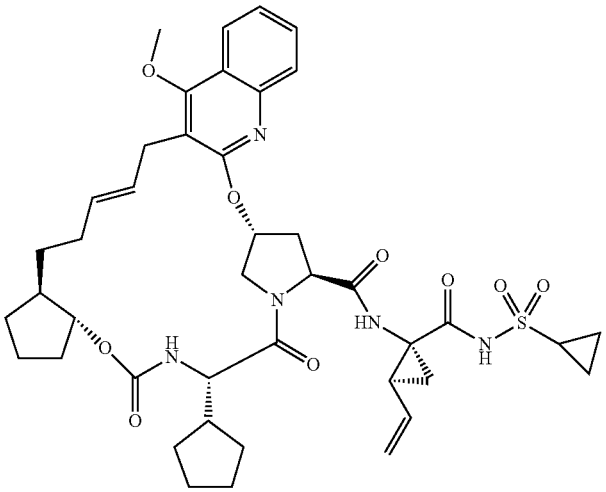 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OC)O2)C(=O)NS(=O)(=O)C1CC1]<br>Int. A1, B2, C1 | (3aR,7S,10S,12R,21E,24aS)-7-cyclo pentyl-N-{(1R,2S)-1-[(cyclopropylsulfonyl)carbamoyl]-2-ethenylcyclopropyl}-19-methoxy-5,8-dioxo-1,2,3,3a,5,6,7,8,11,12,20,23,24,24a-tetradeca hydro-10H-9,12-methanocyclopenta[18,19][1,10,3,6]dioxadiazacyclononadecino[11,12-b]quinoline-10-carboxamide | 804.2 |

| Ex | Structure | Name | LRMS or HRMS (M + H)+ |
|---|---|---|---|
| 5 | Int. A5, B2, C1 | (3aR,7S,10S,12R,21E,24aS)-7-cyclopentyl-N-{(1R,2R)-1-[(cyclopropylsulfonyl)carbamoyl]-2-ethyl cyclopropyl}-19-methoxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 806.2 |
| 6 | Separate isomers Int. A1, B6, C1 | (3aR,7S,10S,12R,21E,24aS)-7-tert-butyl-N-{(1R,2S)-1-[(cyclopropylsulfonyl)carbamoyl]-2-ethenylcyclo propyl}-19-methoxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 792.8 |
| 7 | Int. A1, B6, C1 | (3aR,7S,10S,12R,21Z,24aS)-7-tert-butyl-N-{(1R,2S)-1-[(cyclopropylsulfonyl)carbamoyl]-2-ethenylcyclo propyl}-19-methoxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 792.8 |

-continued

| Ex | Structure | Name | LRMS or HRMS (M + H)+ |
|---|---|---|---|
| 8 | 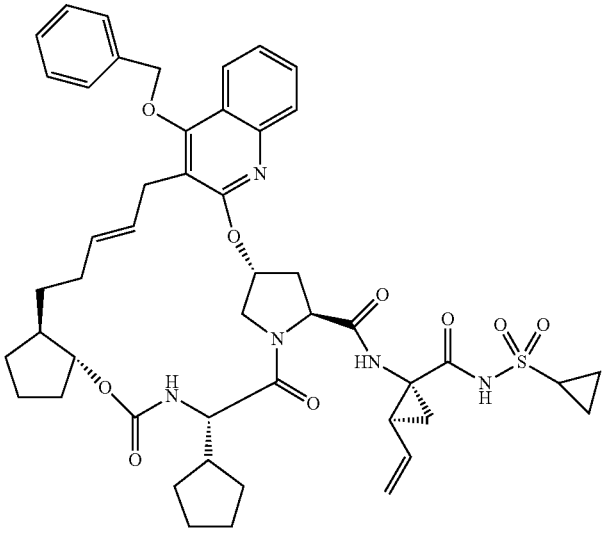 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OCc1ccccc1)O2)C(=O)NS(=O)(=O)C1CC1]<br>Int. A1, B2, C3 | (3aR,7S,10S,12R,21E,24aS)-19-(benzyloxy)-7-cyclopentyl-N-{(1R,2S)-1-[(cyclopropylsulfonyl)carbamoyl]-2-ethenylcyclopropyl}-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 880.3 |
| 9 | 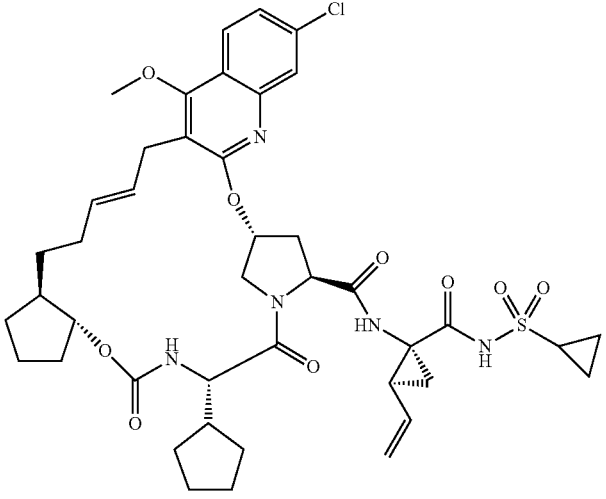 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3cc(Cl)ccc3c1OC)O2)C(=O)NS(=O)(=O)C1CC1]<br>Int. A1, B2, C5<br>Rx. A | (3aR,7S,10S,12R,21E,24aS)-16-chloro-7-cyclopentyl-N-{(1R,2S)-1-[(cyclopropylsulfonyl)carbamoyl]-2-ethenylcyclopropyl}-19-methoxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 838.3 |

US 9,328,138 B2

-continued

| Ex | Structure | Name | LRMS or HRMS (M + H)+ |
|---|---|---|---|
| 10 | 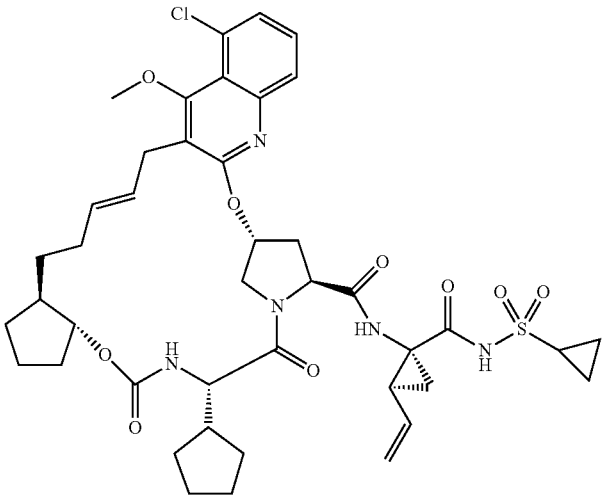 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3cccc(Cl)c3c1OC)O2)C(=O)NS(=O)(=O)C1CC1]<br>Int. A1, B2, C5<br>Rx. B | (3aR,7S,10S,12R,21E,24aS)-18-chloro-7-cyclopentyl-N-{(1R,2S)-1-[(cyclopropylsulfonyl)carbamoyl]-2-ethenylcyclopropyl}-19-methoxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 838.3 |
| 11 | 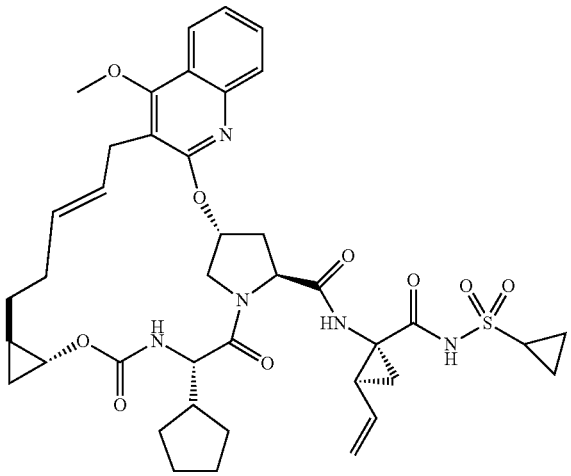 [SMILES: C=C[C@@H]1C[C@]1(NC(=O)[C@@H]1C[C@@H]2CN1C(=O)[C@H](C1CCCC1)NC(=O)O[C@@H]1C[C@H]1CC/C=C/Cc1c(nc3ccccc3c1OC)O2)C(=O)NS(=O)(=O)C1CC1]<br>Int. A1, B1, C1 | (1aR,5S,10R,19E,22aR)-5-cyclo pentyl-N-{(1R,2S)-1-[(cyclopropylsulfonyl)carbamoyl]-2-ethenylcyclo propyl}-17-methoxy-3,6-dioxo-1,1a,3,4,5,6,9,10,18,21,22,22a-dodeca hydro-8H-7,10-methanocyclopropa[18,19][1,10,3,6]dioxadiazacyclononadecino[11,12-b]quinoline-8-carboxamide | 776.8 |

-continued

| Ex | Structure | Name | LRMS or HRMS (M + H)+ |
|---|---|---|---|
| 12 | Int. A1, B1, C1 | (1aS,5S,8S,10R,19E,22aS)-5-cyclo pentyl-N-{(1R,2S)-1-[(cyclopropylsulfonyl)carbamoyl]-2-ethenylcyclo propyl}-17-methoxy-3,6-dioxo-1,1a,3,4,5,6,9,10,18,21,22,22a-dodecahydro-8H-7,10-methanocyclopropa[18,19][1,10,3,6]dioxadiazacyclononadecino[11,12-&]quinoline-8-carboxamide | 776.7 |
| 13 | Int. A3, B2, C1 | (3aR,7S,10S,12R,21E,24aS)-7-cyclopentyl-N-[(1S,2R)-2-[(cyclo propylsulfonyl)carbamoyl]-1,1'-bi(cyclopropyl)-2-yl]-19-methoxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 818.4 |

| Ex | Structure | Name | LRMS or HRMS (M + H)+ |
|---|---|---|---|
| 14 | 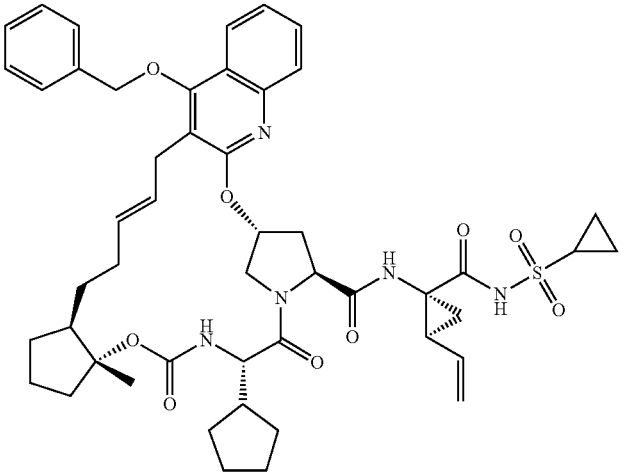 [SMILES: C=C[C@@H]1C[C@]1(NC(=O)[C@@H]1C[C@@H]2CN1C(=O)[C@H](C1CCCC1)NC(=O)O[C@]1(C)CCC[C@H]1CC/C=C/Cc1c(nc3ccccc3c1OCc1ccccc1)O2)C(=O)NS(=O)(=O)C1CC1]<br>Int. A1, B7, C3 | (3aR,7S,10S,12R,21E,24aS)-19-(benzyloxy)-7-cyclopentyl-N-{(1R,2S)-1-[(cyclopropylsulfonyl)carbamoyl]-2-ethenylcyclopropyl}-3a-methyl-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 894.4 |
| 15 | 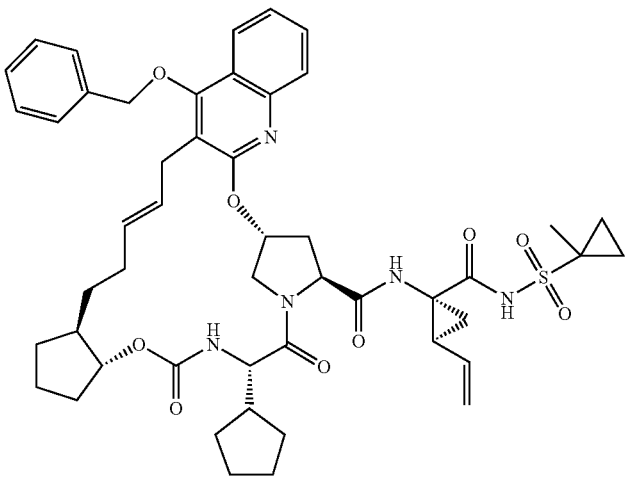 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OCc1ccccc1)O2)C(=O)NS(=O)(=O)C1(C)CC1]<br>Int. A2, B2, C3 | (3aR,7S,10S,12R,21E,24aS)-19-(benzyloxy)-7-cyclopentyl-N-[(1H,2S)-2-ethenyl-1-{[(1-methylcyclopropyl)sulfonyl]carbamoyl}cyclopropyl]-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 894.4 |

| Ex | Structure | Name | LRMS or HRMS (M + H)+ |
|---|---|---|---|
| 16 | Int. A1, B3, C2 | (2R,4S,7S,13S,18E)-7-cyclopentyl-N-{(1R,2S)-1-[(cyclopropylsulfonyl)carbamoyl]-2-ethenylcyclopropyl}-21-ethoxy-6,9-dioxo-3,4,6,7,8,9,12,13,15,16,17,20-dodecahydro-2H,11H-2,5:10,13-dimethano[1,14,5,7,10]dioxatriazacyclodocosino[15,16-b]quinoline-4-carboxamide | 833.4 |

Example 17

(3aR,7S,10S,12R,21E,24aS)-7-cyclopentyl-N-{(1R,2S)-1-[(cyclopropylsulfonyl)carbamoyl]-2-ethenylcyclopropyl}-19-hydroxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

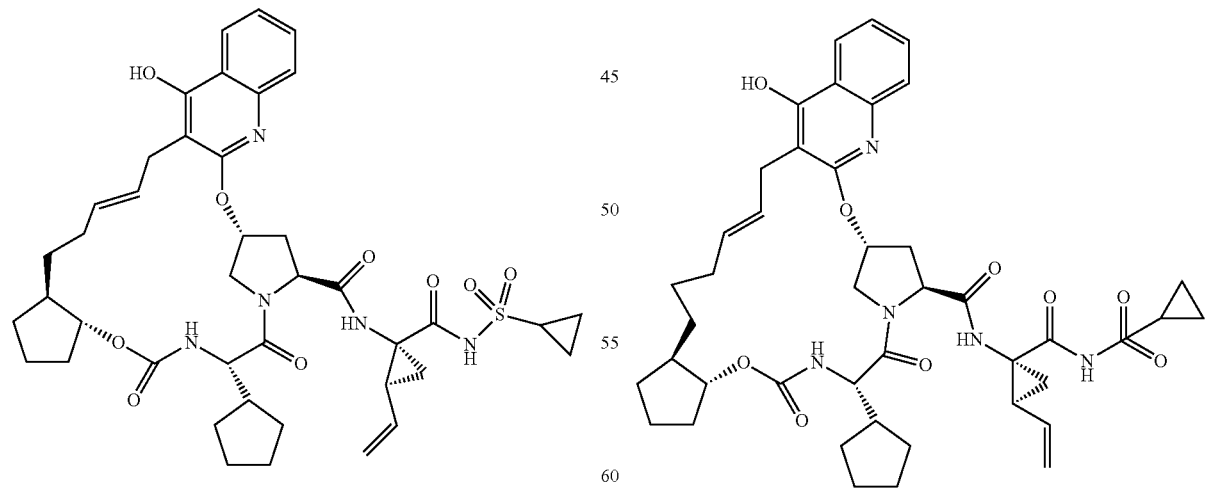

Example 8 (19 mg) was treated with TFA (1 ml) in a sealed tube and warmed to 55° C. After 30 minutes, the reaction was concentrated and the residue was dissolved in ACN and purified by reverse phase HPLC to provide the desired product as a white foam (13 mg). LRMS (ES+) m/z (M+H)+ 790.2.

Example 18

(3aR,7S,10S,12R,21E,25aR)-7-cyclopentyl-N-{(1R,2S)-1-[(cyclopropylsulfonyl)carbamoyl]-2-ethenylcyclopropyl}-19-hydroxy-5,8-dioxo-2,3,3a,5,6,7,8,11,12,20,23,24,25,25a-tetradecahydro-1H,10H-9,12-methanocyclopenta[19,20]11,10,3,6]dioxa diazacycloicosino[11,12-b]quinoline-10-carboxamide

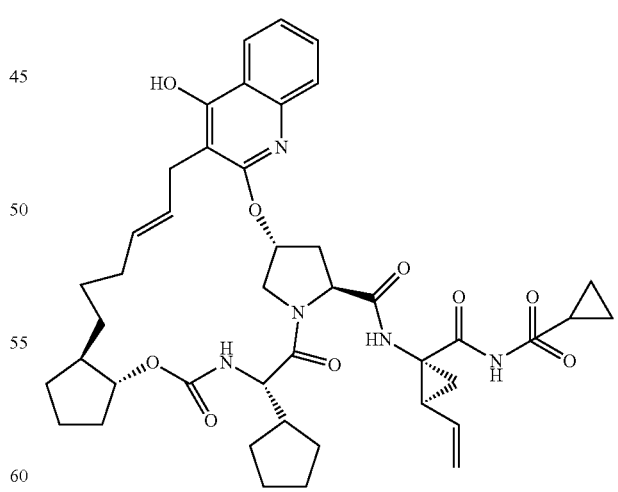

(3aR,7S,10S,12R,21E,25aR)-19-(benzyloxy)-7-cyclopentyl-N-{(1R,2S)-1-[(cyclopropylsulfonyl)carbamoyl]-2-ethenylcyclopropyl}-5,8-dioxo-2,3,3a,5,6,7,8,11,12,20,23,24,25,25a-tetradecahydro-1H,10H-9,12-methanocyclopenta[19,20][1,10,3,6]dioxa diazacycloicosino[11,12-b]quinoline-10-carboxamide prepared by the method described for Example 1 using intermediates A1, B4, and C3 was deprotected using the method described for Example 17. FIRMS (ES+) m/z 804.3639 (M+H)+.

Example 19

(1aR,5S,8S,10R,19E,22aR)-5-cyclopentyl-N-{(1R,2S)-1-[(cyclopropylsulfonyl)carbamoyl]-2-ethenyl-cyclopronyl}-17-hydroxy-1a-methyl-3,6-dioxo-1,1a,3,4,5,6,9,10,18,21,22,22a-dodecahydro-8H-7,10-methanocyclopropa[18,19][1,10,3,6]dioxadiazacyclononadecino[11,12-b]quinoline-8-carboxamide

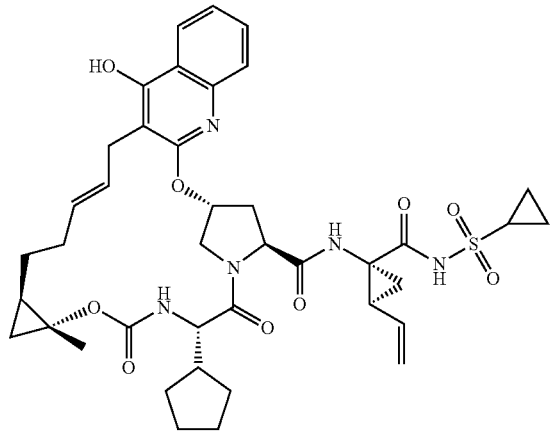 [SMILES: C=C[C@@H]1C[C@]1(NC(=O)[C@@H]1C[C@@H]2CN1C(=O)[C@H](C1CCCC1)NC(=O)O[C@]1(C)C[C@H]1CC/C=C/Cc1c(nc3ccccc3c1O)O2)C(=O)NS(=O)(=O)C1CC1]

(1aR,5S,8S,10R,19E,22aR)-17-(benzyloxy)-5-cyclopentyl-N-{(1R,2S)-1-[(cyclopropylsulfonyl)carbamoyl]-2-ethenylcyclopropyl}-1a-methyl-3,6-dioxo-1,1a,3,4,5,6,9,10,18,21,22,22a-dodecahydro-8H-7,10-methanocyclopropa[18,19][1,10,3,6]dioxadiazacyclononadecino[11,12-b]quinoline-8-carboxamide prepared by the method described for Example 1 using intermediates A1, B7, and C3 (with separation of isomers after ring closing metathesis) was deprotected using the method described for Example 17. HRMS (ES+) m/z 776.3309 (M+H)+.

Example 20

(1aS,5S,8S,10R,19E,22aS)-5-cyclopentyl-N-{(1R,2S)-1-[(cyclopropylsulfonyl)carbamoyl]-2-ethenyl-cyclopropyl}-17-hydroxy-1a-methyl-3,6-dioxo-1,1a,3,4,5,6,9,10,18,21,22,22a-dodecahydro-8H-7,10-methanocyclopropa[18,19][1,10,3,6]dioxadiazacyclononadecino[11,12-b]quinoline-8-carboxamide

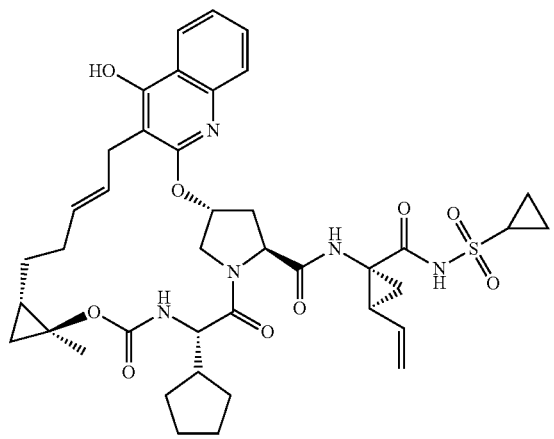 [SMILES: C=C[C@@H]1C[C@]1(NC(=O)[C@@H]1C[C@@H]2CN1C(=O)[C@H](C1CCCC1)NC(=O)O[C@@]1(C)C[C@@H]1CC/C=C/Cc1c(nc3ccccc3c1O)O2)C(=O)NS(=O)(=O)C1CC1]

(1aS,5S,8S,10R,19E,22aS)-17-(benzyloxy)-5-cyclopentyl-N-{(1R,2S)-1-[(cyclopropylsulfonyl)carbamoyl]-2-ethenylcyclopropyl}-1a-methyl-3,6-dioxo-1,1a,3,4,5,6,9,10,18,21,22,22a-dodecahydro-8H-7,10-methanocyclopropa[18,19][1,10,3,6]dioxadiazacyclononadecino[11,12-b]quinoline-8-carboxamide prepared by the method described for Example 1 using intermediates A1, B7, C3 (with separation of isomers after ring closing metathesis) was deprotected using the method described for Example 17. LRMS (ES+) m/z 776.7 (M+H)+.)+.

Example 21

(3aR,7S,10S,12R,21E,24aS)-7-cyclopentyl-N-[(1S,2R)-2-[(cyclopropylsulfonyl)carbamoyl]-1,1'-bi(cyclopropyl)-2-yl]-19-hydroxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

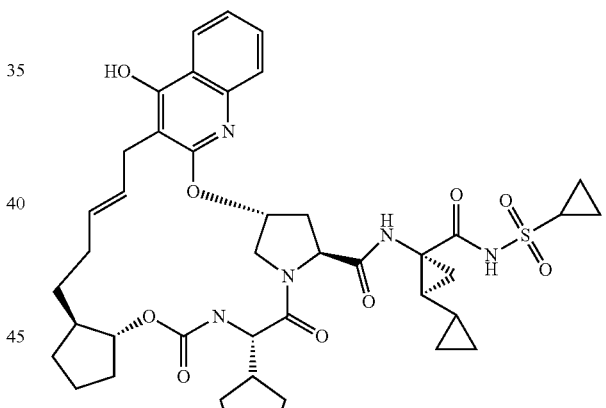

(3aR,7S,10S,12R,21E,24aS)-19-(benzyloxy)-7-cyclopentyl-N-[(1S,2R)-2-[(cyclopropylsulfonyl)carbamoyl]-1,1'-bi(cyclopropyl)-2-yl]-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide prepared by the method described for Example 1 using intermediates A3, B2, and C3 was deprotected using the method described for Example 17. LRMS (ES+) m/z 804.8 (M+H)+.

Example 22

(3aR,7S,10S,12R,21E,24aS)-17-bromo-7-cyclopentyl-N-{(1R,2S)-1-[(cyclopropylsulfonyl)carbamoyl]-2-ethenylcyclopropyl}-19-hydroxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

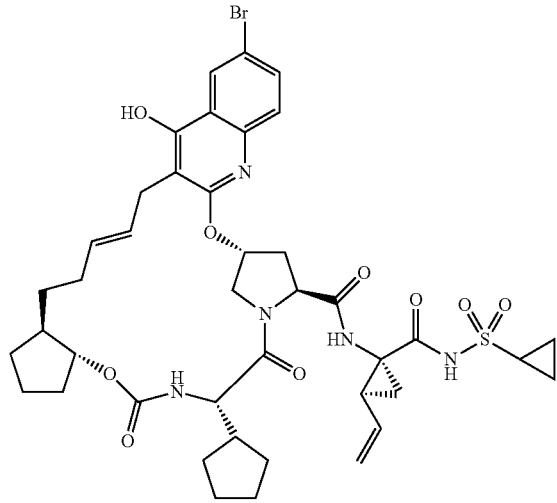 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccc(Br)cc3c1O)O2)C(=O)NS(=O)(=O)C1CC1]

(3aR,7S,10S,12R,21E,24aS)-19-(benzyloxy)-17-bromo-7-cyclopentyl-N-{(1R,2S)-1-[(cyclopropylsulfonyl)carbamoyl]-2-ethenylcyclopropyl}-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide prepared by the method described for Example 1 using intermediates A1, B2, and C4 was deprotected using the method described for Example 17. LRMS (ES+) m/z 868.2602 (M+H)$^+$.

Example 23

(3aR,7S,10S,12R,21E,24aS)-7-cyclopentyl-N-[(1R,2S)-2-ethenyl-1-{[(1-methylcyclopropyl)sulfonyl]carbamoyl}cyclopropyl]-19-hydroxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

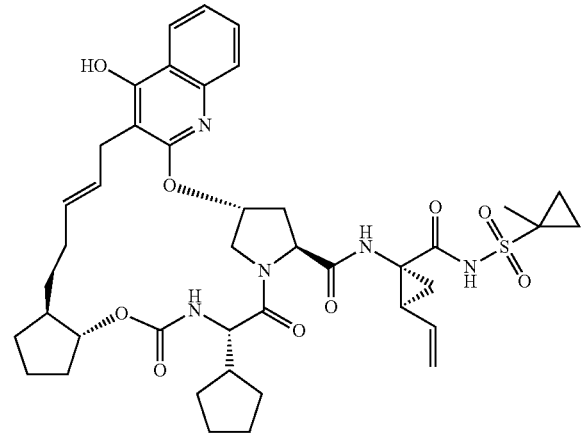 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1O)O2)C(=O)NS(=O)(=O)C1(C)CC1]

The title compound was prepared using the same method as described for Example 17 using Example 15. HRMS (ES+) m/z 804.3642 (M+H)$^+$.

Example 24

(3aR,7S,10S,12R,24aR)-7-cyclopentyl-N-{(1R,2S)-1-[(cyclopropylsulfonyl)carbamoyl]-2-ethenylcyclopropyl}-19-ethoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide

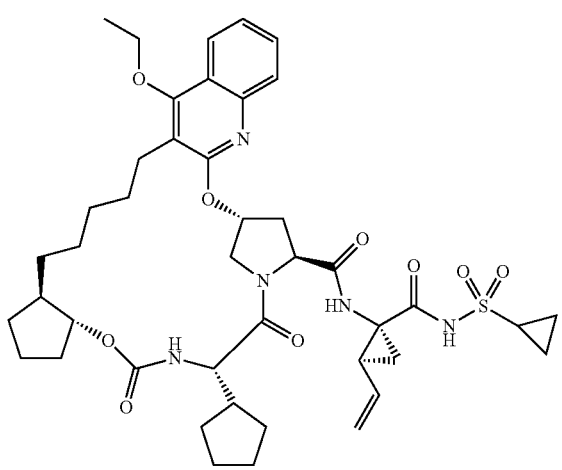 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCc1c(nc3ccccc3c1OCC)O2)C(=O)NS(=O)(=O)C1CC1]

Step 1: methyl (3aR,7S,10S,12R,24aR)-7-cyclopentyl-19-ethoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxylate

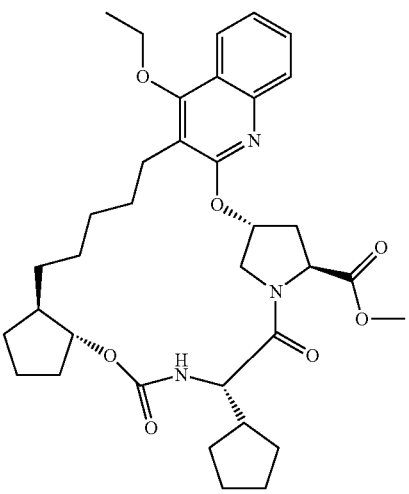 [SMILES: CCOc1c2c(nc3ccccc13)O[C@@H]1C[C@@H](C(=O)OC)N(C1)C(=O)[C@H](C1CCCC1)NC(=O)O[C@@H]1CCC[C@H]1CCCCC2]

To a solution of methyl (3aR,7S,10S,12R,21E,24aS)-7-cyclopentyl-19-ethoxy-5,8-dioxo-1,2,3,3a,5,6,7,8,11,12,20,23,24,24a-tetradecahydro- 10H-9,12-methanocyclopenta

[18,19][1,10,3,6]dioxadiazacyclononadecino[11,12-b]quinoline-10-carboxylate (Example 1, Step 4) (100 mg) in ethyl acetate (20 ml) and methanol (20 ml) was added 5% Rh/C (20 mg) and the mixture was stirred for 18 hours under hydrogen atmosphere. After exchanging the atmosphere for nitrogen, the reaction mixture was filtered and concentrated to give the desired product as a foam (100 mg). LRMS (ES+) M/Z (M+H)$^+$ 622.1.

Step 2: (3aR,7S,10S,12R,24aR)-7-cyclopentyl-19-ethoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxylic acid

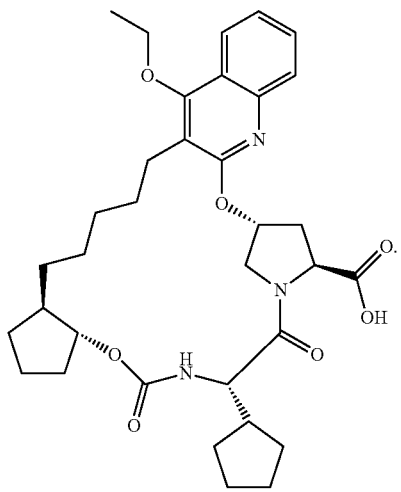 [SMILES: CCOc1c2c(nc3ccccc13)O[C@@H]1C[C@@H](C(=O)O)N(C1)C(=O)[C@H](C1CCCC1)NC(=O)O[C@@H]1CCC[C@H]1CCCCC2]

Using the product from Step 1, the title compound was prepared according to the procedure in Example 1, Step 5. LRMS (ES+) m/z 608.2 (M+H)$^+$.

Step 3: (3aR,7S,10S,12R,24aR)-7-cyclopentyl-N-{(1R,2S)-1-[(cyclopropylsulfonyl)carbamoyl]-2-ethenylcyclopropyl}-19-ethoxy-5,8-dioxo-1,2,3,3a,5,6,7,8,11,12,20,21,22,23,24,24a-hexadeca hydro-10H-9,12-methanocyclopenta[18,19][1,10,3,6]dioxadiazacyclononadecino[11,12-b]quinoline-10-carboxamide

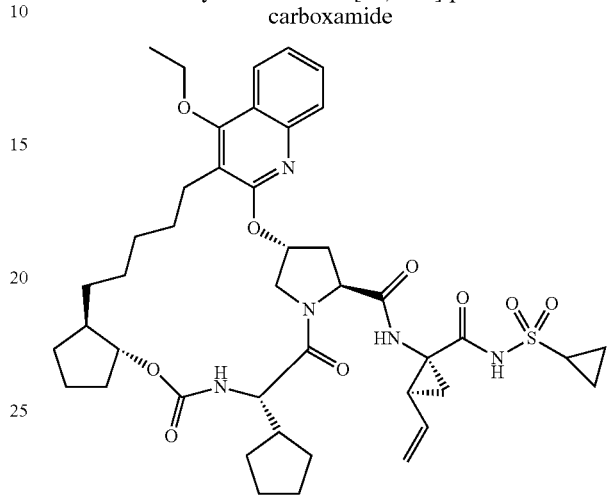

Using the product from Step 2, the title compound was prepared according to the procedure in Example 1, Step 6. LRMS (ES+) m/z 820.3 (M+H)$^+$.

Examples 25-28

By following the procedures outlined in Example 24 and using the appropriate A, B and C intermediates (depicted below the structure as Int.), the following compounds were prepared.

| Ex. | Structure | Name | LRMS (M + H)$^+$ |
|---|---|---|---|
| 25 | Int. A5, B2, C2 | (3aR,7S,10S,12R,24aR)-7-cyclo pentyl-N-{(1R,2R)-1-[(cyclopropylsulfonyl)carbamoyl]-2-ethyl cyclopropyl}-19-ethoxy-5,8-dioxo-1,2,3,3a,5,6,7,8,11,12,20,21,22,23,24,24a-hexadecahydro-10H-9,12-methanocyclopenta[18,19][1,10,3,6]dioxa diazacyclononadecino[11,12-b]quinoline-10-carboxamide | 822.3 |

| Ex. | Structure | Name | LRMS (M + H)+ |
|---|---|---|---|
| 26 | 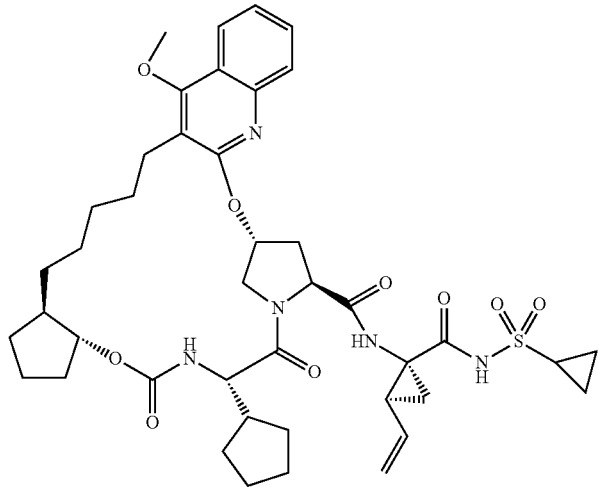<br>Int. A1, B2, C1 | (3aR,7S,10S,12R,24aR)-7-cyclo pentyl-N-{(1R,2S)-1-[(cyclopropylsulfonyl)carbamoyl]-2-ethenylcyclo propyl}-19-methoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 806.2 |
| 27 | 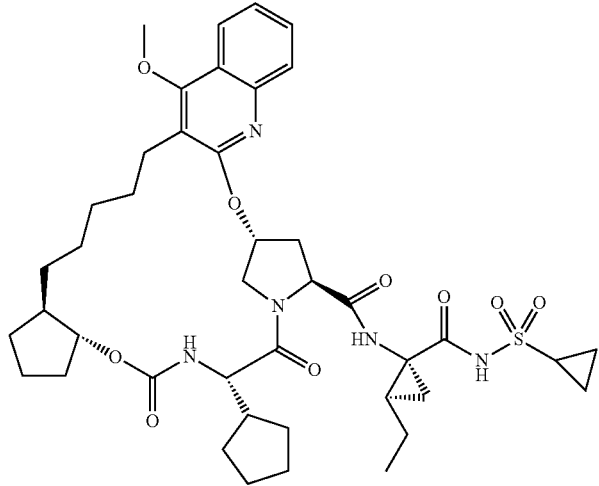<br>Int. A5, B2, C1 | (3aR,7S,10S,12R,24aR)-7-cyclo pentyl-N-{(1R,2R)-1-[(cyclopropyl sulfonyl)carbamoyl]-2-ethylcyclo propyl}-19-methoxy-5,8-dioxo-1,2,3,3a,5,6,7,8,11,12,20,21,22,23,24,24a-hexadeca hydro-10H-9,12-methanocyclopenta[18,19][1,10,3,6]dioxadiazacyclononadecino[11,12-b]quinoline-10-carboxamide | 808.3 |

| Ex. | Structure | Name | LRMS (M + H)+ |
|---|---|---|---|
| 28 | Int. A1, B1, C1 | (1aR,5S,8S,10R,22aR)-5-cyclo pentyl-N-{(1R,2S)-1-[(cyclopropylsulfonyl)carbamoyl]-2-ethenylcyclo propyl}-17-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 778.8 |

Example 29

(3aR,7S,10S,12R,24a?)-7-cyclopentyl-N-{(1R,2S)-1-[(cyclopropylsulfonyl)carbamoyl]-2-ethenylcyclopropyl}-19-hydroxy-3a-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide Step 1: (3aR,7S,10S,12R,24aR)-7-cyclopentyl-19-hydroxy-3a-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxylic acid

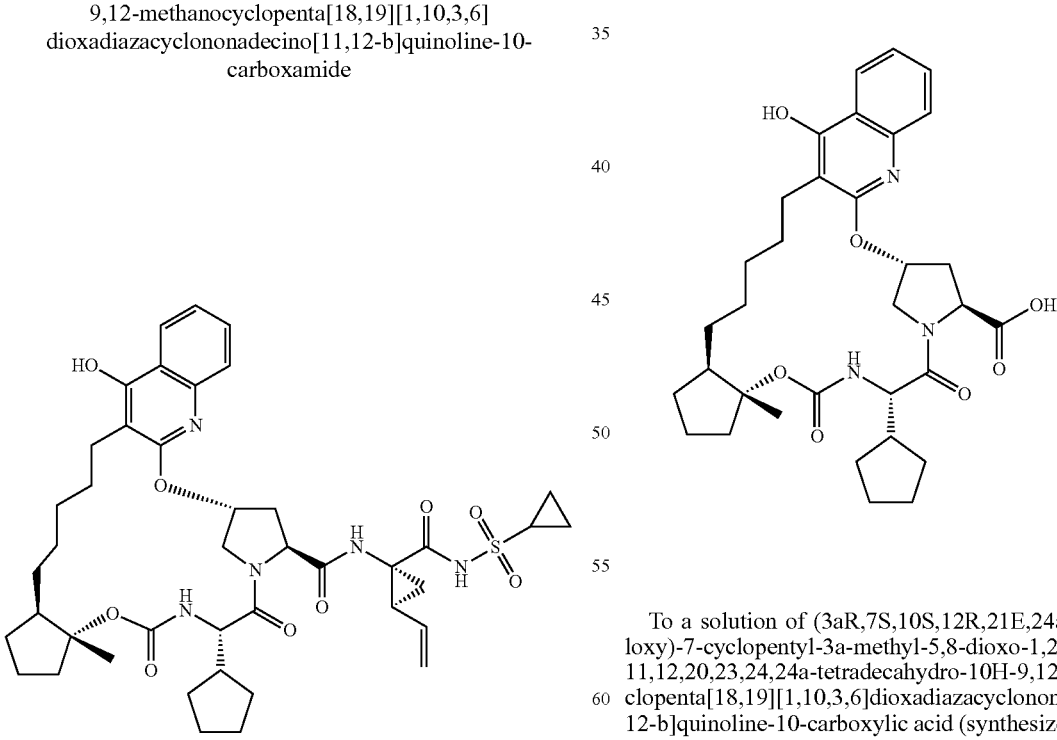

To a solution of (3aR,7S,10S,12R,21E,24aS)-19-(benzyloxy)-7-cyclopentyl-3a-methyl-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxylic acid (synthesized as described in Example 1 with intermediates B7 and C3) (113 mg) in ethyl acetate (5 ml) was added 10% Pd/C (20 mg) and the mixture was stirred for 18 hours under hydrogen atmosphere. After exchanging the atmosphere for nitrogen, the reaction mixture was filtered and concentrated to give the desired product (93 mg). LRMS (ES+) M/Z (M+H)+ 594.7.

Step 2: (3aR,7S,10S,12R,24aR)-7-cyclopentyl-N-{(1R,2S)-1-[(cyclopropylsulfonyl)carbamoyl]-2-ethenylcyclopropyl}-19-hydroxy-3a-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide

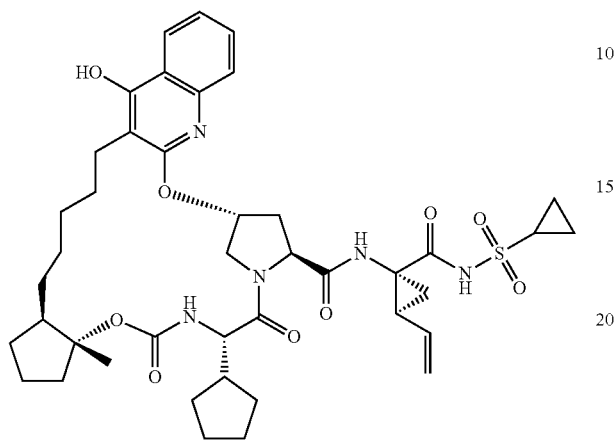

Using the product from Step 1, the title compound was prepared according to the procedure in Example 1 Step 6 using Intermediate A1. The two diastereoisomers were separated by reverse phase HPLC (40%400% ACN/water/0.15% TFA) to provide the desired product (38 mg) HRMS (ES+) m/z 806.3802 (M+H)+.

Examples 30-34

By following the procedures outlined in Example 29 and using the appropriate A, B and C intermediates (depicted below the structure as Int.), the following compounds were prepared.

| Ex. | Structure | Name | HRMS (M + H)+ |
|---|---|---|---|
| 30 | Int. A1, B7, C3 | (3aS,7S,10S,12R,24aS)-7-cyclopentyl-N-{(1R,2S)-1-[(cyclopropyl sulfonyl)carbamoyl]-2-ethenyl cyclopropyl}-19-hydroxy-3a-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 806.4 |

| Ex. | Structure | Name | HRMS (M + H)+ |
|---|---|---|---|
| 31 | Int. A5, B7, C3 | (3aS,7S,10S,12R,24aS)-7-cyclopentyl-N-{(1R,2R)-1-[(cyclopropylsulfonyl)carbamoyl]-2-ethylcyclopropyl}-19-hydroxy-3a-methyl-5,8-dioxo-1,2,3-3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 808.4 |
| 32 | Int. A5, B7, C3 | (3aR,7S,10S,12R,24aR)-7-cyclo pentyl-N-{(1R,2R)-1-[(cyclopropyl sulfonyl)carbamoyl]-2-ethylcyclopropyl}-19-hydroxy-3a-methyl-5,8-dioxo-1,2,3,3a,5,6,7,8,11,12,20,21,22,23,24,24a-hexadeca hydro-10H-9,12-methanocyclopenta[18,19][1,10,3,6]dioxadiazacyclononadecino[11,12-b]quinoline-10-carboxamide | 808.4 |
| 33 | Int. A1, B3, C2 | (2R,4S,7S,13S)-7-cyclopentyl-N-{(1R,2S)-1-[(cyclopropylsulfonyl)carbamoyl]-2-ethenyl cyclopropyl}-21-ethoxy-6,9-dioxo-3,4,6,7,8,9,12,13,15,16,17,18,19,20-tetradecahydro-2H,11H-2,5:10,13-dimethano[1,14,5,7,10]dioxatriazacyclodocosino[15,16-b]quinoline-4-carboxamide | 835.8 |

-continued

| Ex. | Structure | Name | HRMS (M + H)+ |
|---|---|---|---|
| 34 | 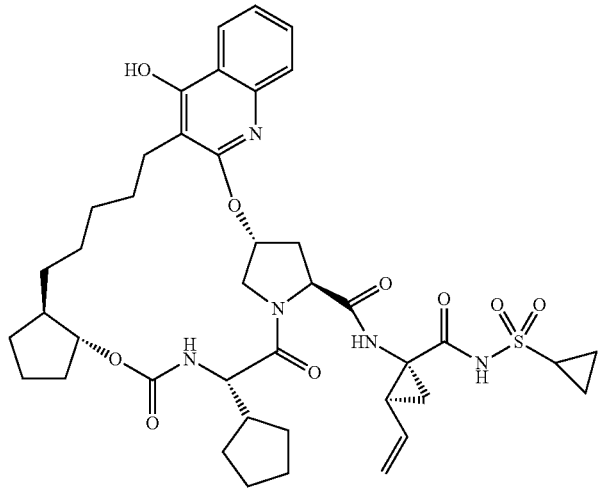<br>Int. A1, B2, C3 | (3aR,7S,10S,12R,24aR)-7-cyclo pentyl-N-{(1R,2S)-1-[(cyclopropyl sulfonyl)carbamoyl]-2-ethenylcyclopropyl}-19-hydroxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 792.3 |

Examples 35-37

By following the procedures outlined in Example 29 and using the appropriate A, B and C intermediates (depicted below the structure as Int.), the following compounds were prepared.

| Ex. | Structure | Name | HRMS (M + H)+ |
|---|---|---|---|
| 35 | 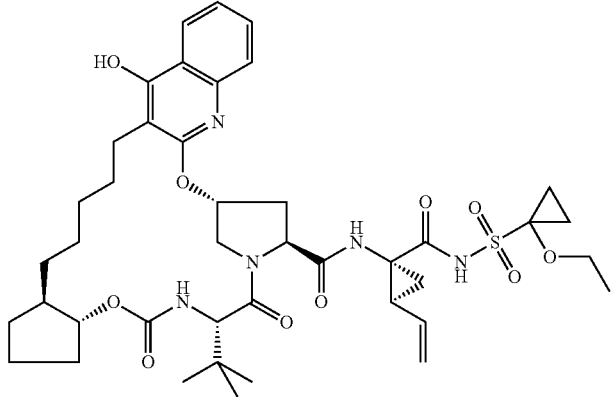<br>Int. A6, B6, C3 | (3aR,7S,10S,12R,24aR)-7-tert-butyl-N-[(1R,2S)-2-ethenyl-1-({[1-(methoxymethyl)cyclopropyl]sulfonyl}carbamoyl)cyclopropyl]-19-hydroxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 824.3 |

| Ex. | Structure | Name | HRMS (M + H)+ |
|---|---|---|---|
| 36 | Int. A8, B6, C3 | (3aR,7S,10S,12R,24aR)-N-{(1R,2S)-1-[({1-[(benzyloxy)methyl]cyclopropyl}sulfonyl)carbamoyl]-2-ethenylcyclopropyl}-7-tert-butyl-19-hydroxy-5,8-dioxo-1,2,3,3a,5,6,7,8,11,12,20,21,22,23,24,24a-hexadeca hydro-10H-9,12-methanocyclopenta[18,19][1,10,3,6]dioxadiazacyclononadecino[11,12-b]quinoline-10-carboxamide | 900.40 |
| 37 | Int. A7, B6, C3 | (3aR,7S,10S,12R,24aR)-7-tert-butyl-N-[(1R,2S)-2-ethenyl-1-({[1-(prop-1-en-2-yl)cyclopropyl]sulfonyl}carbamoyl)cyclopropyl]-19-hydroxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 820.45 |

Example 38

(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl diethyl phosphate

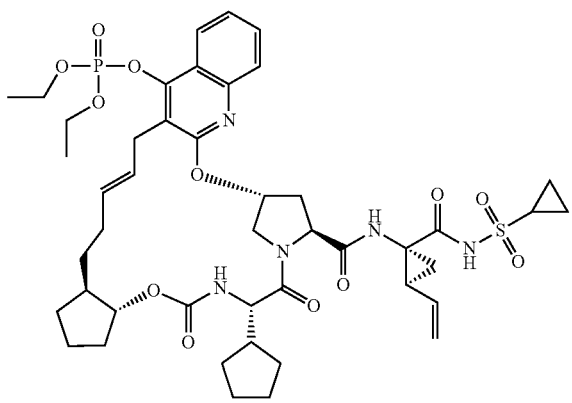 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OP(=O)(OCC)OCC)O2)C(=O)NS(=O)(=O)C1CC1]

To a solution of (3aR,7S,10S,12R,21E,24aS)-7-cyclopentyl-N-{(1R,2S)-1-[(cyclopropylsulfonyl)carbamoyl]-2-ethenylcyclopropyl}-19-hydroxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide (Example 17) (35 mg) in dichloromethane (0.44 mL) was added triethylamine (123 μl) followed by diethyl chlorophosphate (64 μl). The reaction mixture was stirred at room temperature until disappearance of the starting material. The reaction was quenched with water and extracted with ethyl acetate (3×). The combined organic fractions were dried over magnesium sulfate, filtered and concentrated. Purification by reverse phase HPLC (40-100% ACN/0.015% TFA-water) afforded the desired product (20 mg). LRMS (ES+) m/z 926.4 (M+H)+.

Example 39

(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl acetate

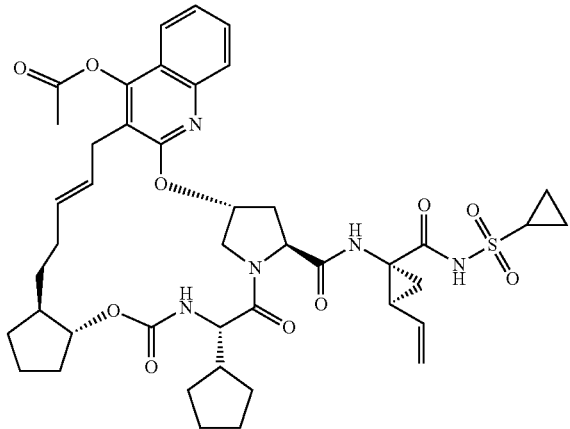 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OC(C)=O)O2)C(=O)NS(=O)(=O)C1CC1]

To a solution of (3aR,7S,10S,12R,21E,24aS)-7-cyclopentyl-N-{(1R,2S)-1-[(cyclopropylsulfonyl)carbamoyl]-2-ethenylcyclopropyl}-19-hydroxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide (Example 17) (35 mg) in pyridine (0.44 mL) was added acetic anhydride (42 μl). The reaction mixture was stirred at room temperature until disappearance of the starting material. The reaction was quenched with water and extracted with ethyl acetate (3×). The combined organic fractions were dried over magnesium sulfate, filtered and concentrated. Purification by reverse phase HPLC (40% ACN/0.05% TFA water to 100%) afforded the desired product (26 mg) after workup with NaHCO$_3$ and ethyl acetate. LRMS (ES+) m/z 832.8 (M+H)$^+$.

Example 40

(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl 2-methylpropanoate

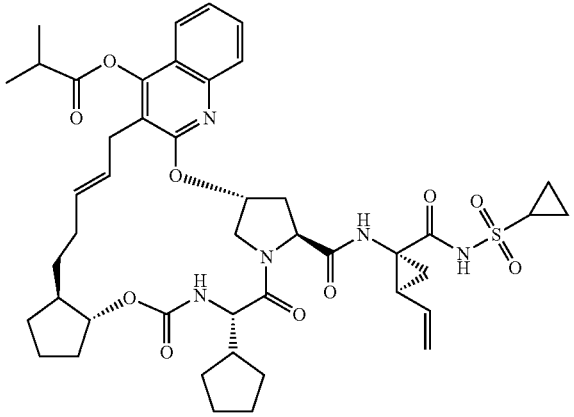 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OC(=O)C(C)C)O2)C(=O)NS(=O)(=O)C1CC1]

The title compound was prepared using the same method as described in Example 39, using isobutyric anhydride. HRMS (ES+) m/z 860.3863 (M+H)$^+$.

Example 41

(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl 3-methylbutanoate

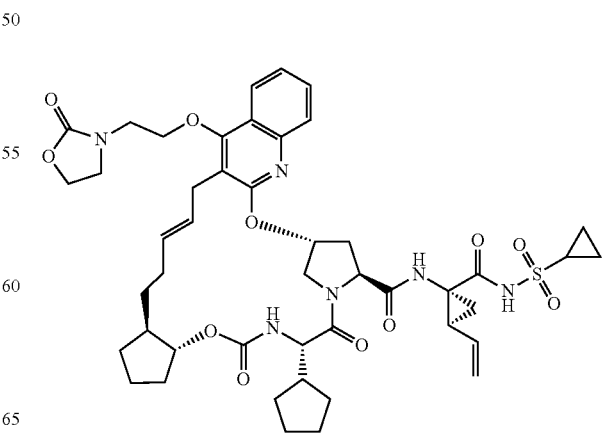

The title compound was prepared using the same method as described for Example 39, using isovaleric anhydride. HRMS (ES+) m/z 874.4027 (M+H)$^+$.

Example 42

(3aR,7S,10S,12R,21E,24aS)-7-cyclopentyl-N-{(1R,2S)-1-[(cyclopropylsulfonyl)carbamoyl]-2-ethenylcyclopropyl}-5,8-dioxo-19-[2-(2-oxo-1,3-oxazolidin-3-yl)ethoxy]-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide To a solution of (3aR,7S,10S,12R,21E,24aS)-7-cyclopentyl-N-{(1R,2S)-1-[(cyclopropylsulfonyl)carbamoyl]-2-ethenylcyclopropyl}-19-hydroxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide (Example 17) (40 mg) in DMF (0.75 mL) under nitrogen was added cesium carbonate (495 mg) followed by 2-(2-oxo-1,3-oxazolidin-3-yl)ethyl 4-methylbenzenesulfonate (144 mg). The reaction mixture was stirred at room temperature for 30 minutes and at 50° C. for 3 hours. After cooling back to room temperature, the reaction was quenched with water and extracted with ethyl acetate (3×). The combined organic fractions were dried over magnesium sulfate, filtered and concentrated. Purification by reverse phase HPLC (40%-100% ACN/0.15% TFA-water) afforded the desired product (39 mg) after workup with NaHCO$_3$ and ethyl acetate. HRMS (ES+) m/z 903.3933 (M+H)$^+$.

Examples 43-60

By following the procedures outlined in Example 42 and using the appropriate A, B and C intermediates and reagent (depicted below the structure as Int. and Rg., respectively), the following compounds were prepared.

| Ex. | Structure | Name | LRMS or HRMS (M + H)$^+$ |
|---|---|---|---|
| 43 | 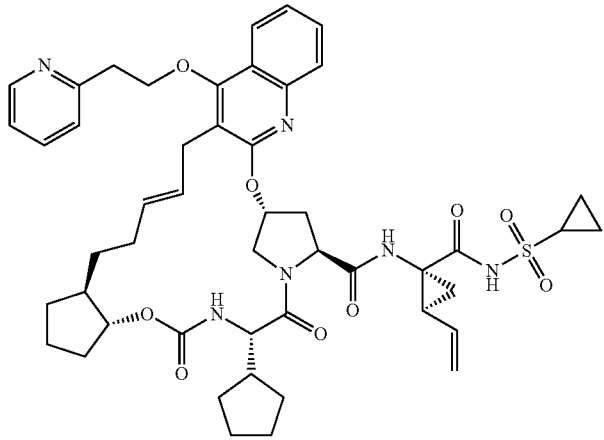<br>Int. A1, B2, C3<br>Rg. 2-bromoethyl pyridine hydrochloride | (3aR,7S,10S,12R,21E,24aS)-7-cyclopentyl-N-{(1R,2S)-1-[(cyclopropylsulfonyl)carbamoyl]-2-ethenylcyclo propyl}-5,8-dioxo-19-[2-(pyridin-2-yl)ethoxy]-1,2,3,3a,5,6,7,8,11,12,20,23,24,24a-tetradecahydro-10H-9,12-methanocyclopenta[18,19][1,10,3,6]dioxadiazacyclonona decino[11,12-b]quinoline-10-carboxamide | 895.4 |
| 44 | 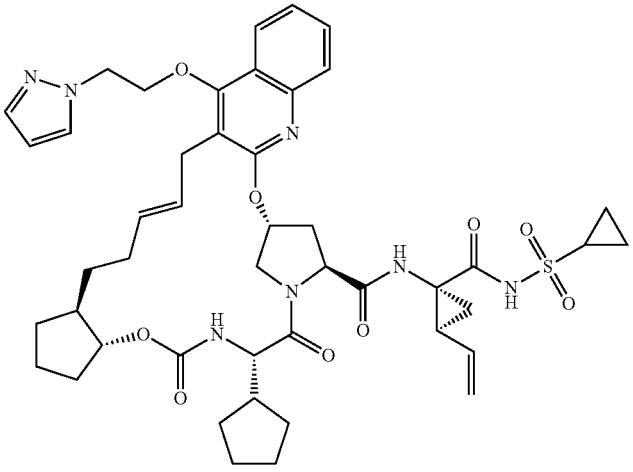<br>Int. A1, B2, C3<br>Rg. 1-(2-chloroethyl)-1H-pyrazole | (3aR,7S,10S,12R,21E,24aS)-7-cyclopentyl-N-{(1R,2S)-1-[(cyclopropylsulfonyl)carbamoyl]-2-ethenylcyclopropyl}-5,8-dioxo-19-[2-(1H-pyrazol-1-yl)ethoxy]-1,2,3,3a,5,6,7,8,11,12,20,23,24,24a-tetra decahydro-10H-9,12-methanocyclopenta[18,19][1,10,3,6]dioxadiazacyclonona decino[11,12-b]quinoline-10-carboxamide | 884.4 |

| Ex. | Structure | Name | LRMS or HRMS (M + H)+ |
|---|---|---|---|
| 45 | Int. A1, B6, C3<br>Rg. 1-(3-bromopropyl) piperidine hydrochloride | (3aR,7S,10S,12R,21E,24aS)-7-tert-butyl-N-{(1R,2S)-1-[(cyclopropylsulfonyl)carbamoyl]-2-ethenylcyclopropyl}-5,8-dioxo-19-[3-(piperidin-1-yl)propoxy]-1,2,3,3a,5,6,7,8,11,12,20,23,24,24a-tetradecahydro-10H-9,12-methanocyclopenta[18,19][1,10,3,6]dioxa diazacyclononadecino[11,12-b]quinoline-10-carboxamide | 903.5 |
| 46 | Int. A1, B2, C3<br>Rg. 2-bromoethyl methyl ether | (3aR,7S,10S,12R,21E,24aS)-7-cyclopentyl-N-{(1R,2S)-1-[(cyclopropylsulfonyl)carbamoyl]-2-ethenylcyclopropyl}-19-(2-methoxyethoxy)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 848.4 |
| 47 | Int. A1, B2, C3<br>Rg. Methoxyethoxy propylbromide | (3aR,7S,10S,12R,21E,24aS)-7-cyclopentyl-N-{(1R,2S)-1-[(cyclopropyl sulfonyl)carbamoyl]-2-ethenylcyclopropyl}-19-[3-(2-methoxyethoxy)propoxy]-5,8-dioxo-1,2,3,3a,5,6,7,8,11,12,20,23,24,24a-tetradeca-hydro-10H-9,12-methanocyclopenta[18,19][1,10,3,6]dioxadiazacyclononadecino[11,12-b]quinoline-10-carboxamide | 903.4 |

| Ex. | Structure | Name | LRMS or HRMS (M + H)+ |
|---|---|---|---|
| 48 | Int. A2, B2, C3<br>Rg. 1-(3-chloropropyl) imidazolidin-2-one | (3aR,7S,10S,12R,21E,24aS)-7-cyclopentyl-N-[(1R,2S)-2-ethenyl-1-{[(1-methyl-cyclopropyl)sulfonyl]carbamoyl}cyclopropyl]-5,8-dioxo-19-[3-(2-oxoimidazolidin-1-yl)propoxy]-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 930.4 |
| 49 | Int. A2, B2, C3<br>Rg. 3-hydroxy-3-methylbutyl 4-methyl benzenesulfonate[1] | (3aR,7S,10S,12R,21E,24aS)-7-cyclopentyl-N-[(1R,2S)-2-ethenyl-1-{[(1-methylcyclopropyl)sulfonyl]carbamoyl}cyclopropyl]-19-(3-hydroxy-3-methylbutoxy)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 890.4 |

| Ex. | Structure | Name | LRMS or HRMS (M + H)+ |
|---|---|---|---|
| 50 | Int. A2, B2, C3<br>Rg. 2-(2-bromoethyl)-1,3-dioxolane | (3aR,7S,10S,12R,21E,24aS)-7-cyclopentyl-19-[2-(1,3-dioxolan-2-yl)ethoxy]-N-[(1R,2S)-2-ethenyl-1-{[(1-methylcyclopropyl)sulfonyl]carbamoyl}cyclopropyl]-5,8-dioxo-1,2,3,3a,5,6,7,8,11,12,20,23,24,24a-tetradeca hydro-10H-9,12-methanocyclopenta[18,19][1,10,3,6]dioxadiazacyclononadecino[11,12-b]quinoline-10-carboxamide | 904.4 |
| 51 | Int. A1, B6, C3<br>Rg. 4-(2-bromoethyl) morpholine | (3aR,7S,10S,12R,21E,24aS)-7-tert-butyl-N-{(1R,2S)-1-[(cyclopropylsulfonyl)carbamoyl]-2-ethenylcyclo propyl}-19-[2-(morpholin-4-yl)ethoxy]-5,8-dioxo-1,2,3,3a,5,6,7,8,11,12,20,23,24,24a-tetradeca hydro-10H-9,12-methanocyclopenta[18,19][1,10,3,6]dioxadiazacyclononadecino[11,12-b]quinoline-10-carboxamide | 891.4 |
| 52 | Int. A1, B6, C3<br>Rg. 1-(2-bromoethyl)-1H-pyrrole | (3aR,7S,10S,12R,21E,24aS)-7-tert-butyl-N-{(1R,2S)-1-[(cyclopropylsulfonyl)carbamoyl]-2-ethenylcyclopropyl}-5,8-dioxo-19-[2-(1H-pyrrol-1-yl)ethoxy]-1,2,3,3a,5,6,7,8,11,12,20,23,24,24a-tetradeca hydro-10H-9,12-methano cyclopenta[18,19][1,10,3,6]dioxadiazacyclo nonadecino[11,12-b]quinoline-10-carboxamide | 871.4 |

| Ex. | Structure | Name | LRMS or HRMS (M + H)+ |
|---|---|---|---|
| 53 | Int. A2, B2, C3<br>Rg. 3-(4H-1,2,4-triazol-4-yl)propyl 4-methyl benzene sulfonate (A11) | (3aR,7S,10S,12R,21E,24aS)-7-cyclopentyl-N-[(1R,2S)-2-ethenyl-1-{[(1-methylcyclo propyl)sulfonyl]carbamoyl}cyclopropyl]-5,8-dioxo-19-[3-(4H-1,2,4-triazol-4-yl)propoxy]-1,2,3,3a,5,6,7,8,11,12,20,23,24,24a-tetra decahydro-10H-9,12-methanocyclopenta[18,19][1,10,3,6] dioxadiazacyclononadecino[11,12-b] quinoline-10-carboxamide | 93.4 |
| 54 | Int. A2, B2, C3<br>Rg. 1-(3-chloropropyl)-pyrrolidine, hydrochloride | (3aR,7S,10S,12R,21E,24aS)-7-cyclopentyl-N-[(1R,2S)-2-ethenyl-1-{[(1-methylcyclopropyl)sulfonyl]carbamoyl}cyclopropyl]-5,8-dioxo-19-[3-(pyrrolidin-1-yl)propoxy]-1,2,3,3a,5,6,7,8,11,12,20,23,24,24a-tetradecahydro-10H-9,12-methanocyclopenta[18,19][1,10,3,6] dioxadiazacyclononadecino[11,12-b] quinoline-10-carboxamide | 915.5 |
| 55 | Int. A2, B2, C3<br>Rg. 3-(1H-pyrrol-1-yl) propyl 4-methyl benzene sulfonate | (3aR,7S,10S,12R,21E,24aS)-7-cyclopentyl-N-[(1R,2S)-2-ethenyl-1-{[(1-methylcyclo propyl)sulfonyl]carbamoyl}cyclopropyl]-5,8-dioxo-19-[3-(1H-pyrrol-1-yl)propoxy]-1,2,3,3a,5,6,7,8,11,12,20,23,24,24a-tetradecahydro-10H-9,12-methanocyclopenta[18,19][1,10,3,6] dioxadiazacyclononadecino[11,12-b] quinoline-10-carboxamide | 911.4 |

-continued

| Ex. | Structure | Name | LRMS or HRMS (M + H)+ |
|---|---|---|---|
| 56 | Int. A2, B6, C3<br>Rg. 1-bromo-3-(2-methoxyethoxy) propane | (3aR,7S,10S,12R,21E,24aS)-7-tert-butyl-N-[(1R,2S)-2-ethenyl-1-{[(1-methylcyclo propyl)sulfonyl]carbamoyl}cyclopropyl]-19-[3-(2-methoxyethoxy)propoxy]-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 908.5 |
| 57 | Int. A2, B2, C3<br>Rg. 1-bromo-3-(2-methoxyethoxy) propane | (3aR,7S,10S,12R,21E,24aS)-7-cyclopentyl-N-[(1R,2S)-2-ethenyl-1-{[(1-methylcyclo propyl)sulfonyl]carbamoyl}cyclopropyl]-19-[3-(2-methoxyethoxy)propoxy]-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 920.4 |
| 58 | Int. A2, B2, C3<br>Rg 1-(3-chloropropyl) piperidine | (3aR,7S,10S,12R,21E,24aS)-7-cyclopentyl-N-[(1R,2S)-2-ethenyl-1-{[(1-methylcyclo propyl)sulfonyl]carbamoyl}cyclopropyl]-5,8-dioxo-19-[3-(piperidin-1-yl)propoxy]-1,2,3,3a,5,6,7,8,11,12,20,23,24,24a-tetra decahydro-10H-9,12-methanocyclopenta[18,19][1,10,3,6]dioxadiazacyclononadecino[11,12-b]quinoline-10-carboxamide | 929.5 |

| Ex. | Structure | Name | LRMS or HRMS (M + H)+ |
|---|---|---|---|
| 59 | Int. A2, B6, C3<br>Rg. 1-(3-chloropropyl) piperidine, hydrochloride | (3aR,7S,10S,12R,21E,24aS)-7-tert-butyl-N-[(1R,2S)-2-ethenyl-1-{[(1-methylcyclo propyl) sulfonyl]carbamoyl}cyclopropyl]-5,8-dioxo-19-[3-(piperidin-1-yl)propoxy]-1,2,3,3a,5,6,7,8,11,12,20,23,24,24a-tetra decahydro-10H-9,12-methanocyclopenta[18,19][1,10,3,6] dioxadiazacyclononadecino[11,12-b]quinoline-10-carboxamide | 917.7 |
| 60 | Int. A1, B2, C3<br>Rg. 2-(2-chloroethyl)-2-azabicyclo[2.2.1] heptane hydrochloride | (3aR,7S,10S,12R,24aR)-19-[2-(2-aza bicycle [2.2.1]hept-2-yl)ethoxy]-7-cyclo pentyl-N-{(1R,2S)-1-[(cyclopropyl sulfonyl) carbamoyl]-2-ethenylcyclopropyl}-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 915.5 |

[1] See International Patent Publication No. WO2002040019

Example 61

(3aR,7S,10S,12R,24aR)-7-tert-butyl-N-[(1R,2S)-2-ethenyl-1-({[1-(methoxymethyl)cyclopropyl]sulfonyl}carbamoyl)cyclopropyl]-19-[2-(morpholin-4-yl)ethoxy]-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide

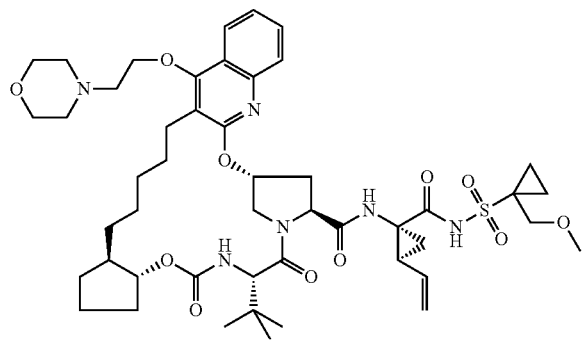 [SMILES: C=C[C@@H]1C[C@]1(NC(=O)[C@@H]1C[C@@H]2CN1C(=O)[C@H](C(C)(C)C)NC(=O)O[C@@H]1CCC[C@H]1CCCCCc1c(nc3ccccc3c1OCCN1CCOCC1)O2)C(=O)NS(=O)(=O)C1(COC)CC1]

The title compound was prepared using the same method as described for Example 42 using 4-(2-bromoethyl)morpholine and (3aR,7S,10S,12R,24aR)-7-tert-butyl-N-[(1R,2S)-2-ethenyl-1-({[1-(methoxymethyl)cyclopropyl]sulfonyl}carbamoyl)cyclopropyl]-19-hydroxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide (Example 35). Purification by flash chromatography (ISCO) afforded the desired product (21.5 mg). LRMS (ES+) m/z 937.3 (M+H)+.

Examples 62-65

By following the procedures outlined in Example 61 and using the appropriate A, B and C intermediates and reagent (depicted below the structure as Int. and Rg., respectively), the following compounds were prepared.

| Ex. | Structure | Name | LRMS (M + H)+ |
|---|---|---|---|
| 62 | ![structure]<br>Int. A7, B6, C3<br>Rg. 4-(2-bromoethyl)morpholine | (3aR,7S,10S,12R,24aR)-7-tert-butyl-N-[(1R,2S)-2-ethynyl-1-({[1-(prop-1-en-2-yl)cyclopropyl]sulfonyl}carbamoyl)cyclopropyl]-19-[2-(morpholin-4-yl)ethoxy]-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 933.3 |

| Ex. | Structure | Name | LRMS (M + H)+ |
|---|---|---|---|
| 63 | 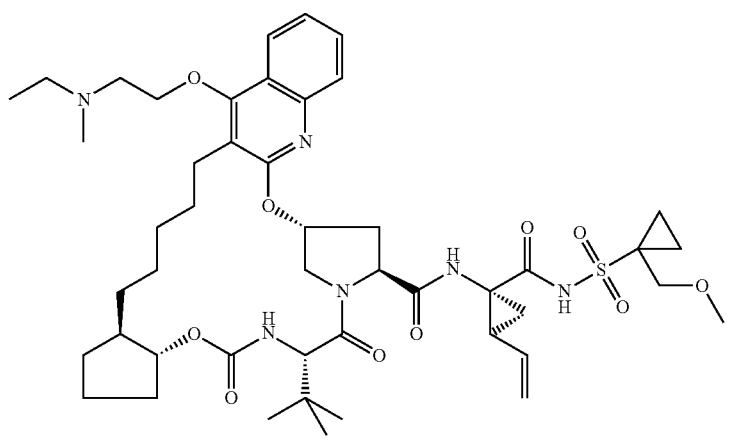<br>Int. A6, B6, C3<br>Rg. 2-chloro-N,N-dimethylethanamine hydrochloride | (3aR,7S,10S,12R, 24aR)-7-tert-butyl-19-[2-(dimethylamino) ethoxy]-N-[(1R,2S)-2-ethenyl-1-({[1-(methoxymethyl) cyclopropyl]sulfonyl} carbamoyl) cyclopropyl]-5,8-dioxo-1,2,3,3a, 5,6,7,8,11,12,20, 21,22,23,24,24a-hexadecahydro-10H-9,12-methanocyclopenta [18,19][1,10,3,6]dioxa-diazacyclononadecino [11,12-b]quinoline-10-carboxamide | 895.5 |
| 64 | 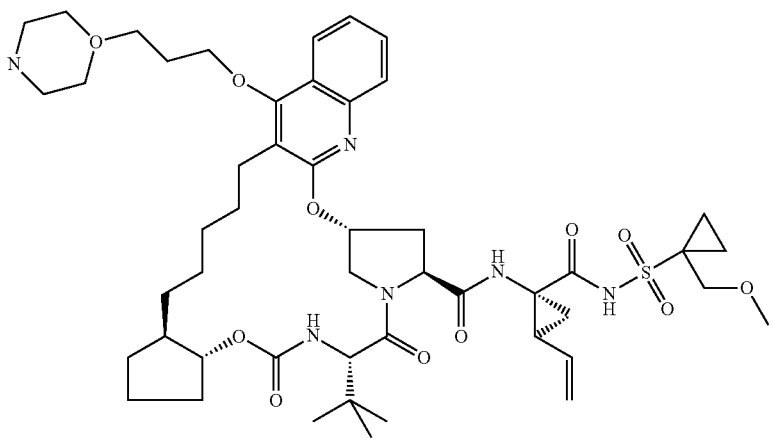<br>Int. A6, B5, C3<br>Rg. 4-(3-bromo propyl)morpholine | (3aR,7S,10S,12R, 24aR)-7-tert-butyl-N-[(1R,2S)-2-ethenyl-1-({[1-(methoxymethyl) cyclopropyl]sulfonyl} carbamoyl) cyclopropyl]-19-[3-(morpholin-4-yl) propoxy]-5,8-dioxo-1,2,3,3a,5,6,7,8, 11,12,20,21,22,23,24, 24a-hexadecahydro-10H-9,12-methanycyclopenta [18,19][1,10,3,6] dioxadiazacyclo-nonadecino [11,12-b]quinoline-10-carboxamide | 951.4 |

| Ex. | Structure | Name | LRMS (M + H)+ |
|---|---|---|---|
| 65 | 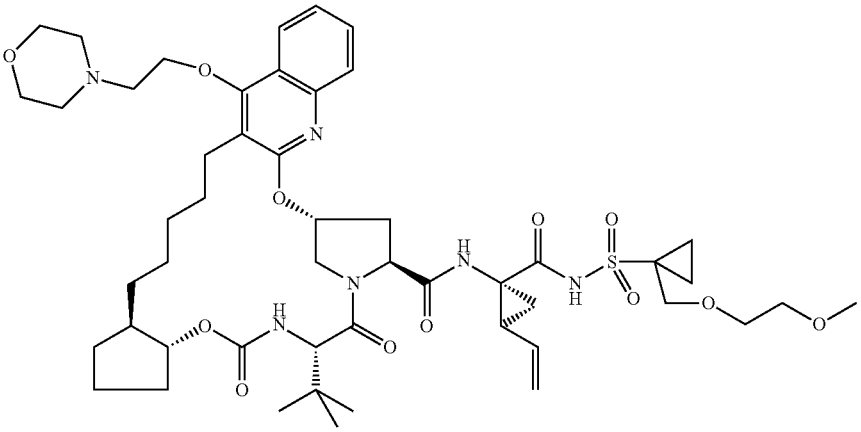<br>Int. A9, B6, C3<br>Rg. 4-(2-bromoethyl)morpholine | (3aR,7S,10S,12R,24aR)-7-tert-butyl-N-{(1R,2S)-2-ethenyl-1-[({1-[(2-methoxyethoxy)methyl]cyclopropyl}sulfonyl)carbamoyl]cyclopropyl}-19-[2-(morpholin-4-yl)ethoxy]-5,8-dioxo-1,2,3,3a,5,6,7,8,11,12,20,21,22,23,24,24a-hexadecahydro-10H-9,12-methanocyclopenta[18,19][1,10,3,6]dioxadiaza-cyclononadecino[11,12-b]quinoline-10-carboxamide | 981.4 |

Example 66

{[(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl]oxy}acetic acid Step 1: methyl {[(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl]oxy}acetate

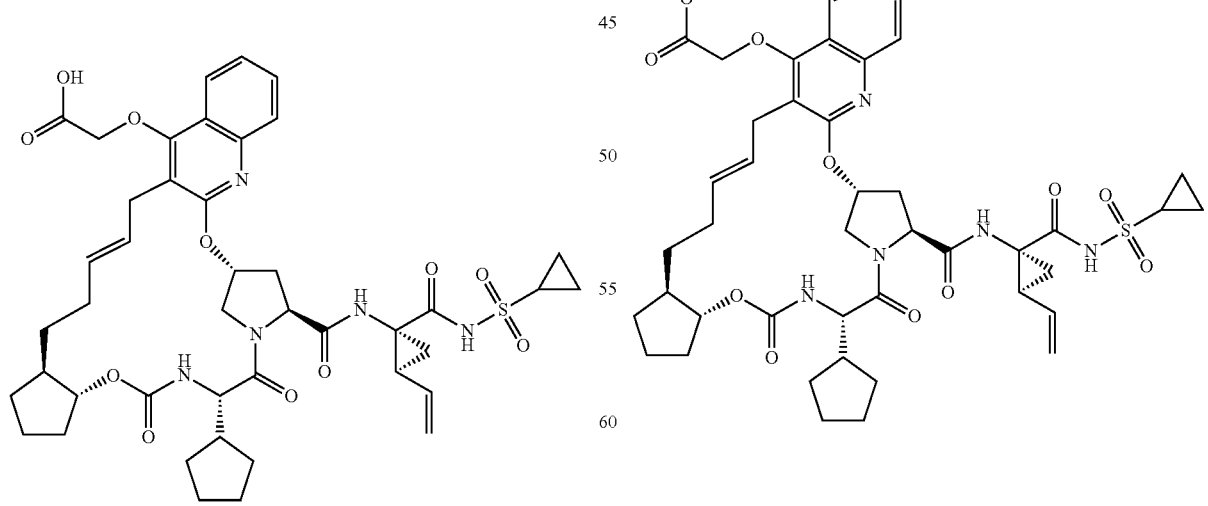

The title compound was prepared using the same method as described in Example 42, using methyl bromoacetate. LRMS (ES+) m/z 862.6 (M+H)+.

Step 2: {[(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl]oxy}acetic acid

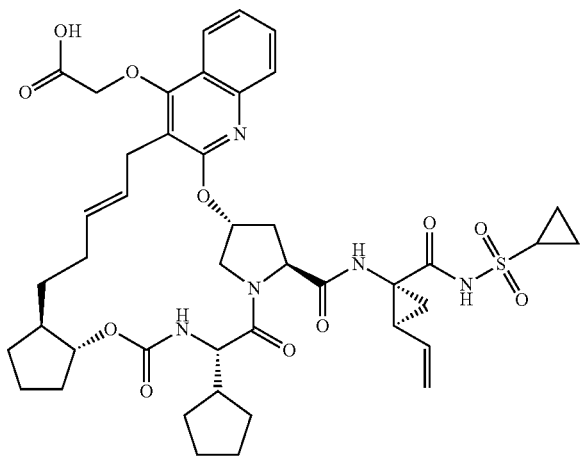 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OCC(=O)O)O2)C(=O)NS(=O)(=O)C1CC1]

The product of Step 1 (43 mg) was dissolved in THF (1 ml) and methanol (0.2 ml). Water (0.5 ml) and LiOH (11.95 mg) were added and the reaction was stirred until complete conversion. The reaction was quenched with 1N HCl (0.4 mL) and 5% KHSO$_4$ was added until the pH was 3. The mixture was extracted with ether then ethyl acetate. The combined organics were washed with water (5×) then brine, dried over magnesium sulfate, filtered and concentrated to yield 42 mg of pure product. HRMS (ES+) m/z 848.3522 (M+H)$^+$.

Example 67

(3aR,7S,10S,12R,21E,24aS)-7-cyclopentyl-N-{(1R,2S)-1-[(cyclopropylsulfonyl)carbamoyl]-2-ethenylcyclopropyl}-5,8-dioxo-19-[2-oxo-2-(pyrrolidin-1-yl)ethoxy]-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

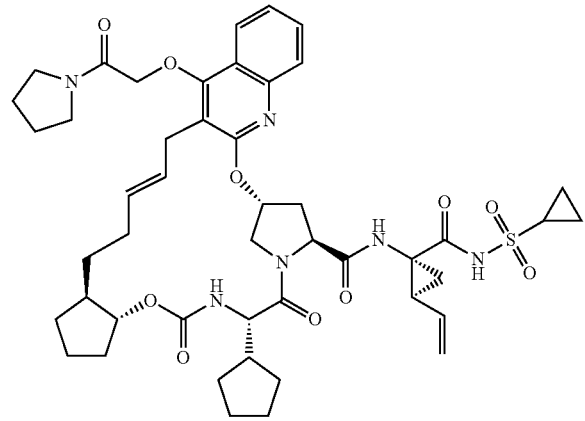 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OCC(=O)N1CCCC1)O2)C(=O)NS(=O)(=O)C1CC1]

To a solution of {[(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl]oxy}acetic acid (Example 66) (27 mg) in DMF (0.5 mL) was added pyrrolidine (5.27 µL), DIPEA (0.028 mL) and HATU (14.53 mg). The reaction mixture was stirred at room temperature for 15 minutes. The reaction was quenched with water and 5% KHSO$_4$ until pH=3. More water was added and the mixture was stirred 5 minutes. The white solid was filtered (washed with water). This solid was dissolved in ethyl acetate and the mixture was dried over magnesium sulfate, filtered and concentrated to afford the desired product (26 mg). HRMS (ES+) m/z 901.4109 (M+H)$^+$.

Example 68

(3aR,7S,10S,12R,21E,24aS)-7-cyclopentyl-N-{(1R,2S)-1-[(cyclopropylsulfonyl)carbamoyl]-2-ethenylcyclopropyl}-19-(4-hydroxybutoxy)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

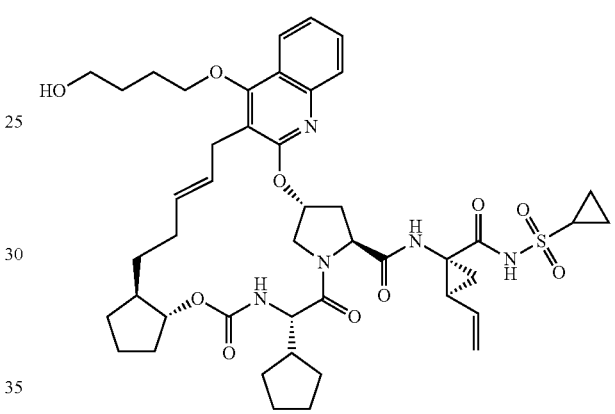

Step 1: (3aR,7S,10S,12R,21E,24aS)-19-(4-{[tert-butyl(dimethyl)silyl]oxy}butoxy)-7-cyclopentyl-N-{(1R,2S)-1-[(cyclopropylsulfonyl)carbamoyl]-2-ethenylcyclopropyl}-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

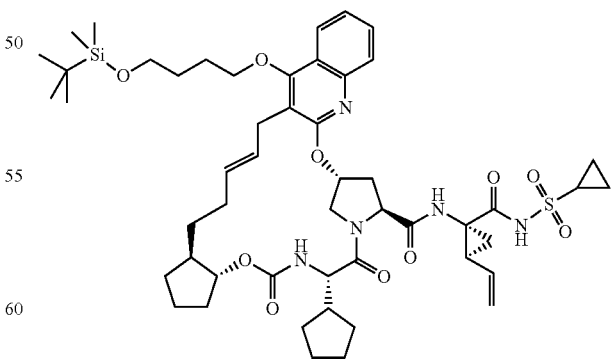

The title compound was prepared using the same method as described in Example 42, using 3-chlorobutanol-TBS ether and heating to 100° C. for 8 hours. LRMS (ES+) m/z 976.9 (M+H)$^+$.

Step 2: (3aR,7S,10S,12R,21E,24aS)-7-cyclopentyl-N-{(1R,2S)-1-[(cyclopropylsulfonyl)carbamoyl]-2-ethenylcyclopropyl}-19-(4-hydroxybutoxy)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

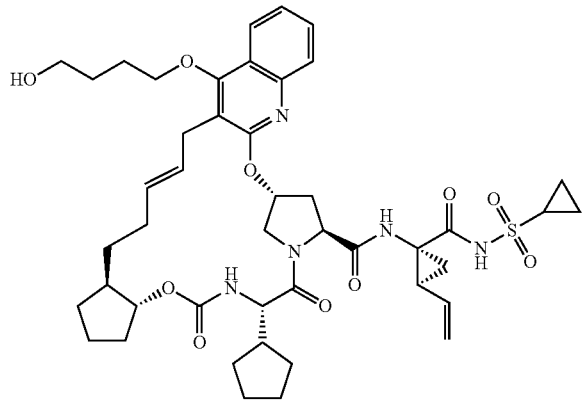 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OCCCCO)O2)C(=O)NS(=O)(=O)C1CC1]

To a solution of the product of Step 1 (50 mg) in THF (0.5 mL) was added HF-TEA (0.334 mL) at room temperature. The solution was heated to 50° C. for 30 minutes. The reaction mixture was concentrated to remove THF and then diluted with EtOAc (10 mL) and water was added (10 mL). To that mixture was added Na₂CO₃ (353 mg) portion wise at 0° C. When the quench was complete, the layers were separated. The organic layer was washed with 10% Na₂CO₃, water and brine. The aqueous layer was re-extracted with ethyl acetate (2×). The combined organics were dried over magnesium sulfate, filtered and concentrated. Purification by reverse phase HPLC (40-100% ACN/water with 0.15% TFA) afforded the desired product (7.2 mg) after workup with NaHCO₃ and ethyl acetate. HRMS (ES+) m/z 862.4073 (M+H)⁺.

Example 69

(3aR,7S,10S,12R,21E,24aS)-7-cyclopentyl-N-{(1R,2S)-1-[(cyclopropylsulfonyl)carbamoyl]-2-ethenylcyclopropyl}-19-(2-hydroxyethoxy)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

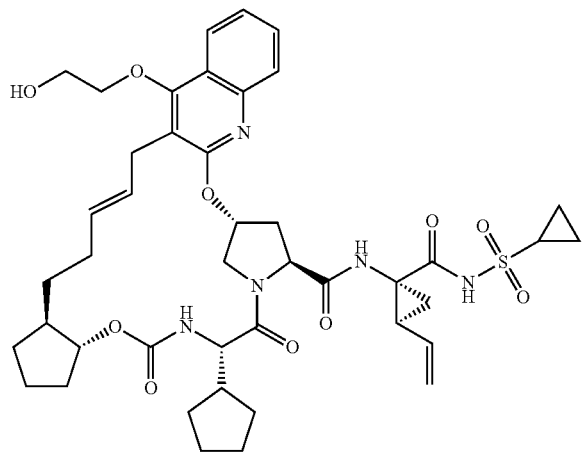 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OCCO)O2)C(=O)NS(=O)(=O)C1CC1]

The title compound was prepared using the same method as described in Example 68, using the (2-bromoethoxy)-tert-butyldimethylsilane (See Zink et al., 2006, *J. Org. Chem.* 71:202). LRMS (ES+) m/z 834.6 (M+H)⁺.

Example 70

(3aR,7S,10S,12R,21E,24aS)-7-tert-butyl-N-{(1R,2S)-1-[(cyclopropylsulfonyl)carbamoyl]-2-ethenylcyclopropyl}-19-(3-hydroxypropoxy)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

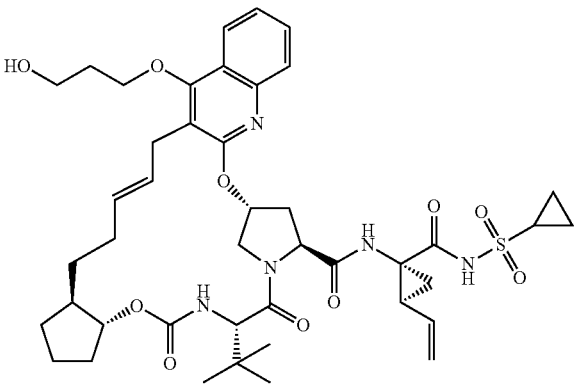 [SMILES: C=C[C@@H]1C[C@]1(NC(=O)[C@@H]1C[C@@H]2CN1C(=O)[C@H](C(C)(C)C)NC(=O)O[C@@H]1CCC[C@H]1CC/C=C/Cc1c(nc3ccccc3c1OCCCO)O2)C(=O)NS(=O)(=O)C1CC1]

The title compound was prepared using the same method as Example 70, using 3-bromopropanol-TBS ether and (3aR,7S,10S,12R,21E,24aS)-7-tert-butyl-N-{(1R,2S)-1-[(cyclopropylsulfonyl)carbamoyl]-2-ethenylcyclopropyl}-19-hydroxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide that was synthesized by the method described in Example 17 with intermediates A1, B6, and C3. HRMS (ES+) m/z 836.3922 (M+H)⁺.

Example 71

(3aR,7S,10S,12R,21E,24aS)-7-tert-butyl-N-[(1R,2S)-2-ethenyl-1-{[(1-methylcyclopropyl)sulfonyl]carbamoyl}cyclopropyl]-19-(3-hydroxypropoxy)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

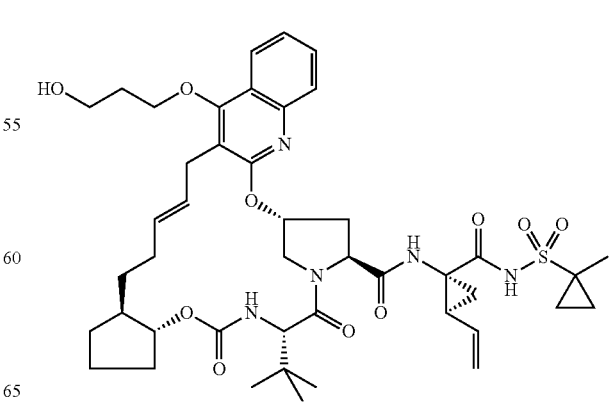

The title compound was prepared using the same method as Example 68, using 3-bromopropanol-TBS ether and (3aR,7S, 10S,12R,21E,24aS)-7-tert-butyl-N-[(1R,2S)-2-ethenyl-1-{[(1-methylcyclopropyl)sulfonyl]carbamoyl}cyclopropyl]-19-hydroxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide that was synthesized by the method described in Example 17 with intermediates A2, B6, and C3. HRMS (ES+) m/z 850.5 (M+H)$^+$.

Example 72

(3aR,7S,10S,12R,21E,24aS)-7-cyclopentyl-N-{(1R, 2S)-1-[(cyclopropylsulfonyl)carbamoyl]-2-ethenyl-cyclopropyl}-19-(3-hydroxypropoxy)-5,8-dioxo-1,2, 3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

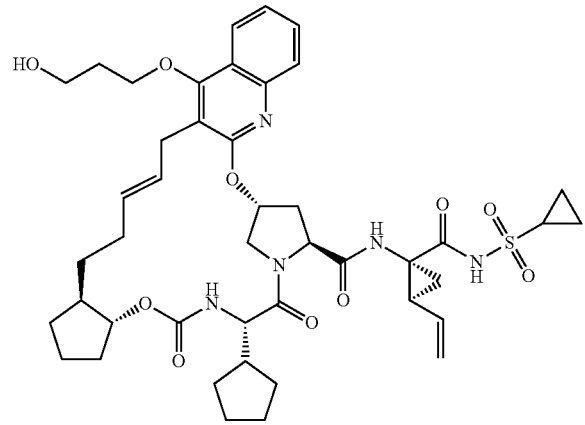 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OCCCO)O2)C(=O)NS(=O)(=O)C1CC1]

The title compound was prepared using the same method as described in Example 68 using 3-bromopropanol-TBS ether. HRMS (ES+) m/z 848.3923 (M+H)$^+$.

Example 73

(3aR,7S,10S,12R,21E,24aS)-7-cyclopentyl-N-{(1R, 2S)-1-[(cyclopropylsulfonyl)carbamoyl]-2-ethenyl-cyclopropyl}-19-(2,2-difluoro-3-hydroxypropoxy)-5, 8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

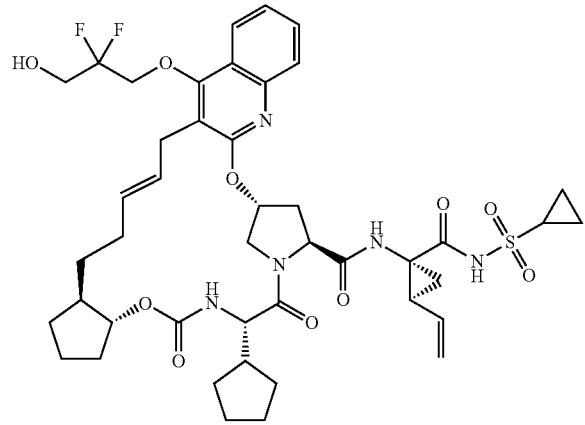 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OCC(F)(F)CO)O2)C(=O)NS(=O)(=O)C1CC1]

The title compound was prepared using the same method as described in Example 68 using 3-{[tert-butyl(dimethyl)silyl]oxy}-2,2-difluoropropyltrifluoro methanesulfonate (See International Patent Application Publication No. WO 2009/101917). HRMS (ES+) m/z 884.3722 (M+H)$^+$.

Example 74

3-{[3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a, 5,6,7,8,11,12,20,23,24,24a-tetradecahydro-10H-9, 12-methanocyclopenta[18,19][1,10,3,6]dioxadiazacyclononadecino[11,12-b]quinolin-19-yl]oxy}propyl N,N-dimethylglycinate

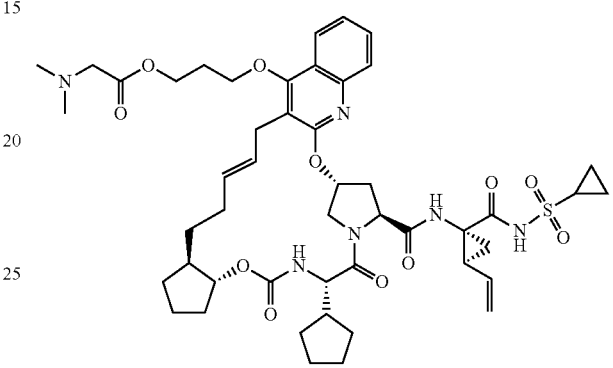

To a solution of Example 72 (31 mg) in dichloromethane (0.5 mL) was added N,N-dimethylglycine (11.3 mg) then triethylamine (0.015 ml), N,N-dicyclo hexylcarbodiimide (18.9 mg) and DMAP (1.1 mg). The solution was stirred at room temperature for 3 days. The mixture was diluted with ether and the solids that were formed were filtered off. The filtrate was concentrated in vacuo. Purification by reverse phase HPLC (30-100% ACN/water w/ 0.15% TFA) yielded 21 mg of the desired product after workup with NaHCO$_3$ and ethyl acetate. HRMS (ES+) m/z 933.4454 (M+H)$^+$.

Example 75

(3aR,7S,10S,12R,21E,24aS)-7-tert-butyl-N-{(1R, 2S)-1-[(cyclopropylsulfonyl)carbamoyl]-2-ethenyl-cyclopropyl}-5,8-dioxo-19-[2-(piperidin-1-yl)ethoxy]-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

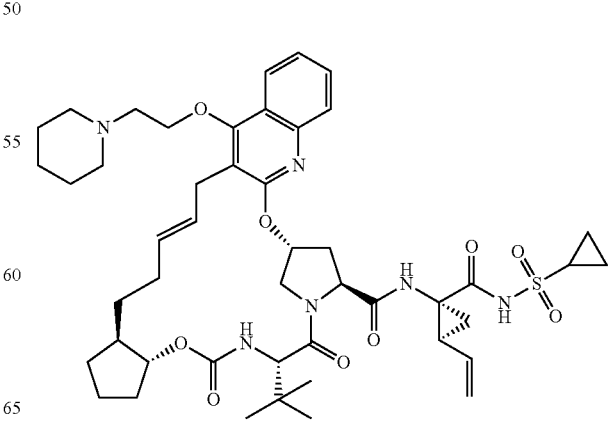

To a solution of (3aR,7S,10S,12R,21E,24aS)-7-tert-butyl-N-{(1R,2S)-1-[(cyclopropylsulfonyl)carbamoyl]-2-ethenyl-cyclopropyl}-19-hydroxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide (synthesized by the method described in Example 17 with intermediates A1, B6, C3) (40 mg) in THF (0.8 mL) under nitrogen was added 2-(piperidin-1-yl)ethanol (0.137 mL), trimethylphosphine (1.028 mL) and diisopropylazodicarboxylate (0.200 mL). After stirring for 18 hours, the mixture was diluted with ethyl acetate and water was added. The mixture was extracted with ethyl acetate (3×).

The combined organics were dried over magnesium sulfate, filtered and concentrated. Purification by reverse phase HPLC (30%-100% ACN/0.015% TFA-water) yielded 13.2 mg of the desired product. HRMS (ES+) m/z 889.4523 (M+H)$^+$.

Examples 76-92

By following the procedures outlined in Example 75 and using the appropriate A, B and C intermediates and reagent (depicted below the structure as Int. and Rg., respectively), the following compounds were prepared.

| Ex | Structure | Name | LRMS or HRMS (M + H)$^+$ |
|---|---|---|---|
| 76 | Int. A1, B2, C3<br>Rg. 1-(2-hydroxyethyl)pyrrolidine-2,5-dione | (3aR,7S,10S,12R,21E,24a)-7-cyclopentyl-N-{(1R,2S)-1-[(cyclopropylsulfonyl)carbamoyl]-2-ethenylcyclopropyl}-19-[2-(2,5-dioxopyrrolidin-1-yl)ethoxy]-5,8-dioxo-1,2,3,3a,5,6,7,8,11,12,20,23,24,24a-tetradeca hydro-10H-9,12-methanocyclopenta[18,19][1,10,3,6]dioxadiazacyclononadecino[11,12-b]quinoline-10-carboxamide | 915.4 |
| 77 | Int. A1, B2, C3<br>Rg. 2-dimethylamino propanol | (3aR,7S,10S,12R,21E,24aS)-7-cyclopentyl-N-{(1R,2S)-1-[(cyclopropyl sulfonyl)carbamoyl]-2-ethenylcyclo propyl}-19-[3-(dimethylamino)propoxy]-5,8-dioxo-1,2,3,3a,5,6,7,8,11,12,20,23,24,24a-tetradecahydro-10H-9,12-methano cyclopenta[18,19][1,10,3,6]dioxadiazacyclo-nonadecino[11,12-b]quinoline-10-carboxamide | 875.4 |

| Ex | Structure | Name | LRMS or HRMS (M + H)+ |
|---|---|---|---|
| 78 | 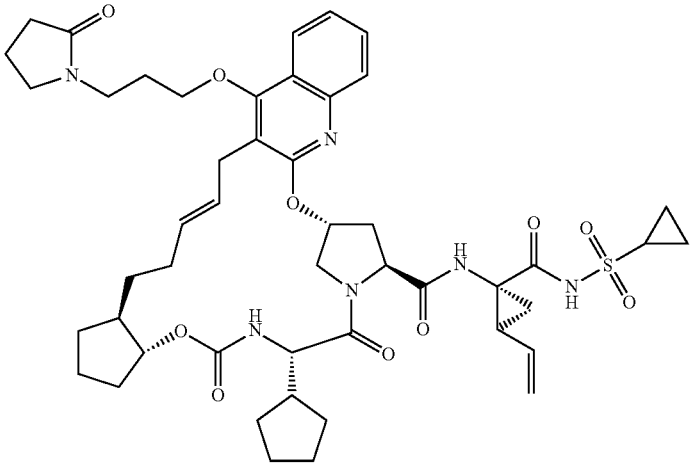<br>Int. A1, B2, C3<br>Rg. 1-(3-hydroxypropyl) pyrrolidin-2-one | (3aR,7S,10S,12R,21E,24aS)-7-cyclopentyl-N-{(1R,2S)-1-[(cyclopropyl sulfonyl)carbamoyl]-2-ethenylcyclo propyl}-5,8-dioxo-19-[3-(2-oxo pyrrolidin-1-yl)propoxy]-1,2,3,3a,5,6,7,8,11,12,20,23,24,24a-tetradecahydro-10H-9,12-methano-cyclopenta[18,19][1,10,3,6]dioxa diazacyclonona decino[11,12-b]quinoline-10-carboxamide | 915.4 |
| 79 | 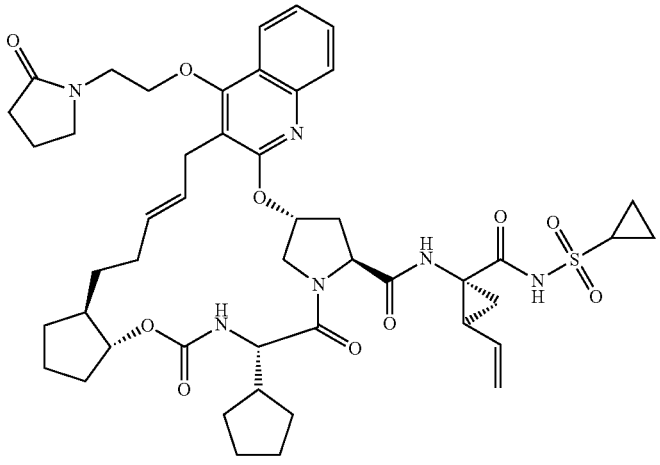<br>Int. A1, B2, C3<br>Rg. 1-(2-hydroxyethyl) pyrrolidin-2-one | (3aR,7S,10S,12R,21E,24aS)-7-cyclopentyl-N-{(1R,2S)-1-[(cyclopropyl sulfonyl)carbamoyl]-2-ethenylcyclopropyl}-5,8-dioxo-19-[2-(2-oxo pyrrolidin-1-yl)ethoxy]-1,2,3,3a,5,6,7,8,11,12,20,23,24,24a-tetradeca hydro-10H-9,12-methanocyclopenta[18,19][1,10,3,6]dioxadiaza cyclononadecino[11,12-b]quinoline-10-carboxamide | 901.4 |

| Ex | Structure | Name | LRMS or HRMS (M + H)+ |
|---|---|---|---|
| 80 | 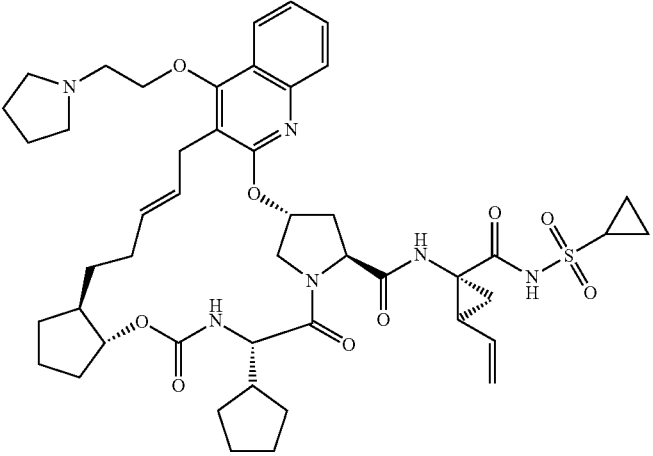<br>Int. A1, B2, C3<br>Rg. 2-(pyrrolidin-1-yl)ethanol | (3aR,7S,10S,12R,21E,24aS)-7-cyclopentyl-N-{(1R,2S)-1-[(cyclopropyl sulfonyl)carbamoyl]-2-ethenylcyclo propyl}-5,8-dioxo-19-[2-(pyrrolidin-1-yl)ethoxy]-1,2,3,3a,5,6,7,7,8,11,12,20,23,24,24a-tetradecahydro-10H-9,12-methanocyclopenta[18,19][1,10,3,6]dioxa diazacyclononadecino[11,12-b]quinoline-10-carboxamide | 887.4 |
| 81 | 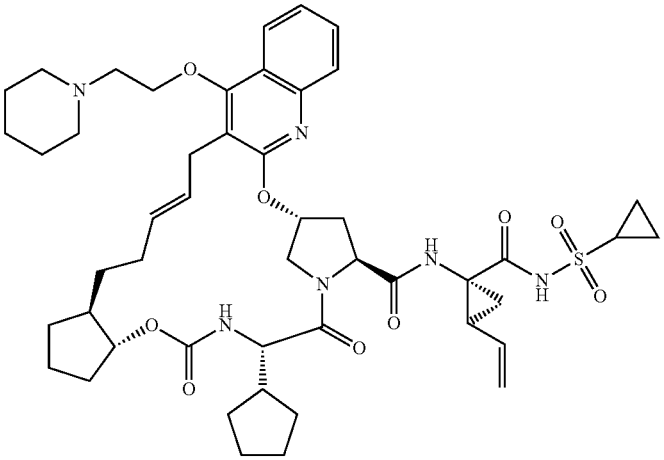<br>Int. A1, B2, C3<br>Rg. 2-(piperidin-1-yl)ethanol | (3aR,7S,10S,12R,21E,24aS)-7-cyclopentyl-N-{(1R,2S)-1-[(cyclopropylsulfonyl)carbamoyl]-2-ethenylcyclopropyl}-5,8-dioxa-19-[2-(piperidin-1-yl)ethoxy]-1,2,3,3a,5,6,7,8,11,12,20,23,24,24a-tetradecahydro-10H-9,12-methanocyclopenta[18,19][1,10,3,6]dioxadiaza cyclononadecino[11,12-b]quinoline-10-carboxamide | 901.5 |

| Ex | Structure | Name | LRMS or HRMS (M + H)⁺ |
|---|---|---|---|
| 82 | 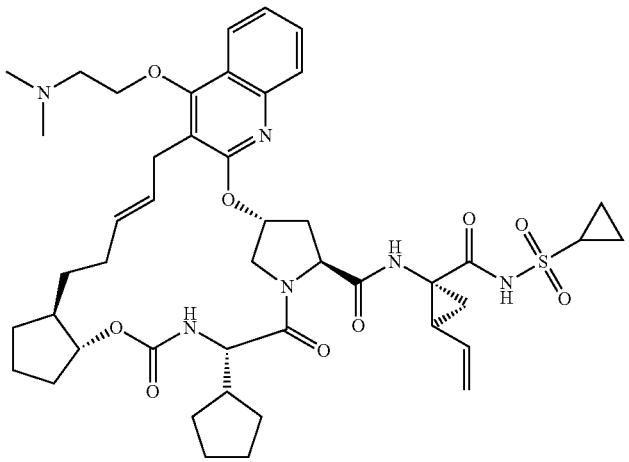<br>Int. A1, B2, C3<br>Rg. 2-(dimethyl amino) ethanol | (3aR,7S,10S,12R,21E,24aS)-7-cyclo pentyl-N-{(1R,2S)-1-[(cyclopropyl sulfonyl)carbamoyl]-2-ethenylcyclo propyl}-19-[2-(dimethylamino)ethoxy]-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 861.4 |
| 83 | 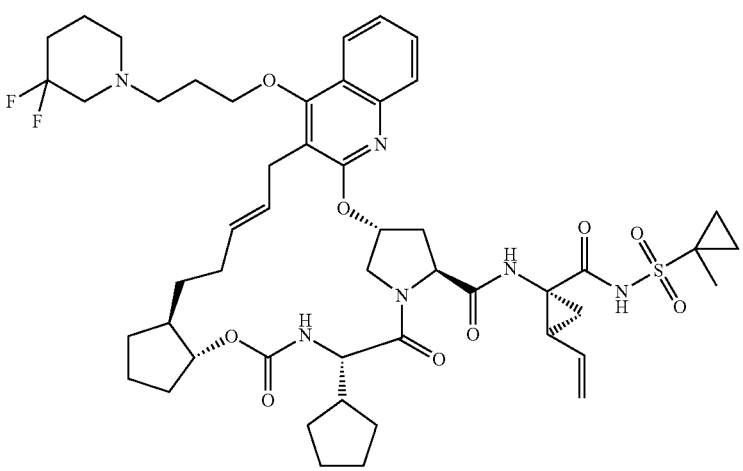<br>Int. A2, B2, C3<br>Rg. 3-(3,3-difluoro piperidin-1-yl) propan-1-ol<br>(Intermediate A12) | (3aR,7S,10S,12R,21E,24aS)-7-cyclo pentyl-19-[3-(3,3-difluoropiperidin-1-yl)propoxy]-N-[(1R,s)-2-ethenyl-1-{[(1-methylcyclopropyl)sulfonyl]carbamoyl}cyclopropyl]-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 965.5 |

| Ex | Structure | Name | LRMS or HRMS (M + H)+ |
|---|---|---|---|
| 84 | 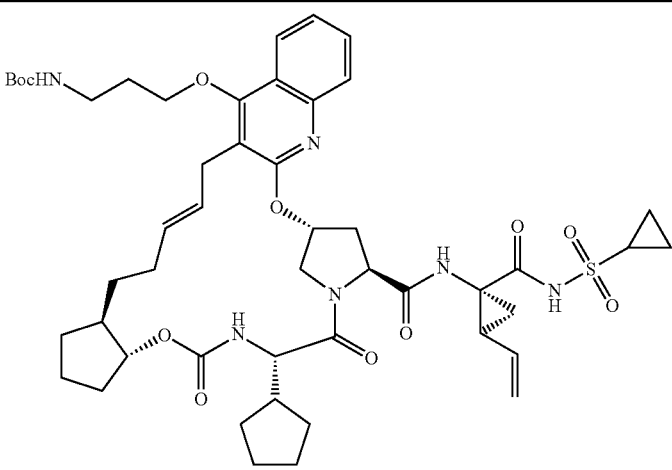 | tert-butyl (3-{[(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl]oxy}propyl)carbamate | 947.5 |
| | Int. A1, B2, C3 Rg. tert-butyl (3-hydroxypropyl) carbamate | | |
| 85 | 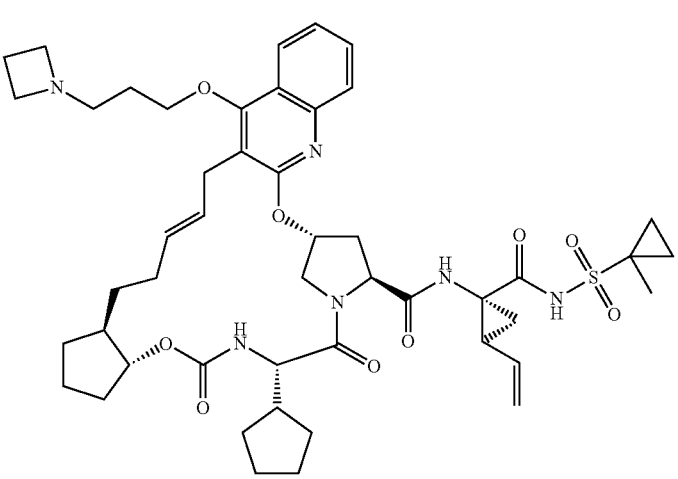 | (3aR,7S,10S,12R,21E,24aS)-19-[3-(azetidin-1-yl)propoxy]-7-cyclopentyl-N-[(1R,2S)-2-ethenyl-1-{[(1-methylcyclopropyl)sulfonyl]carbamoyl}cyclopropyl]-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 901.5 |
| | Int. A2, B2, C3 Rg. 3-(azetidin-1-yl)propan-1-ol[1] | | |

| Ex | Structure | Name | LRMS or HRMS (M + H)+ |
|---|---|---|---|
| 86 | 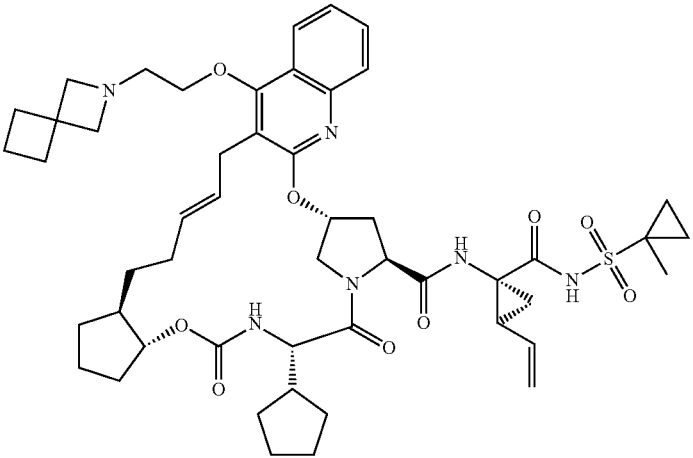<br>Int. A2, B2, C3<br>Rg. 2-(2-azaspiro[3.3]hept-2-yl)ethanol | (3aR,7S,10S,12R,21E,24aS)-19-[2-(2-azaspiro[3.3]hept-2-yl)ethoxy]-7-cyclopentyl-N-[(1R,2S)-2-ethenyl-1-{[(1-methylcyclopropyl)sulfonyl]carbamoyl}cyclopropyl]-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 927.5 |
| 87 | 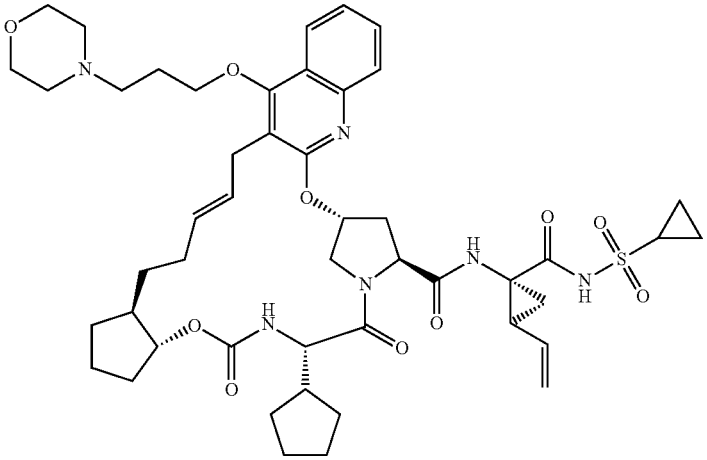<br>Int. A1, B2, C3<br>Rg. 3-(morpholin-4-yl)propan-1-ol | (3aR,7S,10S,12R,21E,24aS)-7-cyclopentyl-N-{(1R,2S)-1-[(cyclopropylsulfonyl)carbamoyl]-2-ethenylcyclopropyl}-19-[3-(morpholin-4-yl)propoxy]-5,8-dioxo-1,2,3,3a,5,6,7,8,11,12,20,23,24,24a-tetradeca hydro-10H-9,12-methano cyclopenta[18,19][1,10,3,6]dioxadiazacyclononadecino[11,12-b]quinoline-10-carboxamide | 917.4 |

| Ex | Structure | Name | LRMS or HRMS (M + H)+ |
|---|---|---|---|
| 88 | 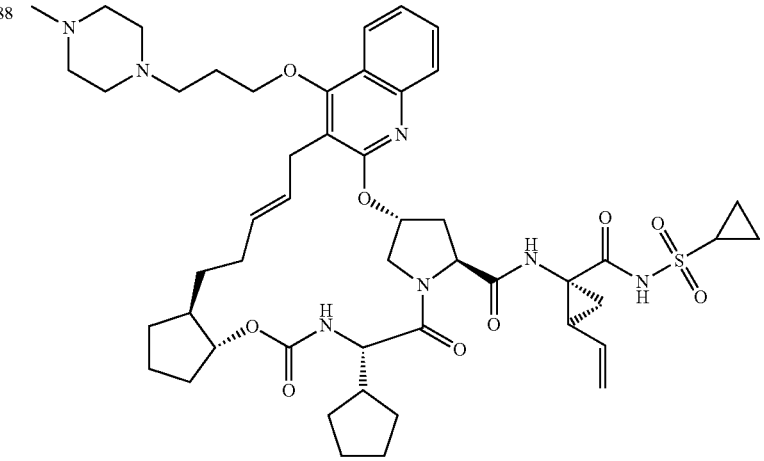<br>Int. A1, B2, C3<br>Rg. 3-(4-methylpiperazin-1-yl)propan-1-ol | (3aR,7S,10S,12R,21E,24aS)-7-cyclopentyl-N-{(1R,2S)-1-[(cyclopropylsulfonyl)carbamoyl]-2-ethenylcyclopropyl}-19-[3-(4-methylpiperazin-1-yl)propoxy]-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,2-b]quinoline-10-carboxamide | 930.5 |
| 89 | 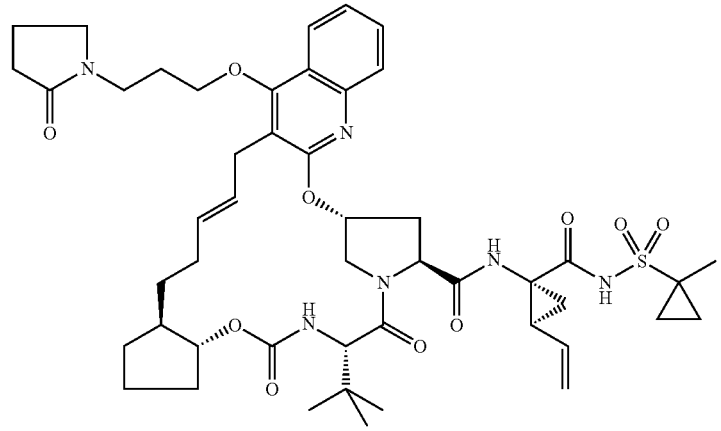<br>Int. A2, B6, C3<br>Rg. 1-(3-hydroxypropyl)pyrrolidin-3-one | (3aR,7S,10S,12R,21E,24aS)-7-tert-butyl-N-[(1R,2S)-2-ethenyl-1-{[(1-methycyclopropyl)sulfonyl]carbamoyl}cyclopropyl]-5,8-dioxo-19-[3-(2-oxopyrrolidin-1-yl)propoxy]-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 917.5 |

| Ex | Structure | Name | LRMS or HRMS (M+H)+ |
|---|---|---|---|
| 90 | 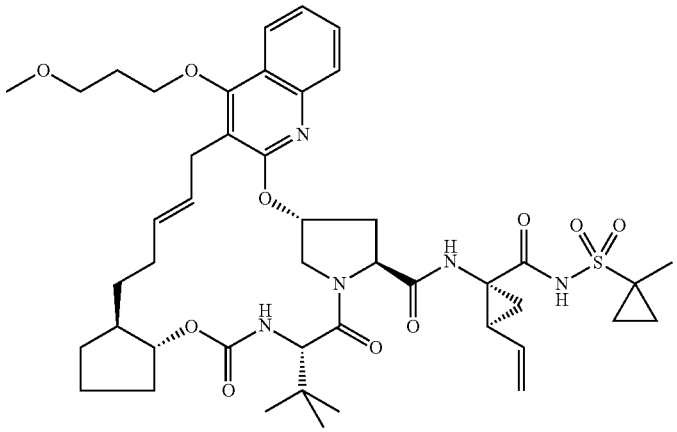<br>Int. A2, B6, C3<br>Rg. 3-methoxypropan-1-ol | (3aR,7S,10S,12R,21E,24aS)-7-tert-butyl-N-[(1R,2S)-2-ethenyl-1-{[(1-methylcyclopropyl)sulfonyl]carbamoyl}cyclopropyl]-19-(3-methoxypropoxy)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 864.5 |
| 91 | 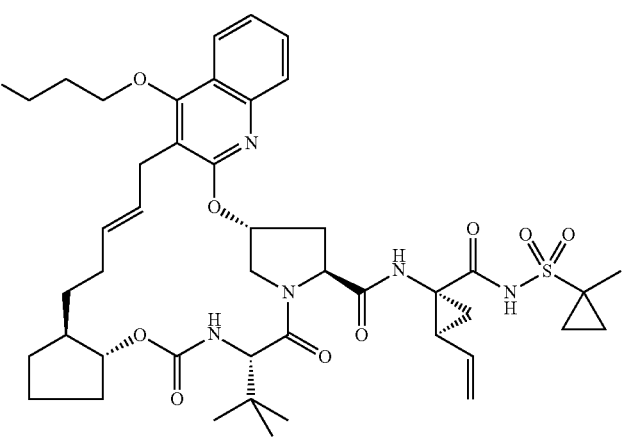<br>Int. A2, B6, C3<br>Rg. 3-(morpholin-4-yl)propan-1-ol | (3aR,7S,10S,12R,21E,24aS)-7-tert-butyl-N-[(1R,2S)-2-ethenyl-1-{[(1-methyl cyclopropyl)sulfonyl]carbamoyl}cyclopropyl]-19-[3-(morpholin-4-yl)propoxy]-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide | 919.6 |

| Ex | Structure | Name | LRMS or HRMS (M + H)+ |
|---|---|---|---|
| 92 | 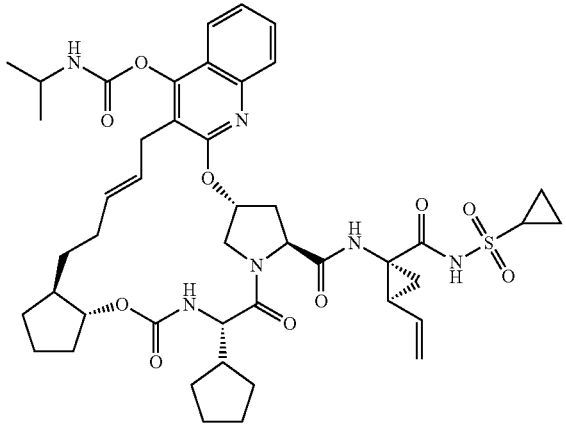 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OC(=O)NC(C)C)O2)C(=O)NS(=O)(=O)C1CC1]Int. A1, B2, C3<br>Rg. 3-(3,3-dimethyl piperidin-1-yl)propan-1-ol[2] | (3aR,7S,10S,12R,21E,24aS)-7-cyclo pentyl-N-{(1R,2S)-1-[(cyclopropyl sulfonyl)carbamoyl]-2-ethenylcyclo propyl}-19-[3-(3,3-dimethyl piperidin-1-yl)propoxy]-5,8-dioxo-1,2,3,3a,5,6,7,8,11,12,20,23,24,24a-tetradeca hydro-10H-9,12-methano-cyclopenta[18,19][1,10,3,6]dioxa diazacyclononadecino[11,12-b] quinoline-10-carboxamide | 943.7 |

[1]See Wang, et al., 2006, J. Applied Polymer Science 102:4383
[2]See US Pat. No. 2,794,806

Example 93

(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl propan-2-ylcarbamate To a solution of (3aR,7S,10S,12R,21E,24aS)-7-cyclopentyl-N-{(1R,2S)-1-[(cyclopropylsulfonyl)carbamoyl]-2-ethenylcyclopropyl}-19-hydroxy-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide (Example 17) (30 mg) in dichloroethane (0.6 mL) was added isopropylisocyanate (0.037 mL) then DMAP (4.6 mg). The reaction mixture was heated to 50° C. for 1 hour. After cooling back to room temperature, the mixture was diluted with ethyl acetate and water was added. The mixture was extracted with ethyl acetate (3x). The combined organics were dried over magnesium sulfate, filtered and concentrated. Purification by reverse phase HPLC (40% ACN-100% ACN/0.05% TFA/water) yielded 27 mg of the desired product after workup with NaHCO$_3$ and ethyl acetate. HRMS (ES+) m/z 875.3981 (M+H)+.

Example 94

(3aR,7S,10S,12R,21E,24aS)-19-(3-aminopropoxy)-7-cyclopentyl-N-{(1R,2S)-1-[(cyclopropylsulfonyl)carbamoyl]-2-ethenylcyclopropyl}-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxamide

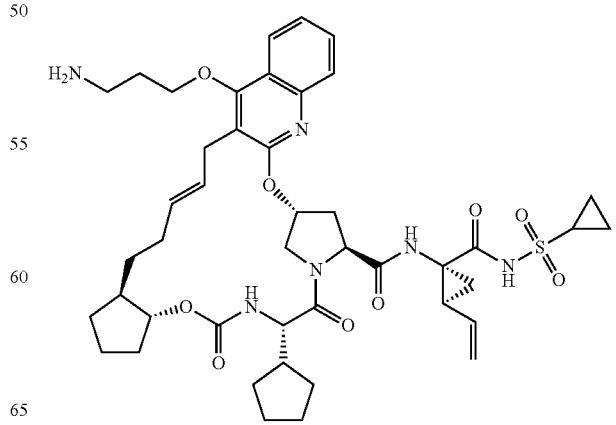

Tert-butyl (3-{[(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19]1,10,3,6]dioxadiazacyclononadecino[11,12-b]quinolin-19-yl]oxy}propyl)carbamate (Example 84) (21 mg) was dissolved in HCl (4M in dioxane) (277 µl) and the resulting mixture was stirred for 30 minutes. The solvent was removed in vacuo. The crude product was dissolved in ethyl acetate and a saturated solution of sodium bicarbonate was added. The mixture was extracted with ethyl acetate (3×). The combined organics were dried over magnesium sulfate, filtered and concentrated to give 17 mg of the desired product. HRMS (ES+) m/z 847.4097 (M+H)+.

Example 95

3-{[(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl]oxy}propyl dihydrogen phosphate

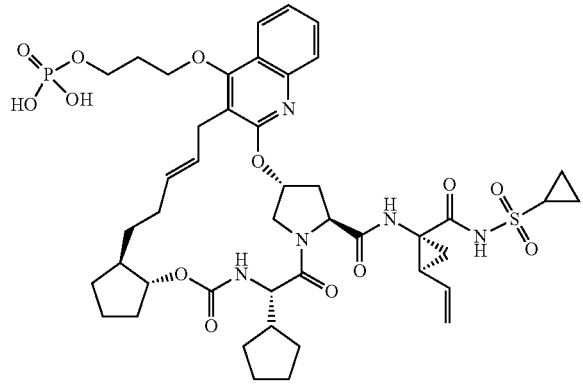 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OCCCOP(=O)(O)O)O2)C(=O)NS(=O)(=O)C1CC1]

Step 1: diethyl(3-{[(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl]oxy}propyl)phosphonate

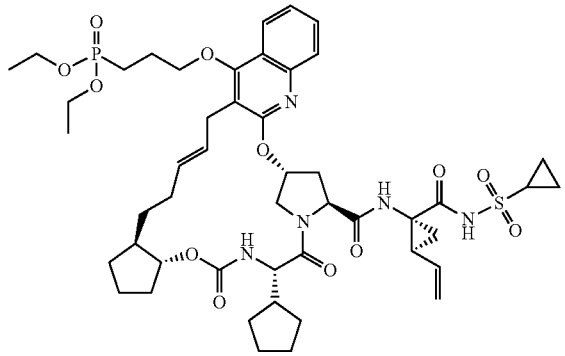 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccc3c1OCCCP(=O)(OCC)OCC)O2)C(=O)NS(=O)(=O)C1CC1]

The title compound was prepared using the same method as Example 42, using diethyl(3-bromopropyl)phosphonate and stirring at room temperature. HRMS (ES+) m/z 968.4214 (M+H)+.

Step 2: 3-{[(3aR,7S,10S,12R,21E,24aS)-7-cyclopentyl-10-({(1R,2S)-1-[(cyclopropylsulfonyl)carbamoyl]-2-ethenylcyclopropyl}carbamoyl)-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinolin-19-yl]oxy}propyl dihydrogen phosphate

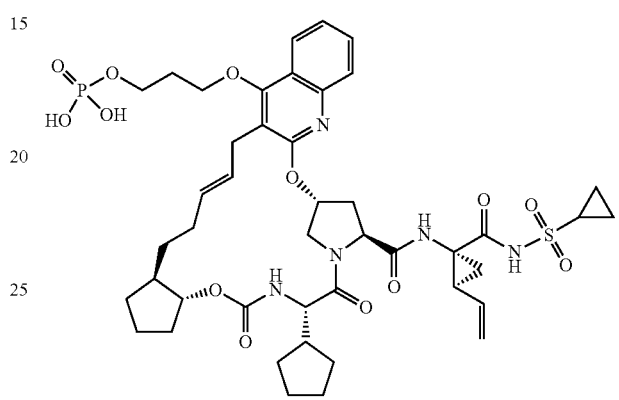

To a solution of the product of Step 1 (43 mg) in dichloromethane (1 mL) was added trimethylsilyl bromide (0.115 mL). After 1 hour at room temperature, another 0.115 mL of trimethylsilyl bromide was added and the mixture was stirred for 2 hours. The reaction was quenched with 0.1 mL water and 1.5 mL ethanol. The solvents were removed in vacuo. The crude product was dissolved in dichloromethane and ether was added to precipitate a white solid. The solid was filtered and washed with ether to yield 36 mg of the desired product. HRMS (ES+) m/z 912.3603 (M+H)+.

Example 96

(3aR,7S,10S,12R,24aR)-7-tert-butyl-N-[(1R,2S)-2-ethenyl-1-({[1-(methoxymethyl)cyclopropyl]sulfonyl}carbamoyl)cyclopropyl]-5,8-dioxo-19-[3-(piperidin-1-yl)propoxy]-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide

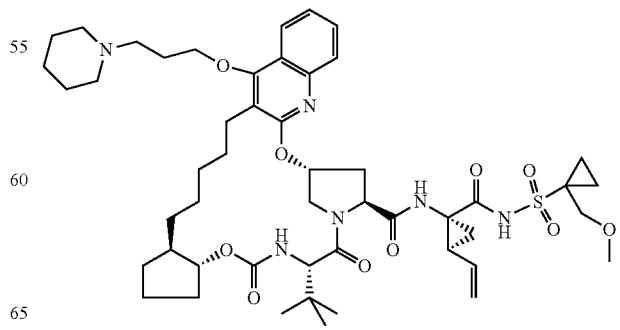

Step 1: methyl (3aR,7S,10S,12R,24aR)-7-tert-butyl-19-hydroxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxylate

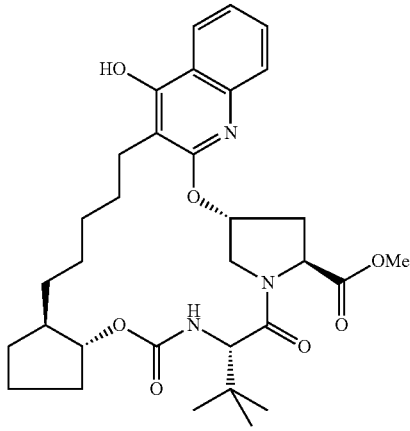 [SMILES: COC(=O)[C@@H]1C[C@@H]2CN1C(=O)[C@H](C(C)(C)C)NC(=O)O[C@@H]1CCC[C@H]1CCCCCc1c(nc3ccccc3c1O)O2]

To a solution of methyl (3aR,7S,10S,12R,21E,24aS)-19-(benzyloxy)-7-tert-butyl-5,8-dioxo-1,2,3,3a,5,6,7,8,11,12,20,23,24,24a-tetradecahydro-10H-9,12-methanocyclopenta[18,19][1,10,3,6]dioxadiazacyclononadecino[11,12-b]quinoline-10-carboxylate (synthesized as in Example 1 with intermediates B6 and C3) (1.16 g) in THF (8.7 ml) and methanol (8.7 mL) was added 10% Pd/C (92 mg) and the mixture was stirred for 18 hours under hydrogen atmosphere. The atmosphere was changed to nitrogen and the reaction was carefully filtered through celite to give 0.88 g of the desired product. LRMS (ES+) m/z 582.40 (M+H)+.

Step 2: methyl (3aR,7S,10S,12R,24aR)-7-tert-butyl-5,8-dioxo-19-[3-(piperidin-1-yl)propoxy]-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxylate

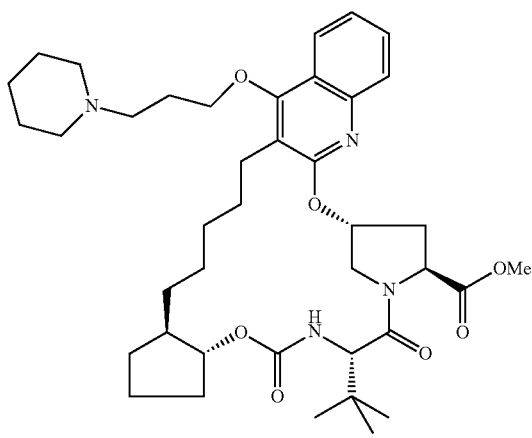 [SMILES: COC(=O)[C@@H]1C[C@@H]2CN1C(=O)[C@H](C(C)(C)C)NC(=O)O[C@@H]1CCC[C@H]1CCCCCc1c(nc3ccccc3c1OCCCN1CCCCC1)O2]

The title compound was prepared using the same method as described in Example 42 using 1-(3-chloropropyl)piperidine hydrochloride as the alkylating agent with the product of Step 1. LRMS (ES+) m/z 707.5 (M+H)+.

Step 3: (3aR,7S,10S,12R,24aR)-7-tert-butyl-5,8-dioxo-19-[3-(piperidin-1-yl)propoxy]-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxylic acid

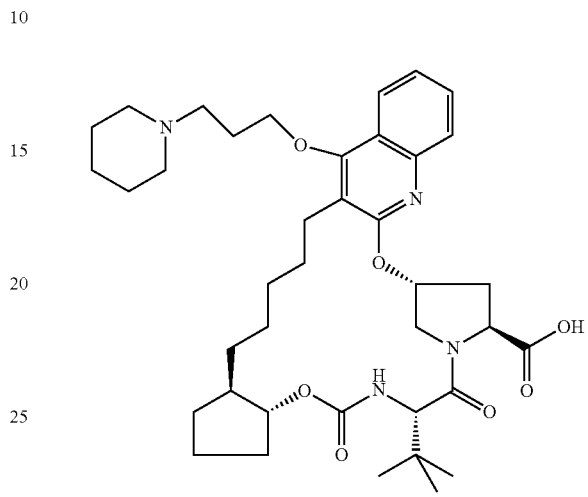

To a solution of the ester from Step 2 (55.8 mg) in THF (0.8 mL) and ethanol (0.2 mL) was added 2M LiOH (0.4 mL). After 1 hour at room temperature, the reaction was done. The mixture was diluted with ethyl acetate and water. Then, acetic acid was added until pH=5. The mixture was extracted with ethyl acetate (3×). The combined organics were dried over sodium sulfate, filtered and concentrated. LRMS (ES−) m/z 691.3 (M−H)−.

Step 4: (3aR,7S,10S,12R,24aR)-7-tert-butyl-N-[(1R,2S)-2-ethenyl-1-({[1-(methoxymethyl)cyclopropyl]sulfonyl}carbamoyl)cyclopropyl]-5,8-dioxo-19-[3-(piperidin-1-yl)propoxy]-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide

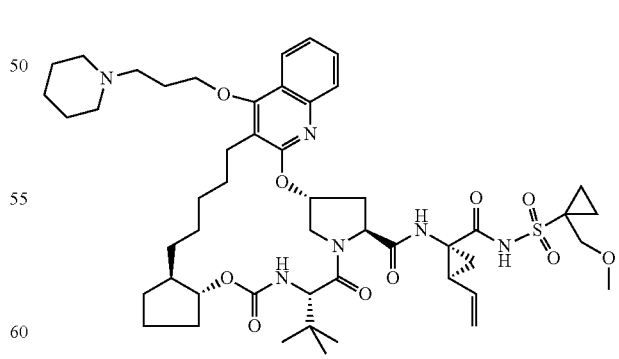

The title compound was prepared using the same method as described in Example 1, Step 6 with intermediate A6. Purification by flash chromatography (ISCO, 0 to 10% methanol in DCM) afforded the desired product (44.6 mg). LRMS (ES+) m/z 949.5 (M+H)+.

US 9,328,138 B2

Examples 97-105

By following the procedures outlined in Example 96 and using the appropriate A, B and C intermediates and reagent (depicted below the structure as Int. and Rg., respectively), the following compounds were prepared.

| Ex | Structure | Name | LRMS (M + H)+ |
|---|---|---|---|
| 97 | 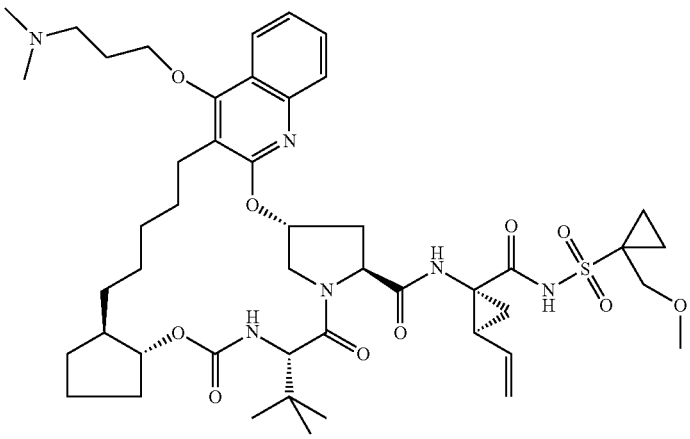<br>Int. A6, B6, C3<br>Rg. 3-chloro-N,N-dimethylpropan-1-amine hydrochloride | (3aR,7S,10S,12R,24aR)-7-tert-butyl-19-[3-(dimethylamino)propoxy]-N-[(1R,2S)-2-ethenyl-1-({[1-(methoxymethyl)cyclopropyl]sulfonyl}carbamoyl)cyclopropyl]-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12,-b]quinoline-10-carboxamide | 909.4 |
| 98 | 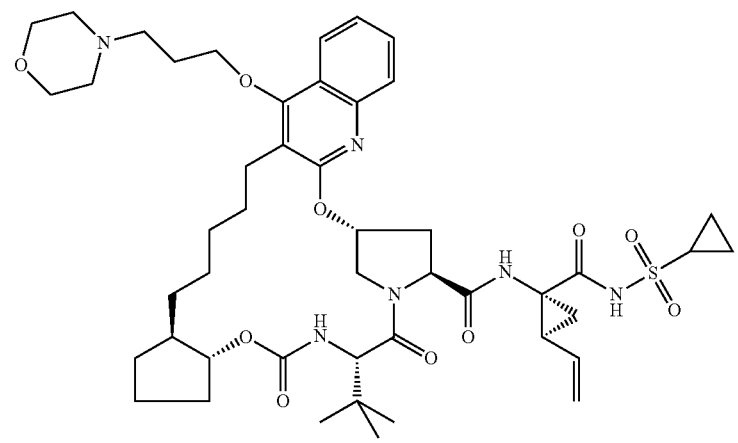<br>Int. A1, B6, C3<br>Rg. 4-(3-bromopropyl)morpholine | (3aR,S,10S,12R,24aR)-7-tert-butyl-N-{(1R,2S)-1-[(cyclopropylsulfonyl)carbamoyl]-2-ethenylcyclopropyl}-19-[3-(morpholin-4-yl)propoxy]-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 907.6 |

| Ex | Structure | Name | LRMS (M + H)+ |
|---|---|---|---|
| 99 | 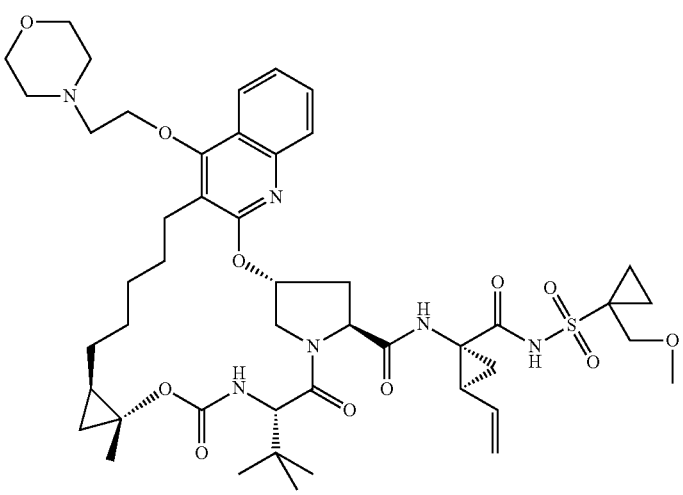<br>Int. A6, B9, C3<br>Rg. 4-(2-bromoethyl) morpholine | (1aR,5S,8S,10R,22aR)-5-tert-butyl-N-[(1R,2S)-2-ethenyl-1-({[1-(methoxy methyl)cyclopropyl] sulfonyl}carbamoyl)cyclopropyl]-1a-methyl-17-[2-(morpholin-4-yl)ethoxy]-3,6-dioxo-1,1a,3,4,5,6,9,10,18,19,20,21,22,22a-tetradecahydro-8H-7,10-methano-cyclopropa[18,19][1,10,3,6] dioxadiazacyclononadecino [11,12-b]quinoline-8-carboxamide | 923.4 |
| 100 | 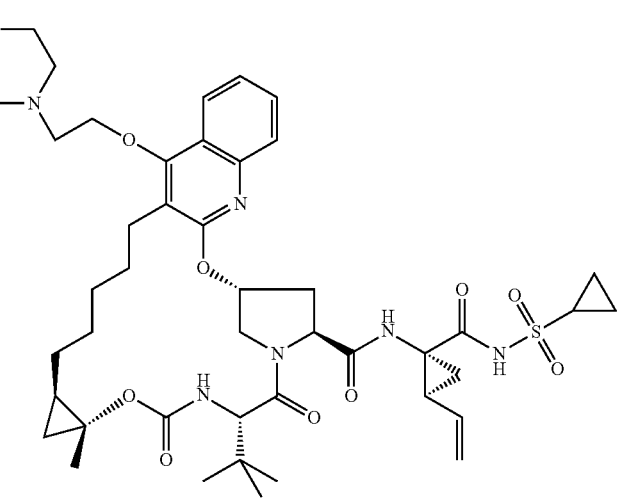<br>Int. A1, B9, C3<br>Rg. 4-(2-bromoethyl) morpholine | (1aR,5S,8S,10R,22aR)-5-tert-butyl-N-{(1R,2S)-1-[(cyclopropylsulfonyl) carbamoyl]-2-ethenylcyclopropyl}-1a-methyl-17-[2-(morpholin-4-yl) ethoxy]-3,6-dioxo-1,1a,3,4,5,6,9,10,18,19,20,21,22,22a-tetradecahydro-8H-7,10-methanocyclopropa[18,19] [1,10,3,6]dioxadiazacyclonona decino[11,12-b]quinoline-8-carboxamide | 879.40 |

| Ex | Structure | Name | LRMS (M + H)+ |
|---|---|---|---|
| 101 | Int. A2, B9, C3<br>Rg. 4-(2-bromoethyl) morpholine | (1aR,5S,8S,10R,22aR)-5-tert-butyl-N-[(1R,2S)-2-ethenyl-1-{[(1-methylcyclopropyl)sulfonyl]carbamoyl}cyclopropyl]-1a-methyl-17-[2-(morpholin-4-yl)ethoxy]-3,6-dioxo-1,1,a,3,4,5,6,9,10,18,19,20,21,22,22a-tetradecahydro-8H-7,10-methano-cyclopropa[18,19][1,10,3,6]dioxadiazacyclononadecino[11,12-b]quinoline-8-carboxamide | 893.35 |
| 102 | Int. A6, B6, C3<br>Rg. 1-(2-chloroethyl)pyrrolidine hydrochloride | (3aR,7S,10S,12R,24aR)-7-tert-butyl-N-[(1R,2S)-2-ethenyl-1-({[1-(methoxy methyl)cyclopropyl]sulfonyl}carbamoyl)cyclopropyl]-5,8-dioxo-19-[2-(pyrrolidin-1-yl)ethoxy]-1,2,3,3a,5,6,7,8,11,12,20,21,22,23,24,24a-hexadecahydro-10H-9,12-methanocyclopenta[18,19][1,10,3,6]dioxadiazacyclo-nonadecino[11,12-b]quinoline-10-carboxamide | 921.55 |

-continued

| Ex | Structure | Name | LRMS (M + H)+ |
|---|---|---|---|
| 103 | Int. A10, B6, C3<br>Rg. 2-chloro-N,N-dimethylethanamine hydrochloride | (3aR,7S,10S,12R,24aR)-7-tert-butyl-19-[2-(dimethylamino)ethoxy]-N-{(1R,2S)-2-ethenyl-1-[({1-[2-(morpholin-4-yl)ethyl]cyclopropyl}sulfonyl)carbamoyl]cyclopropyl}-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 964.5 |
| 104 | Int. A1, B6, C3<br>Rg. 4-(2-bromoethyl)morpholine | (3aR,7S,10S,12R,24aR)-7-tert-butyl-N-{(1R,2S)-1-[(cyclopropylsulfonyl)carbamoyl]-2-ethenylcyclopropyl}-19-[2-(morpholin-4-yl)ethoxy]-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 893.50 |

-continued

| Ex | Structure | Name | LRMS (M + H)+ |
|---|---|---|---|
| 105 | Int. A2, B6, C3<br>Rg. 4-(2-bromoethyl) morpholine | (3aR,7S,10S,12R,24aR)-7-tert-butyl-N-[(1R,2S)-2-ethenyl-1-{[(1-methyl-cyclopropyl)sulfonyl]carbamoyl}cyclopropyl]-19-[2-(morpholin-4-yl)ethoxy]-5,8-dioxo-1,2,3,3a,5,6,7,8,11,12,20,21,22,23,24,24a-hexadeca hydro-10H-9,12-methanocyclopenta[18,19][1,10,3,6]dioxadiazacyclo nonadecino[11,12-b]quinoline-10-carboxamide | 907.45 |

Example 106

(3aR,7S,10S,12R,24aR)-7-tert-butyl-N-{(1R,2S)-1-[(dimethylsulfamoyl)carbamoyl]-2-ethenylcyclopropyl}-19-[2-(morpholin-4-yl)ethoxy]-5,8-dioxo-1,2,3,3a,5,24,24a-hexadecahydro-10H-9,12-methanocyclopenta[18,19][1,10,3,6]dioxadiazacyclononadecino[11,12-b]quinoline-10-carboxamide Step 1: ethyl (1R,2S)-1-[({(3aR,7S,10S,12R,24aR)-7-tert-butyl-19-[2-(morpholin-4-yl)ethoxy]-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinolin-10-yl}carbonyl)amino]-2-ethenylcyclopropanecarboxylate The title compound was prepared using the same method as described in Example 1, Step 6 with intermediate A4 and (3aR,7S,10S,12R,24aR)-7-tert-butyl-19-[2-(morpholin-4-yl)ethoxy]-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxylic acid (Synthesized by the method described for Example 96, Steps 1-3 with 4-(2-bromoethyl)morpholine)). LRMS (ES+) m/z 818.5 (M+H)+.

197

Step 2: (1R,2S)-1-[({(3aR,7S,10S,12R,24aR)-7-tert-butyl-19-[2-(morpholin-4-yl)ethoxy]-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinolin-10-yl}carbonyl)amino]-2-ethenylcyclopropanecarboxylic acid

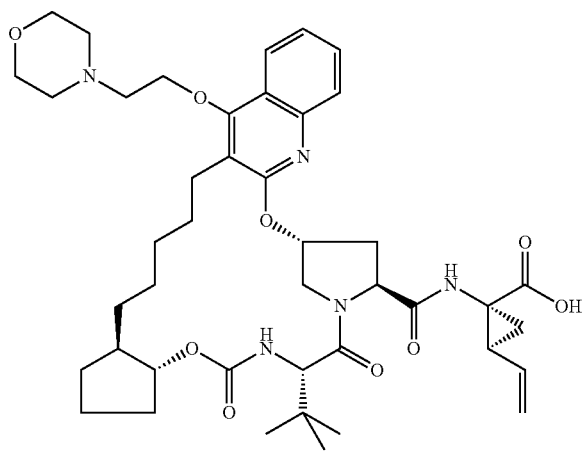 [SMILES: C=C[C@@H]1C[C@]1(NC(=O)[C@@H]1C[C@@H]2CN1C(=O)[C@H](C(C)(C)C)NC(=O)O[C@@H]1CCC[C@H]1CCCCCc1c(nc3ccccc3c1OCCN1CCOCC1)O2)C(=O)O]

The title compound was prepared using the same method as Example 96, Step 3 but the reaction was stirred for 18 hours. LRMS (ES+) m/z 790.60 (M+H)+.

198

Step 3: (3aR,7S,10S,12R,24aR)-7-tert-butyl-N-{(1R,2S)-1-[(dimethylsulfamoyl)carbamoyl]-2-ethenylcyclopropyl}-19-[2-(morpholin-4-yl)ethoxy]-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide

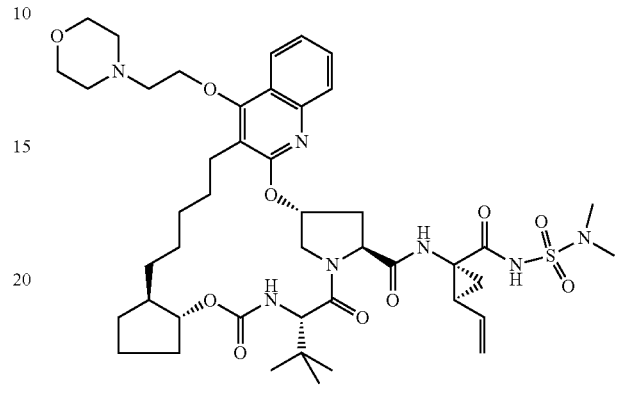

To a solution of the acid from Step 2 (46.6 mg) and N,N-dimethylsulfuric diamide (29.3 mg) in DMF (1 mL) was added DIPEA (52 DMAP (28.8 mg) and DBU (40 µL). The reaction mixture was stirred 5 minutes before adding HATU (26.9 mg). The mixture was stirred at room temperature for 18 hours. The reaction mixture was diluted with Et$_2$O and ethyl acetate and quenched with water and acetic acid (pH=4). The mixture was extracted with diethyl ether (3×). The combined organic phases were washed with water (3×), dried over magnesium sulfate, filtered and concentrated. Purification by flash chromatography (ISCO, 0 to 10% methanol in dichloromethane) afforded the desired product (34.2 mg). LRMS (ES+) m/z 896.50 (M+H)+. By following the procedures outlined in Example 106 and using the appropriate reagent (depicted below the structure as Rg.), the following compounds were prepared.

| Ex. | Structure | Name | LRMS (M + H)+ |
|---|---|---|---|
| 107 | ![structure with Rg. azetidine-1-sulfonamide] | (3aR,7S,10S,12R,24aR)-N-{(1R,2S)-1-[(azetidin-1-ylsulfonyl)carbamoyl]-2-ethenylcyclopropyl}-7-tert-butyl-19-[2-(morpholin-4-yl)ethoxy]-5,8-dioxo-1,2,3,3a,5,6,7,8,11,12,20,21,22,23,24,24a-hexadecahydro-10H-9,12-methanycyclopenta[18,19][1,10,3,6]dioxadiazacyclononadecino[11,12-b]quinoline-10-carboxamide | 908.50 |

-continued

| Ex. | Structure | Name | LRMS (M + H)+ |
|---|---|---|---|
| 108 | Rg. 1-(2-hydroxy propan-2-yl) cyclopropane sulfonamide (Intermediate A13) | (3aR,7S,10S,12R,24aR)-7-tert-butyl-N-[(1R,2S)-2-ethenyl-1-({[1-(2-hydroxy propan-2-yl)cyclopropyl]sulfonyl}carbamoyl)cyclopropyl]-19-[2-(morpholin-4-yl)ethoxy]-5,8-dioxo-1,2,3,3a,5,6,7,8,11,12,20,21,22,23,24,24a-hexadeca hydro-10H-9,12-methanocyclopenta[18,19][1,10,3,6]dioxadiaza-cyclononadecino[11,12-b]quinoline-10-carboxamide | 951.40 |
| 109 | Rg. pyrrolidine-1-sulfonamide | (3aR,7S,10S,12R,24aR)-7-tert-butyl-N-{(1R,2S)-2-ethenyl-1-[(pyrrolidin-1-ylsulfonyl)carbamoyl]cyclopropyl}-19-[2-(morpholin-4-yl)ethoxy]-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 922.45 |
| 110 | Rg. piperidine-1-sulfonamide | (3aR,7S,10S,12R,24aR)-7-tert-butyl-N-{(1R,2S)-2-ethenyl-1-[(piperidin-1-yl sulfonyl)carbamoyl]cyclopropyl}-19-[2-(morpholin-4-yl)ethoxy]-5,8-dioxo-1,2,3,3a,5,6,7,8,11,12,20,21,22,23,24,24a-hexadecahydro-10H-9,12-methanocyclopenta[18,19][1,10,3,6]dioxadiaza-cyclononadecino[11,12-b]quinoline-10-carboxamide | 936.40 |

-continued

| Ex. | Structure | Name | LRMS (M + H)+ |
|---|---|---|---|
| 111 | 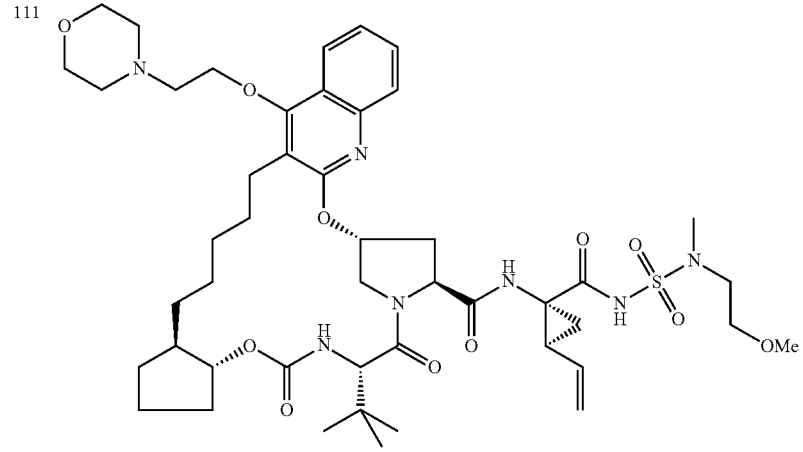 Rg. N-(2-methoxyethyl)-N-methylsulfuric diamide[1] | (3aR,7S,10S,12R,24aR)-7-tert-butyl-N-[(1R,2S)-2-ethenyl-1-{[(2-methoxyethyl)(methyl)sulfamoyl]carbamoyl}cyclopropyl]-19-[2-(morpholin-4-yl)ethoxy]-5,8-dioxo-1,2,3,3a,5,6,7,8,11,12,20,21,22,23,24,24a-hexadecahydro-10H-9,12-methano-cyclopenta[18,19][1,10,3,6]dioxadiazacyclononadecino[11,12-b]quinoline-10-carboxamide | 940.45 |
| 112 | 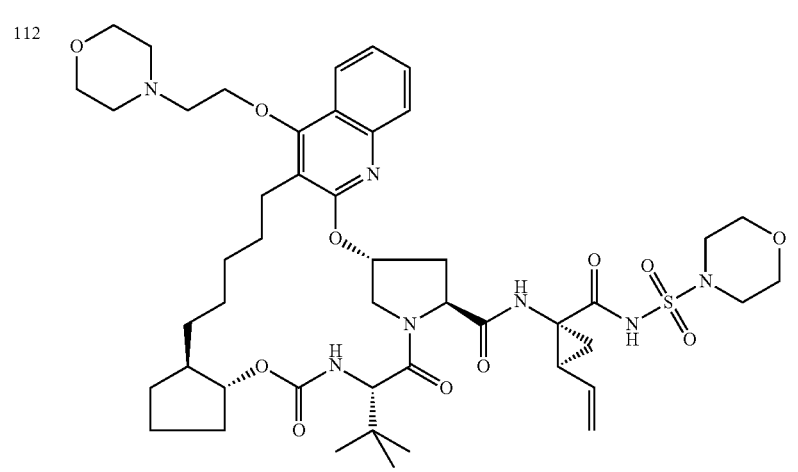 Rg. morpholine-4-sulfonamide | (3aR,7S,10S,12R,24aR)-7-tert-butyl-N-{(1R,2S)-2-ethenyl-1-[(morpholin-4-ylsulfonyl)carbamoyl]cylcopropyl}-19-[2-(morpholin-4-yl)ethoxy]-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoline-10-carboxamide | 938.35 |

[1](See International Patent Application Publication No.: WO2003/029226)

Example 113

(1aR,5S,8S,10R,22aR)-5-tert-butyl-N-[(1R,2S)-2-ethenyl-1-{[(1-methylcyclopropyl)sulfonyl]carbamoyl}cyclopropyl]-17-[2-(morpholin-4-yl)ethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

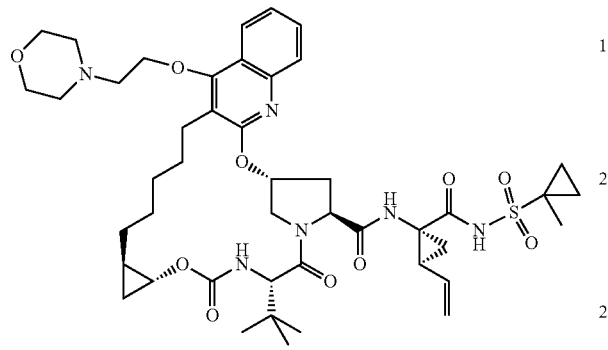

Step 1: 1-tert-butyl 2-methyl(2S,4R)-4-{[4-(benzyloxy)-3-bromoquinolin-2-yl]oxy}pyrrolidine-1,2-dicarboxylate

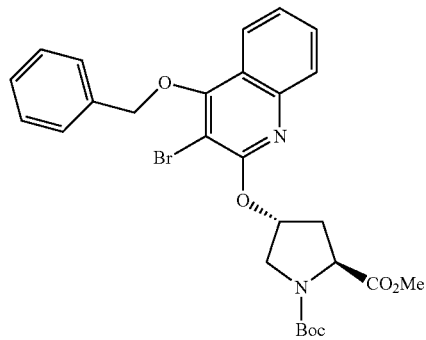 [SMILES: COC(=O)[C@@H]1C[C@@H](Oc2nc3ccccc3c(OCc3ccccc3)c2Br)CN1C(=O)OC(C)(C)C]

To a 0° C. solution of triphenylphosphine (2.54 g) in THF (75 ml) was added dropwise diisopyl azodicarboxylate (1.820 ml). The resulting mixture was stirred at 0° C. for 10 minutes then 1-tert-butyl 2-methyl(2S,4S)-4-hydroxypyrrolidine-1,2-dicarboxylate (2.01 g) followed by intermediate C6 (2.06 g) were added to the mixture. The mixture was stirred another 15 minutes at 0° C. then allowed to reach room temperature and stirred for 2 hours. Silica gel was added and the adsorbed product was purified by flash chromatography (ISCO) to provide the desired product (2.88 g). LRMS (ES+) ink 557.0 (M+H)$^+$.

Step 2: N-({[(1R,2R)-2-{5-[4-(benzyloxy)-2-{[(3R,5S)-1-(tert-butoxycarbonyl)-5-(methoxycarbonyl)pyrrolidin-3-yl]oxy}quinolin-3-yl]pent-4-yn-1-yl}cyclopropyl]oxy}carbonyl)-3-methyl-L-valine

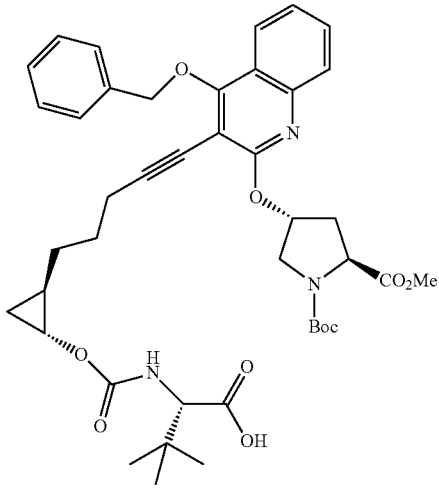 [SMILES: COC(=O)[C@@H]1C[C@@H](Oc2nc3ccccc3c(OCc3ccccc3)c2C#CCCC[C@@H]2C[C@H]2OC(=O)N[C@H](C(=O)O)C(C)(C)C)CN1C(=O)OC(C)(C)C]

PdCl$_2$(MeCN)$_2$ (51 mg), tri-t-butylphosphonium tetrafluoroborate (170 mg), K$_2$CO$_3$ (1.35 g) and intermediate B10 (2.43 g) were added to a reaction flask. The reaction mixture was degassed and refilled with nitrogen (3×). In another flask, bromide from step 1 (2.18 g) was dissolved in 33 mL acetonitrile. This solution was degassed and refilled with nitrogen (3×). Then, this solution was added to the reaction mixture. The complete reaction mixture was degassed and refilled with nitrogen (3×) and stirred at 75° C. for 18 hours. After the reaction mixture was cooled back to room temperature, the acetonitrile was removed in vacuo. The crude reaction mixture was dissolved in ethyl acetate and 1N HCl was slowly added. The reaction mixture was extracted 3× with ethyl acetate. The combined organics were washed with brine, dried over sodium sulfate, filtered and concentrated. The crude mixture was used directly in the next step. LRMS (ES+) m/z 758.3 (M+H)$^+$.

Step 3: N-({[(1R,2R)-2-{5-[4-(benzyloxy)-2-{[(3R,5S)-5-(methoxycarbonyl)pyrrolidinium-3-yl]oxy}quinolin-3-yl]pent-4-yn-1-yl}cyclopropyl]oxy}carbonyl)-3-methyl-L-valine chloride

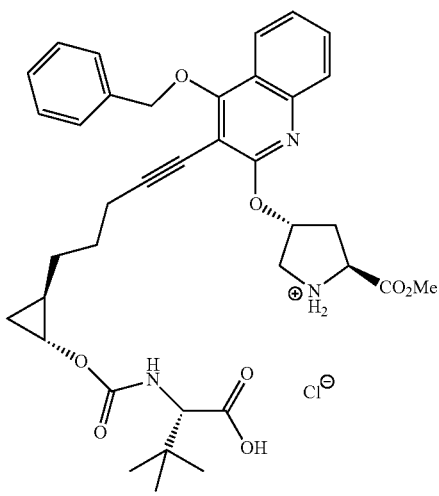 [SMILES: COC(=O)[C@@H]1C[C@@H](Oc2nc3ccccc3c(OCc3ccccc3)c2C#CCCC[C@@H]2C[C@H]2OC(=O)N[C@H](C(=O)O)C(C)(C)C)C[NH2+]1 ; [Cl-]]

The product from step 2 was dissolved in HCl in dioxanes (4M, 9.78 mL). The reaction mixture was stirred at room temperature for 1 hour. The solvent was removed in vacuo. The crude product was used directly in the next step. LRMS (ES+) m/z 658.5 (M+H)+.

Step 4: methyl (1aR,5S,8S,10R,22aR)-17-(benzyloxy)-5-tert-butyl-3,6-dioxo-18,19-didehydro-1,1a,3,4,5,6,9,10,20,21,22,22a-dodecahydro-8H-7,10-methanocyclopropa[18,19][1,10,3,6]dioxadiazacyclononadecino[11,12-b]quinoline-8-carboxylate

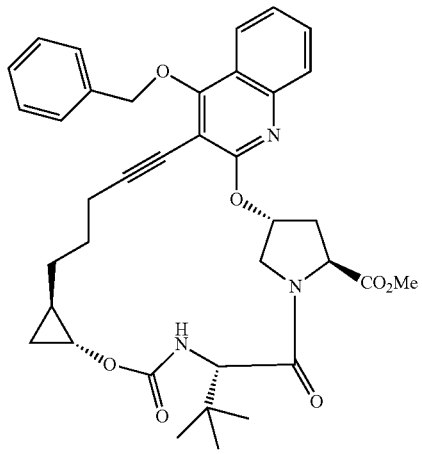 [SMILES: COC(=O)[C@@H]1C[C@@H]2CN1C(=O)[C@H](C(C)(C)C)NC(=O)O[C@@H]1C[C@H]1CCCC#Cc1c(nc3ccccc3c1OCc1ccccc1)O2]

To a solution of the product of step 3 in DMF (52 mL) at 0° C. was added DIPEA (3.1 mL) and HATU (1.64 g). The mixture was stirred at room temperature for 2 hours until disappearance of the starting material. The reaction mixture was diluted with Et$_2$O and quenched with water and HCl (1N). The mixture was extracted (3×) with ether. The combined organic phases were washed with water then brine, dried over sodium sulfate, filtered and concentrated. Purification by flash chromatography (ISCO, 0 to 100% ethyl acetate in hexanes) afforded the desired product (1.3 g). LRMS (ES+) m/z 640.45 (M+H)+.

Step 5: methyl (1aR,5S,8S,10R,22aR)-5-tert-butyl-17-hydroxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

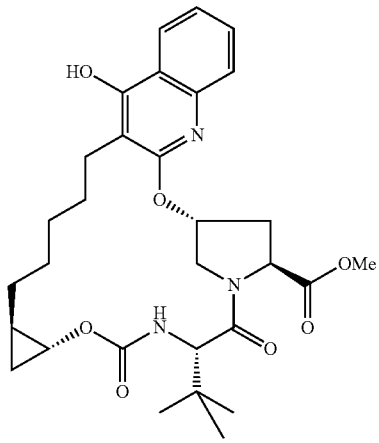 [SMILES: COC(=O)[C@@H]1C[C@@H]2CN1C(=O)[C@H](C(C)(C)C)NC(=O)O[C@@H]1C[C@H]1CCCCCc1c(nc3ccccc3c1O)O2]

The title compound was prepared using the same method as Example 96, Step 1. The reaction was stirred for 4 days at room temperature and additional Pd/C (1 mol %) was added after the third day. LRMS (ES+) m/z 554.35 (M+H)+.

Step 6: methyl (1aR,5S,8S,10R,22aR)-5-tert-butyl-17-[2-(morpholin-4-yl)ethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

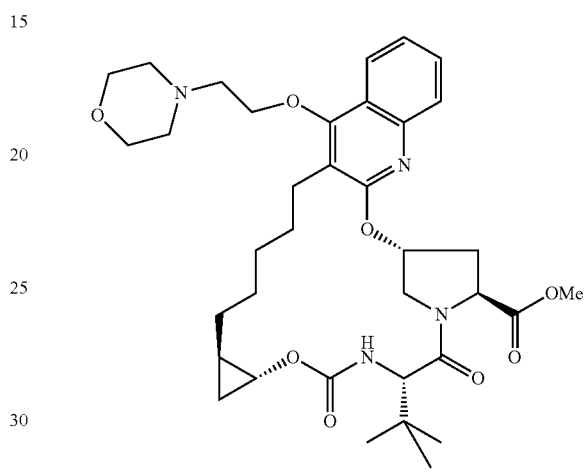

The title compound was prepared using the same method as described in Example 42. LRMS (ES+) m/z 667.45 (M+H)+.

Step 7: (1aR,5S,8S,10R,22aR)-5-tert-butyl-17-[2-(morpholin-4-yl)ethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylic acid

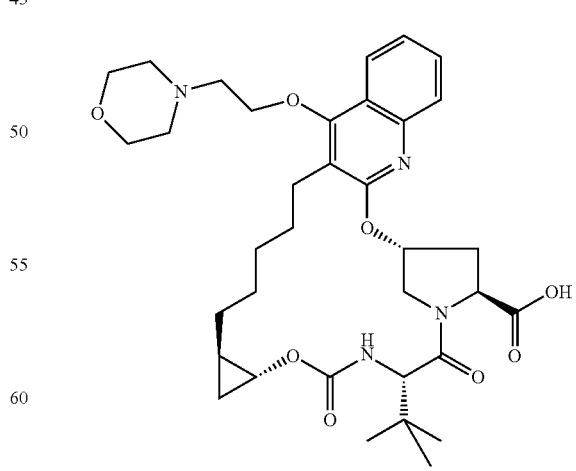

The title compound was prepared using the same method as described in Example 96, Step 3. LRMS (ES+) m/z 653.50 (M+H)+.

Step 8: (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[2-(morpholin-4-yl)ethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

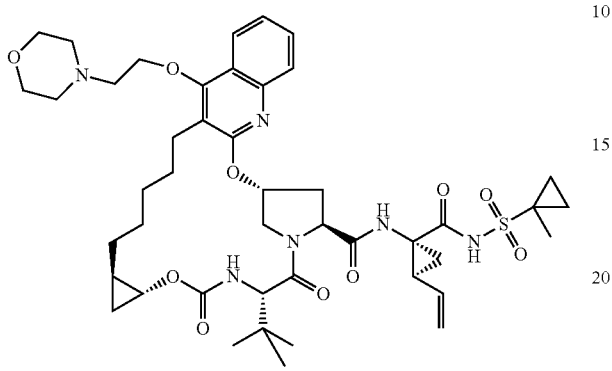

The title compound was prepared using the same method as Example 1, Step 6 with intermediate A2. Purification by flash chromatography (ISCO, 0 to 10% methanol in DCM) afforded the desired product. LRMS (ES+) m/z 879.40 $(M+H)^+$.

Examples 114-130

By following the procedures outlined in Example 113 and using the appropriate A, B and C intermediates and reagent (depicted below the structure as Int. and Rg., respectively), the following compounds were prepared.

| Ex | Structure | Name | LRMS $(M + H)^+$ |
|---|---|---|---|
| 114 | Int. A2, B10, C6<br>Rg. 3-chloro-N,N-dimethylpropan-1-amine hydrochloride | (1aR,5S,8S,10R,22aR)-5-tert-butyl-17-[3-(dimethylamino)propoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 851.50 |

| Ex | Structure | Name | LRMS (M + H)+ |
|---|---|---|---|
| 115 | Int. A2, B10, C6<br>Rg. 1-(3-chloro propyl)piperidine hydrochloride | (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-[3-(piperidin-1-yl)propoxy]-1,1a,3,4,5,6,9,10,18,19,20,21,22,22a-tetradeca hydro-8H-7,10-methano cyclopropa[18,19][1,10,3,6]dioxadiazacyclononadecino[11,12-b]quinoline-8-carboxamide | 891.3 |
| 116 | Int. A2, B10, C6<br>Rg. 4-(3-bromo propyl)morpholine | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[3-(morpholin-4-yl)propoxy]-3,6-dioxo-1,1a,3,4,5,6,9,10,18,19,20,21,22,22a-tetradeca hydro-8H-7,10-methanocyclopropa[18,19][1,10,3,6]dioxadiazacyclononadecino[11,12-b]quinoline-8-carboxamide | 893.50 |
| 117 | Int. A2, B10, C6<br>Rg. 1-(3-bromo propyl)pyrrolidine hydrochloride | (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-[3-(pyrrolidin-1-yl)propoxy]-1,1a,3,4,5,6,9,10,18,19,20,21,22,22a-tetradeca hydro-8H-7,10-methano cyclopropa[18,19][1,10,3,6]dioxadiazacyclononadecino[11,12-b]quinoline-8-carboxamide | 877.45 |

| Ex | Structure | Name | LRMS (M + H)+ |
|---|---|---|---|
| 118 | Int. A2, B10, C6<br>Rg. 1-(3-bromo propyl)pyrrolidin-2-one | (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-[3-(2-oxopyrrolidin-1-yl)propoxy]-1,1a,3,4,5,6,9,10,18,19,20,21,22,22a-tetradeca hydro-8H-7,10-methano cyclopropa[18,19][1,10,3,6]dioxadiazacyclononadecino[11,12-b]quinoline-8-carboxamide | 891.40 |
| 119 | Int. A2, B10, C6<br>Rg. Methyl iodide | (1aR,5S,8S,10R,22aR)-5-tert-butyl-N-[(1R,2S)-2-ethenyl-1-{[1-methylcyclopropyl)sulfonyl]carbamoyl}cyclopropyl]-17-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 780.40 |
| 120 | Int. A2, B10, C6<br>Rg. None | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-hydroxy-3,6-dioxo-1,1a,3,4,5,6,9,10,18,19,20,212,22,22a-tetradeca hydro-8H-7,10-methanocyclopropa[18,19][1,10,3,6]dioxadiazacyclo-nonadecino[11,12-b]quinoline-8-carboxamide | 766.45 |

| Ex | Structure | Name | LRMS (M + H)+ |
|---|---|---|---|
| 121 | 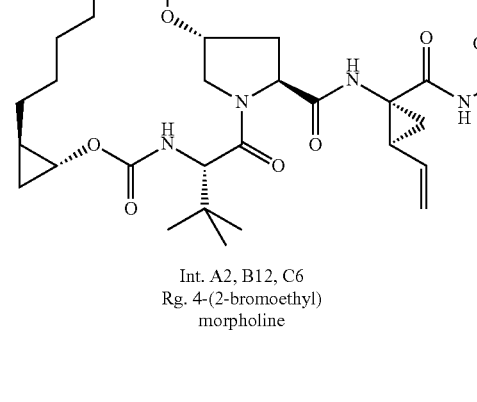<br>Int. A2, B12, C6<br>Rg. 4-(2-bromoethyl) morpholine | (1aR,5S,8S,10R,22aR)-5-cyclopentyl-N-[(1R,2S)-2-ethenyl-1-{[(1-methylcyclopropyl)sulfonyl]carbamoyl}cyclopropyl]-17-[2-(morpholin-4-yl)ethoxy]-3,6-dioxo-1,1a,3,4,5,6,9,10,18,19,20,21,22,22a-tetradeca hydro-8H-7,10-methanocyclopropa[18,19][1,10,3,6]dioxadiazacyclononadecino[11,12-b]quinoline-8-carboxamide | 891.25 |
| 122 | 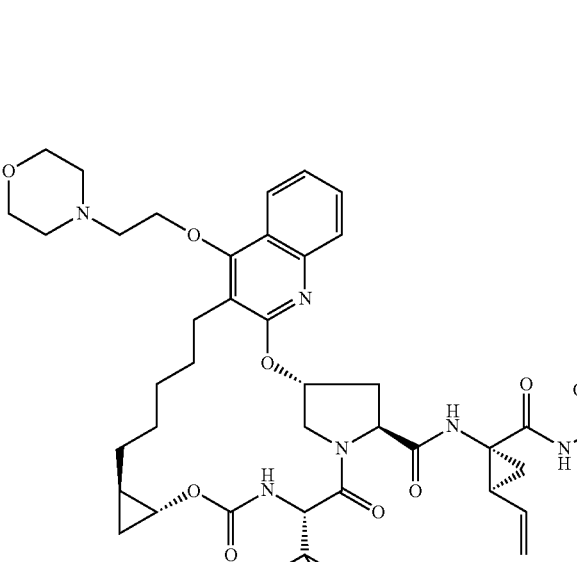<br>Int. A2, B11, C6<br>Rg. 4-(2-bromoethyl) morpholine | (1aR,5S,8S,10R,22aR)-5-cyclohexyl-N-[(1R,2S)-2-ethenyl-1-{[(1-methylcyclopropyl)sulfonyl]carbamoyl}cyclopropyl]-17-[2-(morpholin-4-yl)ethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 905.20 |

| Ex | Structure | Name | LRMS (M + H)+ |
|---|---|---|---|
| 123 | 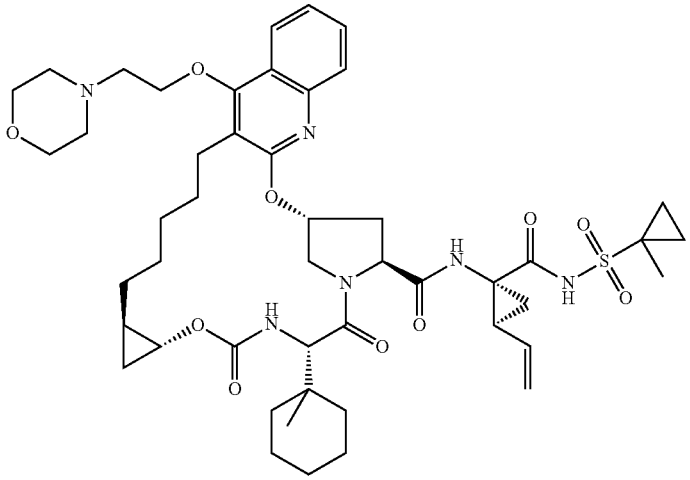<br>Int. A2, B13, C6<br>Rg. 4-(2-bromoethyl) morpholine | (1aR,5S,8S,10R,22aR)-N-[(1R,2S)-2-ethenyl-1-{[(1-methylcyclopropyl)sulfonyl]carbamoyl}cyclopropyl]-5-(1-methylcyclohexyl)-17-[2-(morpholin-4-yl)ethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 919.30 |
| 124 | 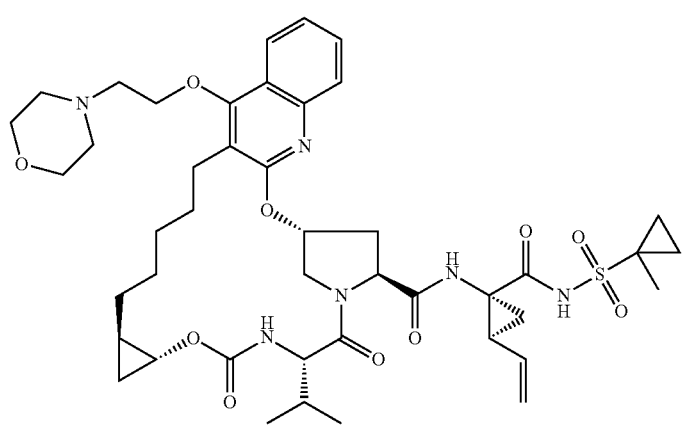<br>Int. A2, B14, C6<br>Rg. 4-(2-bromoethyl) morpholine | (1aR,5S,8S,10R,22aR)-N-[(1R,2S)-2-ethenyl-1-{[(1-methylcyclopropyl)sulfonyl]carbamoyl}cyclopropyl]-17-[2-(morpholin-4-yl)ethoxy]-3,6-dioxo-5-(propan-2-yl)-1,1a,3,4,5,6,9,10,18,19,20,21,22,22a-tetradeca hydro-8H-7,10-methano cyclopropa[18,19][1,10,3,6] dioxadiazacyclonona decino[11,12-b]quinoline-8-carboxamide | 865.30 |

| Ex | Structure | Name | LRMS (M + H)+ |
|---|---|---|---|
| 125 | 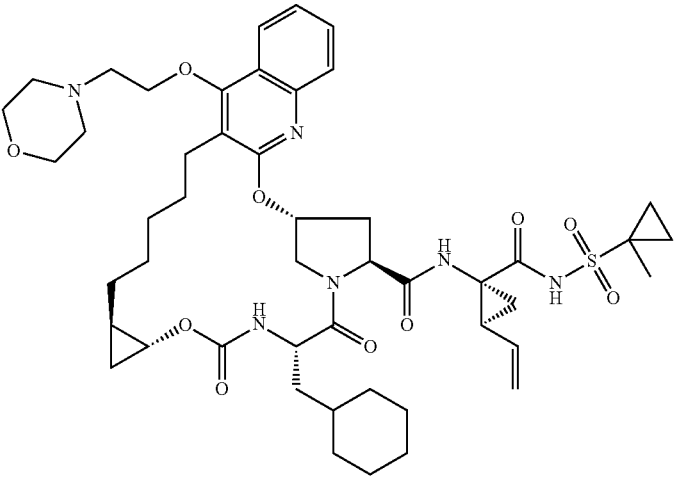<br>Int. A2, B15, C6<br>Rg. 4-(2-bromoethyl) morpholine | (1aR,5S,8S,10R,22aR)-5-(cyclohexyl methyl)-N-[(1R,2S)-2-ethenyl-1-{[(1-methylcyclopropyl)sulfonyl]carbamoyl}cyclopropyl]-17-[2-(morpholin-4-yl)ethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 919.30 |
| 126 | 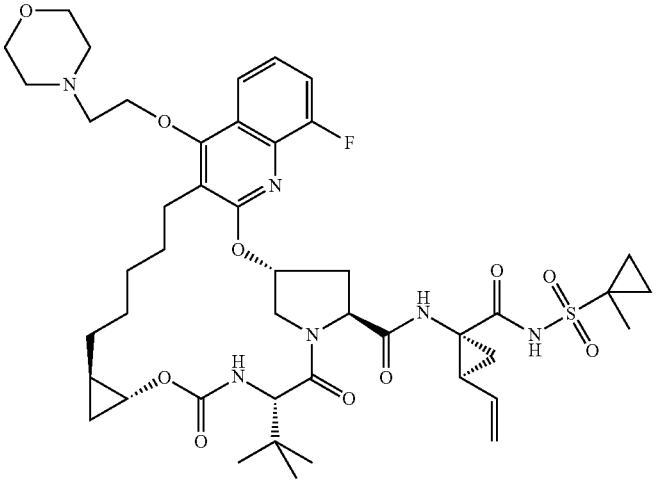<br>Int. A2, B10, C7<br>Rg. 4-(2-bromoethyl) morpholine | (1aR,5S,8S,10R,22aR)-5-tert-butyl-N-[(1R,2S)-2-ethenyl-1-{[(1-methylcyclopropyl)sulfonyl]carbamoyl}cyclopropyl]-13-fluoro-17-[2-(morpholin-4-yl)ethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 897.40 |

| Ex | Structure | Name | LRMS (M + H)+ |
|---|---|---|---|
| 127 | 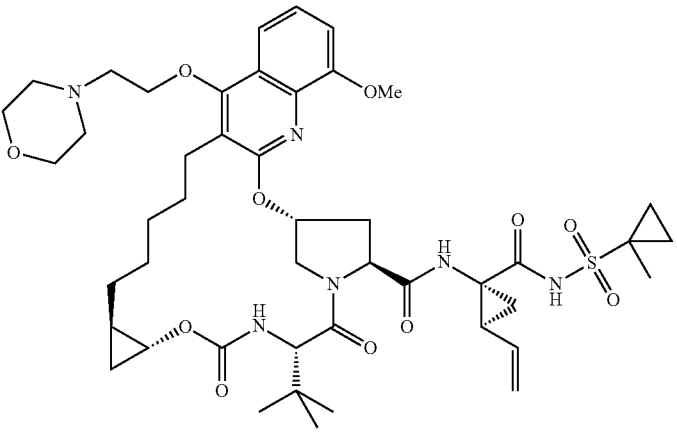<br>Int. A2, B10, C8<br>Rg. 4-(2-bromoethyl) morpholine | (1aR,5S,8S,10R,22aR)-5-tert-butyl-N-[(1R,2S)-2-ethenyl-1-{[(1-methylcyclopropyl)sulfonyl]carbamoyl}cyclopropyl]-13-methoxy-17-[2-(morpholin-4-yl)ethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 909.4 |
| 128 | 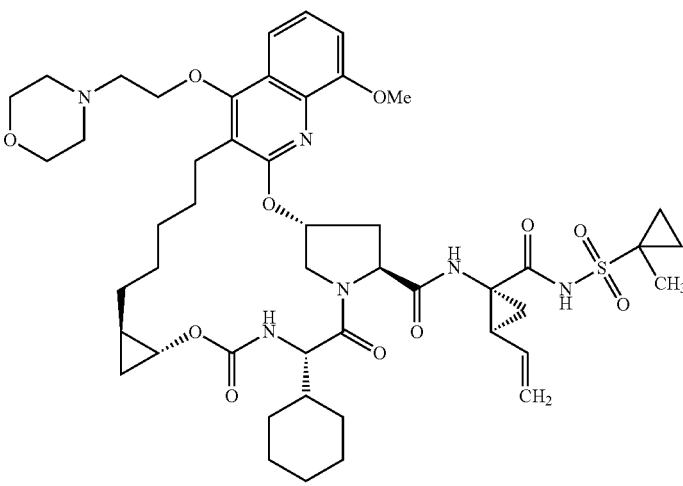<br>Int. A2, B11, C8<br>Rg. 4-(2-bromoethyl) morpholine | (1aR,5S,8S,10R,22aR)-5-cyclohexyl-N-[(1R,2S)-2-ethenyl-1-{[(1-methylcyclo propyl)sulfonyl]carbamoyl}cyclopropyl]-13-methoxy-17-[2-(morpholin-4-yl)ethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 935.2 |

-continued

| Ex | Structure | Name | LRMS (M + H)+ |
|----|-----------|------|---------------|
| 129 | 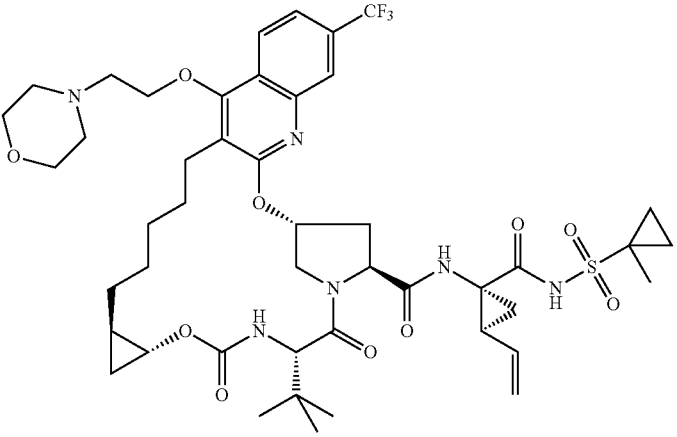<br>Int. A2, B10, C10<br>Rg. 4-(2-bromoethyl) morpholine | (1aR,5S,8S,10R,22aR)-5-tert-butyl-N-[(1R,2S)-2-ethenyl-1-{[(1-methylcyclo propyl)sulfonyl] carbamoyl}cyclopropyl]-17-[2-(morpholin-4-yl)ethoxy]-3,6-dioxo-14-(trifluoro methyl)-1,1a,3,4,5, 6,9,10,18,19,20,21,22,22a-tetradecahydro-8H-7,10-methanocyclopropa[18,19][1,10,3,6] dioxadiazacyclononadecino[11,12-b] quinoline-8-carboxamide | 947.5 |
| 130 | 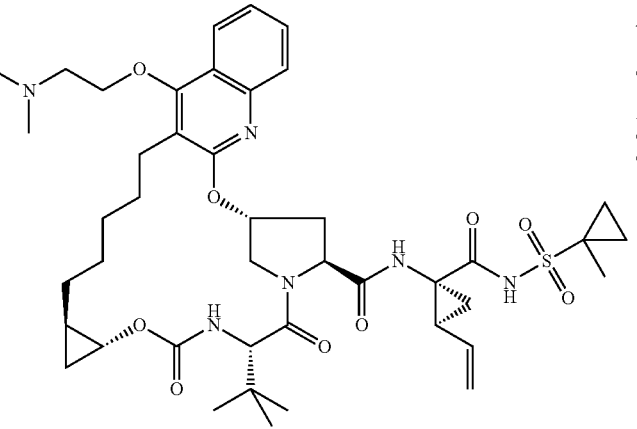<br>Int. A2, B10, C6<br>Rg. N-(2-bromoethyl)-N-methylaniline | (1aR,5S,8S,10R,22aR)-5-tert-butyl-N-[(1R,2S)-2-ethenyl-1-{[(1-methylcyclo propyl)sulfonyl] carbamoyl}cyclopropyl]-17-{2-[methyl(phenyl)amino]ethoxy}-3,6-dioxo-1,1a,3,4,5,6,9,10,18,19, cyclopropa[18,19][1,10,3,6] dioxadiazacyclononadecino [11,12-b]quinoline-8-carboxamide | 899.50 |

Example 131

(1aR,5S,8S,10R,22aR)-5-tert-butyl-N-[(1R,2S)-2-ethenyl-1-{[(1-methylcyclopropyl)sulfonyl]carbamoyl}cyclopropyl]-17-[3-(4-methylpiperazin-1-yl)propoxy]-3,6-dioxo-1,1a,3,4,5,6,9,10,18,19,20,21,22,22a-tetradecahydro-8H-7,10-methanocyclopropa[8,19][1,10,3,6]dioxadiazacyclononadecino[11,12-b]quinoline-8-carboxamide

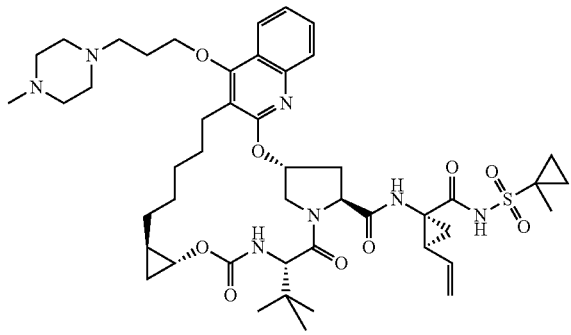 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3ccccc3c1OCCCN1CCN(C)CC1)O2)C(=O)NS(=O)(=O)C1(C)CC1]

The title compound was prepared using the same method as described in Example 42, using the 1-(3-bromopropyl)-4-methylpiperazine and (1aR,5S,8S,10R,22aR)-5-tert-butyl-N-[(1R,2S)-2-ethenyl-1-{[(1-methylcyclopropyl)sulfonyl]carbamoyl}cyclopropyl]-17-hydroxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide (Example 120). LRMS (ES+) m/z 906.40 (M+H)+.

Example 132

(1aR,5S,8S,10R,22aR)-5-tert-butyl-N-[(1R,2S)-2-ethenyl-1-{[(1-methylcyclopropyl)sulfonyl]carbamoyl}cyclopropyl]-17-[2-(morpholin-4-yl)ethoxy]-3,6-dioxo-14-(propan-2-yl)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

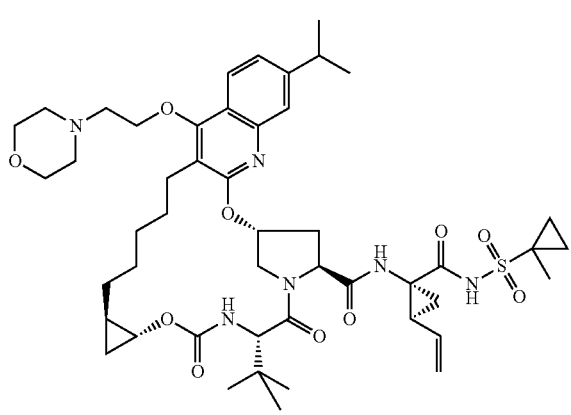 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3cc(C(C)C)ccc3c1OCCN1CCOCC1)O2)C(=O)NS(=O)(=O)C1(C)CC1]

The title compound was prepared using the same method as described in Example 42, using the 4-(2-bromoethyl)morpholine and (1aR,5S,8S,10R,22aR)-5-tert-butyl-N-[(1R,2S)-2-ethenyl-1-{[(1-methylcyclopropyl)sulfonyl]carbamoyl}cyclopropyl]-17-hydroxy-3,6-dioxo-14-(propan-2-yl)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide (synthesized in the same way as Example 120 but using intermediates A2, B10 and C9). LRMS (ES+) m/z 921.55 (M+H)+.

Example 133

(1aR,5S,8S,10R,22aR)-17-[3-(azetidin-1-yl)propoxy]-5-tert-butyl-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

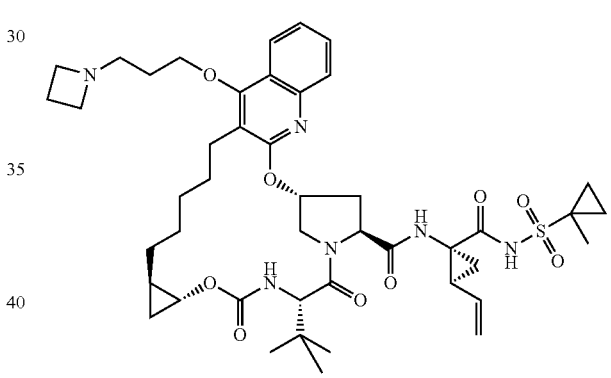

The title compound was prepared using the same method as described in Example 75, using the 3-(azetidin-1-yl)propan-1-ol and (1aR,5S,8S,10R,22aR)-5-tert-butyl-N-[(1R,2S)-2-ethenyl-1-{[(1-methylcyclopropyl)sulfonyl]carbamoyl}cyclopropyl]-17-hydroxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide (Example 120). LRMS (ES+) m/z 863.50 (M+H)+.

Examples 134-136

By following the procedures outlined in Example 133 and using the appropriate reagent (depicted below the structure as Rg.), the following compounds were prepared.

| Ex. | Structure | Name | LRMS (M + H)+ |
|---|---|---|---|
| 134 | Rg. 2-(piperiidn-1-yl)ethanol | (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-[2-(piperidin-1-yl)ethoxy]-1,1a,3,4,5,6,9,10,18,19,20,21,22,22a-tetradeca hydro-8H-7,10-methano cyclopropa[18,19][1,10,3,6]dioxadiazacyclo nonadecino[11,12-b]quinoline-8-carboxamide | 877.45 |
| 135 | Rg. 2-(pyrrolidin-1-yl)ethanol | (1aR,5S8S,10R,22aR)-5-tert-butyl-N-[(1R,2S)-2-ethenyl-1-{[1-methylcyclopropyl)sulfonyl]carbamoyl}cyclopropyl]-3,6-dioxo-17-[2-(pyrrolidin-1-yl)ethoxy]-1,1a,3,4,5,6,9,10,18,19,20,21,22,22a-tetradecahydro-8H-7,10-methano cyclopropa[18,19][1,10,3,6]dioxadiazacyclo nonadecino[11,12-b]quinoline-8-carboxamide | 863.50 |

| Ex. | Structure | Name | LRMS (M + H)+ |
|---|---|---|---|
| 136 | 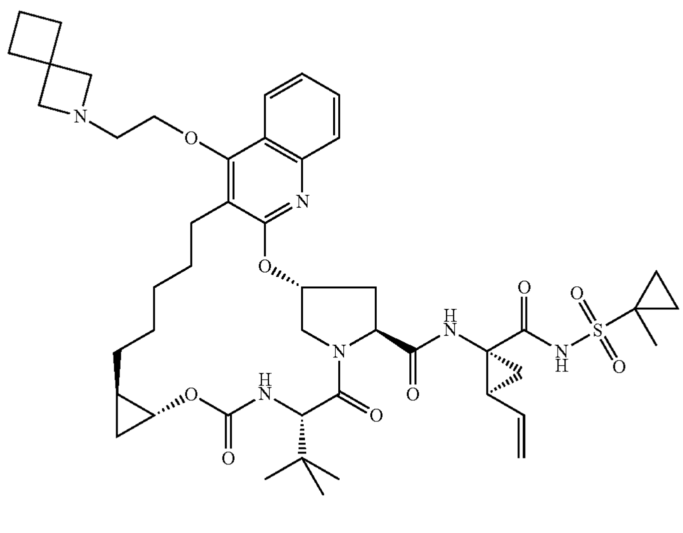 | (1aR,5S,8S,10R,22aR)-17-[2-(2-aza spiro[3.3]hept-2-yl)ethoxy]-5-tert-butyl-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 889.60 |
| | Rg. 2-(2-azaspiro[3.3]hept-2-yl)ethanol | | |

Example 137 tert-butyl (3S)-3-({[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}methyl)pyrrolidine-1-carboxylate

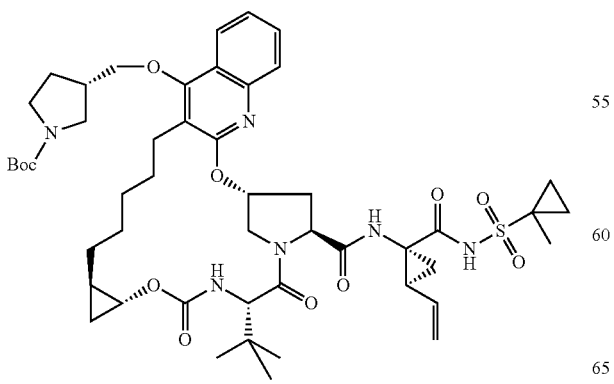

The title compound was prepared using the same method as described in Example 75, using the tert-butyl (3S)-3-(hydroxymethyl)pyrrolidine-1-carboxylate and (1aR,5S,8S,10R,22aR)-5-tert-butyl-N-[(1R,2S)-2-ethenyl-1-{[(1-methylcyclopropyl)sulfonyl]carbamoyl}cyclopropyl]-17-hydroxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide (Example 120). The method was slightly modified as triphenylphosphine was used instead of trimethylphosphine and the reaction was done at a 0.3 M concentration LRMS (ES+) m/z 949.5 (M+H)+.

Examples 138-142

By following the procedures outlined in Example 137 and using the appropriate reagent (depicted below the structure as Rg.), the following compounds were prepared.

| Ex. | Structure | Name | LRMS (M + H)+ |
|---|---|---|---|
| 138 | Rg. tert-butyl (3R)-3-(hydroxymethyl)pyrrolidine-1-carboxylate | tert-butyl (3R)-3-({[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradeca hydro-8H-7,10-methanocyclopropa[18,19][1,10,3,6]dioxadiazacyclononadecino[11,12-b]quinolin-17-yl]oxy}methyl)pyrrolidine-1-carboxylate | 949.5 |
| 139 | Rg. (1-ethylpiperidin-3-yl)methanol | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[(1-ethylpiperidin-3-yl)methoxy]-3,6-dioxo-1,1a,3,4,5,6,9,10,18,19,20,21,22,22a-tetradeca hydro-8H-7,10-methanocyclopropa[18,19][1,10,3,6]dioxadiazacyclononadecino[11,12-b]quinoline-8-carboxamide | 891.45 |

| Ex. | Structure | Name | LRMS (M + H)+ |
|---|---|---|---|
| 140 | Rg. (1,4-dimethyl piperazin-2-yl)methanol | (1ar,5S,8S,10R,22aR)-5-tert-butyl-17-[(1,4-dimethylpiperazin-2-yl)methoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 892.6 |
| 141 | Rg. (1-methylpyrrodin-3-yl)methanol | (1aR,5S,8S,10R,22aR)-5-tert-butyl-N-[(1R,2S)-2-ethenyl-1-{[(1-methyl cyclopropyl)sulfonyl]carbamoyl}cyclopropyl]-17-[(1-methyl pyrrolidin-3-yl)methoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 863.50 |

| Ex. | Structure | Name | LRMS (M + H)+ |
|---|---|---|---|
| 142 | Rg. tert-butyl 3-(hydroxymethyl)azetidine-1-carboxylate | tert-butyl 3-({[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradeca hydro-8H-7,10-methano cyclopropa[18,19][1,10,3,6]dioxadiazacyclononadecino[11,12-b]quinolin-17-yl]oxy}methyl)azetidine-1-carboxylate | 935.5 |

Example 143

(1aR,5S,8S,10R,22aR)-5-tert-butyl-N-[(1R,2S)-2-ethenyl-1-{[(1-methylcyclopropyl)sulfonyl]carbamoyl}cyclopropyl]-13-methoxy-3,6-dioxo-17-[3-(pyrrolidin-1-yl)propoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

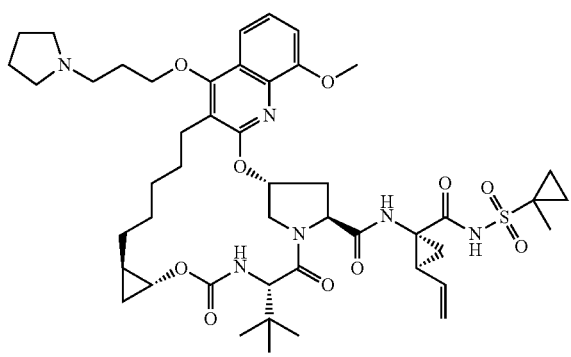 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3c(OC)cccc3c1OCCCN1CCCC1)O2)C(=O)NS(=O)(=O)C1(C)CC1]

Step 1: methyl (1aR,5S,8S,10R,22aR)-17-(3-bromopropoxy)-5-tert-butyl-13-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

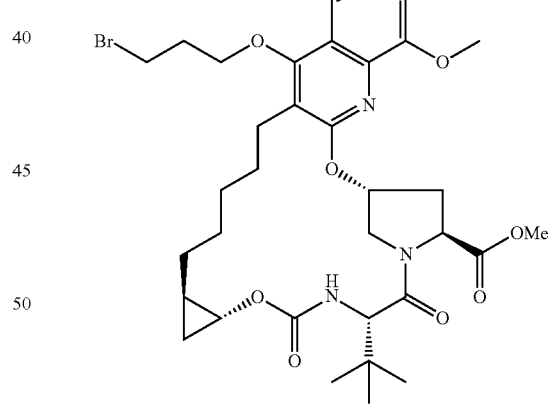

To a solution of methyl (1aR,5S,8S,10R,22aR)-5-tert-butyl-17-hydroxy-13-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate (253 mg) (prepared by the same method as Example 113, Steps 1-5 with intermediates B10 and C8) and 1,3-dibromopropane (500 µl) in DMF (5 ml) was added cesium carbonate (700 mg). After 90 minutes of stirring at room temperature, the reaction mixture was partitioned between water/brine 1:1 and ethyl acetate. The product was extracted twice with ethyl acetate and the combined organic phases were washed with water and brine, dried over sodium sulfate and evaporated. The crude residue was purified by flash chromatography (ISCO 10%-50% ethyl acetate in hexanes) to afford a white solid (231 mg). LRMS (ES+) m/z 704.30 (M+H)$^+$.

Step 2: methyl (1aR,5S,8S,10R,22aR)-5-tert-butyl-13-methoxy-3,6-dioxo-17-[3-(pyrrolidin-1-yl)propoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

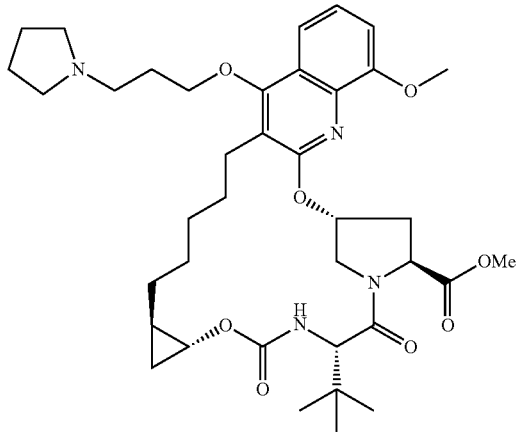 [SMILES: COC(=O)[C@@H]1C[C@@H]2CN1C(=O)[C@H](C(C)(C)C)NC(=O)O[C@@H]1C[C@H]1CCCCCc1c(nc3c(OC)cccc3c1OCCCN1CCCC1)O2]

To a solution of the product resulting from step 1 (72 mg) in DMSO (1.5 ml) were added pyrrolidine (85 μl) and DIPEA (25 μl). After 2 hours of stirring at 50° C., the reaction mixture was poured into water and the product was extracted twice with ethyl acetate. The combined organic phases were washed with water and brine, dried over sodium sulfate and evaporated. The crude product was used as such for the next step. LRMS (ES+) m/z 695.50 (M+H)$^+$.

Step 3: (1aR,5S,8S,10R,22aR)-5-tert-butyl-13-methoxy-3,6-dioxo-17-[3-(pyrrolidin-1-yl)propoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylic acid

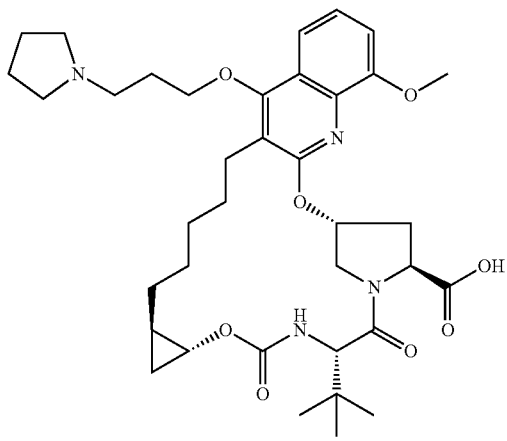 [SMILES: COc1cccc2c(OCCCN3CCCC3)c3c(nc12)O[C@@H]1C[C@@H](C(=O)O)N(C1)C(=O)[C@H](C(C)(C)C)NC(=O)O[C@@H]1C[C@H]1CCCCC3]

The title compound was prepared using the same method as described in Example 113, Step 7. LRMS (ES+) m/z 681.40 (M+H)$^+$.

Step 4: (1aR,5S,8S,10R,22aR)-5-tert-butyl-N-[(1R,2S)-2-ethenyl-1-{[(1-methylcyclopropyl)sulfonyl]carbamoyl}cyclopropyl]-13-methoxy-3,6-dioxo-17-[3-(pyrrolidin-1-yl)propoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

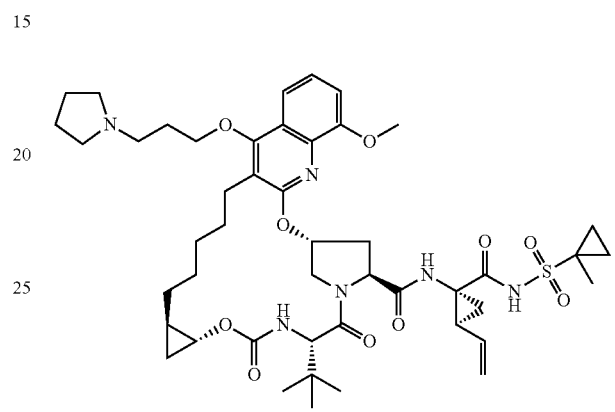

The title compound was prepared using the same method as described in Example 113, Step 8. Purification by flash chromatography (ISCO reverse phase, 15%-70% ACN in water (0.1% TFA buffer)) afforded the desired product (40.5 mg). LRMS (ES+) m/z 907.30 (M+H)$^+$.

Example 144

(1aR,5S,8S,10R,22aR)-5-tert-butyl-N-[(1R,2S)-2-ethenyl-1-{[(1-methylcyclopropyl)sulfonyl]carbamoyl}cyclopropyl]-17-[3-(1H-imidazol-1-yl)propoxy]-13-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

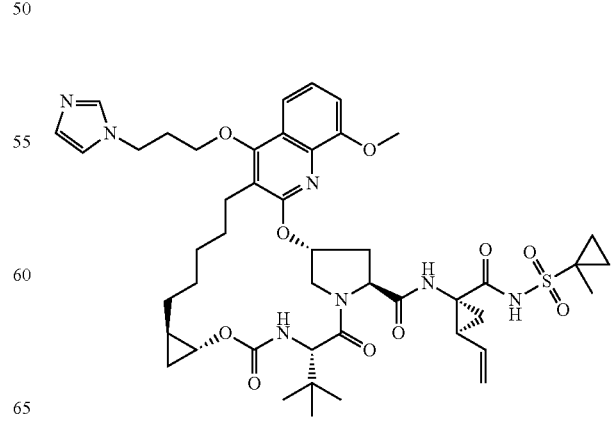

The title compound was prepared using the same method as described in Example 143 using imidazole. LRMS (ES+) m/z 904.45 (M+H)⁺.

Example 145

(1aR,5S,8S,10R,22aR)-5-tert-butyl-17-[3-(cyclopropylamino)propoxy]-N-[(1R,2S)-2-ethenyl-1-{[(1-methylcyclopropyl)sulfonyl]carbamoyl}cyclopropyl]-14-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

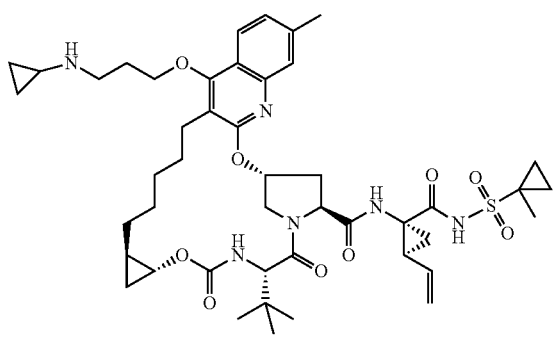 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3cc(C)ccc3c1OCCCNC1CC1)O2)C(=O)NS(=O)(=O)C1(C)CC1]

Step 1

(1aR,5S,8S,10R,22aR)-17-(3-bromopropoxy)-5-tert-butyl-N-[(1R,2S)-2-ethenyl-1-{[(1-methylcyclopropyl)sulfonyl]carbamoyl}cyclopropyl]-14-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

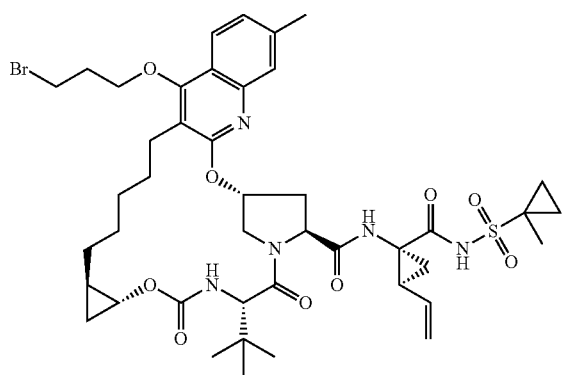 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3cc(C)ccc3c1OCCCBr)O2)C(=O)NS(=O)(=O)C1(C)CC1]

(1aR,5S,8S,10R,22aR)-5-Tert-butyl-N-[(1R,2S)-2-ethenyl-1-{[(1-methylcyclopropyl)sulfonyl]carbamoyl}cyclopropyl]-17-hydroxy-14-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide (synthesized by the method described for Example 120 using intermediates A2,B10,C11) was alkylated using the method for example 143, step 1. LRMS (ES+) m/z 900.30 (M+H)⁺.

Step 2: (1aR,5S,8S,10R,22aR)-5-tert-butyl-17-[3-(cyclopropylamino)propoxy]-N-[(1R,2S)-2-ethenyl-1-{[(1-methylcyclopropyl)sulfonyl]carbamoyl}cyclopropyl]-14-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

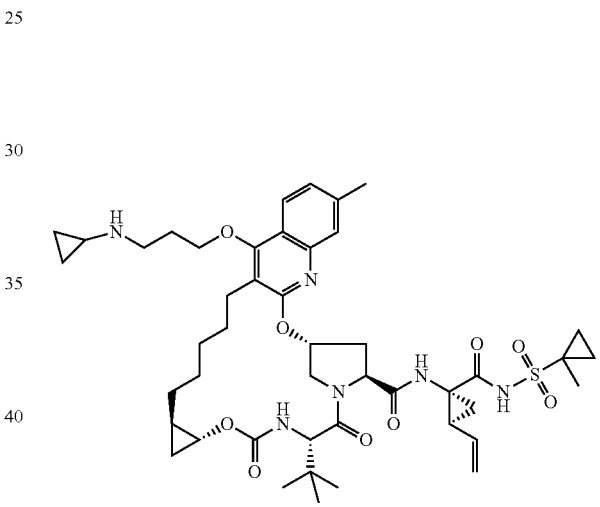

The title compound was prepared using the same method as described in Example 143, Step 2 using cyclopropyl amine. Purification by flash chromatography (ISCO reverse phase, 20%-80% ACN in water (0.1% TFA buffer)) afforded the desired product (40.5 mg). LRMS (ES+) m/z 877.30 (M+H)⁺.

Examples 146-209

By following the procedures outlined in Example 145 and using the appropriate A, B and C intermediates and reagent (depicted below the structure as Int. and Rg., respectively), the following compounds were prepared.

| Ex | Structure | Name | LRMS (M + H)+ |
|---|---|---|---|
| 146 | Int. A2, B10, C11<br>Rg. Pyrrolidine | (1aR,5S,8S,10R,22aR)-5-tert-butyl-N-[(1R,2S)-2-ethenyl-1-{[(1-methylcyclopropyl)sulfonyl]carbamoyl}cyclopropyl]-14-methyl-3,6-dioxo-17-[3-(pyrrolidin-1-yl)propoxy]-1,1a,3,4,5,6,9,10,18,19,20,21,22,22a-tetradecahydro-8H-7,10-methano cyclopropa[18,19][1,10,3,6] dioxadiazacyclonona decino[11,12-b]quinoline-8-carboxamide | 891.55 |
| 147 | Int. A2, B10, C11<br>Rg. Morpholine | (1aR,S,8S,10R,22aR)-5-tert-butyl-N-[(1R,2S)-2-ethenyl-1-{[(1-methylcyclopropyl)sulfonyl]carbamoyl}cyclopropyl]-14-methyl-17-[3-(morpholin-4-yl)propoxy]-3,6-dioxo-1,1a,3,4,5,6,9,10,18,19,20,21,22,22a-tetradecahydro-8H-7,10-methanocyclopropa[18,19][1,10,3,6]dioxadiaza cyclononadecino[11,12-b] quinoline-8-carboxamide | 907.45 |
| 148 | Int. A2, B10, C11<br>Rg. (3S)-(-)-3-(dimethylamino) pyrrolidine | (1aR,5S,8S,10R,22aR)-5-tert-butyl-17-{3-[(3S)-3-(dimethylamino)pyrrolidin-1-yl]propoxy}-N-[(1R,2S)-2-ethenyl-1-{[(1-methylcyclopropyl)ulfonyl]carbamoyl}cyclopropyl]-14-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 934.45 |
| 149 | Int. A2, B10, C11<br>Rg. Methylamine | (1aR,5S,8S,10R,22aR)-5-tert-butyl-N-[(1R,2S)-2-ethenyl-1-{[(1-methylcyclopropyl)sulfonyl]carbamoyl}cyclopropyl]-14-methyl-17-[3-(methylamino)propoxy]-3,6-dioxo-1,1a,3,4,5,6,9,10,18,19,20,21,22,22a-tetradecahydro-8H-7,10-methanocyclopropa[1,19][1,10,3,6]dioxadiazacyclonona decino[11,12-b]quinoline-8-carboxamide | 851.50 |

| Ex | Structure | Name | LRMS (M + H)+ |
|---|---|---|---|
| 150 | Int. A2, B10, C6<br>Rg. Morpholine, 1,4-dibromobutane | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[4-(morpholin-4-yl)butoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 907.50 |
| 151 | Int. A2, B10, C12<br>Rg. Pyrrolidine | (1aR,5S,8S,10R,22aR)-5-tert-butyl-N-[(1R,2S)-2-ethenyl-1-{[(1-methyl cyclopropyl)sulfonyl]carbamoyl}cyclopropyl]-14-fluoro-3,6-dioxo-17-[3-(pyrrolidin-1-yl)propoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 895.30 |
| 152 | Int. A2, B10, C12<br>Rg. Morpholine | (1aR,5S,8S,10R,22aR)-5-tert-butyl-N-[(1R,2S)-2-ethenyl-1-{[(1-methylcyclopropyl)sulfonyl]carbamoyl}cyclopropyl]-14-fluoro-17-[3-(morpholin-4-yl)propoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 911.35 |

| Ex | Name | LRMS (M + H)+ |
|---|---|---|
| 153 | (1aR,5S,8S,10R,22aR)-5-tert-butyl-N-[(1R,2S)-2-ethenyl-1-{[(1-methylcyclopropyl)sulfonyl]carbamoyl}cyclopropyl]-13-methoxy-17-[3-(2-oxa-6-azaspiro[3.3]hept-6-yl)propoxy]-3,6-dioxo-1,1a,3,4,5,6,9,10,18,19,20,21,22,22a-tetradeca hydro-8H-7,10-methanocyclopropa[18,19][1,10,3,6]dioxadiazacyclononadecino[11,12-b]quinoline-8-carboxamide | 935.50 |
| | Int. A2, B10, C8 Rg. 2-oxa-6-azaspiro[3.3]heptane | |
| 154 | (1aR,5S,8S,10R,22aR)-17-[3-(2-azaspiro[3.3]hept-2-yl)propoxy]-5-tert-butyl-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 903.40 |
| | Int. A2, B10, C6 Rg. 2-azaspiro[3.3]heptane | |
| 155 | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[3-(3-fluoro azetidin-1-yl)propoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 881.40 |
| | Int. A2, B10, C6 Rg. 3-fluoroazetidine hydrochloride | |

| Ex | Structure | Name | LRMS (M + H)+ |
|---|---|---|---|
| 156 | 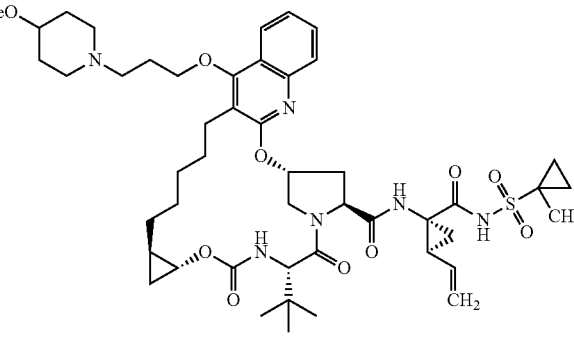<br>Int. A2, B10, C6<br>Rg. 4-methoxypiperidine | (1aR,5S,8S,10R,22aR)-5-tert-butyl-N-[(1R,2S)-2-ethenyl-1-{[(1-methyl cyclopropyl)sulfonyl]carbamoyl}cyclopropyl]-17-[3-(4-methoxypiperidin-1-yl)propoxy]-3,6-dioxo-1,1a,3,4,5,6,9,10,18,19,20,21,22,22a-tetradecahydro-8H-7,10-methanocyclopropa[18,19][1,10,3,6]dioxadiaza cyclononadecino[11,12-b]quinoline-8-carboxamide | 921.55 |
| 157 | 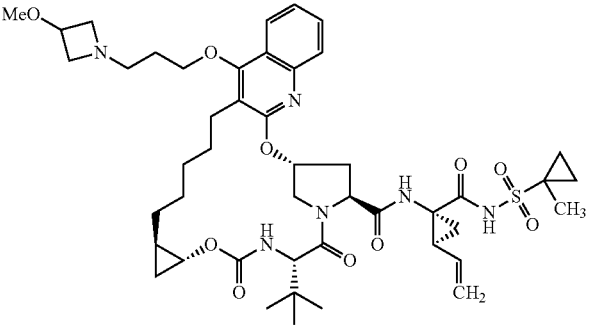<br>Int. A2, B10, C6<br>Rg. 3-methoxyazetidine hydrochloride | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[3-(3-methoxyazetidin-1-yl)propoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 893.50 |
| 158 | 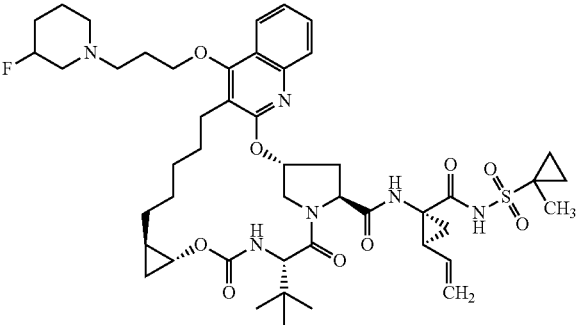<br>Int. A2, B10, C6<br>Rg. 3-fluoropiperidine hydrochloride | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[3-(3-fluoro piperidin-1-yl)propoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 909.45 |

| Ex | Structure | Name | LRMS (M + H)+ |
|---|---|---|---|
| 159 | Int. A2, B10, C9<br>Rg. Pyrrolidine | (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-14-(propan-2-yl)-17-[3-(pyrrolidin-1-yl)propoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 919.45 |
| 160 | Int. A2, B10, C9<br>Rg. Isopropyl amine | (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-14-(propan-2-yl)-17-[3-(propan-2-ylamino)propoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 907.45 |
| 161 | Int. A2, B10, C9<br>Rg. Morpholine | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[3-(morpholin-4-yl)propoxy]-3,6-dioxo-14-(propan-2-yl)-1,1a,3,4,5,6,9,10,18,19,20,21,22,22a-tetradecahydro-8H-7,10-methanocyclopropan[18,19][1,10,3,6]dioxadiazacyclononadecino[11,12-b]quinoline-8-carboxamide | 935.50 |

| Ex | Structure | Name | LRMS (M + H)+ |
|---|---|---|---|
| 162 | Int. A2, B10, C9<br>Rg. Thiomorpholine 1,1-dioxide | (1aR,5S,8S,10R,22aR)-5-tert-butyl-17-[3-(1,1-dioxidothiomorpholin-4-yl)propoxy]-N-[(1R,2S)-2-ethenyl-1-{[(1-methylcyclopropyl)sulfonyl]carbamoyl}cyclopropyl]-3,6-dioxo-14-(propan-2-yl)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 983.50 |
| 163 | Int. A2, B10, C9<br>Rg. 1-methylpiperazin-2-one hydrochloride | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[3-(4-methyl-3-oxopiperazin-1-yl)propoxy]-3,6-dioxo-14-(propan-2-yl)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 962.50 |
| 164 | Int. A2, B10, C9<br>Rg. (1S,4S)-2-oxa-5-azabicyclo[2.2.1]heptane hydrochloride | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-{3-[(1S,4S)-2-oxa-5-azabicyclo[2.2.1]hept-5-yl]propoxy}-3,6-dioxo-14-(propan-2-yl)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 947.50 |

| Ex | Structure | Name | LRMS (M + H)+ |
|---|---|---|---|
| 165 | Int. A2, B11 C6<br>Rg. 1-(methyl sulfonyl)piperazine | (1aR,5S,8S,10R,22aR)-5-cyclohexyl-N-[(1R,2S)-2-ethenyl-1-{[(1-methylcyclopropyl)sulfonyl]carbamoyl}cyclopropyl]-17-{3-[4-(methylsulfonyl)piperazin-1-yl]propoxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 996.3 |
| 166 | Int. A2, B11 C6<br>Rg. 3-(methyl sulfonyl)pyrrolidine | (1aR,5S,8S,10R,22aR)-5-cyclohexyl-N-[(1R,2S)-2-ethenyl-1-{[(1-methylcyclopropyl)sulfonyl]carbamoyl}cyclopropyl]-17-{3-[3-(methylsuflonyl)pyrrolidin-1-yl]propoxy}-3,6-dioxo-1,1a,3,4,5,9,10,18,19,20,21,22,22a-tetradecahydro-8H-7,10-methanocyclopropa[18,19][1,10,3,6]dioxadiazacyclononadecino[11,12-b]quinoline-8-carboxamide | 981.25 |
| 167 | Int. A2, B11 C6<br>Rg. 4-(trifluoro methyl)piperidine hydrochloride | (1aR,5S,8S,10R,22aR)-5-cyclohexyl-N-[(1R,2S)-2-ethenyl-1-{[(1-methylcyclopropyl)sulfonyl]carbamoyl}cyclopropyl]-3,6-dioxo-17-{3-[4-(trifluoromethyl)piperidin-1-yl]propoxy}-1,1a,3,4,5,6,9,10,18,19,20,21,22,22a-tetradecahydro-8H-7,1-methanocyclopropa[18,19][1,10,3,6]dioxadiazacyclononadecino[11,12-b]quinoline-8-carboxamide | 985.3 |

| Ex | Structure | Name | LRMS (M + H)+ |
|---|---|---|---|
| 168 | Int. A2, B11 C6<br>Rg. 1,4-oxazepane hydrochloride | (1aR,5S,8S,10R,22aR)-5-cyclohexyl-N-[(1R,2S)-2-ethenyl-1-{[(1-methylcyclopropyl)sulfonyl]carbamoyl}cyclopropyl]-17-[3-(1,4-oxazepan-4-yl)propoxy]-3,6-dioxo-1,1a,3,4,5,6,9,10,18,19,20,21,22,22a-tetradeca hydro-8H-7,10-methanocyclopropa[18,19][1,10,3,6]dioxadiazacyclononadecino[11,12-b]quinoline-8-carboxamide | 933.2 |
| 169 | Int. A2, B11 C6<br>Rg. (3R)-pyrrolidin-3-ol | (1aR,5S,8S,10R,22aR)-5-cyclohexyl-N-[(1R,2S)-2-ethenyl-1-{[(1-methylcyclopropyl)sulfonyl]carbamoyl}cyclopropyl]-17-{3-[(3R)-3-hydroxypyrrolidin-1-yl]propoxy}-3,6-dioxo-1,1a,3,4,5,6,9,10,18,19,20,21,22,22a-tetradeca hydro-8H-7,10-methanocyclopropa[18,19][1,10,3,6]dioxadiazacyclononadecino[11,12-b]quinoline-8-carboxamide | 919.30 |
| 170 | Int. A2, B11 C6<br>Rg. 4,4-difluoro piperidine hydrochloride | (1aR,5S,8S,10R,22aR)-5-cyclohexyl-17-[3-(4,4-difluoropiperidin-1-yl)propoxy]-N-[(1R,2S)-2-ethenyl-1-{[1-methyl cyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 953.20 |

| Ex | Structure | Name | LRMS (M + H)+ |
|---|---|---|---|
| 171 | 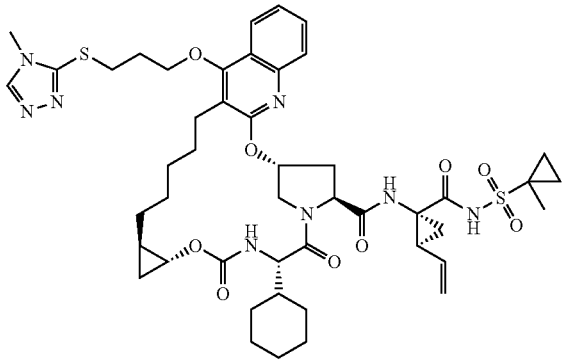<br>Int. A2, B11 C6<br>Rg. 4-methyl-4H-1,2,4-triazole-3-thiol | (1aR,5S,8S,10R,22aR)-5-cyclohexyl-N-[(1R,2S)-2-ethenyl-1-{[(1-methylcyclo propyl)sulfonyl]carbamoyl}cyclopropyl]-17-{3-[(4-methyl-4H-1,2,4-triazol-3-yl)sulfanyl]propoxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 947.50 |
| 172 | 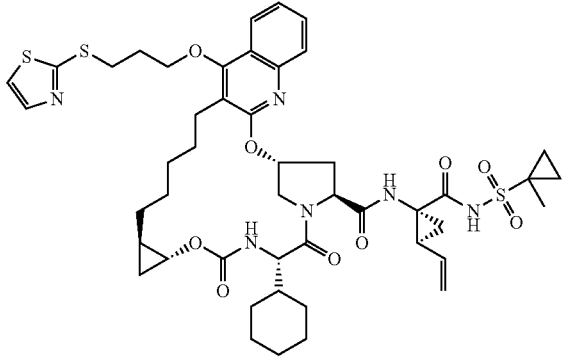<br>Int. A2, B11 C6<br>Rg. 1,3-thiazole-2-thiol | (1aR,5S,8S,10R,22aR)-5-cyclohexyl-N-[(1R,2S)-2-ethenyl-1-{[(1-methylcyclopropyl)sulfonyl]carbamoyl}cyclopropyl]-3,6-dioxo-17-[3-(1,3-thiazol-2-ylsulfonyl)propoxy]-1,1a,3,4,5,6,9,10,18,19,20,21,22,22a-tetradecahydro-8H-7,10-methanocyclo propa[18,19][1,10,3,6]dioxadiazacyclononadecino[11,12-b]quinoline-8-carboxamide | 949.30 |
| 173 | 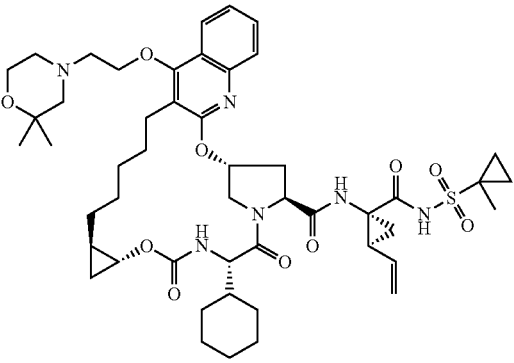<br>Int. A2, B10, C6<br>Rg. 2,2-dimethylmorpholine | (1aR,5S,8S,10R,22aR)-5-tert-butyl-17-[2-(2,2-dimethylmorpholin-4-yl)ethoxy]-N-[(1R,2S)-2-ethenyl-1-{[(1-methylcyclo propyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 907.45 |

| Ex | Structure | Name | LRMS (M + H)+ |
|---|---|---|---|
| 174 | Int. A2, B10, C6<br>Rg. azetidin-3-ol hydrochloride | (1aR,5S,8S,10R,22aR)-5-tert-butyl-N-[(1R,2S)-2-ethenyl-1-{[(1-methyl cyclopropyl)sulfonyl]carbamoyl}cyclopropyl]-17-[2-(3-hydroxyazetidin-1-yl)ethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 865.45 |
| 175 | Int. A2, B10, C6<br>Rg. 4-methylpiperidin-4-ol hydrochloride | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[2-(4-hydroxy-4-methylpiperidin-1-yl)ethoxy]-3,6-dioxo-1,1a,3,4,5,6,9,10,18,19,20,21,22,22a-tetradeca hydro-8H-7,10-methanocyclopropa[18,19][1,10,3,6]dioxadiazacyclononadecino[11,12-b]quinoline-8-carboxamide | 907.45 |
| 176 | Int. A2, B10, C6<br>Rg. Thiomorpholine 1,1-dioxide | (1aR,5S,8S,10R,22aR)-5-tert-butyl-17-[2-(1,1-dioxidothiomorpholin-4-yl)ethoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 927.40 |

-continued

| Ex | Structure | Name | LRMS (M + H)+ |
|---|---|---|---|
| 177 | Int. A2, B10, C6<br>Rg. Tert-butylamine | (1aR,5S,8S,10R,22aR)-5-tert-butyl-17-[2-(tert-butylamino)ethoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 865.45 |
| 178 | Int. A2, B10, C6<br>Rg. Cyclopropylamine | (1aR,5S,8S,10R,22aR)-5-tert-butyl-17-[2-(cyclopropylamino)ethoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 849.40 |
| 179 | Int. A2, B10, C6<br>Rg. 2-methoxy isopropylamine | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-{3-[(1-methoxypropan-2-yl)amino]propoxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 895.45 |

| Ex | Structure | Name | LRMS (M + H)+ |
|---|---|---|---|
| 180 | Int. A2, B10, C6<br>Rg. Cyclobutylamine | (1aR,5S,8S,10R,22aR)-5-tert-butyl-17-[3-(cyclobutylamino)propoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 877.45 |
| 181 | Int. A2, B10, C6<br>Rg. 4-amino tetrahydropyran | (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-[3-(tetrahydro-2H-pyran-4-ylamino)propoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 907.60 |
| 182 | Int. A2, B10, C6<br>Rg. Cyclopentylamine | (1aR,5S,8S,10R,22aR)-5-tert-butyl-17-[3-(cyclopentylamino)propoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 891.40 |

| Ex | Structure | Name | LRMS (M + H)+ |
|---|---|---|---|
| 183 | 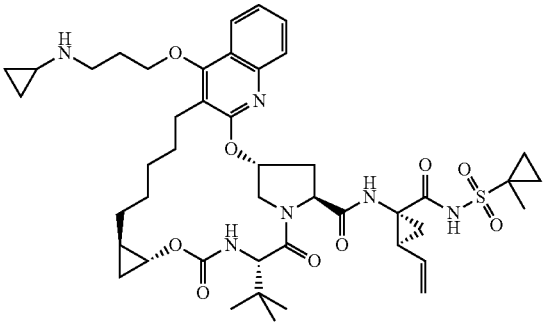<br>Int. A2, B10, C6<br>Rg.<br>Cyclopropylamine | (1aR,5S,8S,10R,22aR)-5-tert-butyl-17-[3-(cyclopropylamino)propoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradeca hydro-8H-7,10-methanocyclopropa[18,19][1,10,3,6]dioxadiazacyclononadecino[11,12-b]quinoline-8-carboxamide | 863.50 |
| 184 | 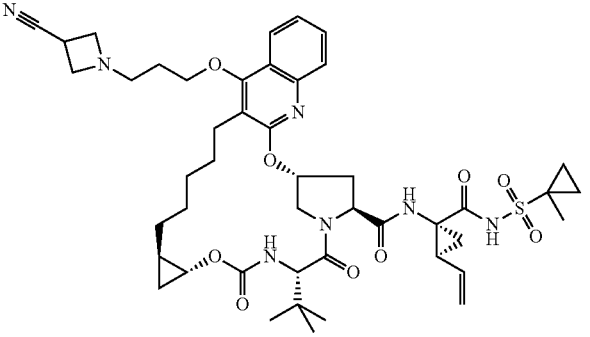<br>Int. A2, B10, C6<br>Rg. azetidine-3-carbonitrile | (1aR,5S,8S,10R,22aR)-5-tert-butyl-17-[3-(3-cyanoazetidin-1-yl)propoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 888.40 |
| 185 | 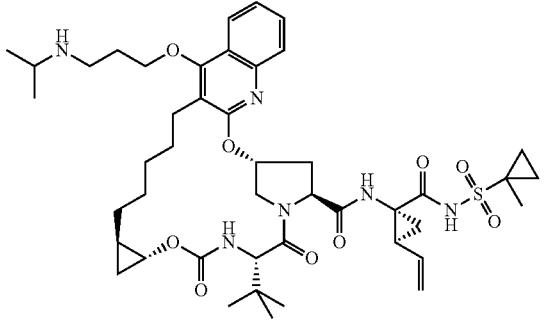<br>Int. A2, B10, C6<br>Rg. Isopropylamine | (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-[3-(propan-2-ylamino)propoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 865.45 |

| Ex | Structure | Name | LRMS (M + H)+ |
|---|---|---|---|
| 186 | 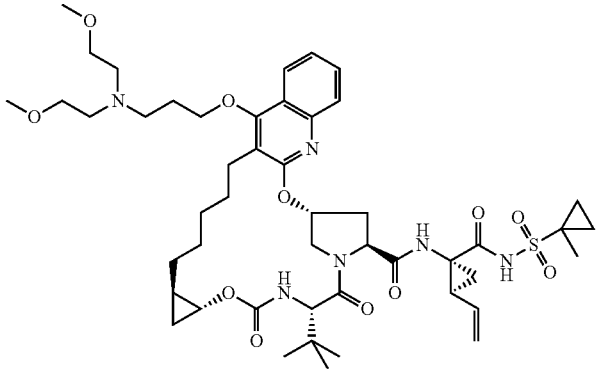<br>Int. A2, B10, C6<br>Rg. bis dimethoxyethylamine | (1aR,5S,8S,10R,22aR)-17-{3-[bis(2-methoxyethyl)amino]propoxy}-5-tert-butyl-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 939.55 |
| 187 | 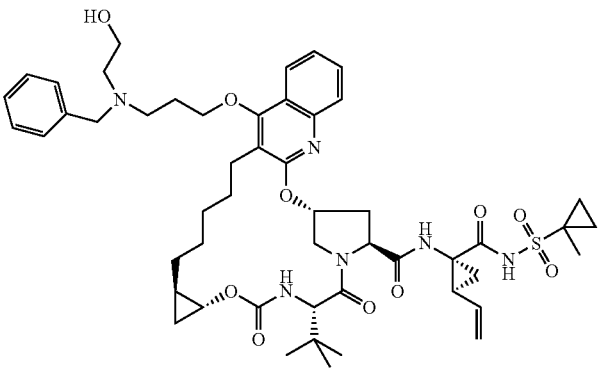<br>Int. A2, B10, C6<br>Rg. 2-(benzylamino)ethanol | (1aR,5S,8S,10R,22aR)-17-{3-[benzyl(2-hydroxyethyl)amino]propoxy}-5-tert-butyl-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 958 |
| 188 | 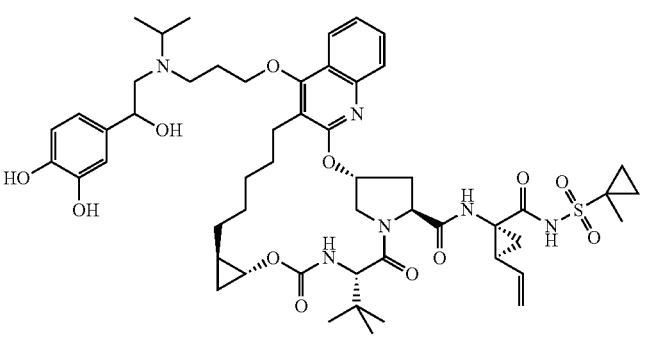<br>Int. A2, B10, C6<br>Rg. 4-[1-hydroxy-2-(propan-2-ylamino)ethyl]benzene-1,2-diol | (1aR,5S,8S,10R,22aR)-5-tert-butyl-17-(3-{[2-(3,4-dihydroxyphenyl)-2-hydroxyethyl](propan-2-yl)amino}propoxy)-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 1018 |

| Ex | Structure | Name | LRMS (M + H)+ |
|---|---|---|---|
| 189 | Int. A2, B10, C6<br>Rg. 2-(naphthalen-1-yl)ethanamine | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-(3-{[2-(naphthalen-1-yl)ethyl]amino}propoxy)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 978 |
| 190 | Int. A2, B10, C6<br>Rg. 2-(methylamino)-1-phenylpropan-1-ol | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-{3-[(1-hydroxy-1-phenylpropan-2-yl)(methyl)amino]propoxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 972 |
| 191 | Int. A2, B10, C6<br>Rg. N-methyl-1-(5-methyl-1H-benzimidazol-2-yl)methanamine | (1aR,5S,8S,10R,22aR)-5-tert-butyl-N-[(1R,2S)-2-ethenyl-1-{[(1-methyl cyclopropyl)sulfonyl]carbamoyl}cyclopropyl]-17-(3-{methyl[(5-methyl-1H-benzimidazol-2-yl)methyl]amino}propoxy)-3,6-dioxo-1,1a,3,4,5,6,9,10,18,19,20,21,22,22a-tetradecahydro-8H-7,10-methano cyclopropa[18,19][1,10,3,6]dioxadiazacyclononadecino[11,12-b]quinoline-8-carboxamide | 982 |

| Ex | Structure | Name | LRMS (M + H)+ |
|---|---|---|---|
| 192 | Int. A2, B10, C6<br>Rg. 2-(1H-benzimidazol-2-yl)-N-ethylethanamine | (1aR,5S,8S,10R,22aR)-17-(3-{[2-(1H-benzimidazol-2-yl)ethyl](ethyl)amino}propoxy)-5-tert-butyl-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 996 |
| 193 | Int. A2, B10, C6<br>Rg. 3-phenylazetidin-3-ol | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[3-(3-hydroxy-3-phenylazetidin-1-yl)propoxy]-3,6-dioxo-1,1a,3,4,5,6,9,10,18,19,20,21,22,22a-tetradeca hydro-8H-7,10-methanocyclopropa[18,19][1,10,3,6]dioxadiazacyclononadecino[11,12-b]quinoline-8-carboxamide | 956 |
| 194 | Int. A2, B10, C6<br>Rg. 2-oxa-6-azaspiro[3.3]heptane | (1aR,5S,8S,10R,22aR)-5-tert-butyl-N-[(1R,2S)-2-ethenyl-1-{[(1-methylcyclo propyl)sulfonyl]carbamoyl}cyclopropyl]-17-[3-(2-oxa-6-azaspiro[3.3]hept-6-yl)propoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 906 |

US 9,328,138 B2

271 272

-continued

| Ex | Structure | Name | LRMS (M + H)+ |
|---|---|---|---|
| 195 | 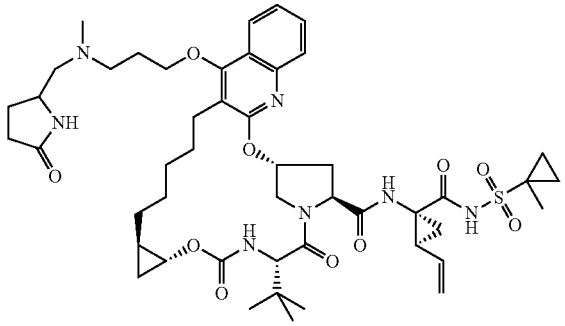<br>Int. A2, B10, C6<br>Rg. 5-[(methylamino)methyl]pyrrolidin-2-one | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-(3-{methyl[(5-oxopyrrolidin-2-yl)methyl]amino}propoxy)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 935 |
| 196 | 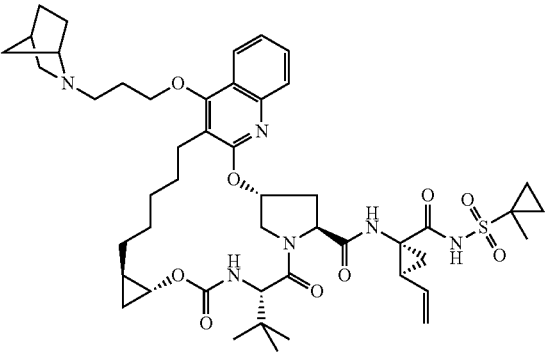<br>Int. A2, B10, C6<br>Rg. 2-azabicyclo[2.2.1]heptane | (1aR,5S,8S,10R,22aR)-17-[3-(2-azabicyclo[2.2.1]hept-2-yl)propoxy]-5-tert-butyl-N-[(1R,2S)-2-ethenyl-1-{[(1-methylcyclopropyl)sulfonyl]carbamoyl}cyclopropyl]-3,6-dioxo-1,1a,3,4,5,7,9,10,18,19,20,21,22,22a-tetradecahydro-8H-7,10-methanocyclopropa[18,19][1,10,3,6]dioxadiazacyclononadecino[11,12-b]quinoline-8-carboxamide | 904 |
| 197 | 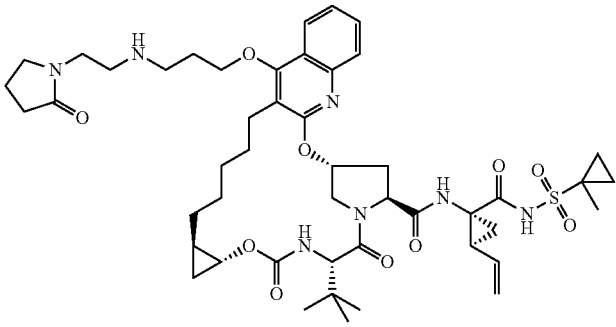<br>Int. A2, B10, C6<br>Rg. 1-(2-aminoethyl)pyrrolidin-2-one | (1aR,5S,8S,10R,22aR)-5-tert-butyl-N-[(1R,2S)-2-ethenyl-1-{[(1-methyl cyclopropyl)sulfonyl]carbamoyl}cyclopropyl]-3,6-dioxo-17-(3-{[2-(2-oxopyrrolidin-1-yl)ethyl]amino}propoxy)-1,1a,3,4,5,7,9,10,18,19,20,21,22,22a-tetra decahydro-8H-7,10-methanocyclopropa[18,19][1,10,3,6]dioxdiazacyclononadecino[11,12-b]quinoline-8-carboxamide | 935 |

| Ex | Structure | Name | LRMS (M + H)+ |
|---|---|---|---|
| 198 | Int. A2, B10, C6<br>Rg. 4-phenylbutan-1-amine | (1aR,5S,8S,10R,22aR)-5-tert-butyl-N-[(1R,2S)-2-ethenyl-1-{[(1-methylcyclopropyl)sulfonyl]carbamoyl}cylcopropoyl]-3,6-dioxo-17-{3-[(4-phenylbutyl)amino]propoxy}-1,1a,3,4,5,6,9,10,18,19,20,21,22,22a-tetra decahydro-8H-7,10-methanocyclopropa[18,19][1,10,3,6]dioxadiazacyclononadecino[11,12-b]quinoline-8-carboxamide | 956 |
| 199 | Int. A2, B10, C6<br>Rg. 5-[(methyl amino)methyl]-2,4-dihydro-3H-1,2,4-triazol-3-one | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-(3-{methyl[(5-oxo-4,5-dihydro-1H-1,2,4-triazol-3-yl)methyl]amino}propoxy)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 935 |
| 200 | Int. A2, B10, C6<br>Rg. 1-(1H-imidazol-2-yl)-N-methylmethanamine | (1aR,5S,8S,10R,22aR)-5-tert-butyl-N-[(1R,2S)-2-ethenyl-1-{[(1-methylcyclopropyl)sulfonyl]carbamoyl}cylcopropyl]-17-{3-[(1H-imidazol-2-yl methyl)(methyl)amino]propoxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 918 |

| Ex | Structure | Name | LRMS (M + H)+ |
|---|---|---|---|
| 201 | Int. A2, B10, C6<br>Rg. N-methy-1-(5-methyl-1H-imidazol-2-yl)methanamine | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-(3-{methyl[(5-methyl1H-imidazol-2-yl)methyl]amino}proopoxy)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 932 |
| 202 | Int. A2, B10, C6<br>Rg. N-methyl-1-(1H-pyrazol-5-yl)methanamine | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-{3-[methyl(1H-pyrazol-5-ylmethyl)amino]propoxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 918 |
| 203 | Int. A2, B10, C6<br>Rg. 5-fluoro-2-(piperidin-2-yl)-1H-benzimidazole | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-{3-[2-(5-fluoro-1H-benzimidazol-2-yl)piperidin-1-yl]propoxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 1026 |

| Ex | Structure | Name | LRMS (M + H)+ |
|---|---|---|---|
| 204 | Int. A2, B10, C6<br>Rg. 1,2,3,4-tetrahydronaphthalen-1-amine | (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-[3-(1,2,3,4-tetrahydronaphthalen-1-ylamino)propoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 954 |
| 205 | Int. A2, B10, C6<br>Rg. 2-(trifluoromethyl)piperazine | (1aR,5S,8S,10R,22aR)-5-tert-butyl-N-[(1R,2S)-2-ethenyl-1-{[(1-methylcyclopropyl)sulfonyl]carbamoyl}cylcopropyl]-3,6-dioxo-17-{3-[3-(trifluoromethyl)piperazin-1-yl]propoxy}-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 961 |
| 206 | Int. A2, B10, C6<br>Rg. 3,3-difluoroazetidine | (1aR,5S,8S,10R,22aR)-5-tert-butyl-17-[3-(3,3-difluoroazetidin-1-yl)propoxy]-N-[(1R,2S)-2-ethenyl-1-{[(1-methylcyclopropyl)sulfonyl]carbamoyl}cyclopropyl]-3,6-dioxo-1,1a,3,4,5,7,9,10,18,19,20,21,22,22a-tetradecahydro-8H-7,10-methanocyclopropa[18,19][1,10,3,6]dioxadiazacyclononadecino[11,12-b]quinoline-8-carboxamide | 900 |

-continued

| Ex | Structure | Name | LRMS (M + H)+ |
|---|---|---|---|
| 207 | Int. A2, B10, C6<br>Rg. 2-azaspiro[4.4]nonane | (1aR,5S,8S,10R,22aR)-17-[3-(2-azaspiro[4.4]non-2-yl)propoxy]-5-tert-butyl-N-[(1R,2S)-2-ethenyl-1-{[(1-methyl cylcopropyl)sulfonyl]carbamoyl} cyclopropyl]-3,6-dioxo-1,1a,3,4,5,7,9, 10,18,19,20,21,22,22a-tetradecahydro-8H-7,10-methanocyclopropa[18,19][1,10,3,6] dioxadiazacyclononadecino[11,12-b] quinoline-8-carboxamide | 932 |
| 208 | Int. A2, B10, C6<br>Rg. D-prolinamide | (1aR,5S,8S,10R,22aR)-5-tert-butyl-17-{3-[(2R)-2-carbamoylpyrrolidin-1-yl]propoxy}-N-[(1R,2S)-2-ethenyl-1-{[(1-methylcyclopropyl)sulfonyl] carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6] dioxadiazacyclononadecino[11,12-b] quinoline-8-carboxamide | 921 |
| 209 | Int. A2, B10, C6<br>Rg. 3-methylpyrrolidin-3-ol | (1aR,5S,8S,10R,22aR)-5-tert-butyl-N-[(1R,2S)-2-ethenyl-1-{[(1-methylcyclopropyl)sulfonyl] carbamoyl}cyclopropyl]-17-[3-(3-hydroxy-3-methylpyrrolidin-1-yl)propoxy]-3,6-dioxo-1,1a,3,4, 5,6,9,10,18,19,20,21,22,22a-tetradeca hydro-8H-7,10-methanocyclopropa[18,19][1,10,3,6] dioxadiazacyclononadecino[11,12-b] quinoline-8-carboxamide | 908 |

Example 210

(1aR,5S,8S,10R,22aR)-5-tert-butyl-N-[(1R,2S)-2-ethenyl-1-{[(1-methylcyclopropyl)sulfonyl]carbamoyl}cyclopropyl]-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

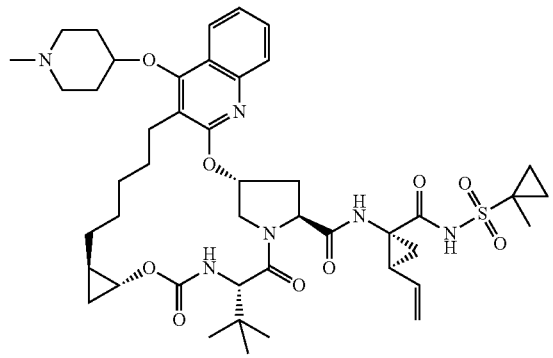 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3ccccc3c1OC1CCN(C)CC1)O2)C(=O)NS(=O)(=O)C1(C)CC1]

Step 1: methyl (1aR,5S,8S,10R,22aR)-5-tert-butyl-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

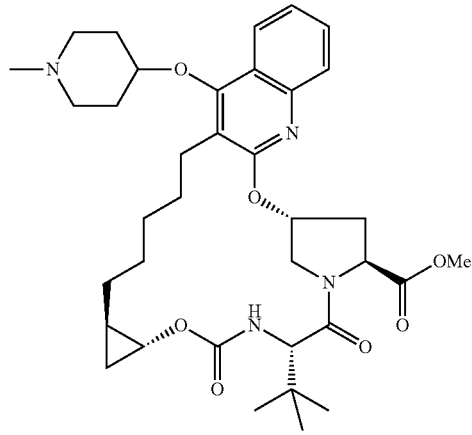 [SMILES: COC(=O)[C@@H]1C[C@@H]2CN1C(=O)[C@H](C(C)(C)C)NC(=O)O[C@@H]1C[C@H]1CCCCCc1c(nc3ccccc3c1OC1CCN(C)CC1)O2]

Methyl (1aR,5S,8S,10R,22aR)-5-tert-butyl-17-hydroxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate synthesized in example 113, step 5 was reacted with 1-methylpiperidin-4-ol using the procedure described for Example 137 (heating was required: 40° C. for 18 hours). LRMS (ES+) m/z 651.55 (M+H)⁺.

Step 2: (1aR,5S,8S,10R,22aR)-5-tert-butyl-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylic acid

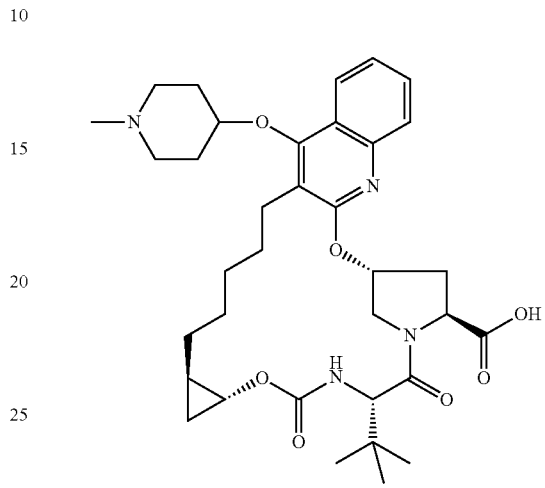

The title compound was prepared using the same method as described for Example 96, Step 3. LRMS (ES+) m/z 637.45 (M+H)⁺.

Step 3: (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

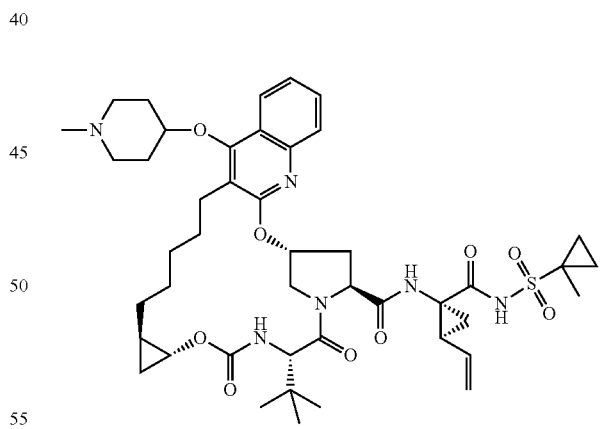

The title compound was prepared using the same method as described in Example 1, Step 6 with intermediate A2. Purification by flash chromatography (ISCO, 0 to 10% methanol in DCM, loading with 0.5% acetic acid in DCM) afforded the desired product. LRMS (ES+) m/z 863.50 (M+H)⁺.

Examples 211-220

By following the procedures outlined in Example 210 and using the appropriate A, B and C intermediates and reagent (depicted below the structure as Int. and Rg., respectively), the following compounds were prepared.

| Ex | Structure | Name | LRMS (M + H)+ |
|---|---|---|---|
| 211 | Int. A2, B11, C6<br>Rg. 1-methylpiperidin-4-ol | (1aR,5S,8S,10R,22aR)-5-cyclohexyl-N-[(1R,2S)-2-ethenyl-1-{[(1-methylcyclopropyl)sulfonyl]carbamoyl}cyclopropyl]-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 889.30 |
| 212 | Int. A2, B10, C7<br>Rg. 2-(azetidin-1-yl)ethanol | (1aR,5S,8S,10R,22aR)-17-[2-(azetidin-1-yl)ethoxy]-5-tent-butyl-N-[(1R,2S)-2-ethenyl-1-{[(1-methylcyclopropyl)sulfonyl]carbamoyl}cyclopropyl]-13-fluoro-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 867.55 |
| 213 | Int. A2, B10, C7<br>Rg. 2-(piperidin-1-yl)ethanol | (1aR,5S,8S,10R,22aR)-5-tent-butyl-N-[(1R,2S)-2-ethenyl-1-{[(1-methylcyclopropyl)sulfonyl]carbamoyl}cyclopropyl]-13-fluoro-3,6-dioxo-17-[2-(piperidin-1-yl)ethoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 895.45 |

| Ex | Structure | Name | LRMS (M + H)+ |
|---|---|---|---|
| 214 | 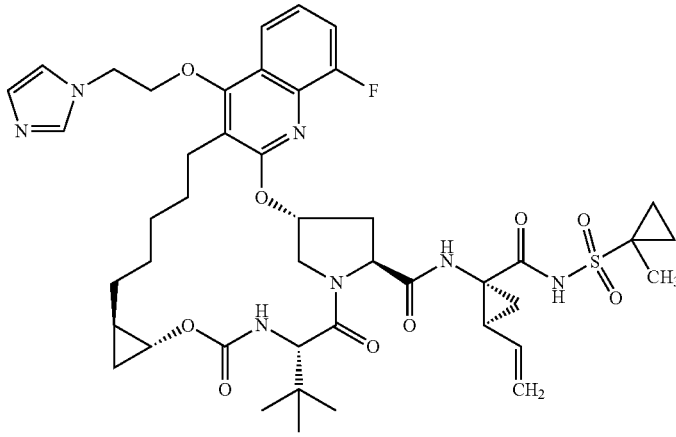<br>Int. A2, B10, C7<br>Rg. 2-(1H-imidazol-1-yl)ethanol | (1aR,5S,8S,10R,22aR)-5-tert-butyl-N-[(1R,2S)-2-ethenyl-1-{[(1-methylcyclopropyl)sulfonyl]carbamoyl}cyclopropyl]-13-fluoro-17-[2-(1H-imidazol-1-yl)ethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 878.20 |
| 215 | 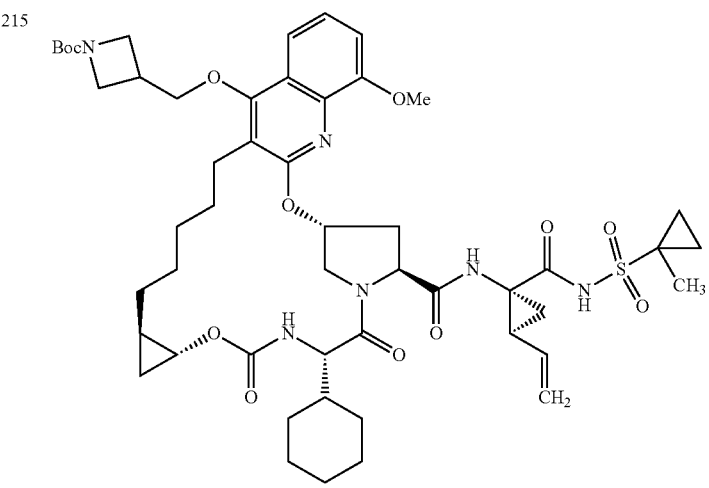<br>Int. A2, B11, C8<br>Rg. tert-butyl 3-(hydroxylmethyl)azetidine-1-carboxylate | tert-butyl 3-[({(1aS,5R,8S,10R,22aR)-5-cyclohexyl-8-[(2-ethenyl-1-{[(1-methylcyclopropyl)sulfonyl]carbamoyl}cyclopropyl)carbamoyl]-13-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-1'7-yl}oxy)methyl]azetidine-1-carboxylate | 991.45 |
| 216 | 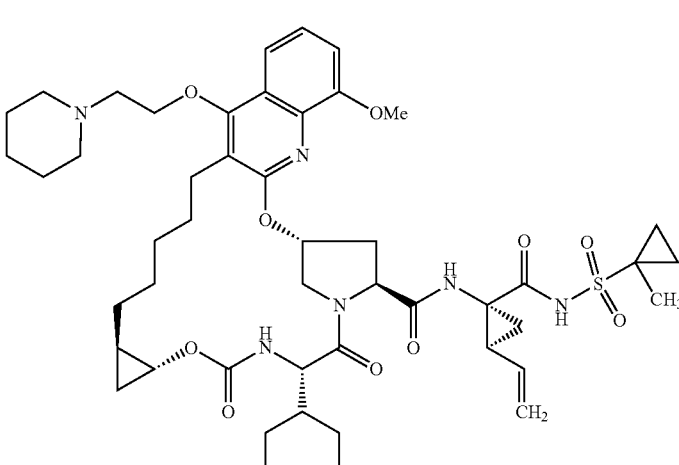<br>Int. A2, B11, C8<br>Rg. 2-(piperidin-1-yl)ethanol, methoxyquinoline | (1aR,5S,8S,10R,22aR)-5-cyclohexyl-N-[(1R,2S)-2-ethenyl-1-{[(1-methylcyclopropyl)sulfonyl]carbamoyl}cyclopropyl]-13-methoxy-3,6-dioxo-17-[2-(piperidin-1-yl)ethoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 933.25 |

-continued

| Ex | Structure | Name | LRMS (M + H)+ |
|---|---|---|---|
| 217 | Int. A2, B10, C6<br>Rg. 2-(pyridin-2-yl)ethanol | (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-[2-(pyridin-2-yl)ethoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 871.45 |
| 218 | Int. A2, B10, C6<br>Rg. 3-(2-hydroxyethyl)pyridine | (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-[2-(pyridin-3-yl)ethoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 871.45 |
| 219 | Int. A2, B10, C6<br>Rg. 4-(2-)hydroxylethyl)pyridine | (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-[2-(pyridine-4-yl)ethoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 871.45 |

| Ex | Structure | Name | LRMS (M + H)+ |
|---|---|---|---|
| 220 | Int. A2, B10, C6<br>Rg. 1-cyclopropylpiperidin-4-ol | (1aR,5S,8S,10R,22aR)-5-tert-butyl-17-[(1-cyclopropylpiperidin-4-yl)oxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 889.60 |

Example 221

(1aR,5S,8S,10R,22aR)-5-tert-butyl-N-[(1R,2S)-2-ethenyl-1-{[(1-methylcyclopropyl)sulfonyl]carbamoyl}cyclopropyl]-17-[(2R)-morpholin-2-ylmethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide Step 1: tert-butyl (2R)-2-({[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}methyl)morpholine-4-carboxylate The title compound was prepared using the same method as described in Example 210, Step 1-3 with tert-butyl (2R)-2-(hydroxymethyl)morpholine-4-carboxylate as the reagent for the Mitsunobu reaction. LRMS (ES+) m/z 965.50 (M+H)+.

Step 2: (1aR,5S,8S,10R,22aR)-5-tert-butyl-N-[(1R,2S)-2-ethenyl-1-{[(1-methylcyclopropyl sulfonyl]carbamoyl}cyclopropyl]-17-[(2R)-morpholin-2-ylmethoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

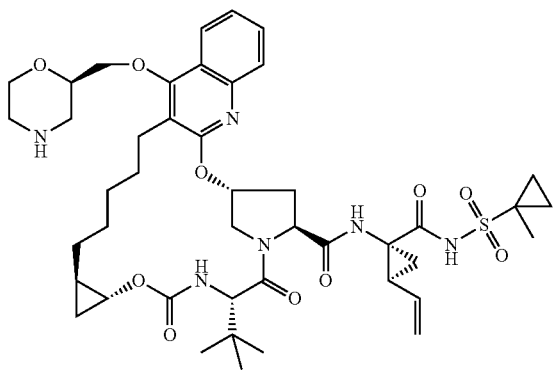 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3ccccc3c1OC[C@H]1CNCCO1)O2)C(=O)NS(=O)(=O)C1(C)CC1]

To a solution of the product from step 1 (92 mg) in dichloromethane (0.5 mL) was added trifluoroacetic acid (0.5 mL) The resulting solution was stirred for 3 hours at room temperature until disappearance of the starting material. The solvent was removed in vacuo. The reaction mixture was dissolved in ethyl acetate and a saturated solution of sodium bicarbonate was added slowly. After extracting 3× with ethyl acetate, the combined organics were dried with sodium sulfate, filtered and concentrated to afford the desired product (77.9 mg). LRMS (ES+) m/z 865.45 (M+H)$^+$.

Example 222

(1aR,5S,8S,10R,22aR)-17-(azetidin-3-yloxy)-5-tert-butyl-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

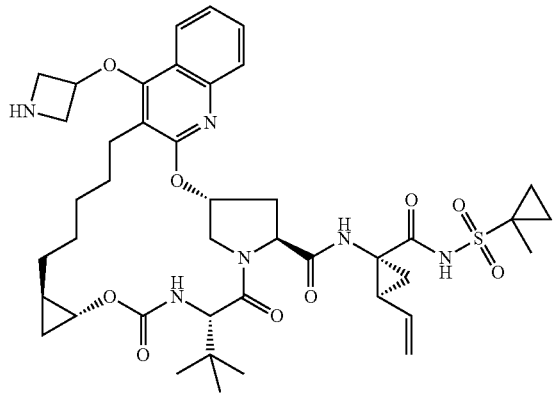 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3ccccc3c1OC1CNC1)O2)C(=O)NS(=O)(=O)C1(C)CC1]

The title compound was prepared using the same method as described in Example 221 using tert-butyl 3-hydroxyazetidine-1-carboxylate for the Mitsunobu reaction. Purification by flash chromatography (ISCO reverse phase, 25 to 70% ACN in water (0.1% TFA buffer)) afforded the desired product LRMS (ES+) m/z 821.50 (M+H)$^+$.

Example 223

(1aR,5S,8S,10R,22aR)-5-tert-butyl-17-{[1-(cyclopropylmethyl)azetidin-3-yl]oxy}-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

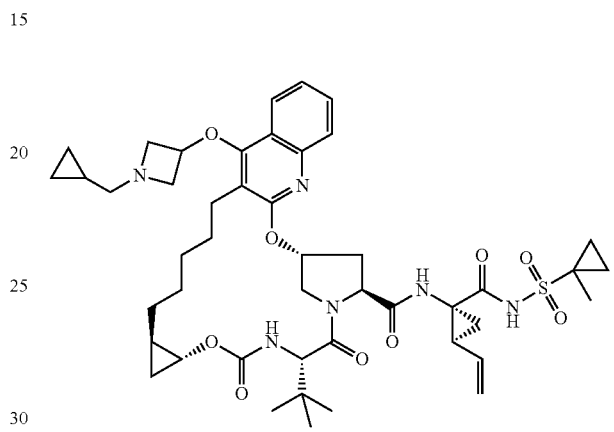

To a solution of Example 222 (100 mg) in DMF (0.5 ml) were added cyclopropyl methyl bromide (28.9 mg) and DIPEA (100 µl). After 18 hours of stirring at 50° C., the reaction mixture was diluted in DMSO (1.5 mL) and it was loaded over a C18 column and purified by flash chromatography (ISCO, 10%-70% ACN in water (0.1% TFA buffer)) to afford a white solid (44 mg of TFA salt). LRMS (ES+) m/z 875.35 (M+H)$^+$.

Example 224

(1aR,5S,8S,10R,22aR)-5-tert-butyl-N-[(1R,2S)-2-ethenyl-1-{[(1-methylcyclopropyl)sulfonyl]carbamoyl}cyclopropyl]-17-[(1-methylazetidin-3-yl)methoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

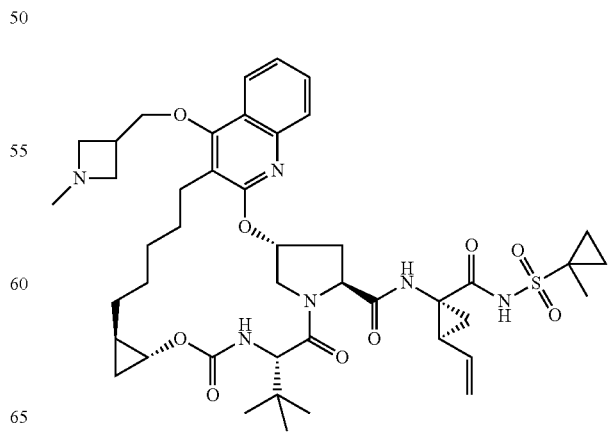

293

Step 1: (1aR,5S,8S,10R,22aR)-17-(azetidin-3-yl-methoxy)-5-tert-butyl-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

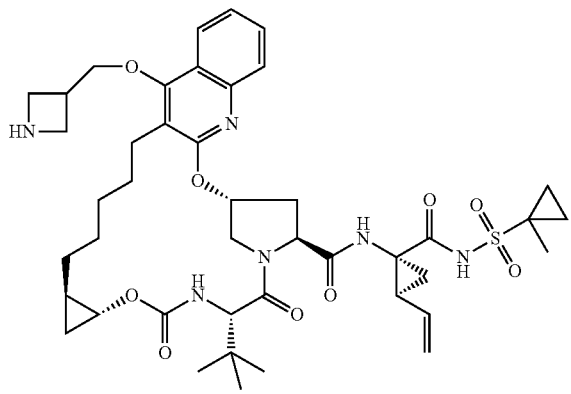 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3ccccc3c1OCC1CNC1)O2)C(=O)NS(=O)(=O)C1(C)CC1]

The title compound was prepared using the same method as described in Example 221, Step 2 with Example 142. LRMS (ES+) m/z 835.45 (M+H)$^+$.

294

Step 2: (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[(1-methylazetidin-3-yl)methoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

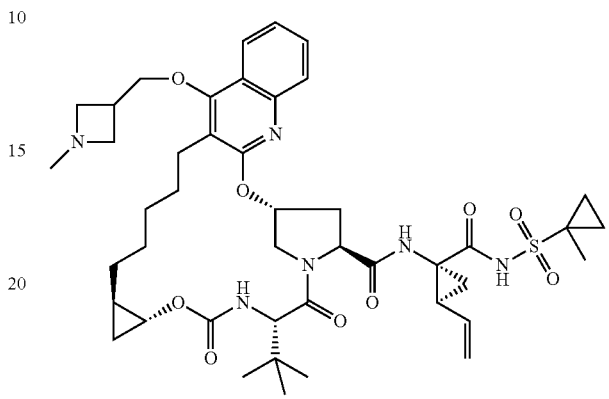

To a suspension of the amine from Step 1 (20.6 mg) in methanol (1 mL) was added formaldehyde (10 μl). Sodium borohydride (5.6 mg) was added slowly. The clear reaction mixture was stirred overnight at room temperature. The solvent was removed in vacuo and the product was dissolved in ethyl acetate and water (with acetic acid to a pH=5). The mixture was extracted (3×) with ethyl acetate. The combined organics were dried with sodium sulfate, filtered and concentrated. Purification by flash chromatography (ISCO reverse phase, 0 to 95% water in acetonitrile followed by ISCO: 0 to 20% methanol in DCM) gave the desired product (1.4 mg). LRMS (ES+) m/z 849.55 (M+H)$^+$.

Example 225

(1aR,5S,8S,10R,22aR)-5-tert-butyl-N-[(1R,2S)-2-ethenyl-1-{[(1-methylcyclopropyl)sulfonyl]carbamoyl}cyclopropyl]-17-{[1-(2-methoxyethyl)piperidin-4-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

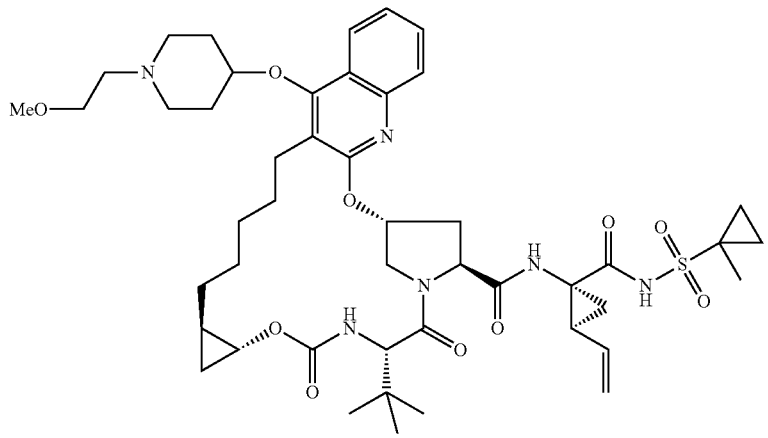 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3ccccc3c1OC1CCN(CCOC)CC1)O2)C(=O)NS(=O)(=O)C1(C)CC1]

Step 1: methyl (1aR,5S,8S,10R,22aR)-17-{[1-(tert-butoxycarbonyl)piperidin-4-yl]oxy}-5-tert-butyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

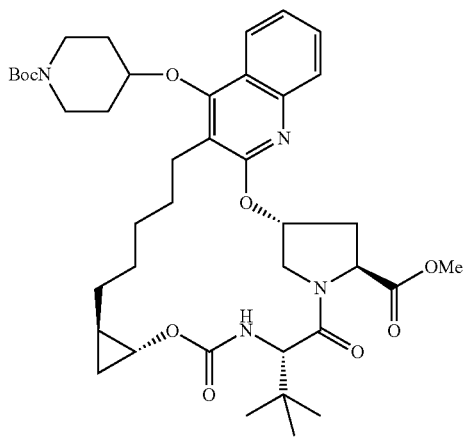 [SMILES: COC(=O)[C@@H]1C[C@@H]2CN1C(=O)[C@H](C(C)(C)C)NC(=O)O[C@@H]1C[C@H]1CCCCCc1c(nc3ccccc3c1OC1CCN(C(=O)OC(C)(C)C)CC1)O2]

The title compound was prepared using the same method as described in Example 210, Step 1 with methyl (1aR,5S,8S,10R,22aR)-5-tert-butyl-17-hydroxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate (Example 113, Step 5) and 1-Boc-4-hydroxypiperidine. LRMS (ES+) m/z 737.5 (M+H)$^+$.

Step 2: methyl (1aR,5S,8S,10R,22aR)-5-tert-butyl-3,6-dioxo-17-(piperidin-4-yloxy)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate trifluoroacetate

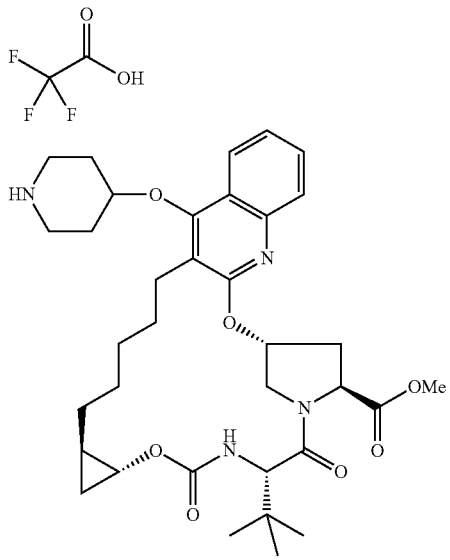

To a solution of the product from step 1 in dichloromethane (2 mL) was added trifluoroacetic acid (2 mL). The resulting solution was stirred for 1 hour at room temperature until disappearance of the starting material. The solvent was removed in vacuo. Purification of the residue by flash chromatography (ISCO reverse phase, 5 to 95% acetonitrile in water (0.5% TFA buffer)) gave the desired product (170 mg). LRMS (ES+) m/z 637.5 (M+H)$^+$.

Step 3: methyl (1aR,5S,8S,10R,22aR)-5-tert-butyl-17-{[1-(2-methoxyethyl)piperidin-4-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

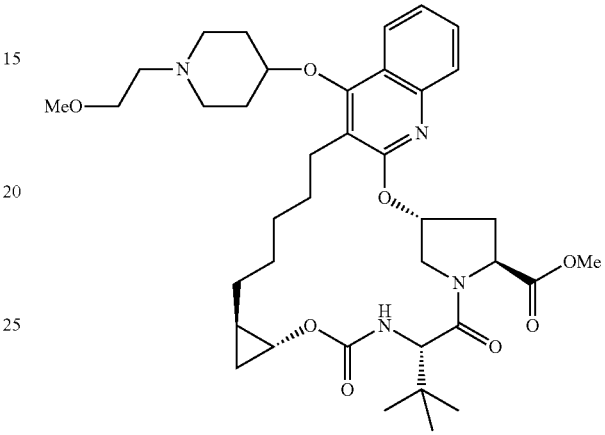

The amine from Step 2 (70.9 mg) was dissolved in DMF (0.3 mL) and triethylamine (53 µl), potassium iodide (1.6 mg) and 2-bromoethyl methyl ether (20 µl) were added sequentially. The reaction mixture was stirred at 60° C. for 24 hours. The reaction mixture was then cooled to room temperature and quenched with a saturated solution of sodium bicarbonate. The mixture was extracted (3×) with ethyl acetate and the combined organics were dried with sodium sulfate, filtered and concentrated. Purification of the residue by flash chromatography (ISCO, 0 to 10% methanol in DCM) gave the desired product (50.6 mg). LRMS (ES+) m/z 695.5 (M+H)$^+$.

Step 4: (1aR,5S,8S,10R,22aR)-5-tert-butyl-17-{[1-(2-methoxyethyl)piperidin-4-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylic acid

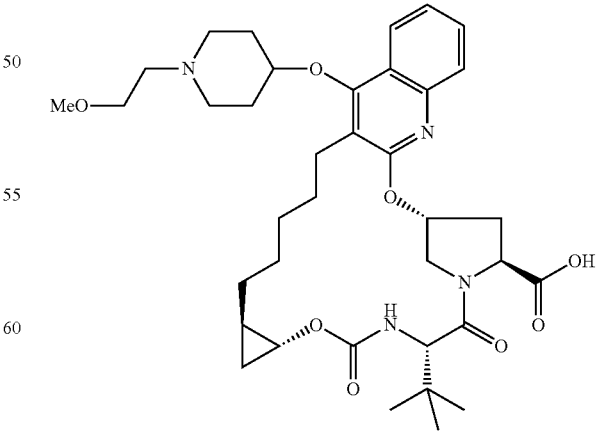

The title compound was prepared using the same method as Example 96, Step 3. LRMS (ES+) m/z 681.5 (M+H)$^+$.

Step 5: (1aR,5S,8S,10R,22aR)-5-tert-butyl-N-[(1R,2S)-2-ethenyl-1-{[(1-methylcyclopropyl)sulfonyl]carbamoyl}cyclopropyl]-17-{[1-(2-methoxyethyl)piperidin-4-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

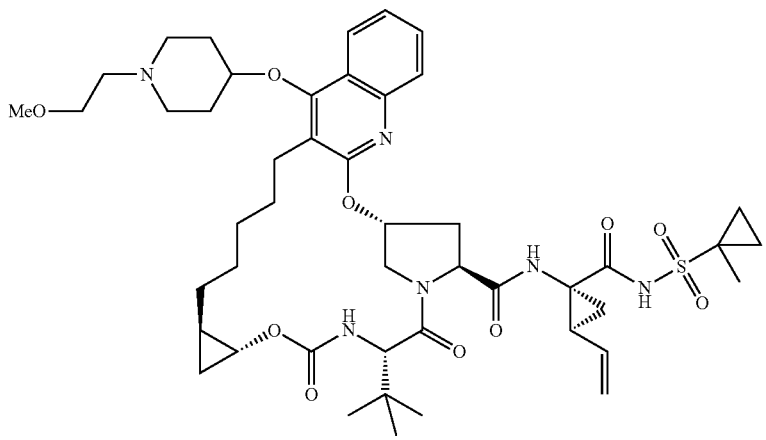 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3ccccc3c1OC1CCN(CCOC)CC1)O2)C(=O)NS(=O)(=O)C1(C)CC1]

The title compound was prepared using the same method as described in Example 1, Step 6 with intermediate A2. Purification of the residue by flash chromatography (ISCO reverse phase, 5 to 95% acetonitrile in water (0.5% TFA buffer)) gave the desired product. LRMS (ES+) m/z 907.45 (M+H)+.

Examples 226

By following the procedures outlined in Example 225 and using the appropriate reagent (depicted below the structure as Rg.), the following compounds were prepared.

| Ex | Structure | Name | LRMS (M + H)+ |
|---|---|---|---|
| 226 | Rg. morpholin-2-ylmethanol, ethyliodide | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[(4-ethylmorpholin-2-yl)methoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 893.50 |

-continued

| Ex | Structure | Name | LRMS (M + H)+ |
|---|---|---|---|
| 227 | Rg. tert-butyl 4-(hydroxylmethyl)piperidine-1-carboxylate, thyliodide | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[(1-ethylpiperidin-4-yl)methoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 891.40 |
| 228 | Rg. tert-butyl 4-(hydroxylmethyl)piperidine-1-carboxylate, 2-bromoethylmethyl ether | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-{[1-(2-methoxyethyl)piperidin-4-yl]methoxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 921.5 |
| 229 | Rg. tert-butyl 4-hydroxypiperidine-1-carboxylate, ethyliodide | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-[(1-ethylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 877.60 |

| Ex | Structure | Name | LRMS (M + H)+ |
|---|---|---|---|
| 230 | Rg. tert-butyl 4-hydroxypiperidine-1-carboxylate, bromomethyl)cyclopropane | (1aR,5S,8S,10R,22aR)-5-tert-butyl-17-{[1-(cyclopropylmethyl)piperidin-4-yl]oxy}-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 903.55 |
| 231 | Rg. tert-butyl (1R,4R,5S)-5-hydroxy-2-azabicyclo[2.2.1]heptane-2-carboxylate, 2-bromoethyl ethyl ether | (1aR,5S,8S,10R,22aR)-5-tert-butyl-N-[(1R,2S)-2-ethenyl-1-{[(1-methylcyclopropyl)sulfonyl]carbamoyl}cyclopropyl]-17-{[(1R,4R,5R)-2-(2-methoxyethyl)-2-azabicyclo[2.2.1]hept-5-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide | 919.45 |

Example 232

(1aR,5S,8S,10R,22aR)—N-[(1R,2S)-2-ethenyl-1-{[(1-methylcyclopropyl)sulfonyl]carbamoyl}cyclopropyl]-5-(1-methylcyclohexyl)-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

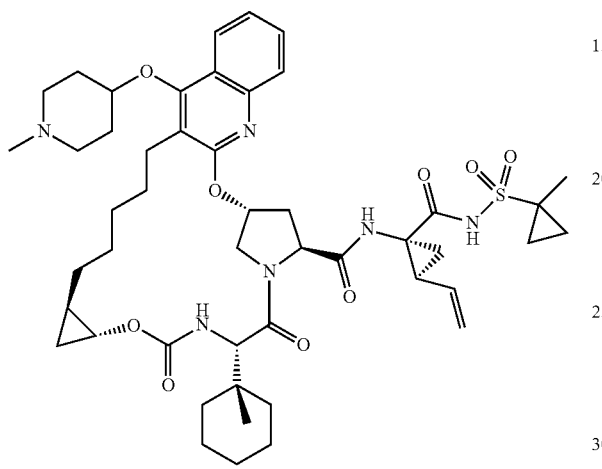

Step 1: (S)-2-(1-methylcyclohexyl)-2-((((1R,2R)-2-(pent-4-yn-1-yl)cyclopropoxy)carbonyl)amino)acetic acid

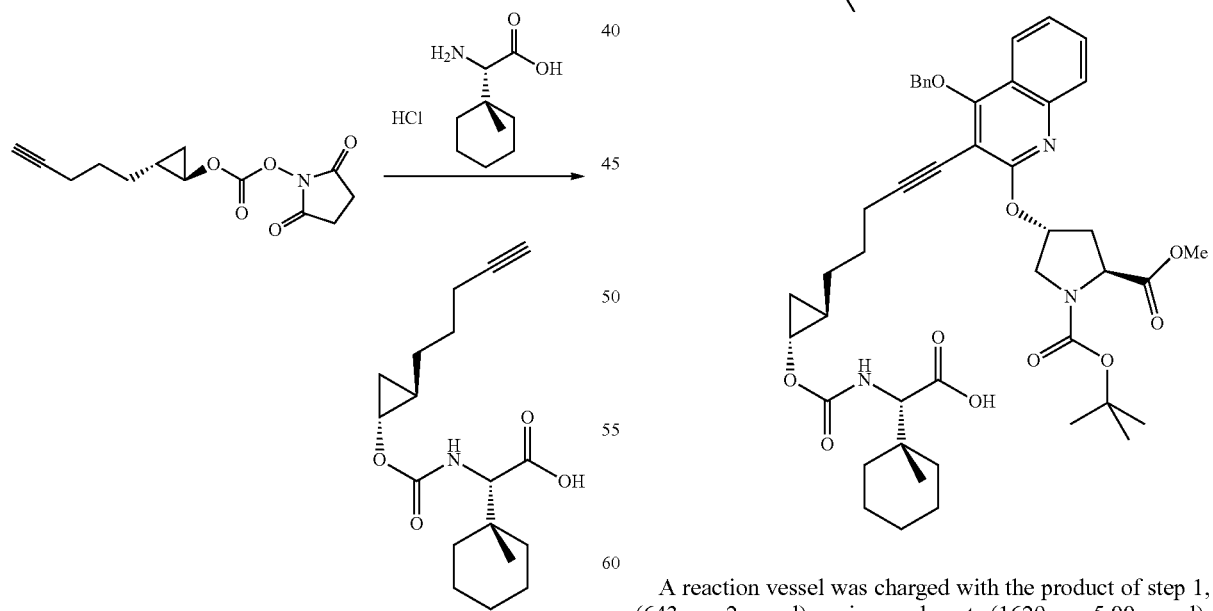

A solution of intermediate D3 (4.3 g, 16.21 mmol) in acetonitrile (81 ml) was treated with intermediate D1 (3.37 g, 16.21 mmol) and triethylamine (9.04 ml, 64.8 mmol). Water (81 ml) was added to facilitate dissolution. The mixture was stirred at room temperature for 4 hours. The mixture was concentrated to half its volume and then diluted with ethyl acetate (500 mL), washed with aq 1M HCl (2×100 mL) and brine (100 mL). The organic layer was dried over magnesium sulfate, filtered and concentrated in the rotavap to give the title compound as a crude product (5.3 g, 16.49 mmol, 102% yield) as a slightly yellow oil.

Step 2: (S)-2-((((1R,2R)-2-(5-(4-(benzyloxy)-24(3R,5S)-1-(tert-butoxycarbonyl)-5-(methoxycarbonyl)pyrrolidin-3-yl)oxy)quinolin-3-yl)pent-4-yn-1-yl)cyclopropoxy)carbonyl)amino)-2-(1-methylcyclohexyl)acetic acid

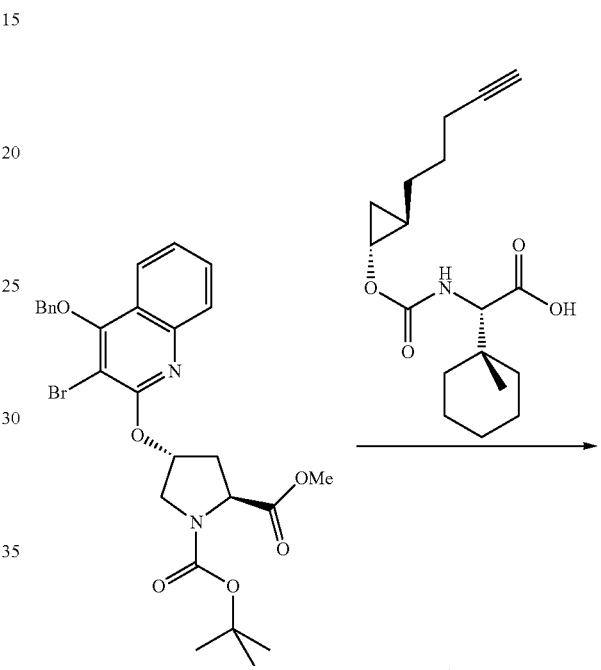

A reaction vessel was charged with the product of step 1, (643 mg, 2 mmol), cesium carbonate (1629 mg, 5.00 mmol), bis(acetonitrile)dichloropalladium(II) (51.9 mg, 0.200 mmol) and tri-tert-butylphosphonium tetrafluoroborate (174 mg, 0.600 mmol). Acetonitrile (5000 µl) was added followed by dibenzylamine (387 µl, 2.000 mmol). The reaction mixture was purged with argon followed by addition of a solution of intermediate D2 (1115 mg, 2.000 mmol) in acetonitrile (5000 µl). The reaction mixture was purged with argon and the tube was sealed. The reaction was heated in an oil bath (80° C.) overnight. Ethyl acetate was added (150 mL) and the mixture was washed with aq 1M HCl (2×50 mL) and brine (50 mL), dried over magnesium sulfate, filtered and concentrated in rotavap to give the crude product. The crude product was purified on a gold cap Redisep (220 g) silica gel column (gradient: 0 to 30% solvent B in dichloromethane (solvent B: 20% methanol in ethyl acetate)) to give the title compound (840 mg, 1.053 mmol, 52.6% yield) as a slightly yellow foam.

Step 3: (S)-2-(((((1R,2R)-2-(5-(4-(benzyloxy)-2-(((3R,5S)-5-(methoxycarbonyl)pyrrolidin-3-yl)oxy)quinolin-3-yl)pent-4-yn-1-yl)cyclopropoxy)carbonyl)amino)-2-(1-methylcyclohexyl)acetic acid

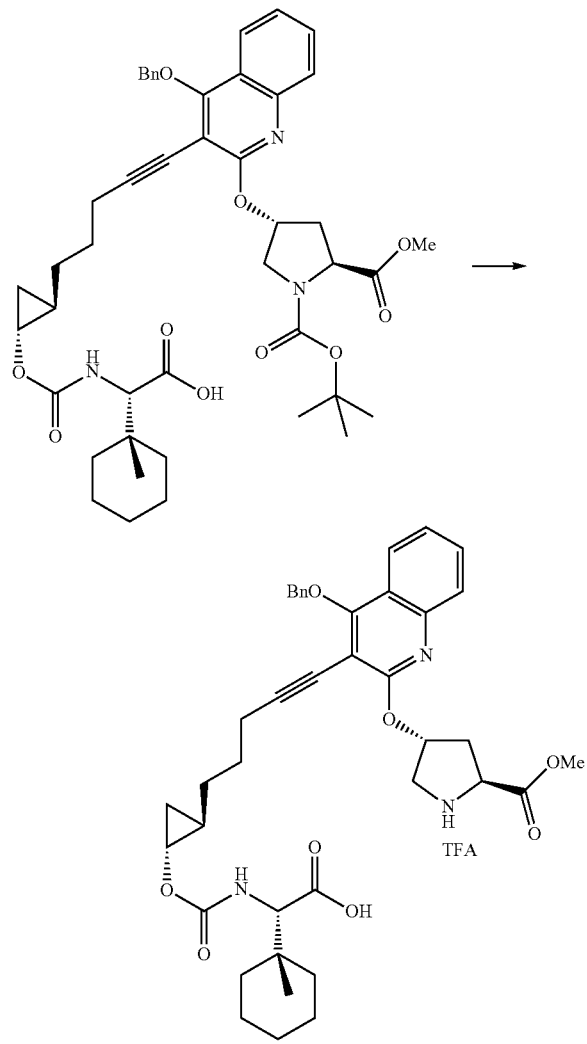

The N-Boc protected product from Step 2 (1.8 g, 2.256 mmol) was dissolved in dichloromethane (15.04 ml) and treated with TFA (7.52 ml). The mixture was stirred at room temp and monitored by LCMS. Reaction was completed after 45 min. The mixture was concentrated to dryness in rotavap. The residual TFA was azeotropically removed with toluene and the title compound (1.83 g, 2.254 mmol, 100% yield) was dried under vacuum. No further purification was carried out.

Step 4: Methyl (1aR,5S,8S,10R,22aR)-17-(benzyloxy)-5-(1-methylcyclohexyl)-3,6-dioxo-18,19-didehydro-1,1a,3,4,5,6,9,10,20,21,22,22a-dodecahydro-8H-7,10-methanocyclopropa[18,19][1,10,3,6]dioxadiazacyclononadecino[11,12-b]quinoline-8-carboxylate

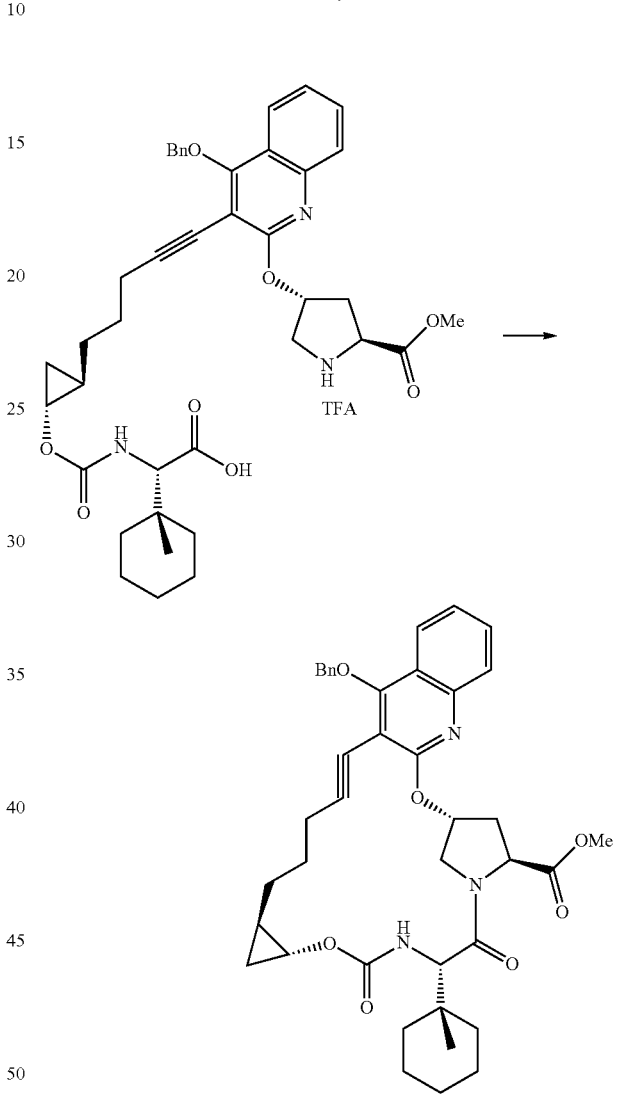

A round-bottom flask was charged with HATU (1711 mg, 4.50 mmol) and dry DMF (2.25E+04 µl) at 0° C. N,N-diisopropylethylamine (1531 µl, 9.00 mmol) was added followed by addition of a solution of the product of step 3 (1827 mg, 2.25 mmol) in dry DMF (2.25E+04 µl) via syringe pump over 1 hour. After addition was complete the reaction was stirred at room temperature for 2 hours. LCMS and MS analyses showed a complete reaction. The reaction mixture was concentrated to almost dryness in rotavap (high vacuum) and the residue was diluted with ethyl acetate (200 mL). The mixture was washed with water (50 mL), aq. 1M HCl (50 mL), half-saturated sodium bicarbonate (50 mL) and brine (50 mL). The organic layer was dried over magnesium sulfate, filtered and concentrated in rotavap. The residue was purified on a Redisep (120 g) silica gel column (gradient: 0 to 40% ethyl acetate in hexanes) to give the title compound (900 mg, 1.324 mmol, 58.8% yield) as a white powder.

Step 5: Methyl (1aR,5S,8S,10R,22aR)-5-(1-methyl-cyclohexyl)-17-hydroxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate column (gradient: 0 to 40% ethyl acetate in hexanes) to give the title compound (710 mg, 1.196 mmol, 93% yield) as a white powder.

Step 6: Methyl (1aR,5S,8S,10R,22aR)-5-(1-methyl-cyclohexyl)-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

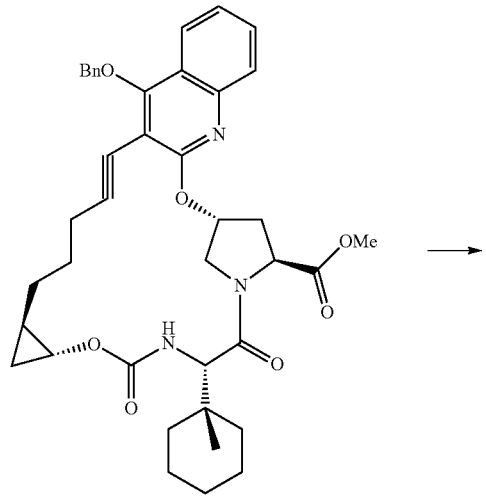

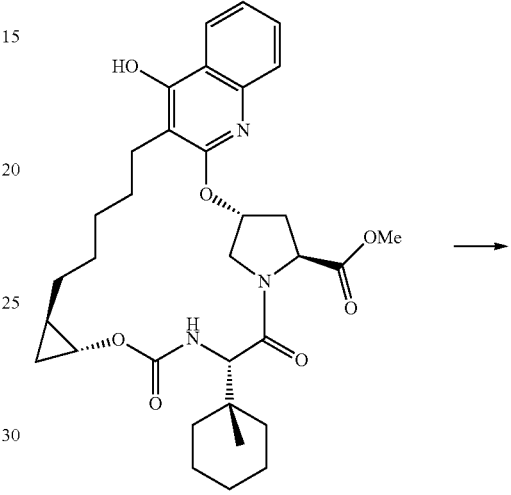

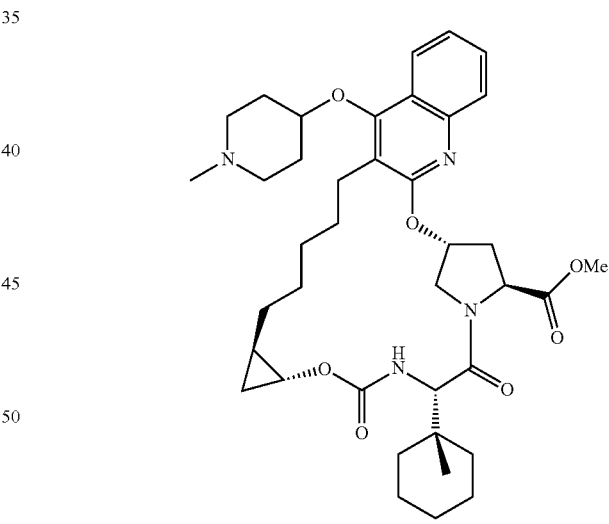

A solution of the product of step 4 (870 mg, 1.280 mmol) in MeOH (8532 μl) and THF (4266 μl) was treated with a catalytic amount of 10% palladium on carbon (68 mg). The mixture was hydrogenated at 30 psi. After 6 hours LCMS showed complete reaction. The mixture was diluted with dichloromethane (50 mL) and the solids were removed by filtration. The filtrate was concentrated in rotavap and the residue was purified on a gold cap RediSep® (80 g) silica gel A reaction tube was charged with the product of step 5 (400 mg, 0.674 mmol) and triphenylphosphine (1414 mg, 5.39 mmol). The tube was sealed and THF (6737 μl) was added via syringe at 0° C. 4-hydroxy-1-methylpiperidine (633 μl, 5.39 mmol) was added followed by slow addition of diisopropyl azodicarboxylate (1044 μl, 5.39 mmol). After 5 min, the cooling bath was removed and the mixture was allowed to reach room temperature and stirred for 10 minutes. The reaction tube was heated at 40° C. LCMS showed complete reaction after 2 hours. The reaction mixture was concentrated to dryness in rotavap and the residue was purified on a gold cap silica gel (120 g) column (gradient: 0 to 50% solvent B in dichloromethane (solvent B: 20% methanol in ethyl acetate)) to give the title compound (450 mg, 0.651 mmol, 97% yield) as a white powder.

Step 7: (1aR,5S,8S,10R,22aR)-5-(1-methylcyclohexyl)-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylic acid Step 8: (1aR,5S,8S,10R,22aR)—N-[(1R,2S)-2-ethenyl-1-{[(1-methylcyclopropyl)sulfonyl]carbamoyl}cyclopropyl]-5-(1-methylcyclohexyl)-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

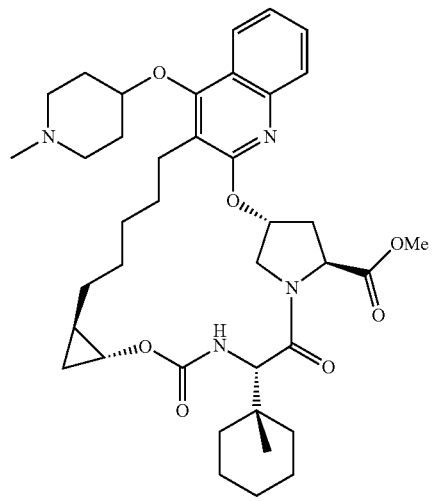

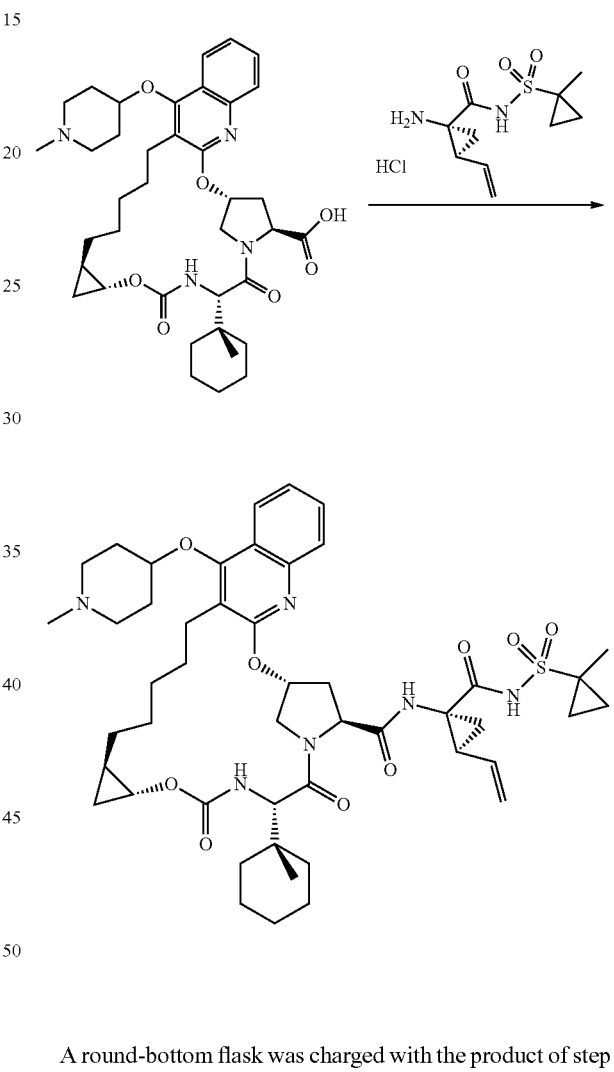

A round-bottom flask was charged with the product of step 6 (450 mg, 0.651 mmol) and lithium hydroxide monohydrate (137 mg, 3.26 mmol). MeOH (2171 µl), THF (2171 µl) and water (2171 µl) were successively added and the mixture was stirred at room temperature LCMS showed complete reaction after 2 hours. The reaction was quenched by addition of acetic acid (373 µl, 6.51 mmol). Water was added (20 mL) and the mixture was extracted with dichloromethane (2×20 mL) and ethyl acetate (20 mL). The combined organic extracts were dried over magnesium sulfate, filtered and concentrated in rotavap. Residual acetic acid was azeotropically removed with toluene to give the title compound as a crude product (450 mg, 0.665 mmol, 102% yield) as a white powder. No further purification was carried out.

A round-bottom flask was charged with the product of step 7 (1.1 g, 1.625 mmol), intermediate D4 (0.684 g, 2.438 mmol) and HATU (0.927 g, 2.438 mmol). Dry DMF (16.25 ml) was added by syringe at 0° C. followed by N,N-diisopropylethylamine (1.106 ml, 6.50 mmol). The cooling bath was removed after 10 minutes and the reaction mixture was stirred overnight. The mixture was concentrated to one third of its volume in rotavap and the residue was diluted with ethyl acetate (200 mL). The organic layer was washed with water (2×25 mL) and brine (25 mL), dried over magnesium sulfate, filtered and concentrated in rotavap. The residue was purified on a gold cap RediSep® (220 g) silica gel column (gradient: 0 to 50% solvent B in dichloromethane (solvent B: 20% MeOH in ethyl acetate)) to give the title compound (810 mg, 0.897 mmol, 55.2% yield) as a white powder. LRMS (ESI) Calcd for $C_{48}H_{67}N_6O_9S$ [M+H]$^+$ 903.46. found 902.8.

Example 233

(1aR,5S,8S,10R,22aR)-5-(2,3-dihydro-1H-inden-2-yl)-17-[3-(dimethylamino)propoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

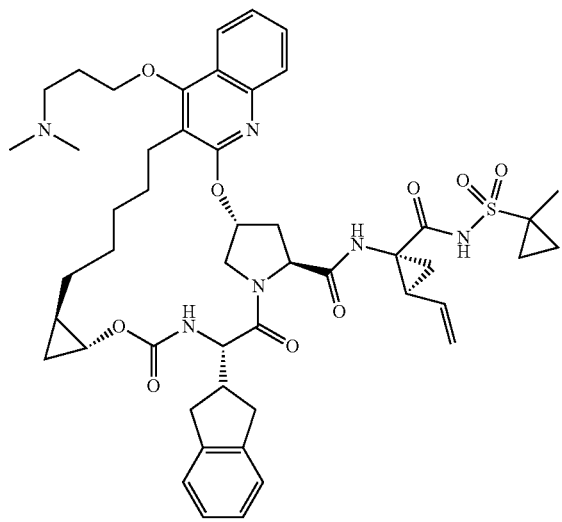

A solution of intermediate D3 (3.54 g, 12.0 mmol) in MeCN (30.0 ml) was treated with intermediate D5 (3.28 g, 14.40 mmol) and triethylamine (6.70 ml, 48.0 mmol). The slurry was vigorously stirred while water (30.0 ml) was added. The resulting mixture was stirred overnight. The mixture was diluted with ethyl acetate (400 mL) and washed with aq. 1M HCl (2×100 mL) and brine (100 mL) The organic layer was dried over magnesium sulfate, filtered and concentrated to half its volume in the rotavap. The solids were recovered by filtration and dried under vacuum to give the first batch of the title compound (2.0 g, 48%). The filtrate was concentrated to dryness in rotavap to give the second batch of the title compound (2.3 g, 56%).

Step 2: (S)-2-(((((1R,2R)-2-(5-(4-(benzyloxy)-24(3R,5S)-1-(tert-butoxycarbonyl)-5-(methoxycarbonyl)pyrrolidin-3-yl)oxy)quinolin-3-yl)pent-4-yn-1-yl)cyclopropoxy)carbonyl)amino)-2-(2,3-dihydro-1H-inden-2-yl)acetic acid Step 1: (S)-2-(2,3-dihydro-1H-inden-2-yl)-2-(((((1R,2R)-2-(pent-4-yn-1-yl)cyclopropoxy)carbonyl)amino)acetic acid

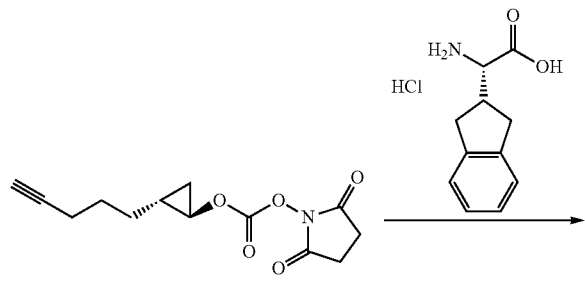

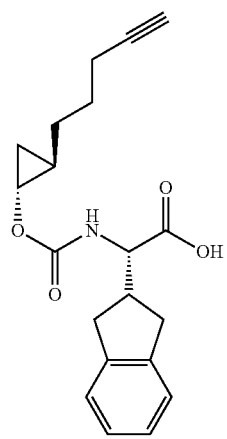

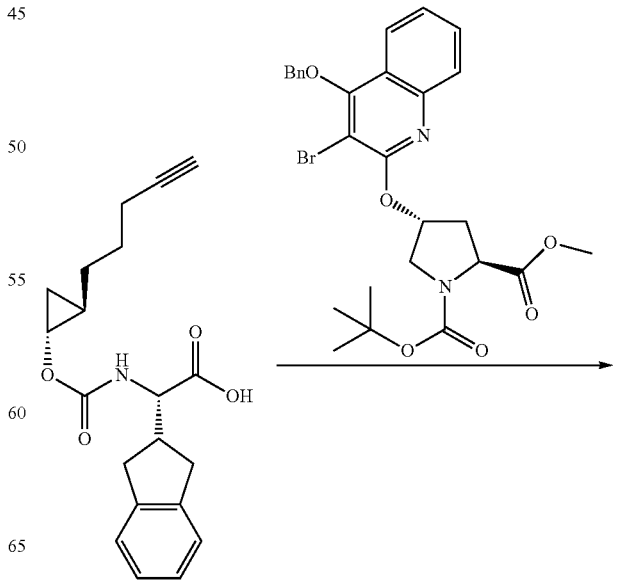

313
-continued

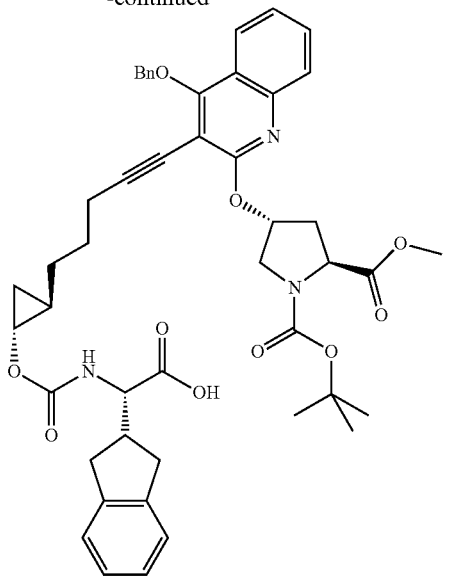

A reaction vessel was charged with the product of step 1 (1990 mg, 5.83 mmol), potassium carbonate (1831 mg, 13.25 mmol), bis(acetonitrile)dichloro palladium(II) (68.7 mg, 0.265 mmol), and tri-tert-butylphosphonium tetrafluoroborate (231 mg, 0.795 mmol). Acetonitrile (1.77E+04 μl) was added followed by dibenzylamine (1017 μl, 5.30 mmol). The reaction mixture was purged with argon followed by addition of a solution of intermediate D2 (2954 mg, 5.3 mmol) in acetonitrile (8833 W). The reaction mixture was purged with argon and the tube was sealed. The reaction was heated in an oil bath (80° C.) overnight. Ethyl acetate was added (300 mL) and the mixture was washed with aq. 1M HCl (2×50 mL) and brine (50 mL), dried over magnesium sulfate, filtered and concentrated in rotavap. The crude product was purified on a gold cap RediSep® (220 g) silica gel column (gradient: 0 to 30% solvent B in dichloromethane (solvent B: 20% methanol in ethyl acetate)). The fractions containing the product were combined and fractions containing impure product were combined, evaporated and purified again under the same conditions (120 g column) to give a second batch of product. The purified products were combined to give the title compound (950 mg, 22%) as a colorless foam.

314
Step 3: (S)-2-(((((1R,2R)-2-(5-(4-(benzyloxy)-2-(((3R,5S)-5-(methoxycarbonyl)pyrrolidin-3-yl)oxy)quinolin-3-yl)pent-4-yn-1-yl)cyclopropoxy)carbonyl)amino)-2-(2,3-dihydro-1H-inden-2-yl)acetic acid

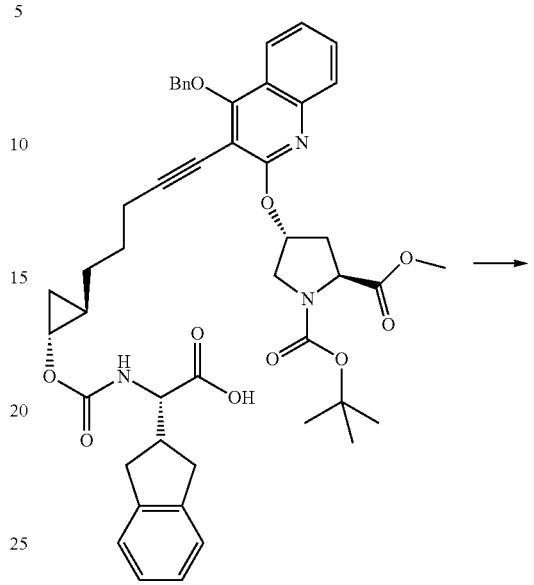

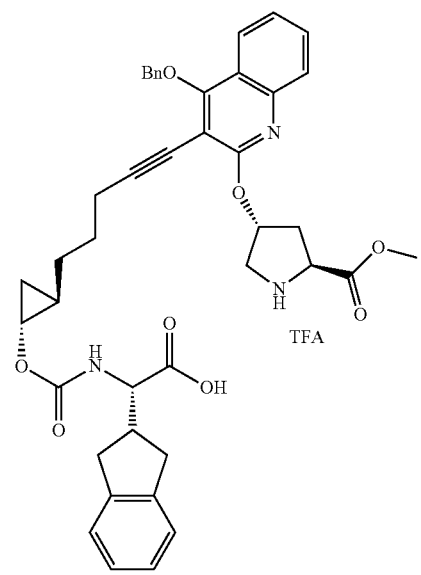

A solution of the product of step 2 (750 mg, 0.917 mmol) in CH$_2$Cl$_2$ (4.58 ml) was treated with trifluoroacetic acid (4.5 ml, 58.8 mmol) and stirred at room temperature. LCMS showed complete reaction after 30 minutes. The mixture was concentrated to dryness in rotavap and residual TFA was azeotropically removed with toluene. The title compound as crude product (760 mg, 100%) was dried under vacuum and used without further purification.

Step 4: Methyl (1aR,5S,8S,10R,22aR)-17-(benzyloxy)-5-(2,3-dihydro-1H-inden-2-yl)-3,6-dioxo-18,19-didehydro-1,1a,3,4,5,6,9,10,20,21,22,22a-dodecahydro-8H-7,10-methanocyclopropa[18,19][1,10,3,6]dioxadiazacyclononadecino[11,12-b]quinoline-8-carboxylate

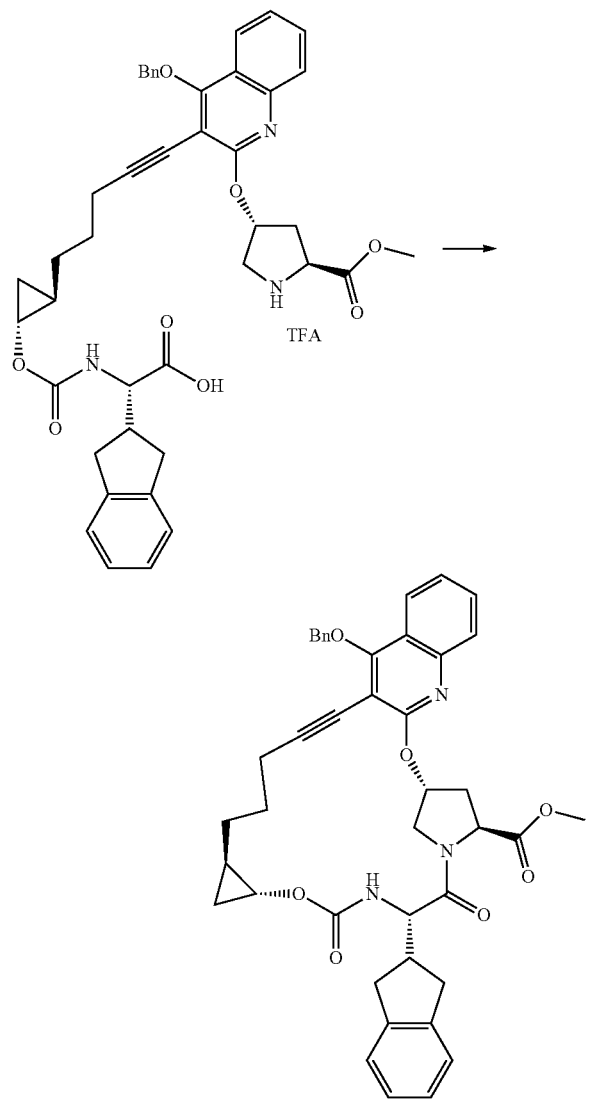

A round-bottom flask was charged with HATU (695 mg, 1.828 mmol) and dry DMF (9140 µl) at 0° C. N,N-diisopropylethylamine (637 µl, 3.66 mmol) was added followed by addition of a solution of the product of step 3 (760 mg, 0.914 mmol) in dry DMF (9140 µl) via syringe pump over 1 hour. After addition was complete the reaction was stirred at room temperature for 1 hour. LCMS and MS analyses showed a complete reaction. The reaction mixture was concentrated to almost dryness in rotavap (high vacuum) and the residue was diluted with ethyl acetate (100 mL). The mixture was washed with water (40 mL), aq. 1M HCl (40 mL), half-saturated sodium bicarbonate (30 mL) and brine (30 mL). The organic layer was dried over magnesium sulfate, filtered and concentrated in rotavap. The residue was purified on a RediSep® (80 g) silica gel column (gradient: 0 to 50% ethyl acetate in hexanes) to give the title compound (510 mg, 0.729 mmol, 80% yield) as a white powder.

Step 5: Methyl (1aR,5S,8S,10R,22aR)-5-(2,3-dihydro-1H-inden-2-yl)-17-hydroxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

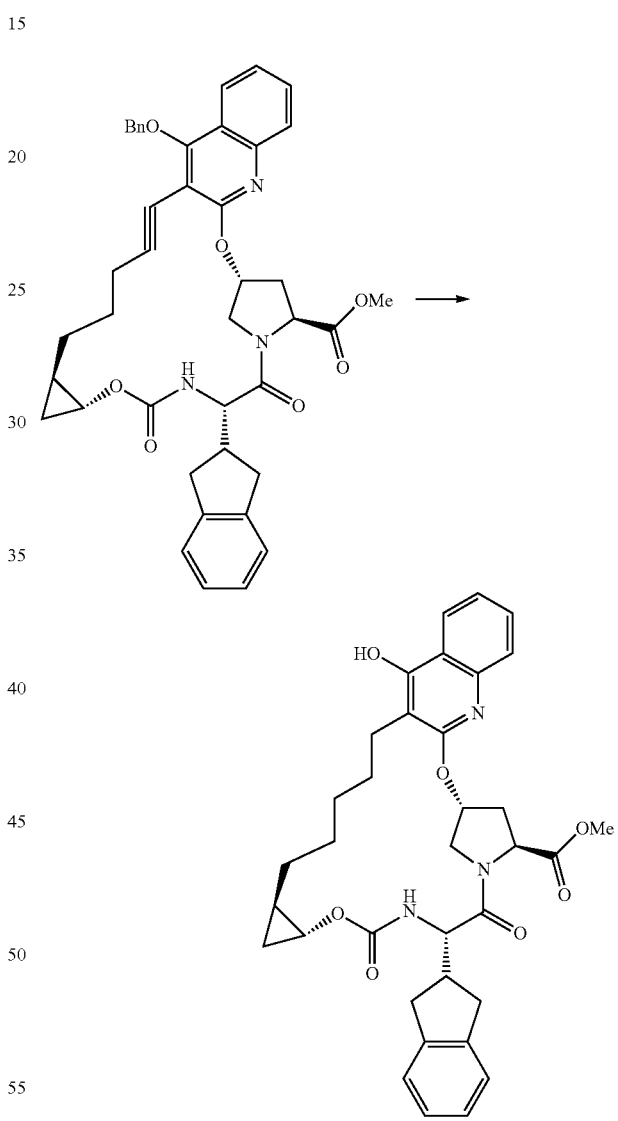

A solution of the product of step 4 (480 mg, 0.686 mmol) in MeOH (9146 µl) and THF (4573 µl) was treated with a catalytic amount of 10% palladium on carbon (36 mg). The mixture was hydrogenated at 20 psi. After 2 hours LCMS showed >70% conversion. Hydrogenation was continued for another 2 h. LCMS showed >90% conversion. The mixture was diluted with ethyl acetate (50 mL) and the solids were removed by filtration. The filtrate was concentrated in rotavap and the residue was purified on a RediSep® (80 g) silica gel column (gradient: 0 to 50% ethyl acetate in hexanes) to give the title compound (420 mg, 0.684 mmol, 100% yield) as a white powder.

Step 6: Methyl (1aR,5S,8S,10R,22aR)-5-(2,3-dihydro-1H-inden-2-yl)-17-[3-(dimethylamino)propoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate Step 7: (1aR,5S,8S,10R,22aR)-5-(2,3-dihydro-1H-inden-2-yl)-17-[3-(dimethylamino)propoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylic acid

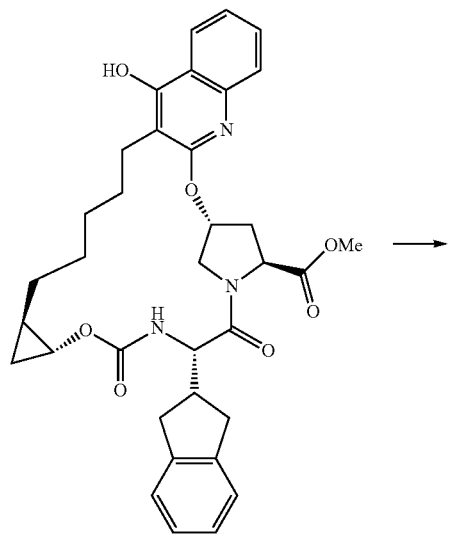

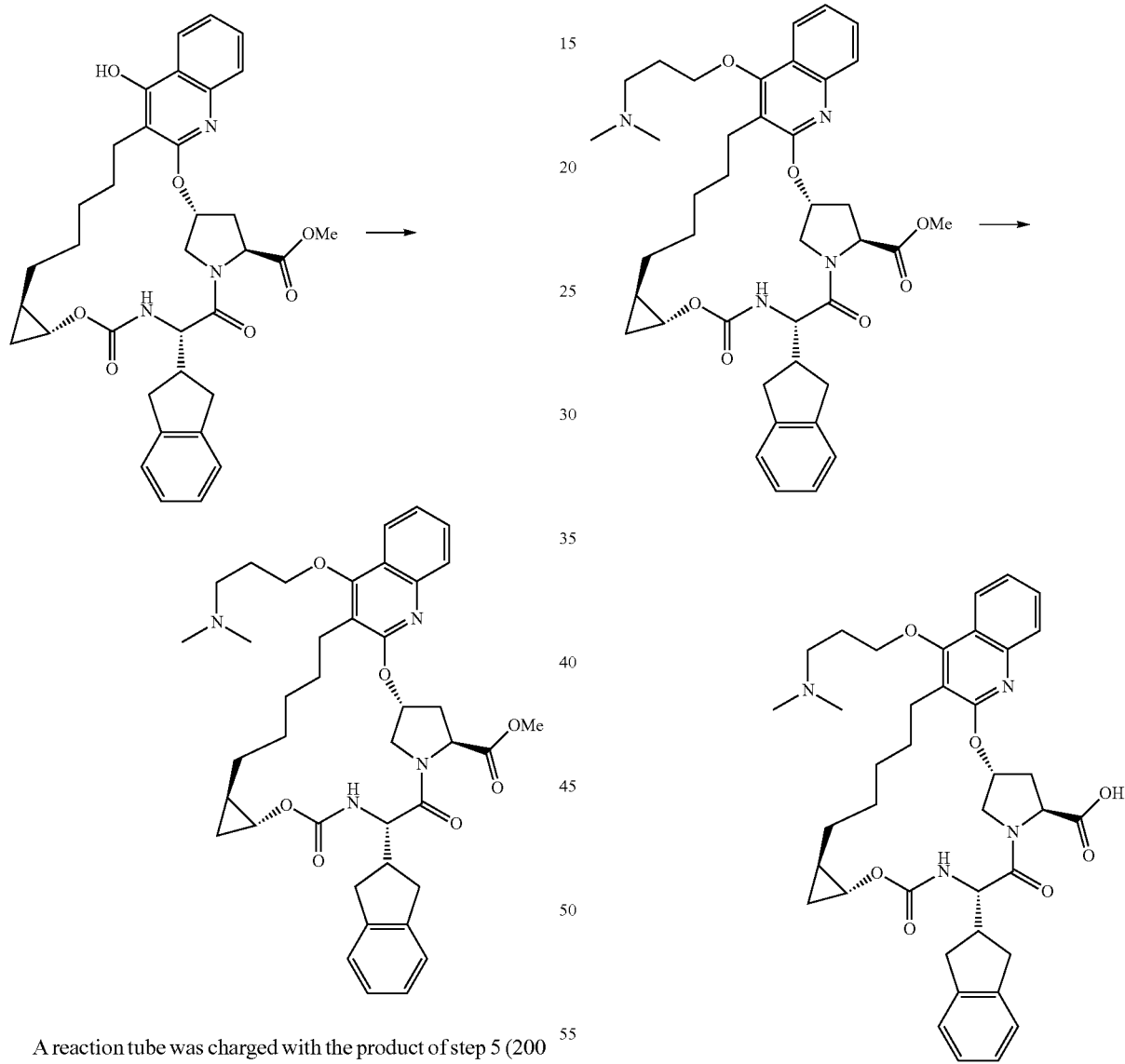

A reaction tube was charged with the product of step 5 (200 mg, 0.326 mmol) and triphenylphosphine (855 mg, 3.26 mmol). The tube was sealed and THF (3259 µl) was added via syringe at 0° C. 3-dimethylamino-1-propanol (381 µl, 3.26 mmol) was added followed by slow addition of diisopropyl azodicarboxylate (631 µl, 3.26 mmol). After 5 minutes the cooling bath was removed and the mixture was allowed to reach room temperature and stirred for 10 minutes. The reaction tube was heated at 40° C. for 3 hours. The reaction mixture was concentrated to dryness in rotavap and the residue was purified on a gold cap silica gel (80 g) column (gradient: 0 to 60% solvent B in dichloromethane (solvent B: 20% methanol in ethyl acetate)) to give the title compound (210 mg, 0.300 mmol, 92% yield) as a white powder.

A solution of the product of step 6 (210 mg, 0.300 mmol) in MeOH (3005 µl), THF (1502 µl) and eater (1502 µl) was treated with lithium hydroxide monohydrate (63.0 mg, 1.502 mmol). The reaction mixture was stirred at room temperature. After 5 hour the reaction was quenched by addition of acetic acid (172 µl, 3.00 mmol) and water (10 mL). The mixture was extracted into dichloromethane (2×10 mL) and ethyl acetate (10 mL). The combined organic extracts were dried over magnesium sulfate filtered and concentrated in rotavap to give the title compound (215 mg, 0.314 mmol, 104% yield) as a white powder. No further purification was carried out for the product.

Step 8: (1aR,5S,8S,10R,22aR)-5-(2,3-dihydro-1H-inden-2-yl)-17-[3-(dimethylamino)propoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

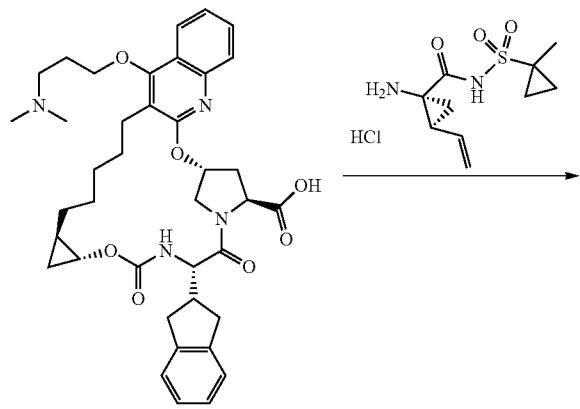

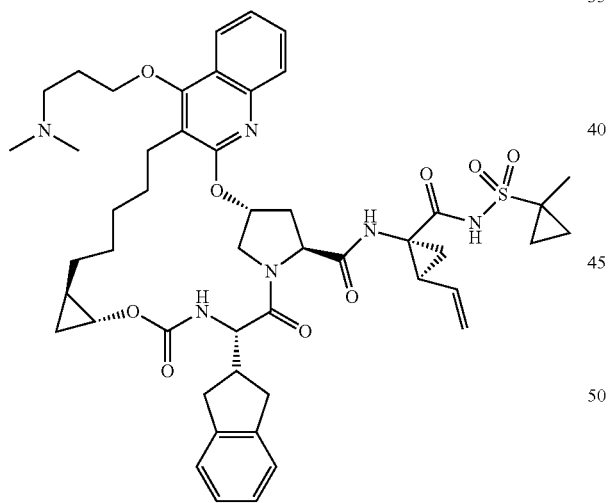

A round-bottom flask was charged with the product of step 7 (105 mg, 0.153 mmol), intermediate D4 (53.8 mg, 0.192 mmol) and HATU (72.9 mg, 0.192 mmol). Dry DMF (3066 µl) was added by syringe followed by 4-methylmorpholine (67.4 µl, 0.613 mmol). The reaction mixture was stirred for 22 hours. Ethyl acetate was added (20 mL) and the mixture was washed with water (2×5 mL), brine (5 mL), dried over magnesium sulfate, filtered and concentrated in rotavap. The residue was purified on a gold cap RediSep® (12 g) silica gel column (gradient: 0 to 60% solvent B in dichloromethane (solvent B: 20% MeOH in ethyl acetate)) to give the title compound (52 mg, 0.057 mmol, 37.2% yield) as a white powder. LRMS (ESI) Calculated for $C_{49}H_{63}N_6O_9S$ [M+H$^+$ 911.4. found 911.2.

Example 234

(1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-{[1-(2,2,2-trifluoroethyl)piperidin-4-yl]oxy}-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

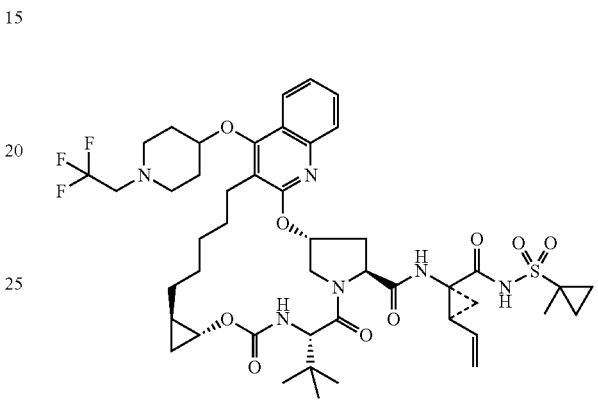

Step 1: methyl (1aR,5S,8S,10R,22aR)-5-tert-butyl-17-{17-(2,2,2-trifluoroethyl)piperidin-4-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

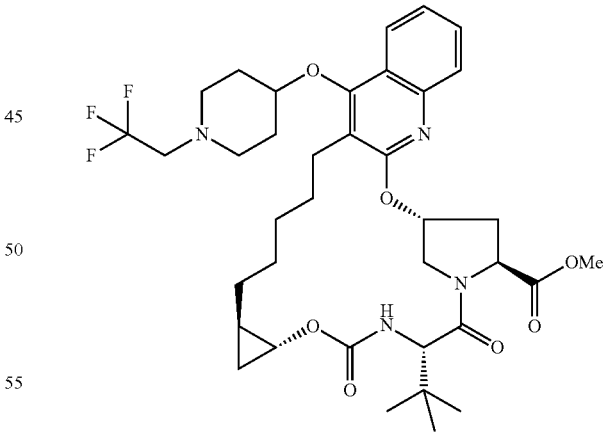

To a solution of the product from Example 225 Step 2 (90 mg, 0.141 mmol) in 2 mL acetonitrile were added cesium carbonate (92 mg, 0.283 mmol) followed by 2,2,2-trifluoroethyl trifluoromethanesulfonate (65.6 mg, 0.283 mmol). The reaction was stirred at room temperature for 2 hours at which stage it was judged to be complete by LCMS. The reaction mixture was filtered through celite, washed with EtOAc, concentrated and purified by PTLC (40% EtOAc/Hexane) to give the title compound (75 mg, 0.104 mmol, 73.8% yield).

Step 2: (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-{[7-(2,2,2-trifluoroethyl)piperidin-4-yl]oxy}-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide The product from Step 1 was converted to Example 234 using the previously described procedures for the synthesis of Example 225. The title compound was purified by PTLC (3% MeOH in CH$_2$Cl$_2$). LRMS m/z 931.4 (M+H)$^+$ Example 235 tert-butyl 4-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}piperidine-1-carboxylate

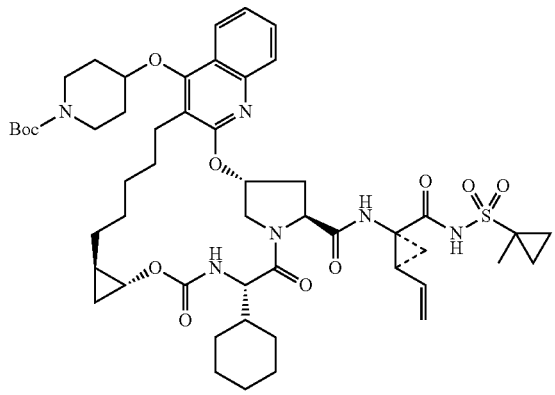

Example 235 was prepared by utilizing the procedures described for the synthesis of Example 211. Tert-butyl 4-hydroxypiperidine-1-carboxylate was used instead of 1-methylpiperidine-4-ol for the Mitsunobu reaction. LRMS m/z 975.4 (M+H)$^+$ Example 236

4-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-1-(2,2,2-trifluoroethyl)piperidinium formate

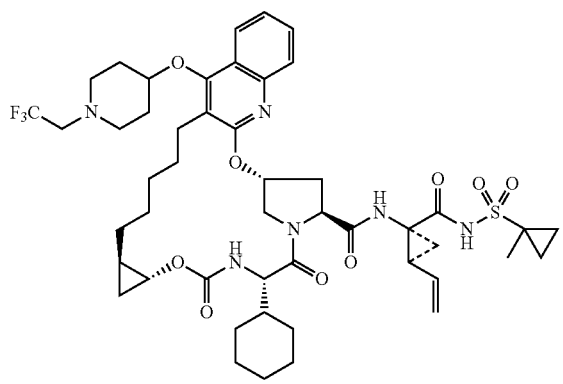

Step 1: 4-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-piperidinium trifluoroacetate

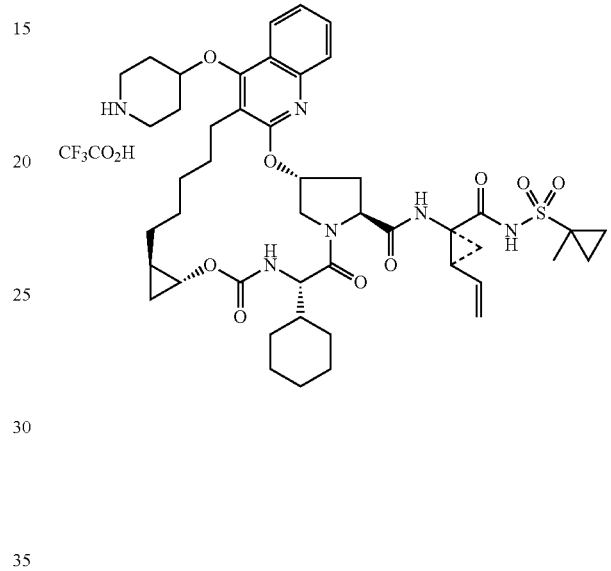

To a solution of Example 235 (100 mg, 0.103 mmol) in dichloromethane (5 ml) was added trifluoroacetic acid (1.025 ml, 0.103 mmol). The reaction was stirred at room temperature for 2 hours at which stage LCMS indicated complete hydrolysis of the NBoc group. The volatiles were evaporated under reduced pressure and the residue was diluted with DCM and azeotroped twice with toluene. The resulting residue (~101 mg) was dried under vacuum and used for the next step without purification.

Step 2: 4-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8 H-7,10-methanocyclopropa[18,19][1,10,3,6]dioxadiazacyclononadecino[11,12-b]quinolin-17-yl]oxy}-1-(2,2,2-trifluoroethyl)piperidinium formate To a solution of the product from Step 1 (101 mg, 0.102 mmol) in acetonitrile (5 mL) was added Hunig's base (0.089 mL, 0.511 mmol) followed by 2,2,2-trifluoroethyl trifluoromethanesulfonate (71.1 mg, 0.306 mmol). The reaction was stirred at 55° C. for 3 hours after which it was quenched with water and extracted with EtOAc. Purification by PTLC (3% MeOH in CH$_2$Cl$_2$) followed by reverse phase HPLC (0 to 90% acetonitrile in water; with 0.1% HCOOH) provided the title compound.

Example 237

4-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-1-(2-methoxyethyl)piperidinium formate

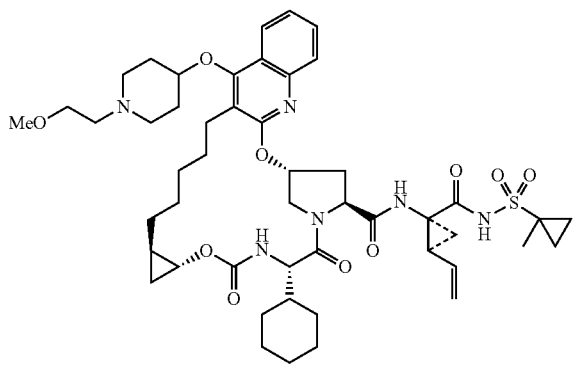

To a solution of the product from Step 1, Example 236 (100 mg, 0.101 mmol) in DMF (3 mL) was added triethylamine (0.070 mL, 0.506 mmol), potassium iodide (3.36 mg, 0.020 mmol) and 2-bromoethylmethylether (42.2 mg, 0.303 mmol). The reaction was heated to 55° C. and stirred for 4 hours at which stage LCMS indicated no starting material. After cooling to room temperature, water was added and the reaction was extracted with ethyl acetate. The combined organic fractions were washed with brine, dried ($Na_2SO_4$) and concentrated to give an oily residue, which was purified by HPLC (0 to 90% acetonitrile in water; with 0.1% HCOOH) to furnish the title compound.

Example 238

4-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-1-(cyclopropylmethyl)piperidinium formate

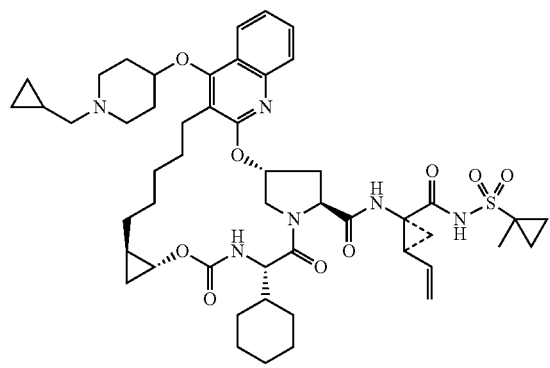

Example 238 was prepared by utilizing procedures described for the synthesis of Example 237. (Bromomethyl)cyclopropane was used instead of 1-bromo-2-methoxyethane in the last step to furnish the title compound.

Example 239

4-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-1-ethylpiperidinium formate

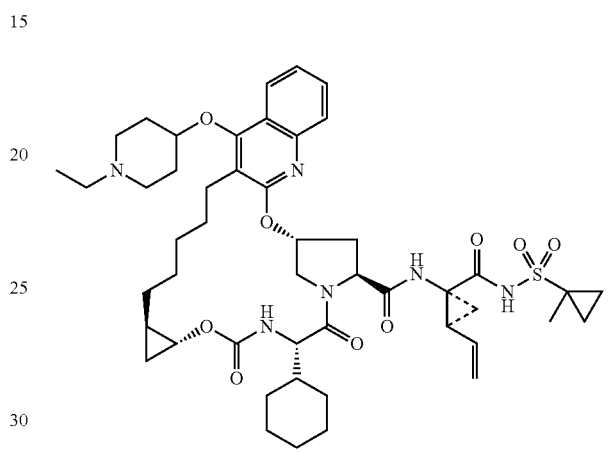

Example 239 was prepared by utilizing procedures described for the synthesis of Example 237. Iodoethane was used instead of 1-bromo-2-methoxyethane and potassium iodide was not utilized in the last step to furnish the title compound.

Example 240

4-(3-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}propyl)morpholin-4-ium formate

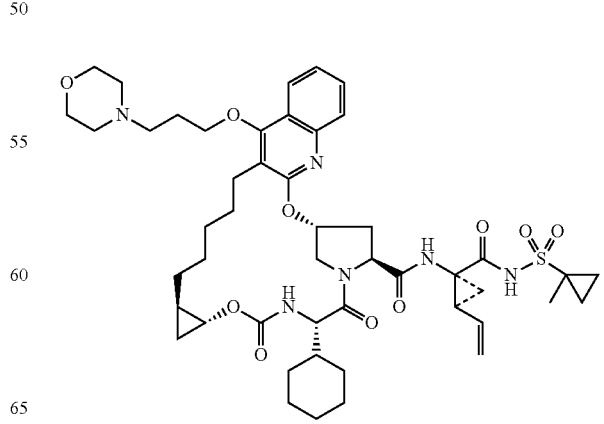

Step 1: (1aR,5S,8S,10R,22aR)-5-cyclohexyl-17-[3-bromopropoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

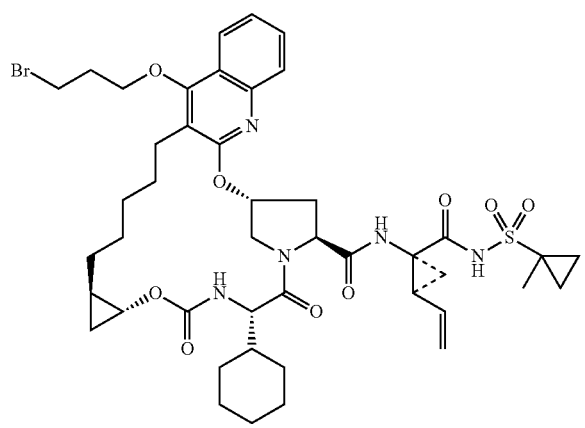

The title compound in step 1 was prepared by utilizing procedures similar to that described for the synthesis of the intermediate obtained in Example 145, Step 1.

Step 2: 4-(3-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}propyl)morpholin-4-ium formate A solution of the intermediate from Step 1 (60 mg, 0.066 mmol), morpholine (28.6 mg, 0.329 mmol), triethylamine (0.046 mL, 0.329 mmol) and potassium iodide (21.82 mg, 0.131 mmol) in DMF (2 mL) was stirred at 55° C. for 4 hours at which stage LCMS indicated complete conversion to the desired product. After cooling the reaction to room temperature, water was added the reaction was extracted with ethyl acetate. The combined organic fractions were dried over $Na_2SO_4$ and concentrated under reduced pressure. Purification by HPLC (0 to 90% acetonitrile in water; with 0.1% HCOOH) provided the title compound. LRMS m/z 919.4 $(M+H)^+$.

Example 241

N-(3-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}propyl)cyclopropanaminium formate

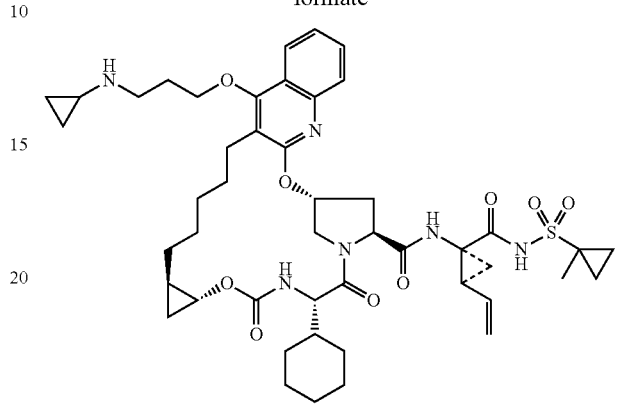

A solution of the intermediate from Example 240, Step 1 (85 mg, 0.093 mmol) and cyclopropyl amine (80 mg, 1.401 mmol) in DMF (2 mL) was stirred at 50° C. for 3 hours; LCMS indicated complete conversion. After cooling the reaction to room temperature, water was added the reaction was extracted with ethyl acetate. The combined organic fractions were dried over $Na_2SO_4$ and concentrated under reduced pressure. Purification by HPLC (0 to 90% acetonitrile in water; with 0.1% HCOOH) furnished the title compound. LRMS ink 889.4 $(M+H)^+$.

Example 242

N-(3-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}propyl)cyclobutanaminium formate

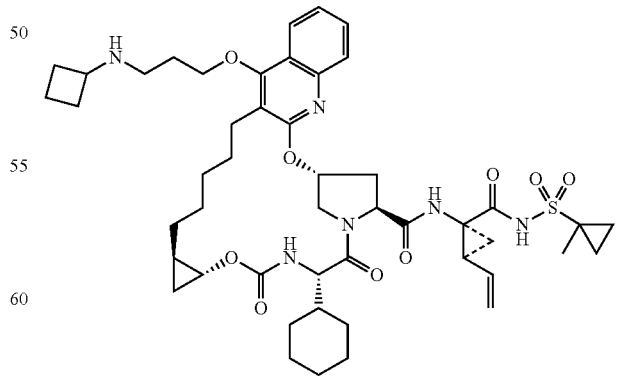

Example 242 was prepared by utilizing procedures similar to that described for the synthesis of Example 241. LRMS m/z 903.4 $(M+H)^+$

Example 243

(1aR,5S,8S,10R,22aR)-5-cyclohexyl-17-{3-[(3,3-difluorocyclobutyl)amino]propoxy}-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

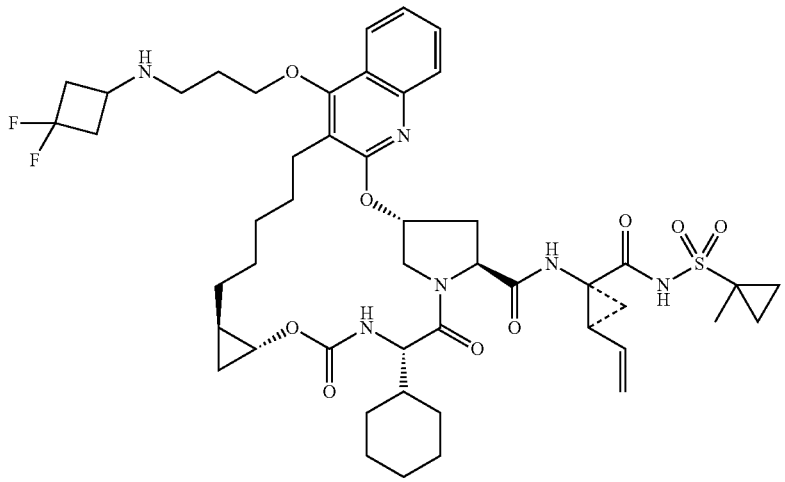

A solution of the intermediate from Example 240, Step 1 (50 mg, 0.055 mmol), 3,3-difluorocyclobutanamine (46.9 mg, 0.438 mmol), triethylamine (0.076 mL, 0.548 mmol) and potassium iodide (91 mg, 0.548 mmol) was stirred at 55° C. for 4 h at which stage LCMS indicated complete conversion to the desired product. After cooling the reaction to room temperature, water was added the reaction was extracted with ethyl acetate. The combined organic fractions were dried over Na$_2$SO$_4$ and concentrated under reduced pressure. Purification by PTLC (5% MeOH in CH2Cl2) furnished the title compound. LRMS m/z 939.4 (M+H)$^+$.

Example 244

(1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-(pyridin-4-yl)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

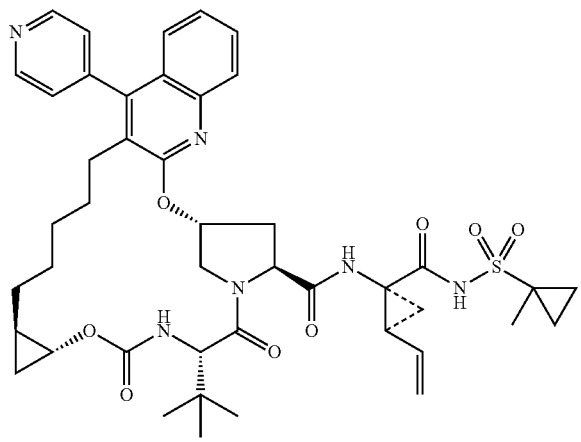

Step 1: methyl (1aR,5S,8S,10R,22aR)-5-tert-butyl-17-{[(trifluoromethyl)sulfonyl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

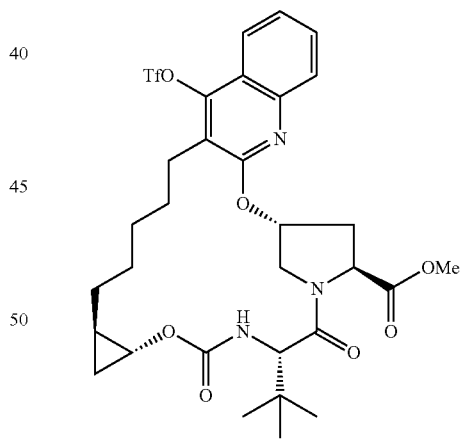

To a solution of the intermediate from Example 113, step 5 (200 mg, 0.361 mmol) in pyridine (2 ml) was added triflic anhydride (0.305 ml, 1.806 mmol) at 0° C. The reaction was stirred at 0° C. for 15 minutes and then at room temperature for 15 minutes after which water was added and an extraction was performed with EtOAc. The combined organics were washed with saturated aq. NH$_4$Cl and then with 10% aq. KHSO$_4$ solution followed by brine. Purification by PTLC (30% EtOAc/hexanes) provided the title compound.

329

Step 2: methyl (1aR,5S,8S,10R,22aR)-5-tert-butyl-17-(pyridin-4-yl)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

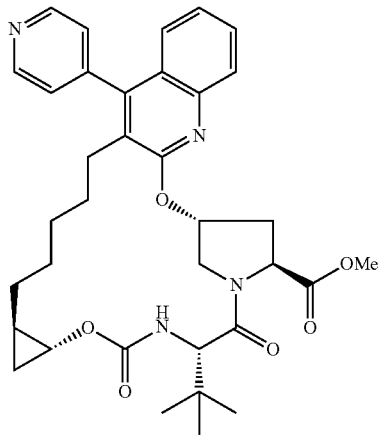 [SMILES: COC(=O)[C@@H]1C[C@@H]2CN1C(=O)[C@H](C(C)(C)C)NC(=O)O[C@@H]1C[C@H]1CCCCCc1c(nc3ccccc3c1-c1ccncc1)O2]

To a solution of the product from step 1 (50 mg, 0.073 mmol) in dioxane (5 ml) was added pyridine-4-boronic acid, (35.9 mg, 0.292 mmol), potassium phosphate tribasic (38.7 mg, 0.182 mmol) and tetrakis (16.85 mg, 0.015 mmol). After purging with $N_2$ for 5 min, the reaction was stirred at 80° C. for 16 hours. After cooling to room temperature, water was added and the reaction was extracted with ethyl acetate, washed with brine, dried ($Na_2SO_4$) and concentrated. Purification by PTLC (40% EtOAc/hexane) provided the desired compound.

Step 3: (1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-(pyridin-4-yl)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

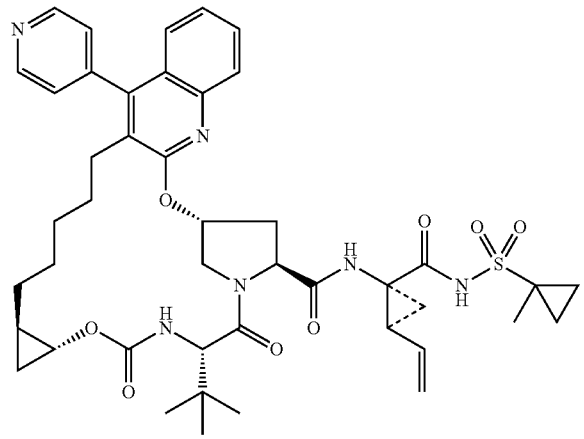

The product from step 2 was converted to Example 244 using the procedures described for the synthesis of Example 113, steps 7 and 8. LRMS m/z 827.2 (M+H)$^+$.

330

Example 245

(1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-(pyridin-2-yl)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

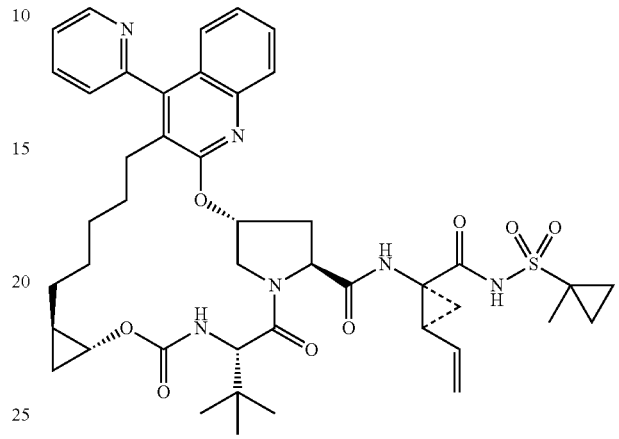

To a solution of the product from Example 244 step 1 (50 mg, 0.073 mmol) in dioxane (3 ml) was added 2-(tributylstannyl)pyridine (53.7 mg, 0.146 mmol), copper(I)iodide (2.78 mg, 0.015 mmol) and tetrakis (16.85 mg, 0.015 mmol). After purging with $N_2$ for 5 minutes, the reaction was stirred at 80° C. for 16 hours. After cooling to room temperature, water was added and the reaction was extracted with ethyl acetate, washed with brine, dried ($Na_2SO_4$) and concentrated. Purification by PTLC (40% EtOAc/hexane) provided the desired compound, which was converted to Example 245 using the procedures described for the synthesis of Example 244. LRMS m/z 827.2 (M+H)$^+$.

Example 246

(1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-(pyridin-3-yl)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

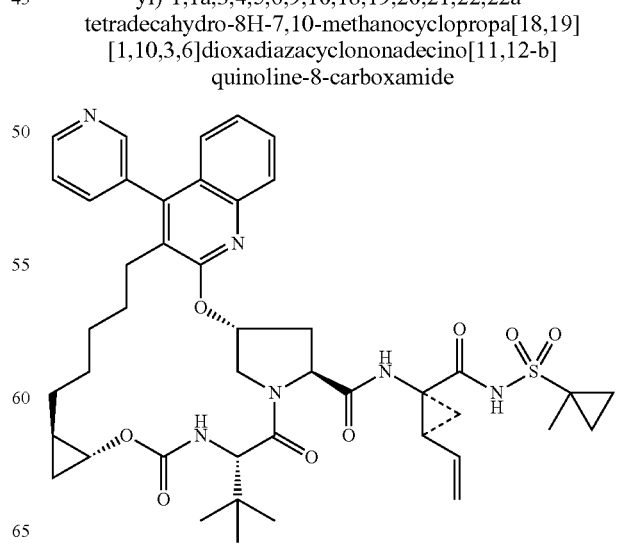

Example 246 was prepared using the procedures described for the synthesis of Example 244. Pyridin-3-ylboronic acid was used instead of pyridin-4-ylboronic acid in the coupling step. LRMS m/z 827.2 (M+H)⁺.

Example 247

(1aR,5S,8S,10R,22aR)-5-tert-butyl-N-[(1R,2S)-2-ethenyl-1-{[(1-methylcyclopropyl)sulfonyl]carbamoyl}cyclopropyl]-3,6-dioxo-17-(1,3-thiazol-2-yl)-1,1a,3,4,5,6,9,10,18,19,20,21,22,22a-tetradecahydro-8H-7,10-methanocyclopropa[18,19][1,10,3,6]dioxadiazacyclononadecino[11,12-13]quinoline-8-carboxamide

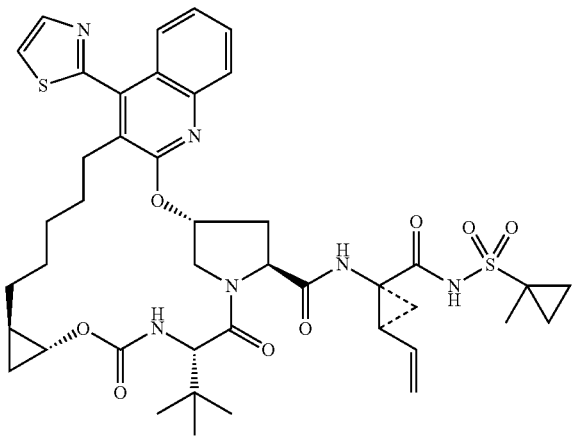

Example 247 was prepared using the procedures described for the synthesis of Example 245. 2-(Tributylstannyl)thiazole was used instead of 2-(tributylstannyl)pyridine. LRMS m/z 833.2 (M+H)⁺

Example 248 potassium {[(1R,2S)-1-({[(1aR,5S,8S,10R,22aR)-5-tert-butyl-17-(morpholin-4-ylmethyl)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl]carbonyl}amino)-2-ethenylcyclopropyl]carbonyl}[(1-methylcyclopropyl)sulfonyl]azanide

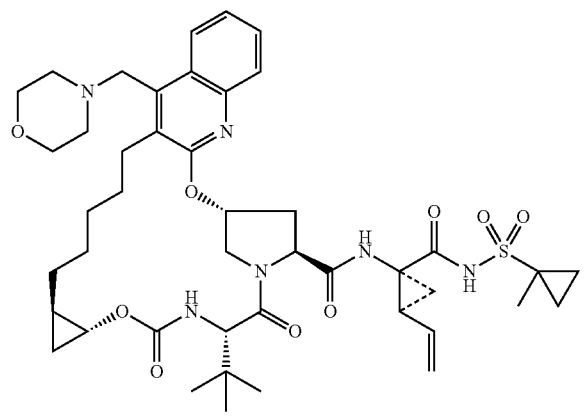

Step 1: methyl (1aR,5S,8S,10R,22aR)-5-tert-butyl-17-vinyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

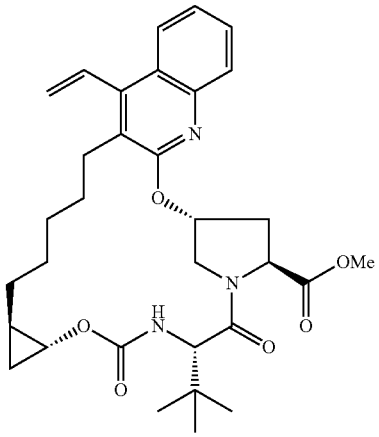 [SMILES: C=Cc1c2c(nc3ccccc13)O[C@@H]1C[C@@H](C(=O)OC)N(C1)C(=O)[C@H](C(C)(C)C)NC(=O)O[C@@H]1C[C@H]1CCCCC2]

To a solution of the product from Example 244 step 1 (100 mg, 0.146 mmol) in dioxane (3 ml) was added tributyl(vinyl)stannane (92 mg, 0.292 mmol), copper (I) iodide (5.55 mg, 0.029 mmol) and tetrakis (33.7 mg, 0.029 mmol). After purging with N₂ for 5 min, the reaction was stirred at 80° C. for 16 hours. After cooling to room temperature, water was added and the reaction was extracted with ethyl acetate, washed with brine, dried (Na₂SO₄) and concentrated. Purification by PTLC (30% EtOAc/hexane) provided the desired compound.

Step 2: methyl (1aR,5S,8S,10R,22aR)-5-tert-butyl-17-formyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

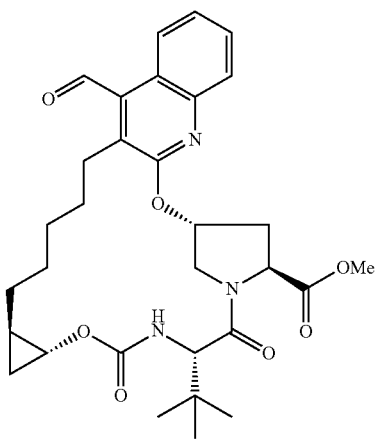

To a solution of the product from Step 1 (30 mg, 0.053 mmol) in acetone (1 ml) and water (1 mL) was added potassium osmate dehydrate (19.61 mg, 0.053 mmol). The reaction was stirred at room temperature for 10 minutes after which sodium periodate (114 mg, 0.532 mmol) was added. After stirring for 2 hours, an additional 15 mg of potassium osmate and 115 mg of sodium periodate were added. After stirring 16 hours, the reaction was filtered and the solid was washed with acetone. The filtrate was concentrated, diluted with EtOAc and washed with Na$_2$S$_2$O$_3$ and NaHCO$_3$ aq. soln. Purification by PTLC (30% EtOAc-hexane) provided the desired aldehyde.

Step 3: methyl (1aR,5S,8S,10R,22aR)-5-tert-butyl-17-(morpholinomethyl)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

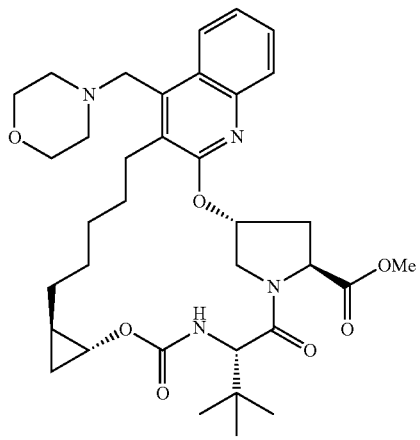 [SMILES: COC(=O)[C@@H]1C[C@@H]2CN1C(=O)[C@H](C(C)(C)C)NC(=O)O[C@@H]1C[C@H]1CCCCCc1c(nc3ccccc3c1CN1CCOCC1)O2]

To a solution of the product from Step 2 (34 mg, 0.060 mmol) in CH$_2$Cl$_2$ (3 ml) was added morpholine (0.016 ml, 0.180 mmol) and acetic acid (10.32 µl, 0.180 mmol) followed by sodium triacetoxyborohydride (38.2 mg, 0.180 mmol). The reaction was complete in 30 minutes at which stage it was quenched with water and extracted with dichloromethane. Purification by PTLC (40% EtOAc/hexane) provided the desired compound.

Step 4: potassium {[(1R,2S)-1-({[(1aR,5S,8S,10R,22aR)-5-tert-butyl-17-(morpholin-4-ylmethyl)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl]carbonyl}amino)-2-ethenylcyclopropyl]carbonyl}[(1-methylcyclopropyl)sulfonyl]azanide

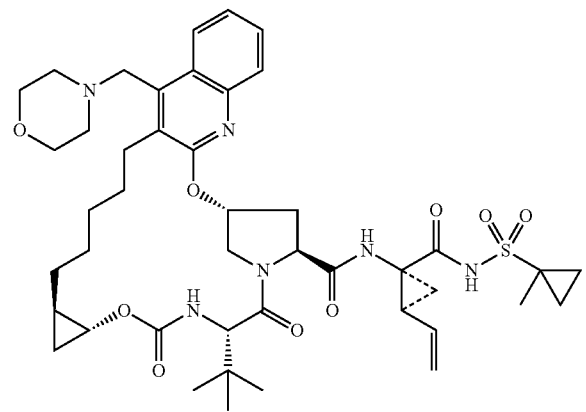

Steps 7 and 8 described for the synthesis of Example 113 were performed on the product from step 3 and the resulting compound was converted to Example 248 after treatment with 1 equivalent of 0.1N aqueous KOH solution. LRMS m/z 849.2 (M+H)$^+$.

Example 249

(1aR,5S,8S,10R,22aR)-5-cyclohexyl-17-[3-(3,3-difluoroazetidin-1-yl)propoxy]-N-[(1R,2S)-2-ethenyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

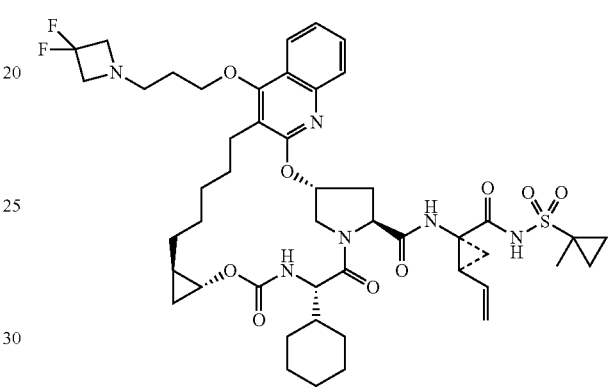

Example 249 was prepared using the procedures described for the synthesis of Example 243. 3,3-Difluoroazetidine hydrochloride was used instead of 3,3-difluorocyclobutanamine in the final alkylation step to provide the title compound. LRMS m/z 925.6 (M+H)$^+$ Example 250

(1aR,5S,8S,10R,22aR)-5-cyclohexyl-N-[(1R,2S)-2-ethenyl-1-{[1-methylcyclopropyl)sulfonyl]carbamoyl}cyclopropyl]-17-[3-(3-fluoroazetidin-1-yl)propoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

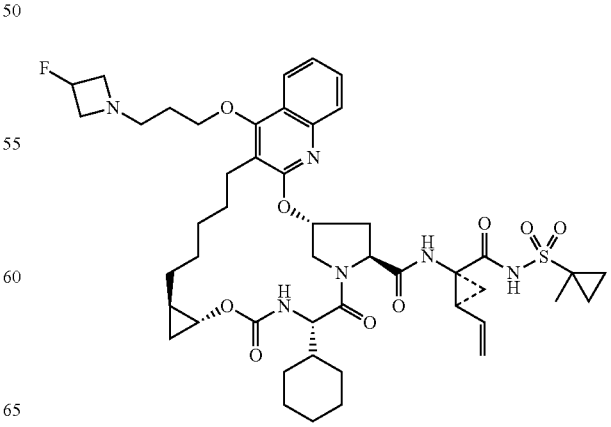

Example 250 was prepared using the procedures described for the synthesis of Example 243. 3-fluoroazetidine hydrochloride was used instead of 3,3-difluorocyclobutanamine in the final alkylation step to provide the title compound. LRMS m/z 907.6 (M+H)+

Example 251

(1aR,5S,8S,10R,22aR)-5-cyclohexyl-N-[(1R,2S)-2-ethenyl-1-{[(1-methylcyclopropyl)sulfonyl]carbamoyl}cyclopropyl]-17-[3-(4-methylpiperazin-1-yl)propoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

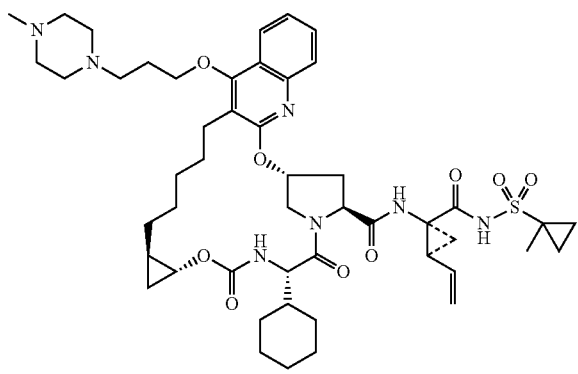

Example 251 was prepared using the procedures described for the synthesis of Example 243. N-methylpiperazine was used instead of 3,3-difluorocyclobutanamine in the final alkylation step to provide the title compound. LRMS m/z 932.6 (M+H)+

Example 252 potassium {[(1R,2S)-2-ethenyl-1-({[(1aR,5S,8S,10R,22aR)-17-[(1-methylpiperidin-4-yl)oxy]-3,6-dioxo-5-(tetrahydro-2H-pyran-4-yl)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl]carbonyl}amino)cyclopropyl]carbonyl}[(1-methylcyclopropyl)sulfonyl]azanide

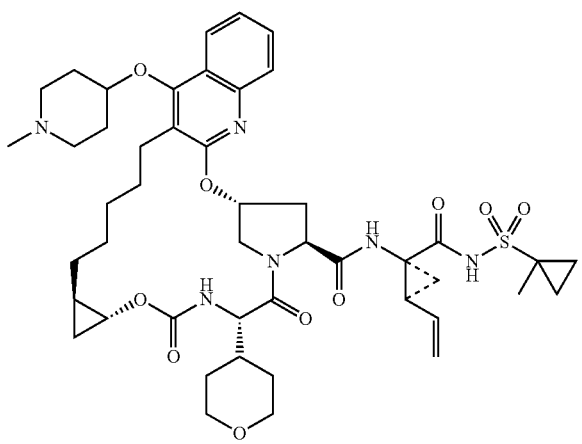

Step 1: (S)-methyl 2-(((((1R,2R)-2-(pent-4-yn-1-yl)cyclopropoxy)carbonyl)amino)-2-(tetrahydro-2H-pyran-4-yl)acetate

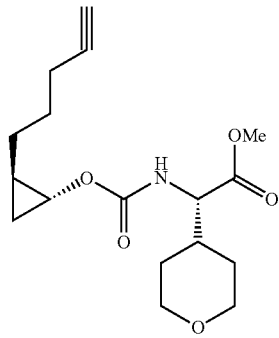 [SMILES: C#CCCC[C@@H]1C[C@H]1OC(=O)N[C@H](C(=O)OC)C1CCOCC1]

The title compound was prepared using the procedures described for Intermediate B11, Step 2. (S)-methyl 2-amino-2-(tetrahydro-2H-pyran-4-yl)acetate was reacted with the product obtained after Step 1 in the preparation of Intermediate B11.

Step 2: (S)-2-(((((1R,2R)-2-(pent-4-yn-1-yl)cyclopropoxy)carbonyl)amino)-2-(tetrahydro-2H-pyran-4-yl)acetic acid

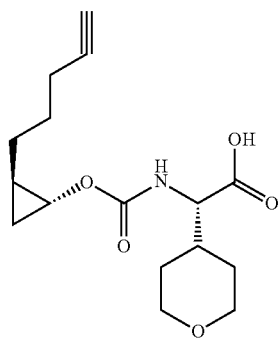 [SMILES: C#CCCC[C@@H]1C[C@H]1OC(=O)N[C@H](C(=O)O)C1CCOCC1]

To a solution of the product from Step 1 (1.88 g, 5.81 mmol) in THF (20 ml) and MeOH (10 mL) was added an aq. 2M solution of lithium hydroxide monohydrate (14.53 ml, 29.1 mmol). The reaction was stirred at 50° C. for 20 hours at which stage TLC indicated no more starting material. The reaction was treated with 10% aq. KHSO4 and extracted with EtOAc. The organic fractions were washed with brine, dried over sodium sulfate, evaporated and dried to provide the desired compound, which was used for the next step without purification.

337

Step 3: potassium {[(1R,2S)-2-ethenyl-1-({[(1aR,5S,8S,10R,22aR)-17-[(1-methylpiperidin-4-yl)oxy]-3,6-dioxo-5-(tetrahydro-2H-pyran-4-yl)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl]carbonyl}amino)cyclopropyl]carbonyl}[(1-methylcyclopropyl)sulfonyl]azanide

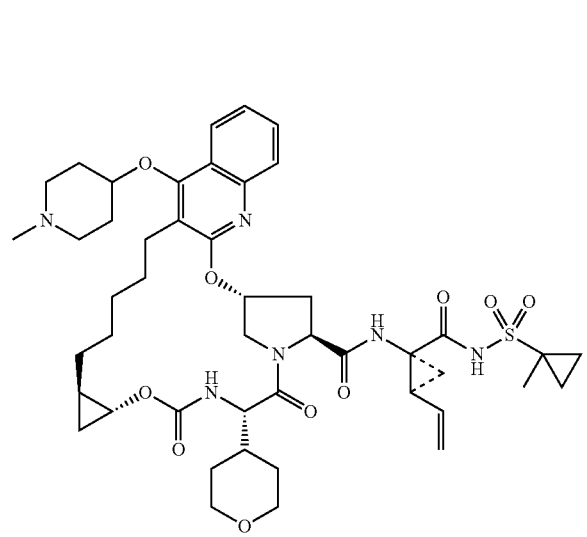

The product from Step 2 was converted to Example 252 using the procedures described for the synthesis of Example 210; the potassium salt was prepared upon treatment of the parent compound with 1 equivalent of 0.1N aqueous KOH solution. LRMS m/z 891.2 (M+H)$^+$

338

Example 253

(1aR,5S,8S,10R,22aR)-5-cyclohexyl-N-[(1R,2S)-2-ethenyl-1-{[(1-methylcyclopropyl)sulfonyl]carbamoyl}cyclopropyl]-3,6-dioxo-17-(tetrahydro-2H-pyran-4-yloxy)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

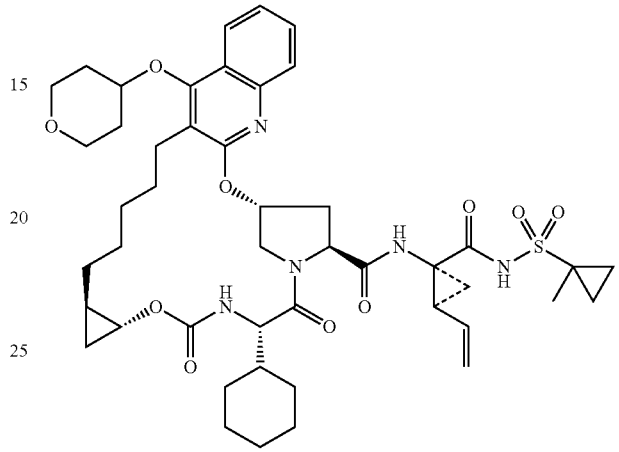

Example 253 was prepared by utilizing the procedures described for the synthesis of Example 211. Tetrahydro-2H-pyran-4-ol was used instead of 1-methylpiperidine-4-ol for the Mitsunobu reaction. LRMS m/z 876.6 (M+H)$^+$ Example 254 tert-butyl 9-{[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-3-oxa-7-azabicyclo[3.3.1]nonane-7-carboxylate

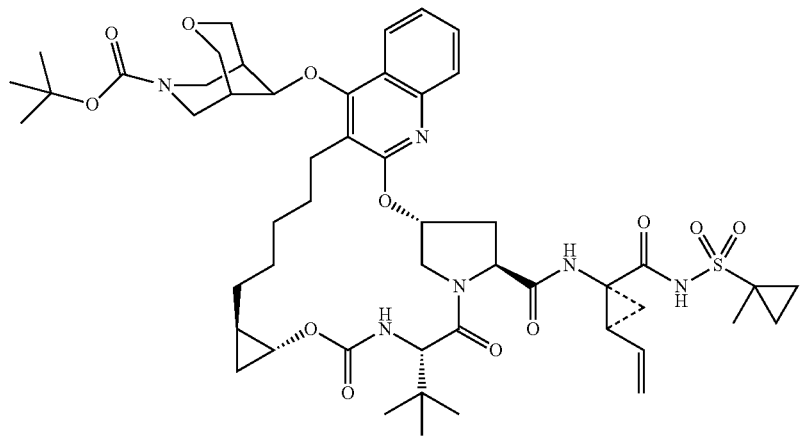

Step 1: methyl (1aR,5S,8S,10R,22aR)-5-tert-butyl-17-{syn-[7-(tert-butoxycarbonyl)-3-oxa-7-azabicyclo[3.3.1]non-9-yl]-oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

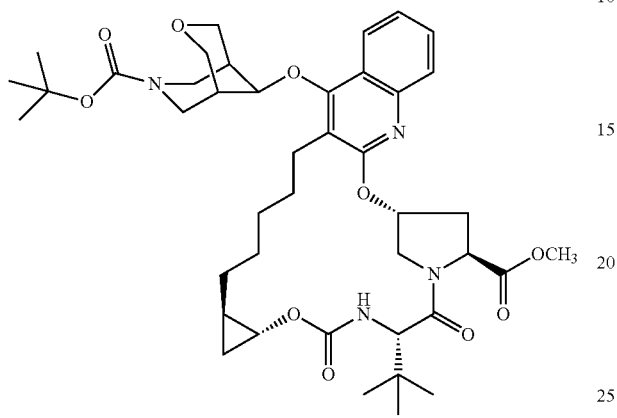

The title compound was prepared using the procedure described for the synthesis of Example 210, Step 1. (1R,5S)-tert-butyl 9-hydroxy-3-oxa-7-azabicyclo[3.3.1]nonane-7-carboxylate (1:2 mixture of anti:syn alcohols; prepared as described in International Patent Publication No. WO2009055331) was used instead of 1-methylpiperidin-4-ol. The title compound (syn isomer) was separated from the anti isomer by column chromatography (0-40% EtOAc in hexane); the syn isomer eluted first and was collected as the minor isomer.

Step 2: tert-butyl 9-{[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-3-oxa-7-azabicyclo[3.3.1]nonane-7-carboxylate Example 254 was prepared from the product of Step 1 by utilizing the procedures described for the synthesis of Example 210. LRMS m/z 991.2 (M+H)$^+$ Example 255 tert-butyl 9-{[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-3-oxa-7-azabicyclo[3.3.1]nonane-7-carboxylate

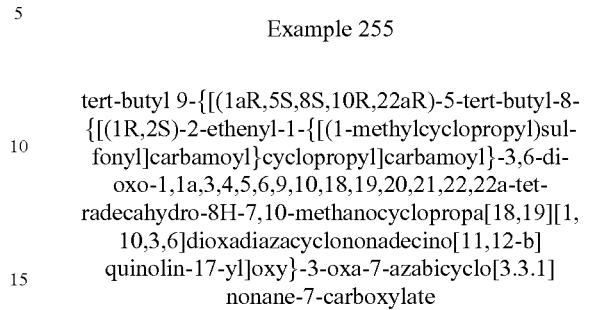

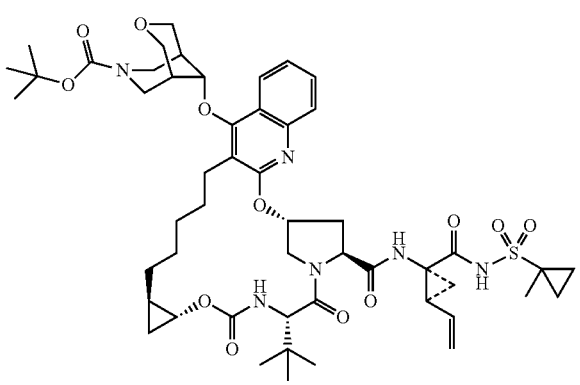

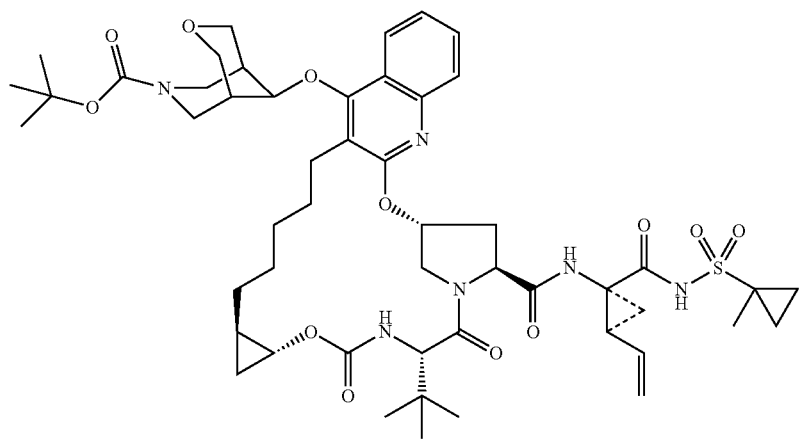

Step 1: methyl (1aR,5S,8S,10R,22aR)-5-tert-butyl-17-{anti-[7-(tert-butoxycarbonyl)-3-oxa-7-azabicyclo[3.3.1]non-9-yl]-oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

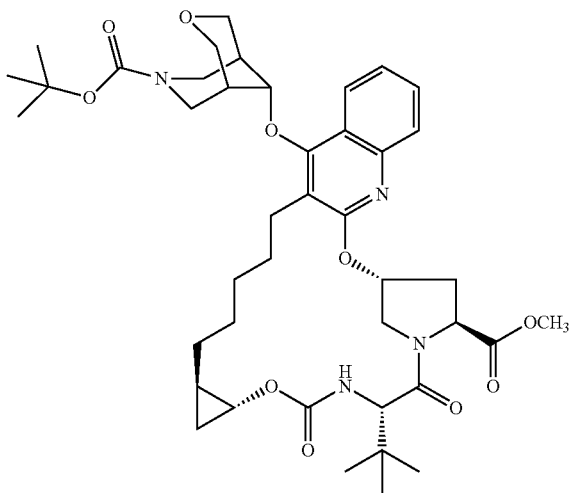 [SMILES: COC(=O)[C@@H]1C[C@@H]2CN1C(=O)[C@H](C(C)(C)C)NC(=O)O[C@@H]1C[C@H]1CCCCCc1c(nc3ccccc3c1OC1C3COCC1CN(C(=O)OC(C)(C)C)C3)O2]

The title compound was prepared using the procedure described for the synthesis of Example 210, Step 1. (1R,5S)-tert-butyl 9-hydroxy-3-oxa-7-azabicyclo[3.3.1]nonane-7-carboxylate (1:2 mixture of anti:syn alcohols; prepared as described in International Patent Publication No. WO2009055331) was used instead of 1-methylpiperidin-4-ol. The title compound (anti isomer) was separated from the syn isomer by column chromatography (0-40% EtOAc in hexane); the anti isomer eluted after the syn isomer and was collected as the major isomer.

Step 2: tert-butyl 9-{[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-3-oxa-7-azabicyclo[3.3.1]nonane-7-carboxylate

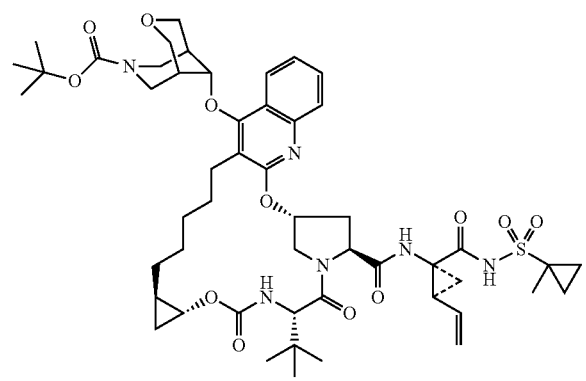

Example 255 was prepared from the product of Step 1 by utilizing the procedures described for the synthesis of Example 210. LRMS m/z 991.2 (M+H)⁺

Example 256

9-{[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-7-(cyclopropylmethyl)-3-oxa-7-azoniabicyclo[3.3.1]nonane formate

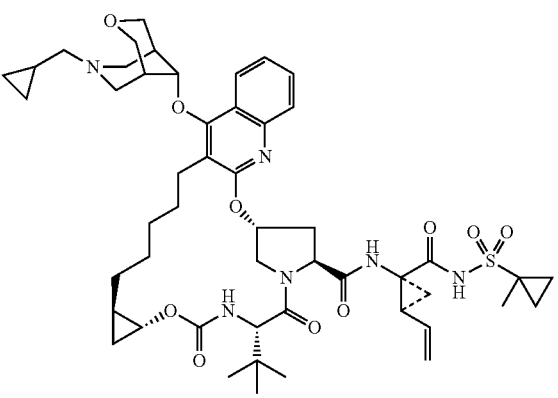

Example 256 was prepared from Example 255 by utilizing the procedures described for the synthesis of Example 238. LRMS m/z 945.2 (M+H)⁺

Example 257

9-{[(1aR,5S,8S,10R,22aR)-5-tert-butyl-8-{[(1R,2S)-2-ethenyl-1-{[1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-7-(2-methoxyethyl)-3-oxa-7-azoniabicyclo[3.3.1]nonane formate

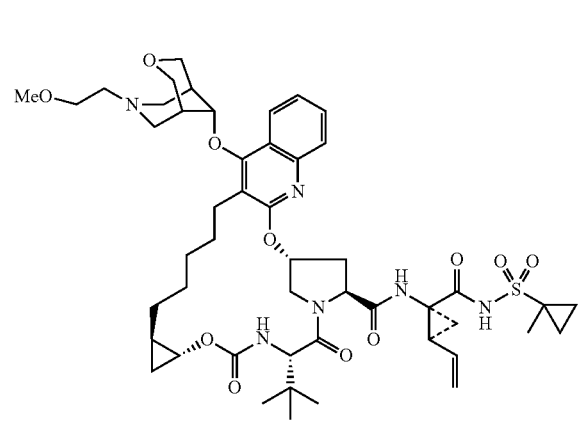

Example 257 was prepared from Example 255 by utilizing the procedures described for the synthesis of Example 237. LRMS m/z 949.2 (M+H)$^+$ Example 258

9-{[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-3-oxa-7-azoniabicyclo[3.3.1]nonane trifluoroacetate

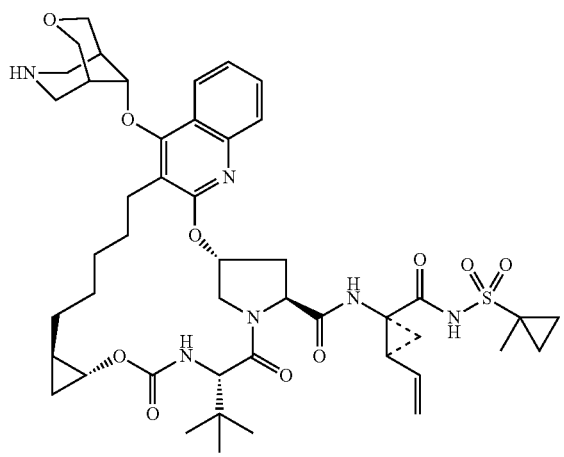

Example 258 was prepared from Example 255 by utilizing the procedure described for the synthesis of Example 236, Step 1. LRMS m/z 891.2 (M+H)$^+$.

Example 259

9-{[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-3-oxa-7-azoniabicyclo[3.3.1]nonane trifluoroacetate

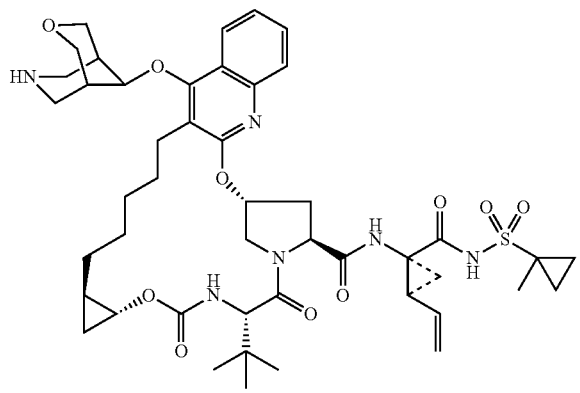

Example 259 was prepared from Example 254 by utilizing the procedure described for the synthesis of Example 236, Step 1. LRMS m/z 891.2 (M+H)$^+$.

Example 260

(1aR,5S,8S,10R,22aR)-5-tert-butyl-N-[(1R,2S)-2-ethenyl-1-{[(1-methylcyclopropyl)sulfonyl]carbamoyl}cyclopropyl]-17-[(7-ethyl-3-oxa-7-azabicyclo[3.3.1]non-9-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

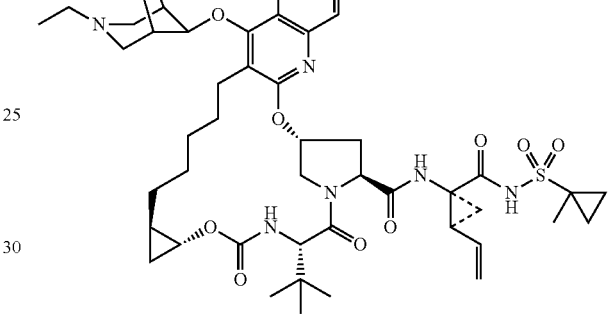

Example 260 was prepared from Example 254 by utilizing the procedure described for the synthesis of Example 239. LRMS m/z 919.2 (M+H)$^+$.

Example 261

(1aR,5S,8S,10R,22aR)-5-tert-butyl-N-[(1R,2S)-2-ethenyl-1-{[(1-methylcyclopropyl)sulfonyl]carbamoyl}cyclopropyl]-17-{[7-(2-methoxyethyl)-3-oxa-7-azabicyclo[3.3.1]non-9-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

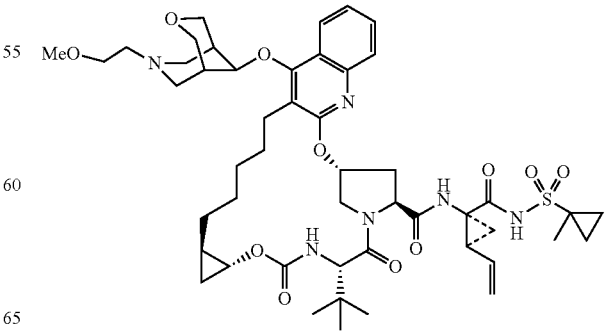

Example 261 was prepared from Example 254 by utilizing the procedures described for the synthesis of Example 237. LRMS m/z 949.2 (M+H)+.

Example 262 potassium {[(1R,2S)-1-({[(1aR,5S,8S,10R,22aR)-5-cyclohexyl-3,6-dioxo-17-({1-[2-(trifluoromethoxy)ethyl]piperidin-4-yl}oxy)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl]carbonyl}amino)-2-ethenylcyclopropyl]carbonyl}[(1-methylcyclopropyl)sulfonyl]azanide

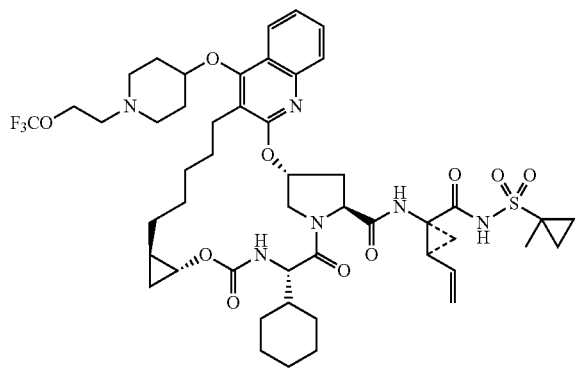

Example 262 was prepared by utilizing the procedures described for the synthesis of Example 236. 2-(Trifluoromethoxy)ethyl trifluoromethanesulfonate was used instead of 2,2,2-trifluoroethyl trifluoromethanesulfonate in the final alkylation step. LRMS m/z 987.2 (M+H)+.

Example 263

(1aR,5S,8S,10R,22aR)—N-[(1R,2S)-2-ethenyl-1-{[(1-methylcyclopropyl)sulfonyl]carbamoyl}cyclopropyl]-17-[(8-methyl-8-azabicyclo[3.2.1]oct-3-yl)oxy]-5-(1-methylcyclohexyl)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

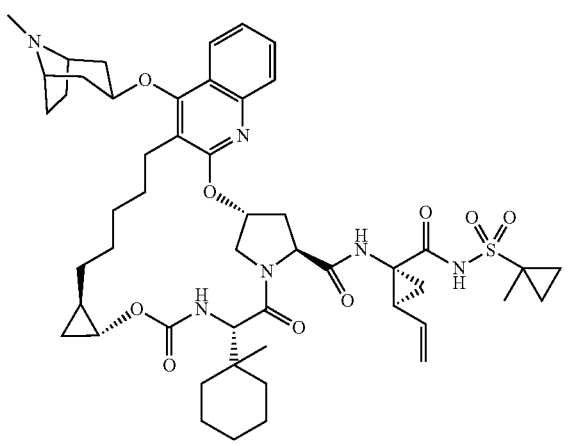 [SMILES: C=C[C@@H]1C[C@]1(NC(=O)[C@@H]1C[C@@H]2CN1C(=O)[C@H](C1(C)CCCCC1)NC(=O)O[C@@H]1C[C@H]1CCCCCc1c(nc3ccccc3c1OC1CC3CCC(C1)N3C)O2)C(=O)NS(=O)(=O)C1(C)CC1]

Example 263 was prepared by utilizing the procedures described for the synthesis of Example 232; tropine was used instead of 1-methylpiperidin-4-ol. LRMS m/z 929.2 (M+H)+.

Example 264 tert-butyl 4-(3-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}propyl)piperazine-1-carboxylate

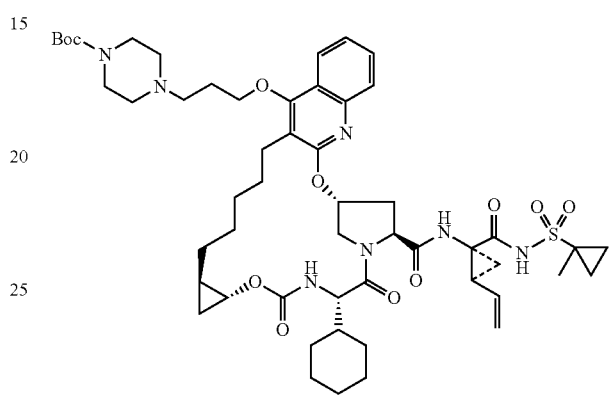

Example 264 was prepared by utilizing the procedures described for the synthesis of Example 251; NBoc-piperazine was used instead of N-methylpiperazine. LRMS m/z 1019.2 (M+H)+.

Example 265 potassium ({(1R,2S)-1-[({(1aR,5S,8S,10R,22aR)-5-cyclohexyl-3,6-dioxo-17-[3-(piperazin-1-yl)propoxy]-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl}carbonyl)amino]-2-ethenylcyclopropyl}carbonyl)[(1-methylcyclopropyl)sulfonyl]azanide

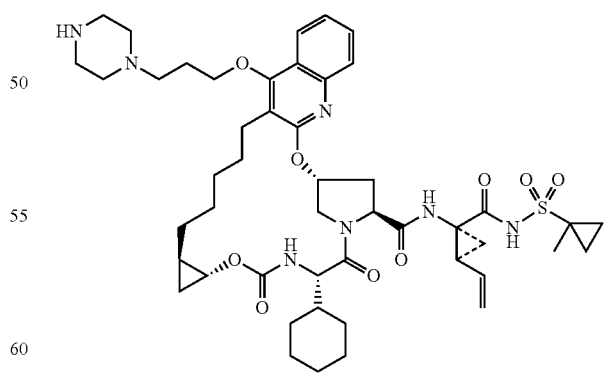

Example 265 was prepared from Example 262 by utilizing the procedure described for the synthesis of Example 236, Step 1; the potassium salt was prepared upon treatment of the parent compound with 0.1N aqueous KOH solution. LRMS m/z 918.4 (M+H)+.

Example 266 potassium ({(1R,2S)-1-[({(1aR,5S,8S,10R,22aR)-5-cyclohexyl-17-[(4-methylpiperazin-1-yl)methyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl}carbonyl)amino]-2-ethenylcyclopropyl}carbonyl)[(1-methylcyclopropyl)sulfonyl]azanide

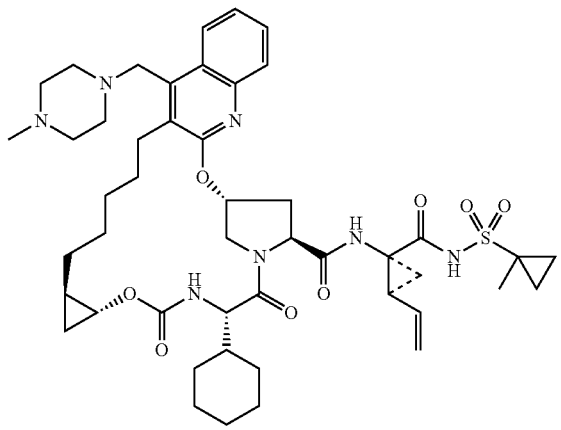

Example 266 was prepared by utilizing the procedures described for the synthesis of Example 248. LRMS m/z 888.3 (M+H)$^+$.

Example 267 tert-butyl 4-{[(1aR,5S,8S,10R,22aR)-8-{[(1R,2S)-2-ethenyl-1-{[(1-methylcyclopropyl)sulfonyl]carbamoyl}cyclopropyl]carbamoyl}-5-(1-methylcyclohexyl)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}piperidine-1-carboxylate

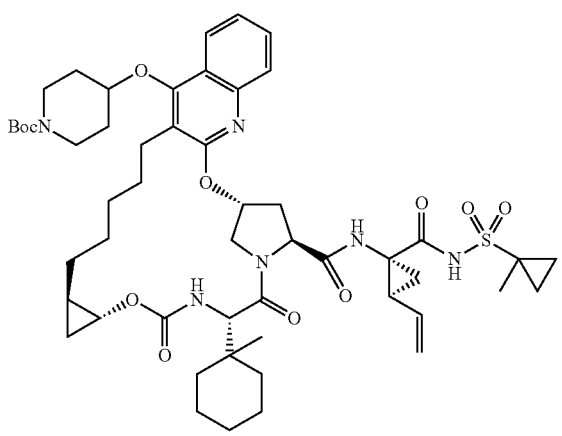 [SMILES: C=C[C@@H]1C[C@]1(NC(=O)[C@@H]1C[C@@H]2CN1C(=O)[C@H](C1(C)CCCCC1)NC(=O)O[C@@H]1C[C@H]1CCCCCc1c(nc3ccccc3c1OC1CCN(C(=O)OC(C)(C)C)CC1)O2)C(=O)NS(=O)(=O)C1(C)CC1]

Example 267 was prepared by utilizing the procedures described for Example 263; NBoc-piperidine was used instead of tropine. LRMS m/z 989.2 (M+H)$^+$.

Example 268

(1aR,5S,8S,10R,22aR)—N-[(1R,2S)-2-ethenyl-1-{[(1-methylcyclopropyl)sulfonyl]carbamoyl}cyclopropyl]-5-(1-methylcyclohexyl)-3,6-dioxo-17-(piperidin-4-yloxy)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

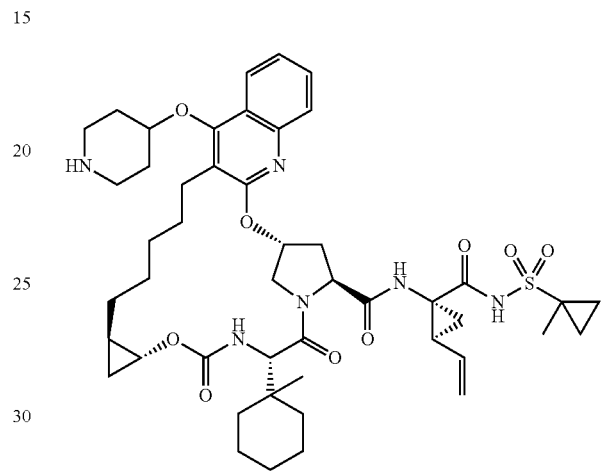

Example 268 was prepared from Example 267 by utilizing the procedure described for the synthesis of Example 236, Step 1. LRMS m/z 889.2 (M+H)$^+$.

Example 270

(1aR,5S,8S,10R,22aR)—N-[(1R,2S)-2-ethenyl-1-{[(1-methylcyclopropyl)sulfonyl]carbamoyl}cyclopropyl]-5-(1-methylcyclohexyl)-17-[3-(1,4-oxazepan-4-yl)propoxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

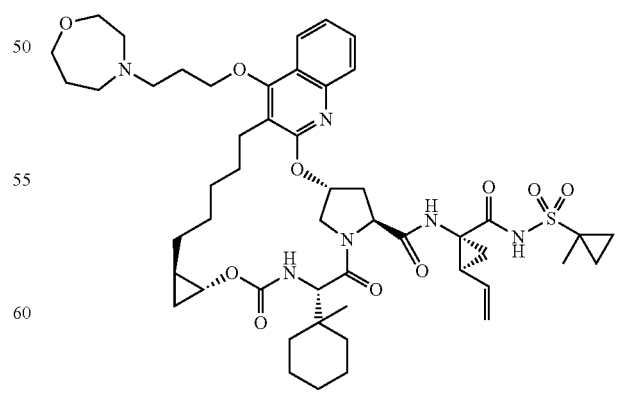

Example 270 was prepared by utilizing the procedures described for the synthesis of Example 240. LRMS m/z 947.2 (M+H)$^+$.

Example 271

(1aR,5S,8S,10R,22aR)-5-cyclohexyl-N-[(1R,2S)-2-ethenyl-1-{[(1-methylcyclopropyl)sulfonyl]carbamoyl}cyclopropyl]-17-({1-[2-(methylsulfonyl)ethyl]piperidin-4-yl}oxy)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

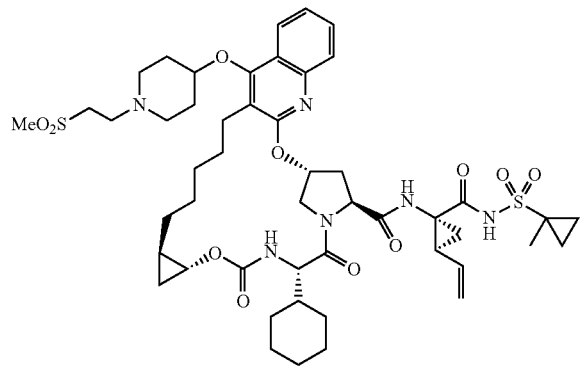 [SMILES: C=C[C@@H]1C[C@]1(NC(=O)[C@@H]1C[C@@H]2CN1C(=O)[C@H](C1CCCCC1)NC(=O)O[C@@H]1C[C@H]1CCCCCc1c(nc3ccccc3c1OC1CCN(CCS(C)(=O)=O)CC1)O2)C(=O)NS(=O)(=O)C1(C)CC1]

To a solution of the product from Step 1, Example 236 (50 mg, 0.057 mmol) in $CH_2Cl_2$ (3 ml) was added DIPEA (0.030 ml, 0.171 mmol) followed by methyl vinyl sulfone (12.10 mg, 0.114 mmol). The reaction was stirred in a sealed vial for 16 h at which stage LCMS indicated complete conversion to one peak corresponding to a product with desired mass. After removing the solvent the crude mixture was purified by PTLC (5% MeOH in $CH_2Cl_2$) and then repurified by PTLC using 40% acetone in hexane to furnish the title compound. LRMS m/z 981.6 $(M+H)^+$.

Example 272

4-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-1-(2-fluoroethyl)piperidinium formate

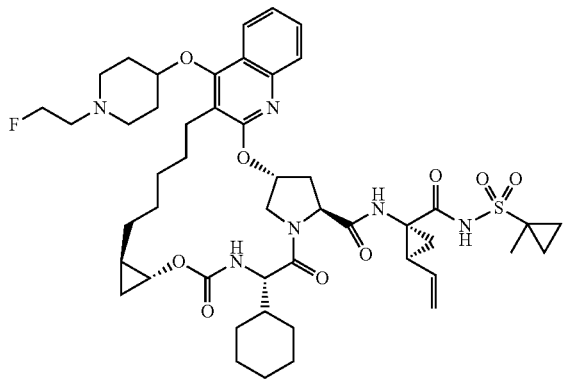 [SMILES: C=C[C@@H]1C[C@]1(NC(=O)[C@@H]1C[C@@H]2CN1C(=O)[C@H](C1CCCCC1)NC(=O)O[C@@H]1C[C@H]1CCCCCc1c(nc3ccccc3c1OC1CCN(CCF)CC1)O2)C(=O)NS(=O)(=O)C1(C)CC1]

The product from Step 1, Example 236 was reacted with 1-bromo-2-fluoro ethane as described for the synthesis of Example 237 to give Example 272. LRMS m/z 921.2 $(M+H)^+$.

Example 273 tert-butyl 3-{[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-8-azabicyclo[3.2.1]octane-8-carboxylate

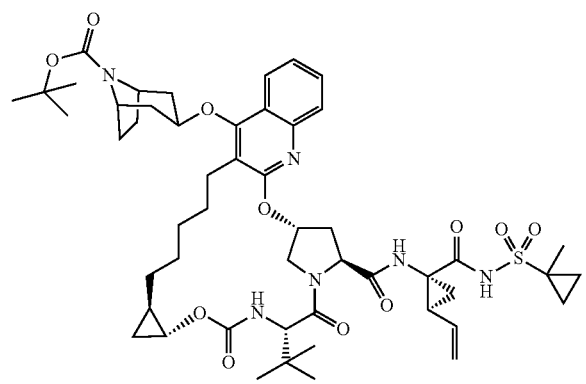 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3ccccc3c1OC1CC3CCC(C1)N3C(=O)OC(C)(C)C)O2)C(=O)NS(=O)(=O)C1(C)CC1]

Example 273 was prepared using the procedures described for the synthesis of Example 210. The endo isomer of tert-butyl 3-hydroxy-8-azabicyclo[3.2.1]octane-8-carboxylate (as prepared in International Patent Application No. WO2009055331) was used instead of 1-methylpiperidin-4-ol. LRMS m/z 975.4 $(M+H)^+$.

Example 274

3-{[(1aR,5S,8S,10R,22aR)-5-tert-butyl-8-{[(1R,2S)-2-ethenyl-1-{[1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-8-azoniabicyclo[3.2.1]octane trifluoroacetate

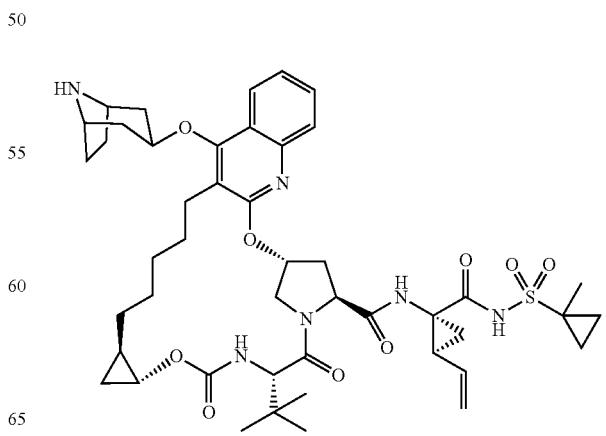

Example 274 was prepared from Example 273 by utilizing the procedure described for the synthesis of Example 236, Step 1. LRMS m/z 875.4 (M+H)$^+$ Example 275 potassium {[(1R,2S)-1-({[(1aR,5S,8S,10R,22aR)-5-tert-butyl-3,6-dioxo-17-{[8-(2,2,2-trifluoroethyl)-8-azabicyclo[3.2.1]oct-3-yl]oxy}-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl]carbonyl}amino)-2-ethenylcyclopropyl]carbonyl}[(1-methylcyclopropyl)sulfonyl]azanide

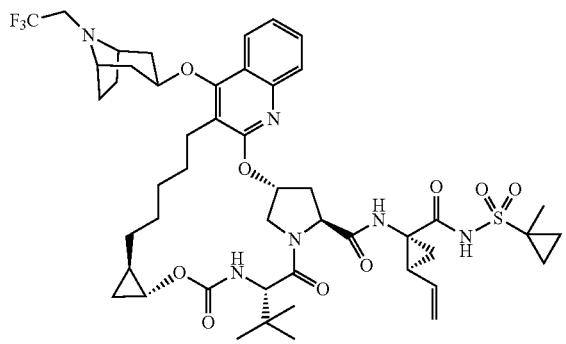 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3ccccc3c1OC1CC3CCC(C1)N3CC(F)(F)F)O2)C(=O)NS(=O)(=O)C1(C)CC1]

Example 274 was converted into Example 275 by utilizing the procedures described for the synthesis of Example 236; the potassium salt was prepared upon treatment of the free base with 0.1N aqueous KOH solution. LRMS m/z 957.4 (M+H)$^+$.

Example 276 potassium {[(1R,2S)-1-({[(1aR,5S,8S,10R,22aR)-5-tert-butyl-17-{[8-(2-methoxyethyl)-8-azabicyclo[3.2.1]oct-3-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl]carbonyl}amino)-2-ethenylcyclopropyl]carbonyl}[(1-methylcyclopropyl)sulfonyl]azanide

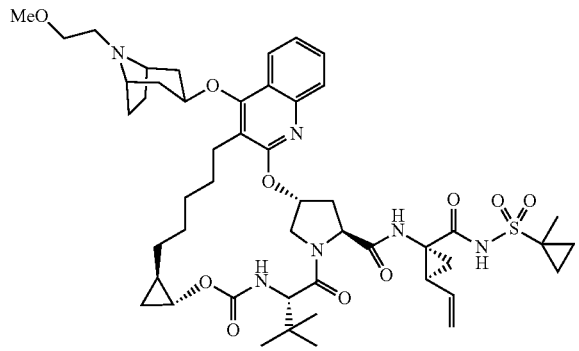 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3ccccc3c1OC1CC3CCC(C1)N3CCOC)O2)C(=O)NS(=O)(=O)C1(C)CC1]

Example 274 was converted into Example 276 by utilizing the procedures described for the synthesis of Example 237; the potassium salt was prepared upon treatment of the free base with 0.1N aqueous KOH solution. LRMS m/z 933.4 (M+H)$^+$.

Example 277 potassium ({(1R,2S)-1-[({(1aR,5S,8S,10R,22aR)-5-tert-butyl-17-[(8-ethyl-8-azabicyclo[3.2.1]oct-3-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl}carbonyl)amino]-2-ethenylcyclopropyl}carbonyl)[(1-methylcyclopropyl)sulfonyl]azanide

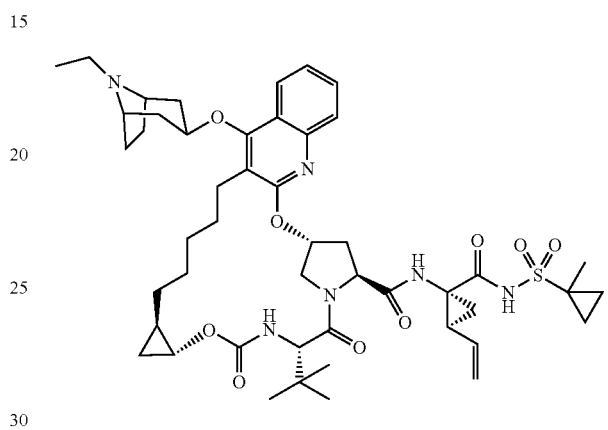

Example 274 was converted into Example 277 by utilizing the procedures described for the synthesis of Example 238; the potassium salt was prepared upon treatment of the free base with 0.1N aqueous KOH solution. LRMS m/z 903.4 (M+H)$^+$.

Example 278 tert-butyl 3-{[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-8-azabicyclo[3.2.1]octane-8-carboxylate

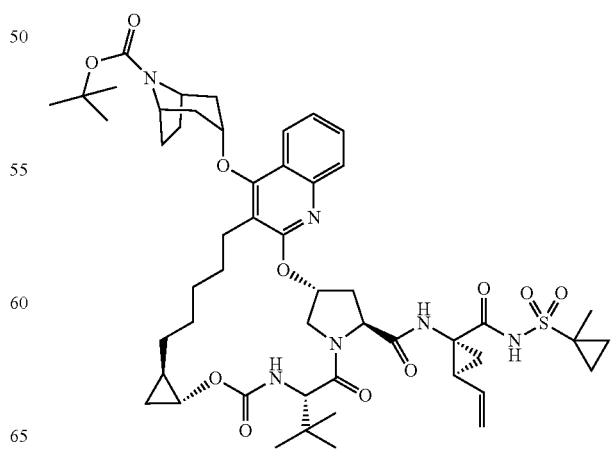

Example 278 was prepared using the procedures described for the synthesis of Example 210. The exo isomer of tert-butyl 3-hydroxy-8-azabicyclo[3.2.1]octane-8-carboxylate (as prepared in International Patent Publication No. WO2009055331) was used instead of 1-methylpiperidin-4-ol. LRMS m/z 975.4 (M+H)+.

Example 279

3-{[(1aR,5S,8S,10R,22aR)-5-tert-butyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-8-azoniabicyclo[3.2.1]octane trifluoroacetate

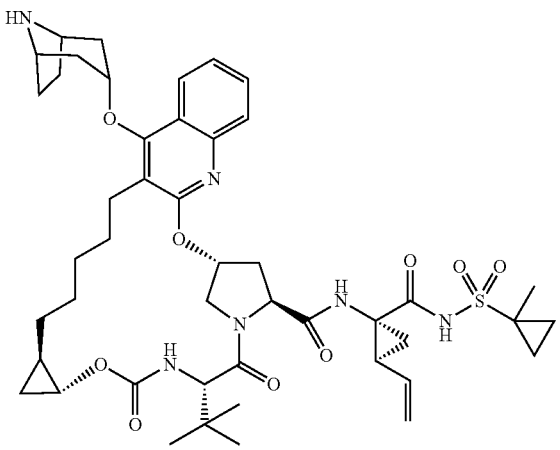 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1c(nc3ccccc3c1OC1CC3CCC(C1)N3)O2)C(=O)NS(=O)(=O)C1(C)CC1]

Example 279 was prepared from Example 278 by utilizing the procedure described for the synthesis of Example 236, Step 1. LRMS m/z 875.4 (M+H)+.

Example 280 potassium {[(1R,2S)-1-({[(1aR,5S,8S,10R,22aR)-5-tert-butyl-17-{[8-(2-methoxyethyl)-8-azabicyclo[3.2.1]oct-3-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl]carbonyl}amino)-2-ethenylcyclopropyl]carbonyl}[(1-methylcyclopropyl)sulfonyl]azanide

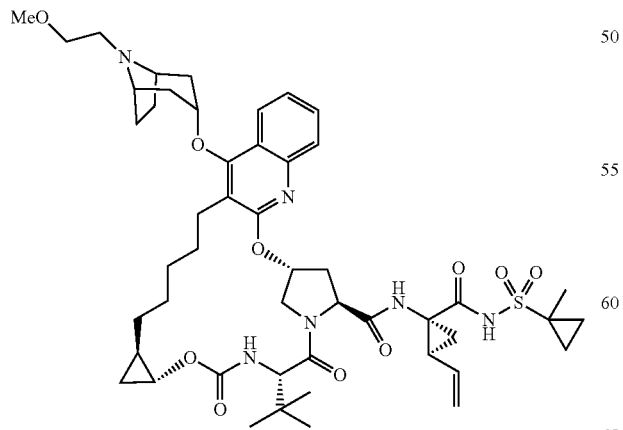

Example 279 was converted into Example 280 by utilizing the procedures described for the synthesis of Example 237; the potassium salt was prepared upon treatment of the free base with 0.1N aqueous KOH solution. LRMS m/z 933.5 (M+H)+.

Example 281 potassium ({(1R,2S)-1-[({(1aR,5S,8S,10R,22aR)-5-tert-butyl-17-[(8-ethyl-8-azabicyclo[3.2.1]oct-3-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl}carbonyl)amino]-2-ethenylcyclopropyl}carbonyl)[(1-methylcyclopropyl)sulfonyl]azanide

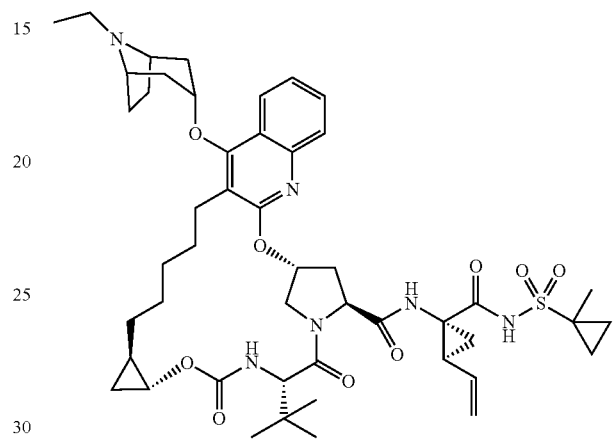

Example 279 was converted into Example 281 by utilizing the procedures described for the synthesis of Example 238; the potassium salt was prepared upon treatment of the free base with 0.1N aqueous KOH solution. LRMS m/z 903.4 (M+H)+.

Example 282 tert-butyl 3-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-8-azabicyclo[3.2.1]octane-8-carboxylate

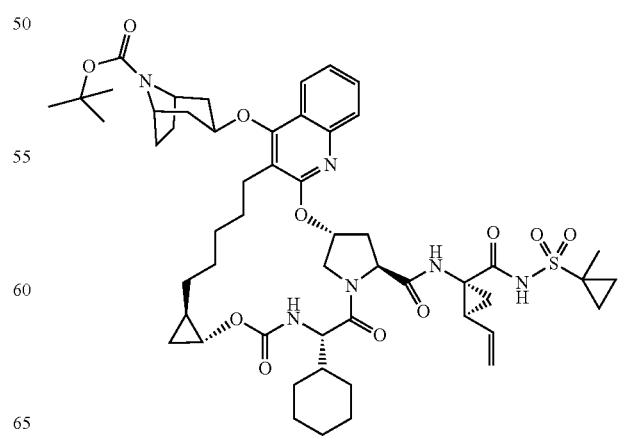

Example 282 was prepared by utilizing the procedure described for the synthesis of Example 273. LRMS m/z 945.3 (M+H-tBu)⁺.

Example 283 potassium {[(1R,2S)-1-({[(1aR,5S,8S,10R,22aR)-17-(8-azabicyclo[3.2.1]oct-3-yloxy)-5-cyclohexyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl]carbonyl}amino)-2-ethenylcyclopropyl]carbonyl}[(1-methylcyclopropyl)sulfonyl]azanide

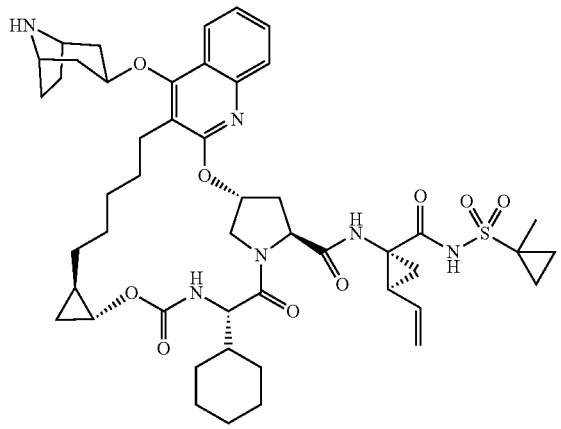 [SMILES: C=C[C@@H]1C[C@]1(NC(=O)[C@@H]1C[C@@H]2CN1C(=O)[C@H](C1CCCCC1)NC(=O)O[C@@H]1C[C@H]1CCCCCc1c(nc3ccccc3c1OC1CC3CCC(C1)N3)O2)C(=O)NS(=O)(=O)C1(C)CC1]

Example 283 was prepared from Example 282 by utilizing the procedure described for the synthesis of Example 274; the potassium salt was prepared upon treatment of the free base with 0.1N aqueous KOH solution. LRMS m/z 901.2 (M+H)⁺.

Example 284

(1aR,5S,8S,10R,22aR)-5-cyclohexyl-N-[(1R,2S)-2-ethenyl-1-{[(1-methylcyclopropyl)sulfonyl]carbamoyl}cyclopropyl]-17-{[8-(2-methoxyethyl)-8-azabicyclo[3.2.1]oct-3-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

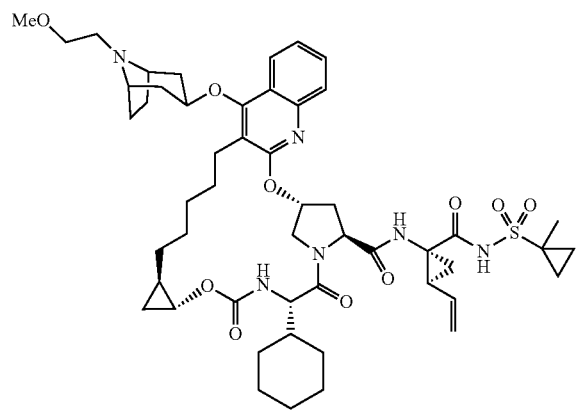 [SMILES: C=C[C@@H]1C[C@]1(NC(=O)[C@@H]1C[C@@H]2CN1C(=O)[C@H](C1CCCCC1)NC(=O)O[C@@H]1C[C@H]1CCCCCc1c(nc3ccccc3c1OC1CC3CCC(C1)N3CCOC)O2)C(=O)NS(=O)(=O)C1(C)CC1]

Example 284 was prepared from Example 283 by utilizing the procedure described for the synthesis of Example 276. LRMS m/z 959.4 (M+H)⁺.

Example 285

(1aR,5S,8S,10R,22aR)-5-cyclohexyl-N-[(1R,2S)-2-ethenyl-1-{[(1-methylcyclopropyl)sulfonyl]carbamoyl}cyclopropyl]-17-[(8-methyl-8-azabicyclo[3.2.1]oct-3-yl)oxy]3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-h]quinoline-8-carboxamide

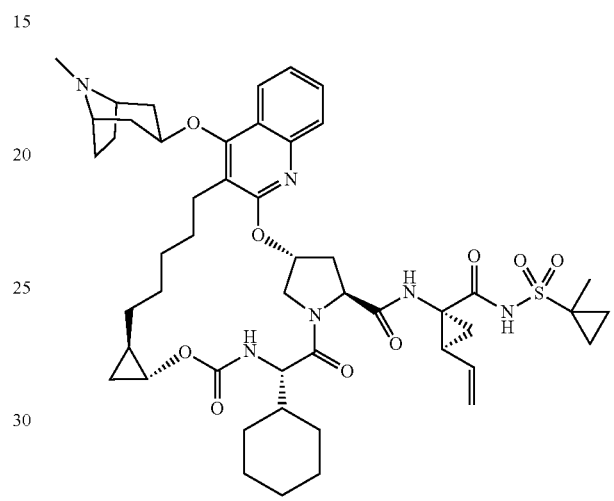

Example 285 was prepared by utilizing the procedures described for the synthesis of Example 211; tropine was used instead of 1-methylpiperidin-4-ol. LRMS m/z 915.2 (M+H)⁺.

Example 286

(1aR,5S,8S,10R,22aR)-5-cyclohexyl-N-[(1R,2S)-2-ethenyl-1-{[(1-methylcyclopropyl)sulfonyl]carbamoyl}cyclopropyl]-13-fluoro-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

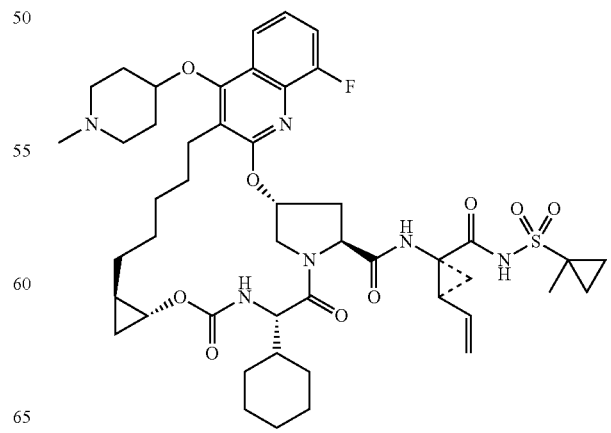

Example 286 was prepared by utilizing the procedures described for the synthesis of Example 211. LRMS m/z 907.6 (M+H)⁺.

Example 287 tert-butyl 7-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-3-oxa-9-azabicyclo[3.3.1]nonane-9-carboxylate

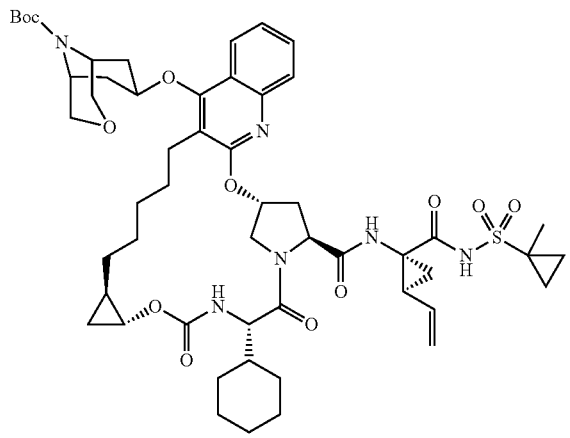 [SMILES: C=C[C@@H]1C[C@]1(NC(=O)[C@@H]1C[C@@H]2CN1C(=O)[C@H](C1CCCCC1)NC(=O)O[C@@H]1C[C@H]1CCCCCc1c(nc3ccccc3c1OC1CC3COCC(C1)N3C(=O)OC(C)(C)C)O2)C(=O)NS(=O)(=O)C1(C)CC1]

The syn isomer of tert-butyl 7-hydroxy-3-oxa-9-azabicyclo[3.3.1]nonane-9-carboxylate (as prepared in International Patent Publication No. WO2009055331) was converted into Example 287 by utilizing the procedures described for the synthesis of Example 282. LRMS m/z 961.2 (M+H-tBu)⁺.

Example 288

(1aR,5S,8S,10R,22aR)-5-cyclohexyl-N-[(1R,2S)-2-ethenyl-1-{[(1-methylcyclopropyl)sulfonyl]carbamoyl}cyclopropyl]-17-(3-oxa-9-azabicyclo[3.3.1]non-7-yloxy)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

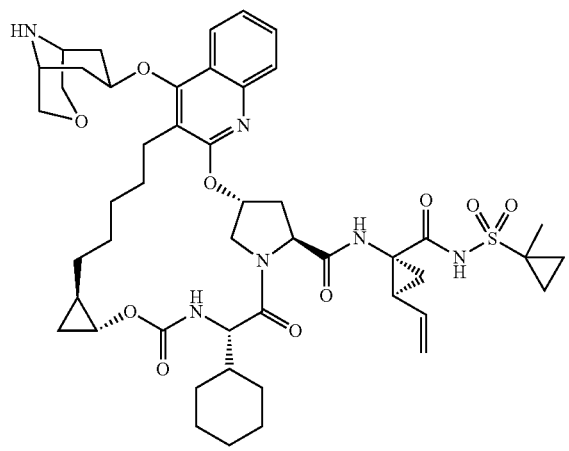 [SMILES: C=C[C@@H]1C[C@]1(NC(=O)[C@@H]1C[C@@H]2CN1C(=O)[C@H](C1CCCCC1)NC(=O)O[C@@H]1C[C@H]1CCCCCc1c(nc3ccccc3c1OC1CC3COCC(C1)N3)O2)C(=O)NS(=O)(=O)C1(C)CC1]

Example 288 was prepared by utilizing the procedure described for the synthesis of Example 274. LRMS m/z 917.2 (M+H)⁺.

Example 289

(1aR,5S,8S,10R,22aR)-5-cyclohexyl-N-[(1R,2S)-2-ethenyl-1-{[(1-methylcyclopropyl)sulfonyl]carbamoyl}cyclopropyl]-17-{[9-(2-methoxyethyl)-3-oxa-9-azabicyclo[3.3.1]non-7-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxamide

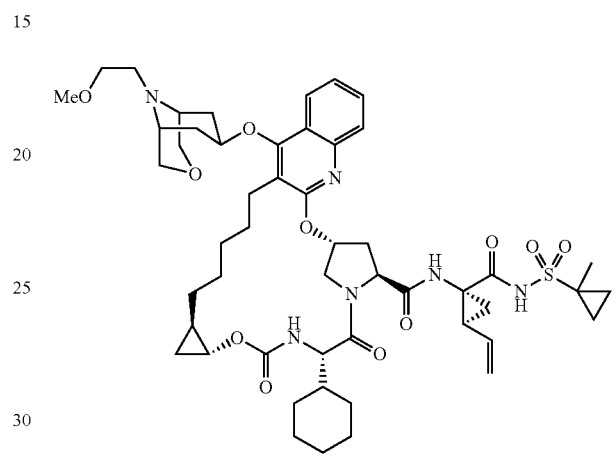

Example 288 was converted into Example 289 by utilizing the procedures described for the synthesis of Example 47. LRMS m/z 975.2 (M+H)⁺.

Example 290

7-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-9-ethyl-3-oxa-9-azoniabicyclo[3.3.1]nonane formate

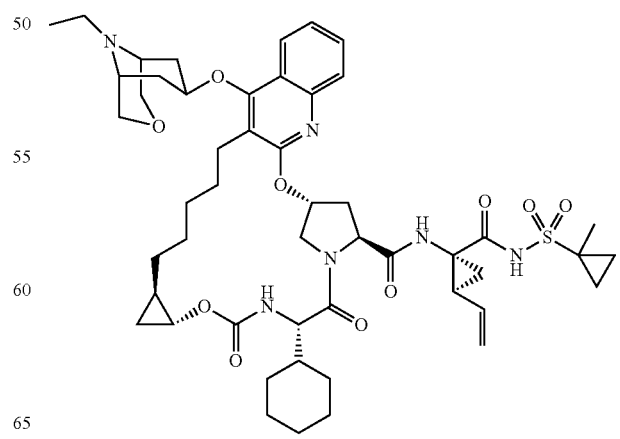

Example 288 was converted into Example 290 by utilizing the procedures described for the synthesis of Example 48. LRMS m/z 945.2 (M+H)⁺.

Example 291

3-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-1-methylpiperidinium formate

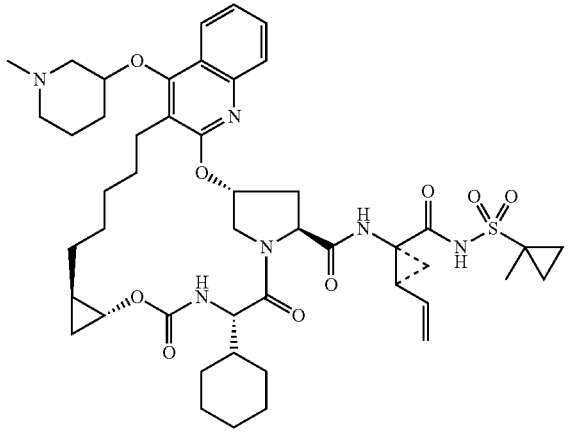

Example 291 was prepared by utilizing the procedures described for the synthesis of Example 211; 1-methylpiperidin-3-ol was used instead of 1-methylpiperidin-4-ol. LRMS m/z 889.2 (M+H)⁺.

Example 292 tert-butyl (3S,4R)-4-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-3-fluoropiperidine-1-carboxylate

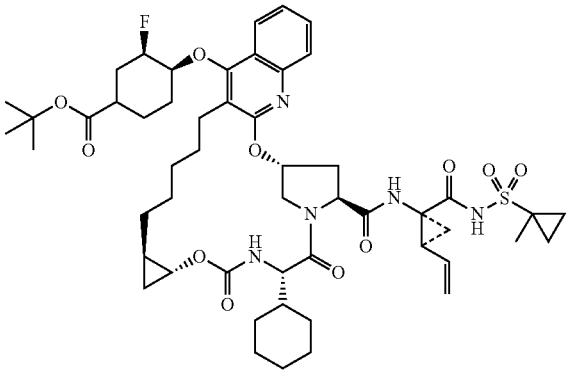

The trans isomer of tert-butyl 3-fluoro-4-hydroxypiperidine-1-carboxylate (as prepared in International Patent Publication No. WO 2011036576) was converted into Example 292 by utilizing the procedures described for the synthesis of Example 282. The substituents at the 3 and 4 position of the piperidine group in the title compound are in cis orientation; only relative stereochemistry is shown. Example 292 is a diastereomeric mixture. LRMS m/z 993.2 (M+H-tBu)⁺.

Example 293

(3S,4R)-4-{[(1aR,5S,8S,10R,22aR)-5-cyclohexyl-8-{[(1R,2S)-2-ethenyl-1-{[(1-methylcyclopropyl)sulfonyl]carbamoyl}cyclopropyl]carbamoyl}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-17-yl]oxy}-3-fluoropiperidinium chloride

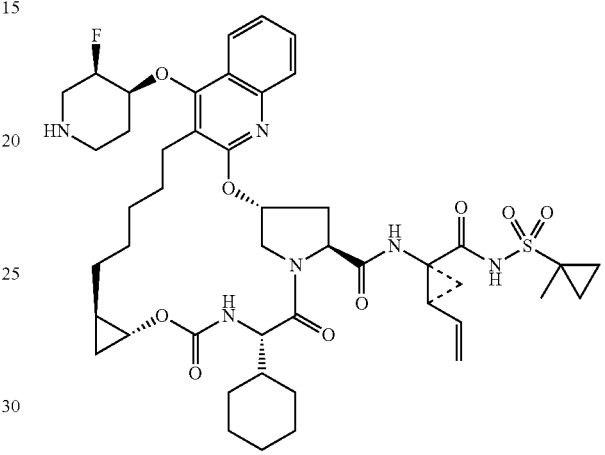

Example 292 was converted into Example 293 by utilizing the procedure described for the synthesis of Example 236, Step 1. LRMS m/z 893.2 (M+H)⁺.

Example 294 potassium {[(1R,2S)-1-({[(1aR,5S,8S,10R,22aR)-5-cyclohexyl-17-{[(3S,4R)-3-fluoro-1-methylpiperidin-4-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl]carbonyl}amino)-2-ethenylcyclopropyl]carbonyl}[(1-methylcyclopropyl)sulfonyl]azanide

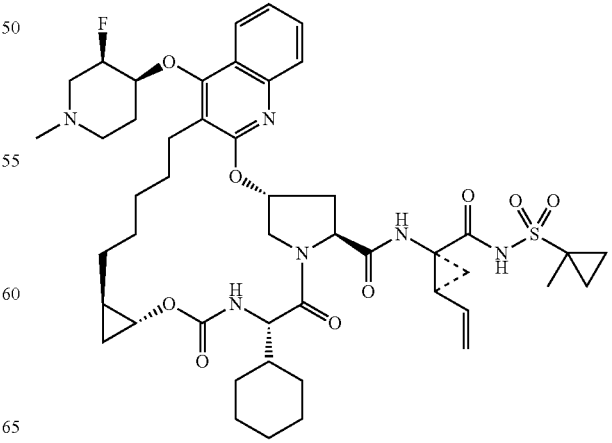

Step 1: methyl (1aR,5S,8S,10R,22aR)-5-cyclohexyl-17-[(cis-3-fluoropiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

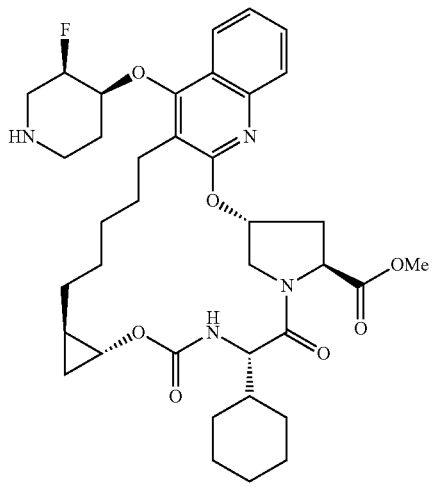 [SMILES: COC(=O)[C@@H]1C[C@@H]2CN1C(=O)[C@H](C1CCCCC1)NC(=O)O[C@@H]1C[C@H]1CCCCCc1c(nc3ccccc3c1O[C@H]1CCNC[C@H]1F)O2]

The trans isomer of tert-butyl 3-fluoro-4-hydroxypiperidine-1-carboxylate (as prepared in International Patent Publication No. WO 2011036576) was converted into the title compound by utilizing the procedures described in Example 225, steps 1 and 2.

Step 2: methyl (1aR,5S,8S,10R,22aR)-5-cyclohexyl-17-[(cis-3-fluoro-1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoline-8-carboxylate

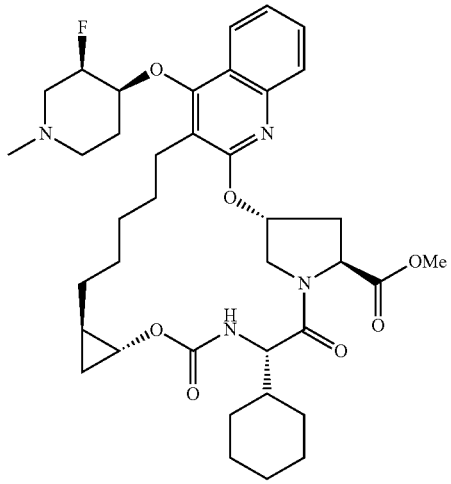 [SMILES: COC(=O)[C@@H]1C[C@@H]2CN1C(=O)[C@H](C1CCCCC1)NC(=O)O[C@@H]1C[C@H]1CCCCCc1c(nc3ccccc3c1O[C@H]1CCN(C)C[C@H]1F)O2]

The product from step 1 (90 mg, 0.132 mmol), formaldehyde (0.107 ml, 1.322 mmol), and acetic acid (11.91 mg, 0.198 mmol) were dissolved in dichloromethane (1.322 ml) and allowed to stir for 30 minutes. Sodium triacetoxyborohydride (84 mg, 0.397 mmol) was added and the reaction was stirred overnight at room temperature, after which it was quenched with water and extracted (×3) with ethyl acetate. The combined organics were washed with brine, dried over sodium sulfate, and concentrated under reduced pressure. Purification by PTLC (25% acetone in hexane) provided the title compound.

Step 3: potassium {[(1R,2S)-1-({[(1aR,5S,8S,10R,22aR)-5-cyclohexyl-17-{[(3S,4R)-3-fluoro-1-methylpiperidin-4-yl]oxy}-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinolin-8-yl]carbonyl}amino)-2-ethenylcyclopropyl]carbonyl}[(1-methylcyclopropyl)sulfonyl]azanide

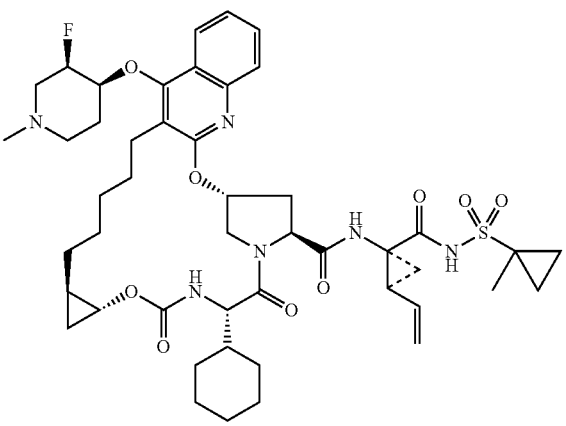

The product from Step 2 was converted into Example 294 by utilizing the procedures described for the synthesis of Example 225, steps 4 and 5.

Example 295

(1aS,5S,8S,10R,22aS)-5-tert-butyl-N-{(1R,2S)-2-ethenyl-1-[(1-methylcyclopropanesulfonamido)carbonyl]cyclopropyl}-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b][1,6]naphthyridine-8-carboxamide

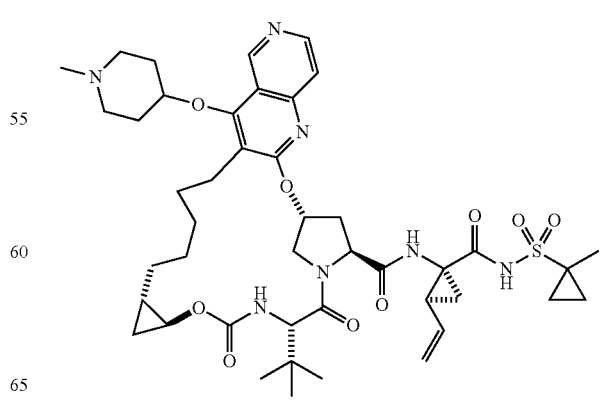

Step 1: sodium 3-(ethoxycarbonyl)-1-oxo-1,2-dihydro-2,6-naphthyridin-4-olate

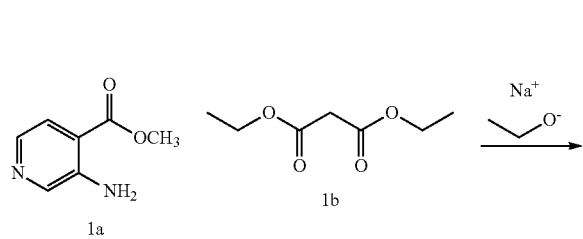

Metallic sodium 1.00 g (43 mmol) was dissolved in 30 mL of ethanol at room temperature to form sodium ethoxide. 25 mL of this solution was added to a mixture of 1a (5.00 g, 32.9 mmol) and diethyl malonate (5.26 g, 32.9 mmol) and heated at 150° C. for 20 hours. The reaction mixture was allowed to cool to room temperature and diluted with ether. The solid separating out was filtered and used as it is in next step as it is without any further purification.

Step 2: 4-hydroxy-2,6-naphthyridin-1(2H)-one hydrobromide

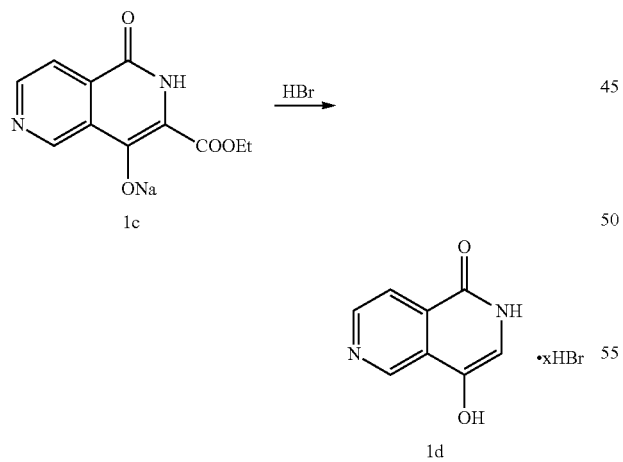

The sodium salt 1c from previous step was dissolved in hydrobromic acid (100 mL) and heated at reflux for 12 hours. The reaction mixture was concentrated in vacuo and the solid 1d was used as it is in next step.

Step 3: 3-bromo-4-hydroxy-2,6-naphthyridin-1(2H)-one hydrobromide

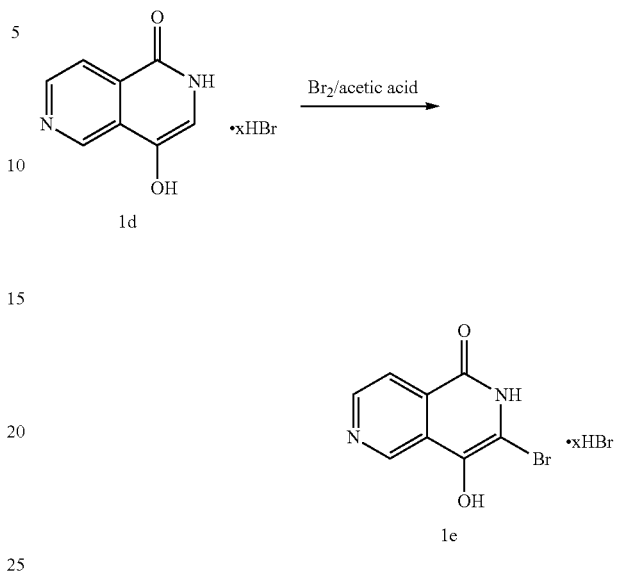

A solution of naphthyridinone 1d (241 mg, 1.49 mmol) in acetic acid (3.00 mL) was treated with bromine (77 micro liters, 1.49 mmol) and stirred at room temperature for 2 hours. The reaction mixture was concentrated in vacuo, triturated with ether and filtered. The filtered solid 1e (1.25 g, 84%) was used as it is in the next step.

Step 4: 4-(benzyloxy)-3-bromo-2,6-naphthyridin-1(2H)-one

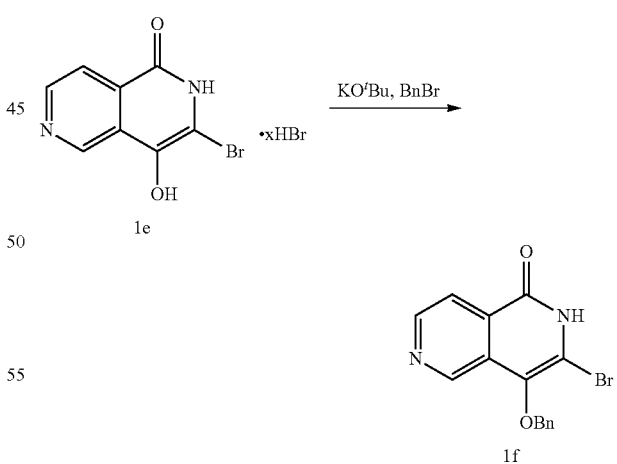

A suspension of 1e (2.75 g, 6.83 mmol) in THF (20 mL) was treated with potassium tert-butoxide (2.30 g, 20.48 mmol), benzyl bromide (1.17 g, 6.83 mmol) and stirred at room temperature overnight. The reaction mixture was concentrated in vacuo and treated with water. The solid separating out was filtered and dried in vacuo. The residue 1f (1.25, 55.3%) was used as it is in next step.

Step 5: (2S,4R)-1-tert-butyl 2-methyl 4-((4-(benzyloxy)-3-bromo-1,6-naphthyridin-2-yl)oxy)pyrrolidine-1,2-dicarboxylate

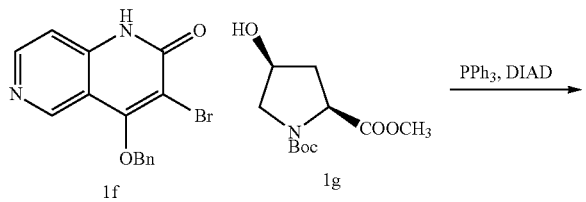

A solution of naphthyridine 1f (1.25 g, 3.77 mmol), triphenylphosphine (1.98 g, 7.55 mmol), and cis-4-hydroxyproline 1g (1.29 g) in CH$_2$Cl$_2$ (40 mL) was cooled to 0° C. and treated with a solution of DIAD (1.145 g) in CH$_2$Cl$_2$ (10 mL). The reaction mixture was stirred at room temperature for overnight concentrated in vacuo and purified by silica gel chromatography using Acetone/Hexanes to yield product 1h (610 mg, 29%) as a yellow solid.

Step 6: (5)-tert-butyl 3,3-dimethyl-2-((((1R,2R)-2-(pent-4-yn-1-yl)cyclopropoxy)carbonyl)amino)butanoate

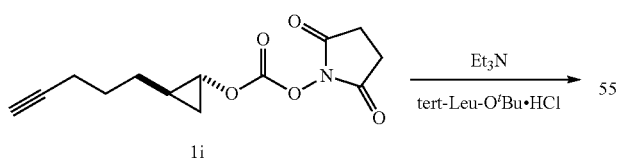

A solution of succinyl carbonate 1i (5.42 g, 20.43 mmol) in dry acetonitrile (50 mL) was treated with tert-butylglycine tert-butyl ester (4.57 g, 20.43 mmol) and cooled to 0° C. The reaction mixture was treated with triethyl amine (2.95 mL, 20.43 mmol) and stirred at room temperature for 36 hours. The reaction mixture was concentrated in vacuo and extracted into EtOAc (300 mL). The combined organic layers were dried (MgSO$_4$), filtered, concentrated in vacuo and purified by silica gel chromatography to yield product 1j (4.2 g, 61%).

Step 7: (S)-tert-butyl 3,3-dimethyl-2-((((1R,2R)-2-((E)-5-(tributylstannyl)pent-4-en-1-yl)cyclopropoxy)carbonyl)amino)butanoate and (S)-tert-butyl 3,3-dimethyl-2-((((1R,2R)-2-(4-(tributylstannyl)pent-4-en-1-yl)cyclopropoxy)carbonyl)amino)butanoate

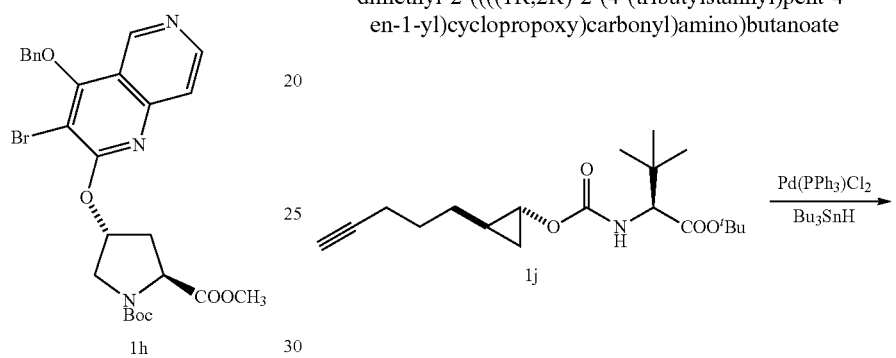

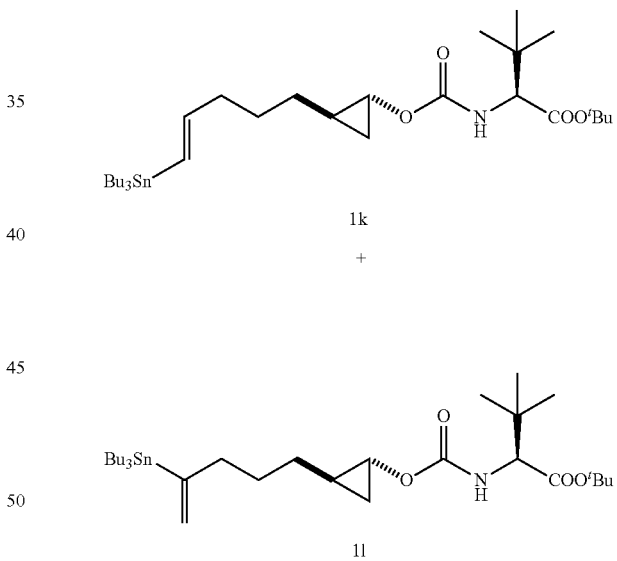

A solution of alkyne 1j (2.00 g, 5.93 mmol) in THF (50 mL) was cooled to 0° C. and treated with Pd(PPh$_3$)$_2$Cl$_2$ and tributyltin hydride (1.73 g, 5.93 mmol). The reaction mixture was stirred at room temperature for 0.5 hours and concentrated in vacuo. The residue was taken in hexane and filtered through a plug of celite. The filtrate was concentrated in vacuo and purified by silica gel chromatography to yield stannanes 1k and 1l as a inseparable mixture (1.99 g, 53%).

Step 8: (2S,4R)-1-tert-butyl 2-methyl 4-((4-(benzyloxy)-3-((E)-5-((1R,2R)-2-((((S)-1-(tert-butoxy)-3,3-dimethyl-1-oxobutan-2-yl)carbamoyl)oxy)cyclopropyl)pent-1-en-1-yl)-1,6-naphthyridin-2-yl)oxy)pyrrolidine-1,2-dicarboxylate and (2S,4R)-1-tert-butyl 2-methyl 4-((4-(benzyloxy)-3-(5-((1R,2R)-2-((((S)-1-(tert-butoxy)-3,3-dimethyl-1-oxobutan-2-yl)carbamoyl)oxy)cyclopropyl)pent-1-en-2-yl)-1,6-naphthyridin-2-yl)oxy)pyrrolidine-1,2-dicarboxylate
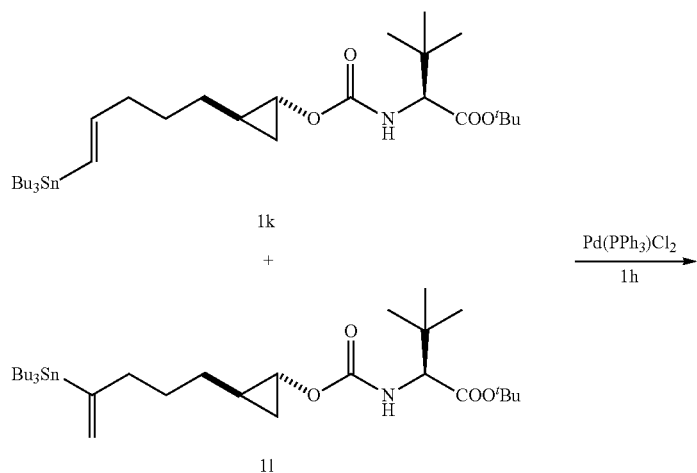
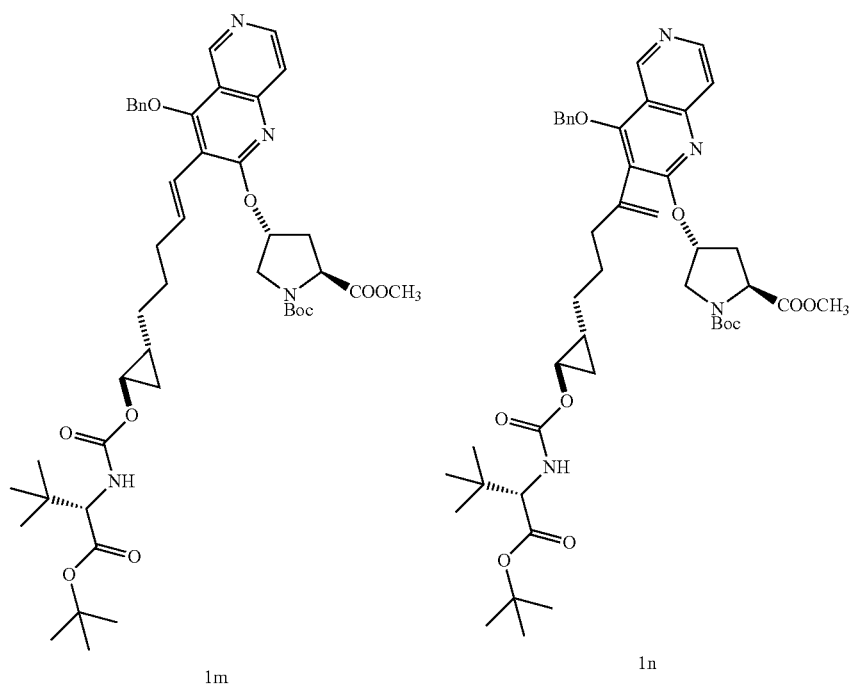

A solution of stannanes 1k & 1l (225 mg, 0.358 mmol), bromide 1h (100 mg, 0.179 mmol) and Pd(PPh$_3$)$_2$Cl$_2$ (20.7 mg) in dioxane (3.0 mL) was degassed and heated at 115° C. for 14 hours. The reaction mixture was cooled and taken in EtOAc, filtered through a plug of celite. The filtrate was concentrated in vacuo and purified by silica gel chromatography to yield coupled product 1m (60 mg).

Step 9: (2S,4R)-1-tert-butyl 2-methyl 4-((3-(5-((1R,2R)-2-((((S)-1-(tert-butoxy)-3,3-dimethyl-1-oxobutan-2-yl)carbamoyl)oxy)cyclopropyl)pentyl)-4-hydroxy-1,6-naphthyridin-2-yl)oxy)pyrrolidine-1,2-dicarboxylate A solution of benzylated derivative 1m (130 mg, 0.159 mmol) in methanol was treated with palladium hydroxide on carbon (10%, 130 mg) and hydrogenated with hydrogen in a balloon for 12 hours. The reaction mixture was filtered through a plug of celite, concentrated in vacuo and purified by silica gel chromatography (Acetone, Hexanes) to yield reduced product 1o.

Step 10: (2S,4R)-1-tert-butyl 2-methyl 4-((3-(5-((1R,2R)-2-((((S)-1-(tert-butoxy)-3,3-dimethyl-1-oxobutan-2-yl)carbamoyl)oxy)cyclopropyl)pentyl)-4-((1-methylpiperidin-4-yl)oxy)-1,6-naphthyridin-2-yl)oxy)pyrrolidine-1,2-dicarboxylate

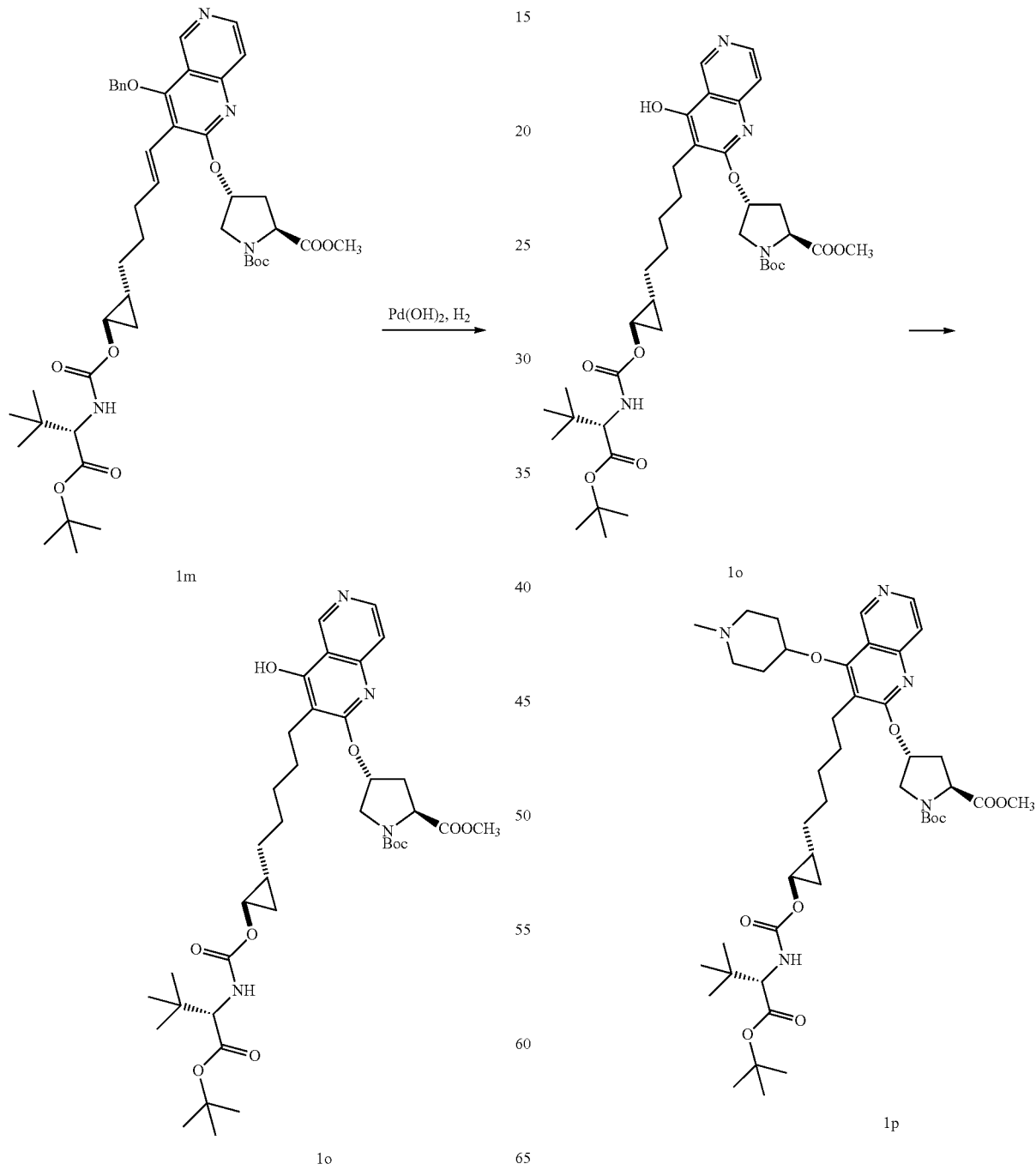

A solution of 1o (60 mg, 0.082 mmol), triphenylphosphine (216 mg, 0.823 mmol), 4-hydroxy-N-methylpiperidine (95 mg, 0.823 mmol) in THF (3.00 mL) in a two necked flask was filled with nitrogen and treated drop wise with DIAD (166 mg, 0.823 mmol). The reaction mixture was stirred at 40° C. for 3 hours. The reaction mixture was concentrated in vacuo and purified by silica gel chromatography to yield 1p. After first purification, the product co-eluted with N-methylpiperidinol. It was therefore subjected to second purification using methylene chloride and ammoniacal methanol, to yield product still containing some N-methylpiperidinol (162 mg).

Step 11: Methyl-(1aS,5S,8S,10R,22aS)-5-tert-butyl-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6] dioxadiazacyclononadecino[11,12-b][1,6] naphthyridine-8-carboxylate and used as it is in next step. The crude mixture was dried in vacuo for 48 hours, dissolved in DMF (2.00 mL) and cooled to 0° C. It was treated with NMM (41.6 mg, 0.412 mmol) and HATU (117 mg, 0.31 mmol) and stirred at 0° C. for 0.5 hours and room temperature for 1 hour. The reaction mixture was diluted with 30 mL aqueous sodium bicarbonate solution and extracted into EtOAc (90 mL). The combined organic layers were dried (MgSO₄), filtered, concentrated in vacuo, and purified by silica gel chromatography using (CH₂Cl₂, and 10% methanol in CH₂Cl₂) to yield cyclized product 1q as colorless solid (30 mg).

Step 12: Methyl-(1aS,5S,8S,10R,22aS)-5-tert-butyl-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][10,3,6] dioxadiazacyclononadecino[11,12-b][1,6] naphthyridine-8-carboxylic acid

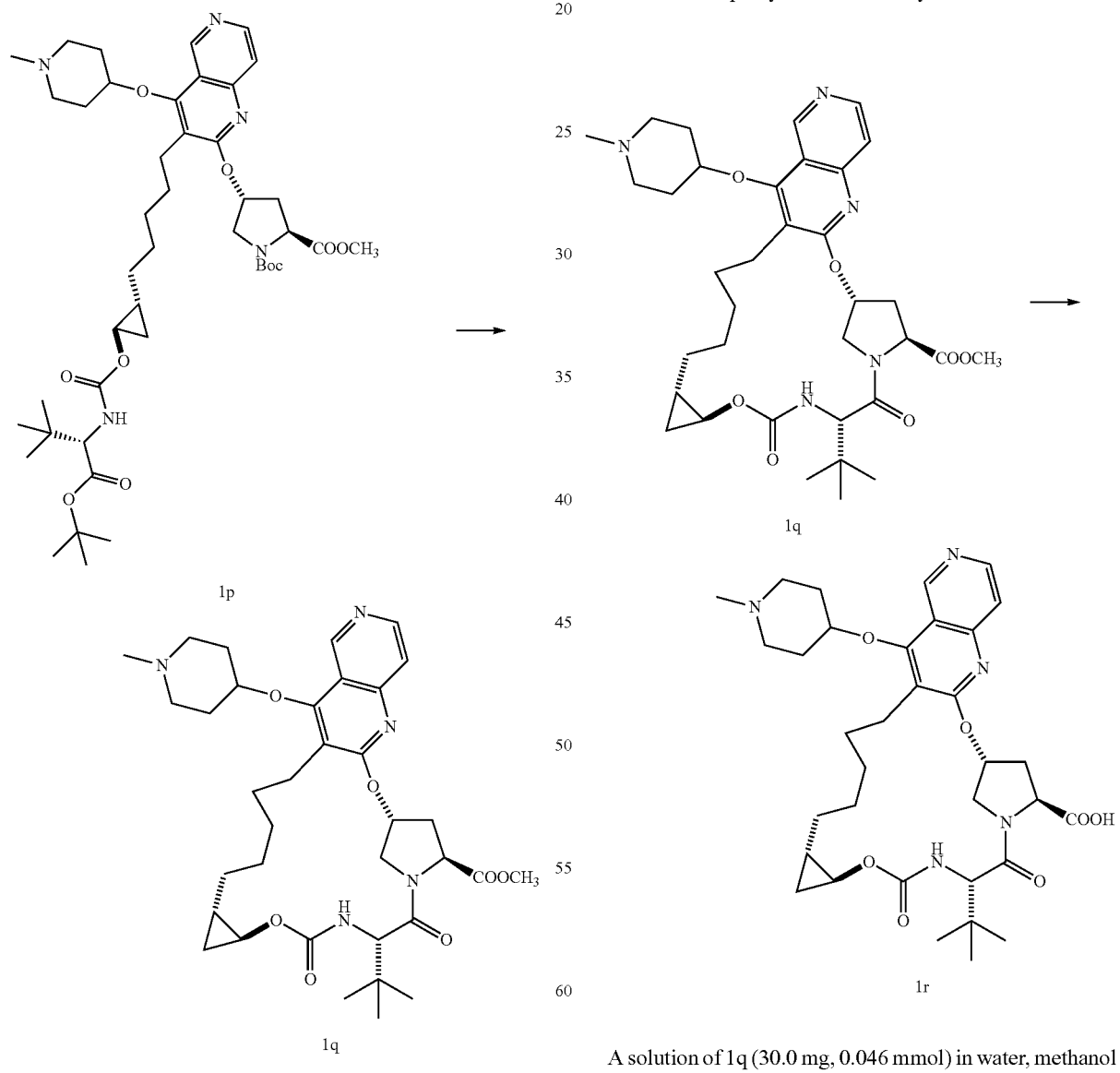

1p

1q

1r

A solution of 1p (85 mg, 0.103 mmol) dissolved in CH₂Cl₂ (2.0 mL) and TFA (2.0 mL) and stirred at room temperature for 2 hours. The reaction mixture was concentrated in vacuo A solution of 1q (30.0 mg, 0.046 mmol) in water, methanol THF (0.6 mL each) was treated with aqueous solution of lithium hydroxide (0.5 M, 0.276 mL) and stirred overnight. The reaction mixture was quenched with acetic acid (30 µl) and extracted into CH₂Cl₂ (7×20 mL) and EtOAc (2×20 mL).

Step 13: (1aS,5S,8S,10R,22aS)-5-tert-butyl-N-{(1R,2S)-2-ethenyl-1-[(1-methylcyclopropanesulfonamido)carbonyl]cyclopropyl}-17-[(1-methylpiperidin-4-yl)oxy]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b][1,6]naphthyridine-8-carboxamide

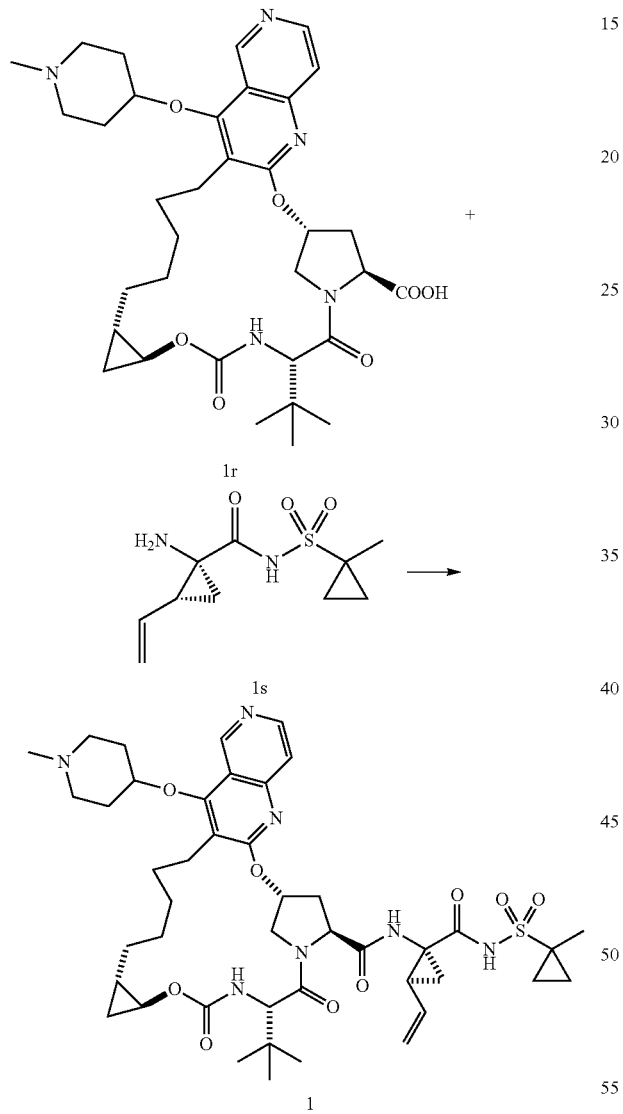

A solution of 1r (22 mg, 0.034 mmol), amine is (12.6 mg, 0.052 mmol) and HATU (26.2 mg, 0.069 mmol) in DMF (0.6 mL) and CH$_2$Cl$_2$ (0.6 mL) was stirred at room temperature for 10 minutes and treated with 4-methyl morpholine (20 µl). The reaction mixture was stirred at room temperature overnight and quenched with 20 µl of acetic acid. The reaction mixture was extracted with methylene chloride and the combined organic layers were dried (MgSO$_4$), filtered, concentrated in vacuo and purified by silica gel chromatography (CH$_2$Cl$_2$, ethanol) to yield 1 (13 mg, 44%) as a colorless solid. LR-MS (ESI) Calculated for C$_{44}$H$_{62}$N$_7$O$_9$S (M+H)$^+$ 864.43. Found 864.45.

Example 296

(1aR,5S,11Z,12aS,13aR,16S,19R,27E,31aR)—N-[(1-methylcyclopropyl)sulfonyl]-3,15,33-trioxo-26-[2-(piperidin-1-yl)ethoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide

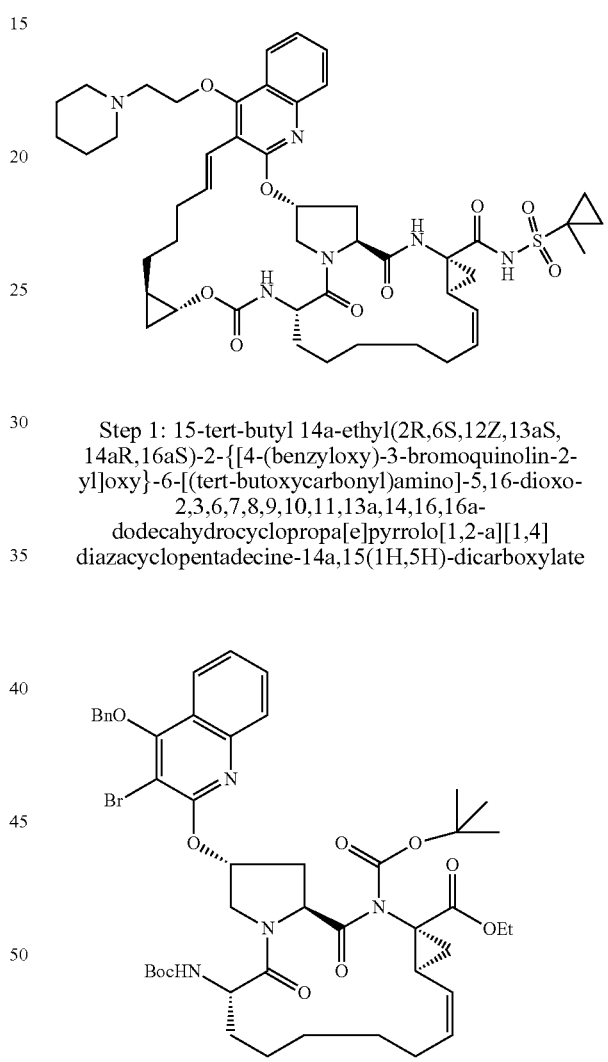

Step 1: 15-tert-butyl 14a-ethyl(2R,6S,12Z,13aS,14aR,16aS)-2-{[4-(benzyloxy)-3-bromoquinolin-2-yl]oxy}-6-[(tert-butoxycarbonyl)amino]-5,16-dioxo-2,3,6,7,8,9,10,11,13a,14,16,16a-dodecahydrocyclopropa[e]pyrrolo[1,2-a][1,4]diazacyclopentadecine-14a,15(1H,5H)-dicarboxylate To a solution of Intermediate C6 (1.48 g) and Intermediate B16 (2.03 g) in DMA (12.5 mL) was added cesium carbonate (1.02 g). The reaction mixture was heated to 60° C. for 5 hours. After cooling to room temperature, the reaction mixture was diluted with ethyl acetate and water. The mixture was extracted (3×) with ethyl acetate. The combined organic layers were washed with water, then brine, dried over magnesium sulfate, filtered and concentrated. The residue was suspended in dichloromethane and filtered to remove the insoluble Intermediate C6. The mother liquors were concentrated and the residue was purified by flash chromatography (ISCO, 0 to 100% ethyl acetate in hexanes) to give the title compound (2.06 g). LRMS (ES+) m/z 905.0 (M+H)$^+$.

Step 2: ethyl (2R,6S,12Z,13aS,14aR,16aS)-6-amino-2-[(3-bromo-4-hydroxyquinolin-2-yl)oxy]-5,16-dioxo-1,2,3,6,7,8,9,10,11,13a,14,15,16,16a-tetradecahydrocyclopropa[e]pyrrolo[1,2-a][1,4]diazacyclopentadecine-14a(5H)-carboxylate

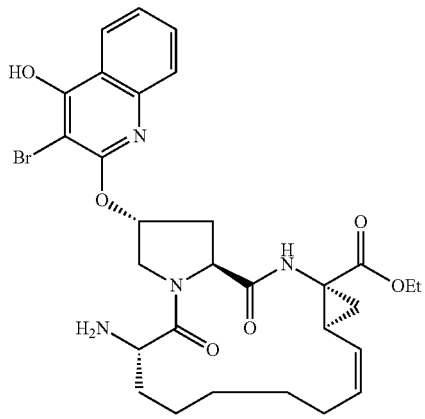 [SMILES: CCOC(=O)[C@@]12C[C@H]1/C=C\CCCCC[C@H](N)C(=O)N1C[C@H](Oc3nc4ccccc4c(O)c3Br)C[C@H]1C(=O)N2]

The product of Step 1 (2.06 g) was dissolved in TFA (22.7 mL) and the reaction was stirred for 5 hours at room temperature. The solvent was removed in vacuo. The residue was dissolved in ethyl acetate and a saturated solution of sodium bicarbonate was added slowly. The layers were separated and the organic layer was washed again with a saturated solution of sodium bicarbonate then with brine, dried over magnesium sulfate, filtered and concentrated. The product was used without further purification. LRMS (ES+) m/z 615.2 (M+H)+.

Step 3: ethyl (2R,6S,12Z,13aS,14aR,16aS)-2-[(3-bromo-4-hydroxyquinolin-2-yl)oxy]-5,16-dioxo-6-{[({(1R,2R)-2-[(4E)-5-(4,4,5,5-tetramethyl-1,3,2-dioxaborolan-2-yl)pent-4-en-1-yl]cyclopropyl}oxy)carbonyl]amino}-1,2,3,6,7,8,9,10,11,13a,14,15,16,16a-tetradecahydrocyclopropa[e]pyrrolo[1,2-a][1,4]diazacyclopentadecine-14a(5H)-carboxylate

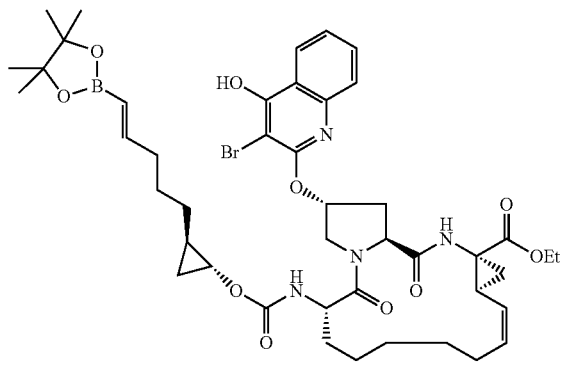 [SMILES: CCOC(=O)[C@@]12C[C@H]1/C=C\CCCCC[C@H](NC(=O)O[C@@H]1C[C@H]1CCC/C=C/B1OC(C)(C)C(C)(C)O1)C(=O)N1C[C@H](Oc3nc4ccccc4c(O)c3Br)C[C@H]1C(=O)N2]

To a solution of the amine from Step 2 (1.58 g) and Intermediate A14 (1.11 g) in acetonitrile (12.8 mL) was added triethylamine (1.78 mL) The reaction mixture was stirred overnight at room temperature. The solvent was removed in vacuo. The residue was dissolved in ethyl acetate and water was added. The mixture was extracted (3×) with ethyl acetate. The combined organics were dried over sodium sulfate, filtered and concentrated. The residue was purified by flash chromatography (ISCO, 0 to 10% methanol in dichloromethane) to give the title compound (1.53 g) as a white solid. LRMS (ES+) m/z 893.3 (M+H)+.

Step 4: ethyl (2R,6S,12Z,13aS,14aR,16aS)-2-({3-bromo-4-[2-(piperidin-1-yl)ethoxy]quinolin-2-yl}oxy)-5,16-dioxo-6-{[({(1R,2R)-2-[(4E)-5-(4,4,5,5-tetramethyl-1,3,2-dioxaborolan-2-yl)pent-4-en-1-yl]cyclopropyl}oxy)carbonyl]amino}-1,2,3,6,7,8,9,10,11,13a,14,15,16,16a-tetradecahydrocyclopropa[e]pyrrolo[1,2-a][1,4]diazacyclopentadecine-14a(5H)-carboxylate

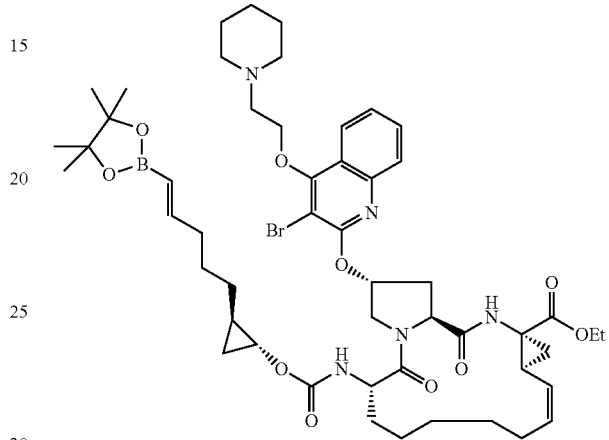

To a solution of phenol from Step 3 (0.513 g) in DMF (5.7 mL) was added 1-(2-bromoethyl)piperidine (0.39 g) and cesium carbonate (1.5 g). The reaction mixture was stirred at room temperature for 18 hours. The reaction was quenched with water and the reaction mixture was diluted with ethyl acetate. The mixture was extracted (3×) with ethyl acetate. The combined organics were washed with water (2×), then brine, dried over magnesium sulfate, filtered and concentrated. The residue was purified by flash chromatography (ISCO, 0 to 10% methanol in dichloromethane) to give the title compound (456 mg) as a colorless oil. LRMS (ES+) m/z 1004.4 (M+H)+.

Step 5: ethyl (1aR,5S,11Z,12aS,13aR,16S,19R,27E,31aR)-3,15,33-trioxo-26-[2-(piperidin-1-yl)ethoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxylate

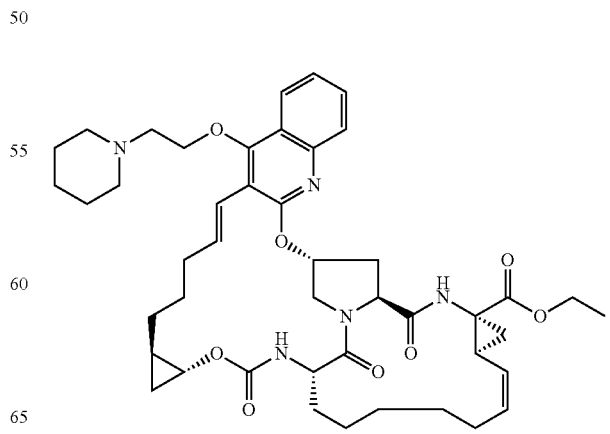

In a reaction flask, boronate from Step 4 (456 mg), Catacxium A (35.4 mg), cesium carbonate (483 mg) were dissolved in 10.3 mL of dioxane and 2.1 mL of water. The reaction mixture was degassed with nitrogen (3 cycles) before the addition of palladium acetate (11.1 mg). The reaction mixture was once again degassed with nitrogen (3 cycles) and heated to 100° C. for 1 hour. After cooling to room temperature, the reaction was quenched with a saturated solution of ammonium chloride. The mixture was extracted (3×) with ethyl acetate. The combined organics were dried over magnesium sulfate, filtered and concentrated. The residue was purified by flash chromatography (ISCO, 0 to 10% methanol in dichloromethane) to give the title compound (232 mg) as a yellow foam. LRMS (ES+) m/z 798.35 (M+H)$^{4"}$.

Step 6: (1aR,5S,11Z,12aS,13aR,16S,19R,27E, 31aR)-3,15,33-trioxo-26-[2-(piperidin-1-yl)ethoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxylic acid

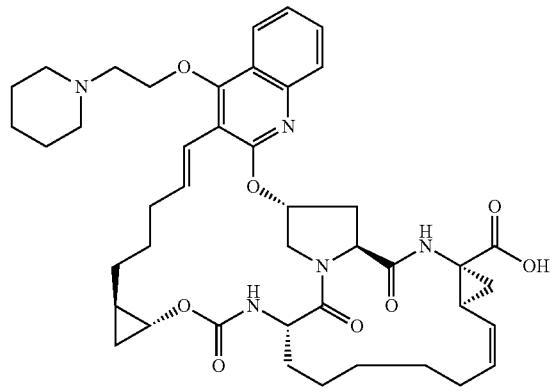 [SMILES: O=C1N[C@H]2CCCCC/C=C\[C@@H]3C[C@@]3(C(=O)O)NC(=O)[C@@H]3C[C@H](CN3C2=O)Oc2nc3ccccc3c(OCCN3CCCCC3)c2/C=C/CCC[C@@H]2C[C@H]2O1]

Ester from step 5 (231 mg) was dissolved in THF (1.4 mL) and methanol (0.7 mL) LiOH (121 mg) in 0.7 mL of water was then added to the reaction mixture. The reaction was stirred overnight at room temperature. The reaction mixture was acidified to pH=4 with acetic acid. The mixture was extracted (3×) with ethyl acetate. The combined organics were dried over magnesium sulfate, filtered and concentrated. The residue was purified by flash chromatography (ISCO reverse phase, 5 to 95% acetonitrile in water) to give the desired product (87.3 mg). LRMS (ES+) m/z 770.60 (M+H)$^+$.

Step 7: (1aR,5S,11Z,12aS,13aR,16S,19R,27E, 31aR)—N-[(1-methylcyclopropyl)sulfonyl]-3,15,33-trioxo-26-[2-(piperidin-1-yl)ethoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide

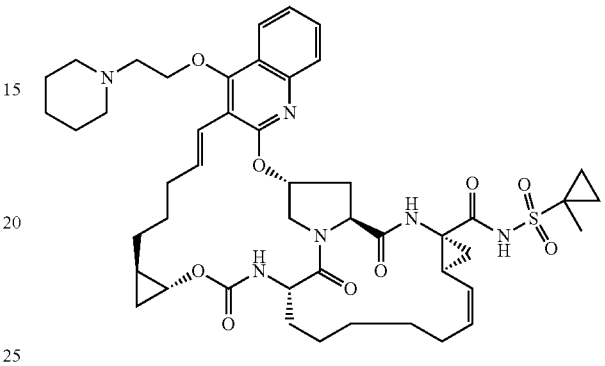

To a solution of acid from Step 6 (87.3 mg) in THF (0.6 mL) was added 1,1'-carbonyldiimidazole (28 mg) and the reaction mixture was heated to 40° C. for 1 hour. The reaction mixture was cooled to room temperature. At this point, 1-methylcyclopropanesulfonamide (61 mg) and DBU (85 µl) were added. The reaction mixture was heated to 40° C. for 18 hours. Once the mixture cooled to room temperature, it was diluted with ethyl acetate. Water was added and the mixture was acidified to pH=4. The mixture was extracted (3×) with ethyl acetate. The combined organics were dried over magnesium sulfate, filtered and concentrated. The residue was purified by flash chromatography (ISCO reverse phase, 5 to 95% acetonitrile in water) to give the desired product (40.8 mg). LRMS (ES+) m/z 887.40 (M+H)$^+$.

Examples 297-299

By following the procedures outlined in Example 296 and using the appropriate reagents (depicted below the structure as Rg.), the following compounds were prepared.

| Ex | Structure | Name | LRMS (M + H)$^+$ |
|---|---|---|---|
| 297 | (structure shown) Rg. 4-(2-bromoethyl)morpholine | (1aR,5S,11Z,12aS,13aR,16S,19R,27E,31aR)-N-[(1-methylcyclopropyl)sulfonyl]-26-[2-(morpholin-4-yl)ethoxy]-3,15,33-trioxo-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide | 889.50 |

| Ex | Structure | Name | LRMS (M + H)+ |
|---|---|---|---|
| 298 | Rg. 4-(3-bromopropyl)morpholine, NaI | (1aR,5S,11Z,12aS,13aR,16S,19R,27E,31aR)-N-[(1-methylcyclopropyl)sulfonyl]-26-[3-(morpholin-4-yl)propoxy]-3,15,33-trioxo-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide | 903.30 |
| 299 | Rg. 1-(2-chloroethyl)pyrrolidine hydrochloride | (1aR,5S,11Z,12aS,13aR,16S,19R,27E,31aR)-N-[(1-methylcyclopropyl)sulfonyl]-3,15,33-trioxo-26-[2-(pyrrolidin-1-yl)ethoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide | 873.55 |

Example 300

(1aR,5S,11Z,12aS,13aR,16S,19R,27E,31aR)-26-methoxy-N-[(1-methylcyclopropyl)sulfonyl]-3,15,33-trioxo-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide Step 1: ethyl (2R,6S,12Z,13aS,14aR,16aS)-2-[(3-bromo-4-methoxyquinolin-2-yl)oxy]-5,16-dioxo-6-{[({(1R,2R)-2-[(4E)-5-(4,4,5,5-tetramethyl-1,3,2-dioxaborolan-2-yl)pent-4-en-1-yl]cyclopropyl}oxy)carbonyl]amino}-1,2,3,6,7,8,9,10,11,13a,14,15,16,16a-tetradecahydrocyclopropa[e]pyrrolo[1,2-a][1,4]diazacyclopentadecine-14a(5H)-carboxylate

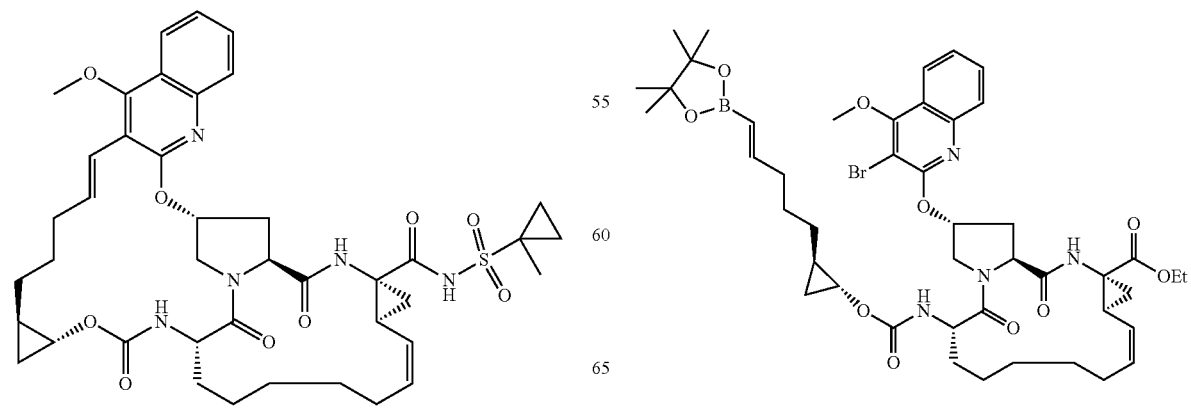

381

To a solution of phenol from Example 296, Step 3 (402 mg) in DMF (2.2 mL) was added methyl iodide (84 µl) and DIPEA (314 µl). The reaction mixture was stirred at room temperature for 18 hours. The reaction was quenched with water and the reaction mixture was diluted with ethyl acetate. The mixture was extracted (3×) with ethyl acetate. The combined organics were washed with brine (2×), dried over magnesium sulfate, filtered and concentrated. The residue was purified by flash chromatography (ISCO, 0 to 10% methanol in dichloromethane) to give the title compound (403 mg, 99%) as a yellow foam. LRMS (ES+) ink 907.3 (M+H)+.

Steps 2 to 4: (1aR,5S,11Z,12aS,13aR,16S,19R,27E,31aR)-26-methoxy-N-[(1-methylcyclopropyl)sulfonyl]-3,15,33-trioxo-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide

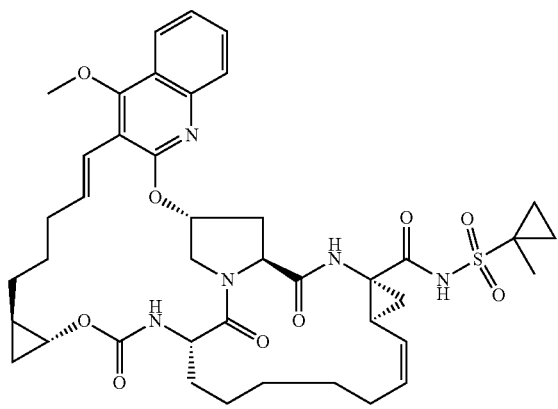 [SMILES: COc1c2c(nc3ccccc13)O[C@@H]1C[C@H]3C(=O)N[C@]4(C(=O)NS(=O)(=O)C5(C)CC5)C[C@H]4/C=C\CCCCC[C@H](NC(=O)O[C@@H]4C[C@H]4CCC/C=C/2)C(=O)N3C1]

The title compound was prepared using the same method as Example 296, Steps 5-7 using the product of step 1. LCMS (ES+) m/z 790.25 (M+H)+.

Example 301

(1aR,5S,11Z,12aS,13aR,16S,19R,31aR)—N-[(1-methylcyclopropyl)sulfonyl]-26-[2-(morpholin-4-yl)ethoxy]-3,15,33-trioxo-1,1a,3,4,5,6,7,8,9,10,12a,13,15,16,18,19,27,28,29,30,31,31a-docosahydro-5,17:16,19-dimethanodicyclopropa[12,13:28,29][1,20,3,14,17]dioxatriazacyclononacosino[21,22-b]quinoline-13a(14H)-carboxamide

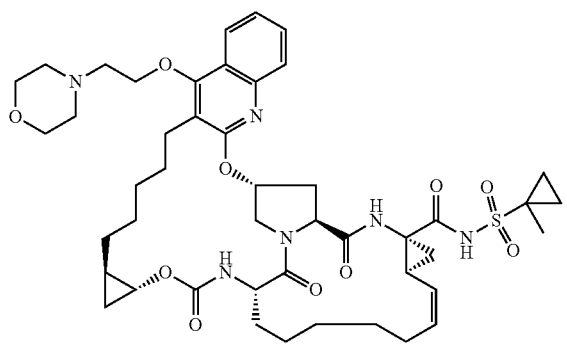 [SMILES: CC1(S(=O)(=O)NC(=O)[C@@]23C[C@H]2/C=C\CCCCC[C@@H]2NC(=O)O[C@@H]4C[C@H]4CCCCCc4c(nc5ccccc5c4OCCN4CCOCC4)O[C@@H]4C[C@@H](C(=O)N3)N(C4)C2=O)CC1]

382

Step 1: 15-tert-butyl 14a-ethyl(2R,6S,12Z,13aS,14aR,16aS)-2-({3-bromo-4-[(4-methoxybenzyl)oxy]quinolin-2-yl}oxy)-6-[(tert-butoxycarbonyl)amino]-5,16-dioxo-2,3,6,7,8,9,10,11,13a,14,16,16a-dodecahydrocyclopropa[e]pyrrolo[1,2-a][1,4]diazacyclopentadecine-14a,15(1H,5H)-dicarboxylate

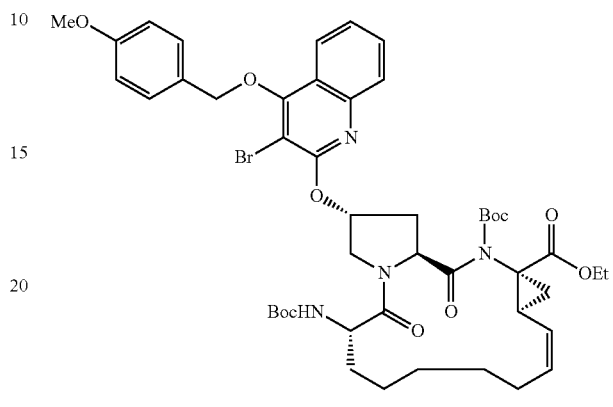

The title compound was prepared using the same method as Example 296, Step 1 using Intermediate C13. LCMS (ES+) ink 957.4 (M+Na)+.

Step 2: 15-tert-butyl 14a-ethyl(2R,6S,12Z,13aS,14aR,16aS)-6-amino-2-({3-bromo-4-[(4-methoxybenzyl)oxy]quinolin-2-yl}oxy)-5,16-dioxo-2,3,6,7,8,9,10,11,13a,14,16,16a-dodecahydrocyclopropa[e]pyrrolo[1,2-a][1,4]diazacyclopentadecine-14a,15(1H,5H)-dicarboxylate

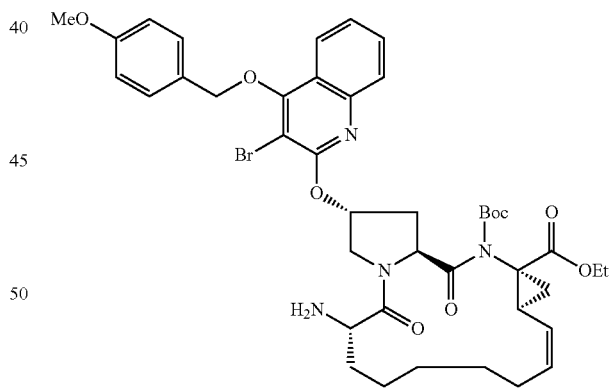

Tert-butyldimethylsilyl trifluoromethanesulfonate (0.655 mL) was added to the solution of 2,6-lutidine (0.31 mL) and the product from Step 1 (1.91 g) in DCM (40 mL). The solution was stirred at room temperature for 1 hour. Tetrabutyl ammonium fluoride (1.0M in THF, 3.06 mL) was added and the solution was stirred at room temperature for 30 minutes. A saturated solution of ammonium chloride was added and the mixture was extracted with dichloromethane (3×). The combined organic fractions were washed with saturated solution of sodium bicarbonate, dried over magnesium sulfate, filtered and concentrated. The crude product was used directly in the next step. LCMS (ES+) ink 835.3 (M+H)+.

Step 3: 15-tert-butyl 14a-ethyl(2R,6S,12Z,13aS, 14aR,16aS)-2-({3-bromo-4-[(4-methoxy benzyl) oxy]quinolin-2-yl}oxy)-5,16-dioxo-6-{[({(1R,2R)-2-[5-(4,4,5,5-tetramethyl-1,3,2-dioxaborolan-2-yl) pentyl]cyclopropyl}oxy)carbonyl]amino}-2,3,6,7,8, 9,10,11,13a,14,16,16a-dodecahydrocyclopropa[e] pyrrolo[1,2-a][1,4]diazacyclopentadecine-14a,15 (1H,5H)-dicarboxylate

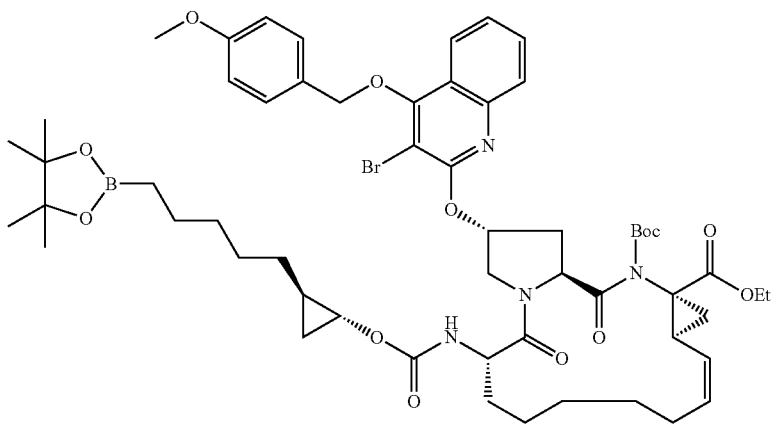 [SMILES: CCOC(=O)[C@@]12C[C@H]1/C=C\CCCCC[C@H](NC(=O)O[C@@H]1C[C@H]1CCCCCB1OC(C)(C)C(C)(C)O1)C(=O)N1C[C@H](Oc3nc4ccccc4c(OCc4ccc(OC)cc4)c3Br)C[C@H]1C(=O)N2C(=O)OC(C)(C)C]

The title compound was prepared using the same method as described in Example 296, Step 3 using intermediate A15.

Step 4: 14-tert-butyl 13a-ethyl(1aR,5S,11Z,12aS, 13aR,19R,31aR)-26-[(4-methoxybenzyl)oxy]-3,15, 33-trioxo-1,1a,3,4,5,6,7,8,9,10,12a,13,15,16,18,19, 27,28,29,30,31,31a-docosahydro-5,17:16,19-dimethanodicyclopropa[12,13:28,29][1,20,3,14,17] dioxatriazacyclononacosino[21,22-b]quinoline-13a, 14-dicarboxylate

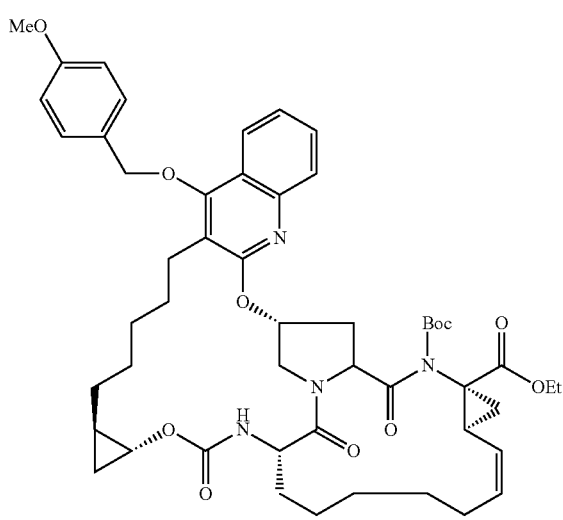 [SMILES: CCOC(=O)[C@@]12C[C@H]1/C=C\CCCCC[C@@H]1NC(=O)O[C@@H]3C[C@H]3CCCCCc3c(nc4ccccc4c3OCc3ccc(OC)cc3)O[C@@H]3CC(C(=O)N2C(=O)OC(C)(C)C)N(C3)C1=O]

The title compound was prepared using the same method as described in Example 296, Step 5 except that cataxium A and palladium acetate were pre-mixed before addition to the reaction mixture. The reaction mixture was heated at 100° C. for 9 hours. LCMS (ES+) m/z 909.45 (M+H)⁺.

Step 5: ethyl (1aR,5S,11Z,12aS,13aR,19R,31aR)-26-hydroxy-3,15,33-trioxo-1,1a,3,4,5,6,7,8,9,10,12a,13, 15,16,18,19,27,28,29,30,31,31a-docosahydro-5,17: 16,19-dimethanodicyclopropa[12,13:28,29][1,20,3, 14,17]dioxatriazacyclononacosino[21,22-b] quinoline-13a(14H)-carboxylate

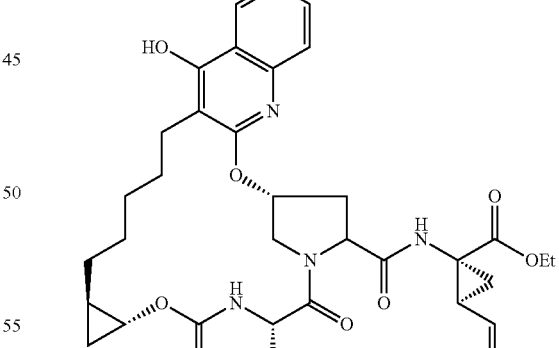

TFA (1.51 ml) was added to the solution of bis-macrocycle from Step 4 (0.412 g) in DCM (3.0 ml) at room temperature. The solution was stirred for 3 hours. The solvent was evaporated under reduced pressure and the residue was purified by flash chromatography (ISCO, reverse phase) to afford the desired product (0.122 g) as a white solid. LCMS (ES+) m/z 689.5 (M+H)+.

Step 6: ethyl (1aR,5S,11Z,12aS,13aR,16S,19R,31aR)-26-[2-(morpholin-4-yl)ethoxy]-3,15,33-trioxo-1,1a,3,4,5,6,7,8,9,10,12a,13,15,16,18,19,27,28,29,30,31,31a-docosahydro-5,17:16,19-dimethanodicyclopropa[12,13:28,29][1,20,3,14,17]dioxatriazacyclononacosino[21,22-b]quinoline-13a(14H)-carboxylate

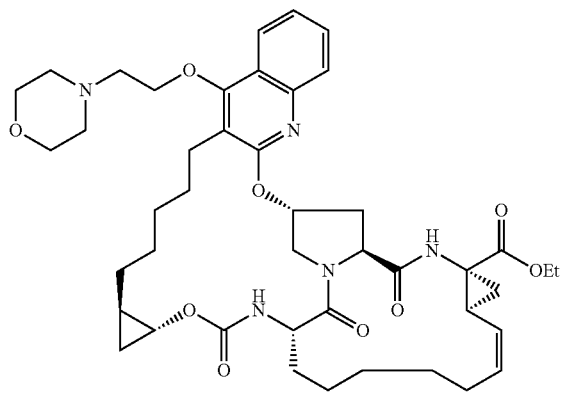 [SMILES: CCOC(=O)[C@@]12C[C@H]1/C=C\CCCCC[C@@H]1NC(=O)O[C@@H]3C[C@H]3CCCCCc3c(nc4ccccc4c3OCCN3CCOCC3)O[C@@H]3C[C@@H](C(=O)N2)N(C3)C1=O]

4-(2-Bromoethyl)morpholine (0.069 g) was added to the mixture of phenol from Step 5 (0.122 g) and cesium carbonate (0.462 g) in DMF (1.77 ml). The mixture was stirred at room temperature for 1 hour 30 minutes. At this point, water was added and the mixture was extracted with ethyl acetate (3×). The combined organic fractions were dried over magnesium sulfate, filtered and concentrated. The residue was purified by flash chromatography (ISCO reverse phase) to give the undesired epimer (19 mg) as a white powder and the desired product (12.9 mg) as a white powder. LCMS (ES+) m/z 802.45 (M+H)+.

Step 7-8: (1aR,5S,11Z,12aS,13aR,16S,19R,31aR)—N-[(1-methylcyclopropyl)sulfonyl]-26-[2-(morpholin-4-yl)ethoxy]-3,15,33-trioxo-1,1a,3,4,5,6,7,8,9,10,12a,13,15,16,18,19,27,28,29,30,31,31a-docosahydro-5,17:16,19-dimethanodicyclopropa[12,13:28,29][1,20,3,14,17]dioxatriazacyclononacosino[21,22-b]quinoline-13a(14H)-carboxamide

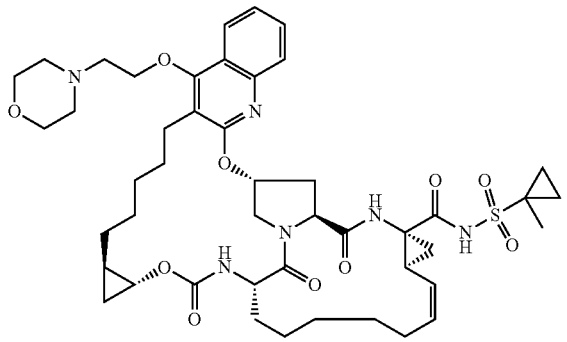 [SMILES: CC1(S(=O)(=O)NC(=O)[C@@]23C[C@H]2/C=C\CCCCC[C@@H]2NC(=O)O[C@@H]4C[C@H]4CCCCCc4c(nc5ccccc5c4OCCN4CCOCC4)O[C@@H]4C[C@@H](C(=O)N3)N(C4)C2=O)CC1]

The title compound was prepared using the same method as Example 296, Steps 6-7. LCMS (ES+) m/z 891.40 (M+H)+.

Example 302

(1aR,5S,11Z,12aS,13aR,16S,19R,27E,31aR)—N-[(1-methylcyclopropyl)sulfonyl]-3,15,33-trioxo-26-[3-(piperidin-1-yl)propoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide

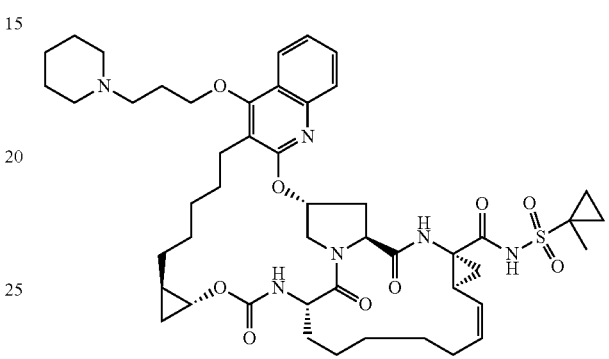

Step 1: ethyl (2R,6S,12Z,13aS,14aR,16aS)-2-{[3-bromo-4-(3-bromopropoxy)quinolin-2-yl]oxy}-5,16-dioxo-6-{[({(1R,2R)-2-[(4E)-5-(4,4,5,5-tetramethyl-1,3,2-dioxaborolan-2-yl)pent-4-en-1-yl]cyclopropyl}oxy)carbonyl]amino}-1,2,3,6,7,8,9,10,11,13a,14,15,16,16a-tetradecahydrocyclopropa[e]pyrrolo[1,2-a][1,4]diazacyclopentadecine-14a(5H)-carboxylate

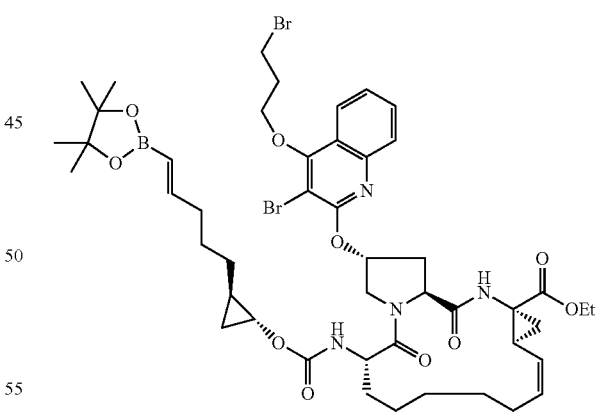

To a 0° C. solution of phenol from Example 296, Step 3 (868 mg) in DMF (6 mL) was added sodium hydride (38 mg). The mixture was stirred 10 minutes and 1,3-dibromopropane (1.98 mL) was added. The reaction mixture was stirred at the same temperature for 30 minutes and then it was warmed up to room temperature and stirred for 18 hours. The reaction was quenched with a saturated solution of ammonium chloride and extracted with ethyl acetate (3×). The combined organic fractions were dried over magnesium sulfate, filtered and concentrated. The residue was purified by flash chromatography (ISCO, 0 to 10% methanol in dichloromethane) to give the title compound (602 mg) as a white foam.

Step 2: ethyl (2R,6S,12Z,13aS,14aR,16aS)-2-({3-bromo-4-[3-(piperidin-1-yl)propoxy]quinolin-2-yl}oxy)-5,16-dioxo-6-{[({(1R,2R)-2-[(4E)-5-(4,4,5,5-tetramethyl-1,3,2-dioxaborolan-2-yl)pent-4-en-1-yl]cyclopropyl}oxy)carbonyl]amino}-1,2,3,6,7,8,9,10,11,13a,14,15,16,16a-tetradecahydrocyclopropa[e]pyrrolo[1,2-a][1,4]diazacyclopentadecine-14a(5H)-carboxylate

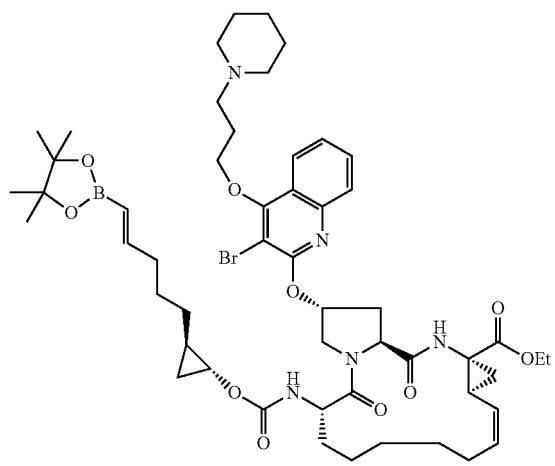 [SMILES: CCOC(=O)[C@@]12C[C@H]1/C=C\CCCCC[C@H](NC(=O)O[C@@H]1C[C@H]1CCC/C=C/B1OC(C)(C)C(C)(C)O1)C(=O)N1C[C@H](Oc3nc4ccccc4c(OCCCN4CCCCC4)c3Br)C[C@H]1C(=O)N2]

Piperidine (317 µl) was added to a solution of bromide from Step 1 (326 mg) in DMSO (2 mL) and the resulting mixture was stirred for 2 hours at room temperature. The reaction was quenched with water and extracted with ethyl acetate (3×). The combined organic fractions were washed with water then brine, dried over magnesium sulfate, filtered and concentrated. The residue was purified by flash chromatography (ISCO reverse phase, 0 to 95% acetonitrile in water) to give the title compound (262 mg) as a mixture with the boronic acid.

Step 3-5: (1aR,5S,11Z,12aS,13aR,16S,19R,27E,31aR)—N-[(1-methylcyclopropyl)sulfonyl]-3,15,33-trioxo-26-[3-(piperidin-1-yl)propoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide

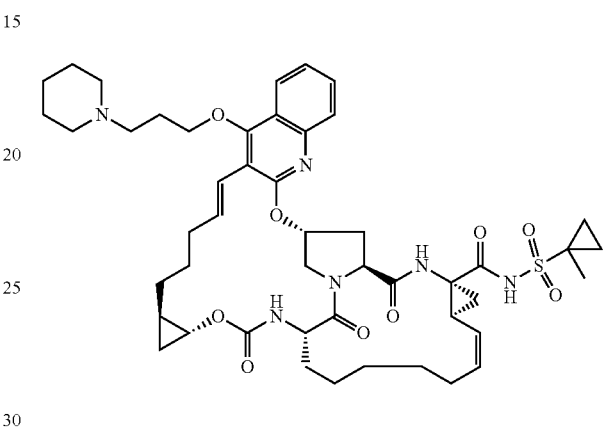

The title compound was prepared using the same method as Example 296, Steps 5-7. LCMS (ES+) m/z 901.20 (M+H)$^+$.

Examples 303-304

By following the procedures outlined in Example 7 and using the appropriate reagents (depicted below the structure as Rg.), the following compounds were prepared.

| Ex | Structure | Name | LRMS (M + H)$^+$ |
|---|---|---|---|
| 303 | (structure shown; Rg. Pyrrolidine) | (1aR,5S,11Z,12aS,13aR,16S,19R,27E,31aR)-N-[(1-methylcyclopropyl)sulfonyl]-3,15,33-trioxo-26-[3-(pyrrolidin-1-yl)propoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide | 887.40 |

| Ex | Structure | Name | LRMS (M + H)+ |
|---|---|---|---|
| 304 | 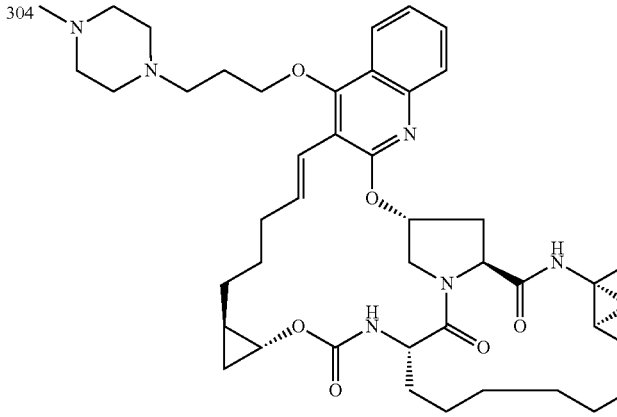 Rg. 1-methyl piperazine | (1aR,5S,11Z,12aS,13aR,16S,19R,27E, 31aR)-N-[(1-methylcyclopropyl)sulfonyl]-26-[3-(4-methylpiperazin-1-yl)propoxy]-3,15,33-trioxo-1,1a,3,4,5,6,7,8,9,10,12a,13,15,16,18, 19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide | 916.50 |

Example 305

(1aR,5S,11Z,12aS,13aR,16S,19R,31aR)-26-methoxy-N-[(1-methylcyclopropyl)sulfonyl]-3,15,33-trioxo-1,1a,3,4,5,6,7,8,9,10,12a,13,15,16,18,19,27, 28,29,30,31,31a-docosahydro-5,17:16,19-dimethanodicyclopropa[12,13:28,29][1,20,3,14,17]dioxatriazacyclononacosino[21,22-b]quinoline-13a(14H)-carboxamide

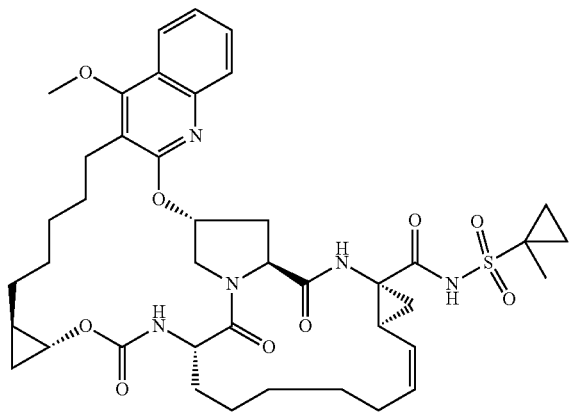

Bismuth trichloride (91 mg) was added to a solution of Example 300 (22.8 mg) in ethanol (2.9 mL) and cooled to 0° C. Then, potassium borohydride (156 mg) was added in small portions. The mixture was stirred at 0° C. for 45 minutes then at room temperature for 18 hours. The reaction mixture was diluted with ethyl acetate and acidified with 4N HCl until pH=3. The mixture was filtered over celite, rinsing with ethyl acetate. The solvent was removed in vacuo. The residue was purified by flash chromatography (ISCO, 0 to 10% methanol in dichloromethane) to give the title compound (5.3 mg) as a white solid. LRMS (ES+) m/z 792.25 (M+H)+.

Example 306

(1aR,5S,11Z,12aS,13aR,16S,19R,31aR)—N-[(1-methylcyclopropyl)sulfonyl]-3,15,33-trioxo-26-[2-(pyrrolidin-1-yl)ethoxy]-1,1a,3,4,5,6,7,8,9,10,12a, 13,15,16,18,19,27,28,29,30,31,31a-docosahydro-5, 17:16,19-dimethanodicyclopropa[12,13:28,29][1,20, 3,14,17]dioxatriazacyclononacosino[21,22-b] quinoline-13a(14H)-carboxamide

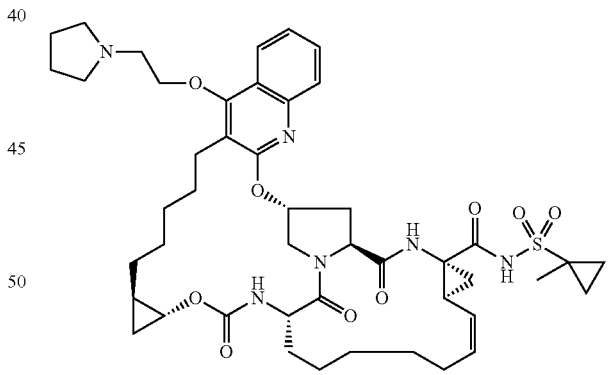

The title compound was prepared using the same method as Example 305 with Example 299 except that 200 equivalents of potassium borohydride and 20 equivalents of bismuth trichloride were used. LRMS (ES+) m/z 875.50 (M+H)+.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound of formula (I) or a pharmaceutically acceptable salt thereof:

(I)

wherein:
Y is CH or N;
$R^1$ is:
- $—OC_{1-6}alkyl$,
- $—OC_{1-6}alkyl-het_1$,
- $—OC_{1-6}alkyl-OH$,
- $—OC_{1-6}alkyl-NR^aR^b$,
- $—O-het_1$,
- $—OC_{1-6}alkylCO_2H$,
- $—OC_{1-6}alkylC(=O)-het_1$,
- $—O(CH_2)_{1-6}OC(=O)CH_2NR^aR^b$,
- $—OC_{1-6}alkyl-C_{1-6}alkoxy$,
- $—OC_{1-6}alkyl-C_{1-6}alkoxy-C_{1-6}alkoxy$,
- $—OC(O)NR^aR^b$,
- $—OC_{1-6}alkyl-S-het_1$,
- $—OC_{1-6}alkyl-phosphate$,
- a phosphate group,
- $—(CH_2)_{1-6}-het_1$,
- pyridinyl, or
- thiazolyl;

wherein
said alkyl is optionally substituted with 1 or 2 fluoro substituents,
said phosphate group is optionally substituted with 1, 2 or 3 $C_{1-6}$alkyl;
said $het_1$ is:
a) naphthyl optionally substituted with 1 or 2 substituents selected from —OH, $C_{1-6}$alkyl, or halo;
b) heteroaryl selected from 5- and 6-membered aromatic rings having 1, 2 or 3 heteroatoms independently selected from N, O and S, wherein said heteroaryl is attached through a ring atom selected from C or N and optionally substituted with 1 or 2 substituents independently selected from $C_{1-6}$alkyl and —OH; or
c) heterocycle selected from 4-7 membered monocyclic or 6-10 membered polycyclic bridged, linearly fused or spirocyclic saturated or unsaturated non-aromatic rings having 1, 2, 3 or 4 heteroatoms independently selected from N, O and S, wherein said heterocycle is attached through a ring atom selected from C or N and optionally substituted with 1 or 2 substituents independently selected from $C_{1-6}$alkyl, oxo, $—(CH_2)_mF$, Boc, $—(CH_2)_mCF_3$, $—(CH_2)_mOCF_3$, —OH, $—NR^aR^b$, $—C_{1-6}$alkoxy, $—(CH_2)_mSO_2CH_3$, aryl, $—C_{1-6}$alkoxy-$C_{1-6}$alkyl, $—C_{1-6}$alkyl-$C_{1-6}$alkoxy optionally substituted with $CF_3$, cyano, $C(=O)NH_2$, $C_{3-6}$cycloalkyl,
$—C_{1-6}$alkyl-$C_{3-6}$cycloalkyl, $—COOC_{1-6}$alkyl,
$C_{1-6}$alkyl-$SO_2C_{1-6}$alkyl, and benzimidazolyl wherein the benzimidazolyl is optionally substituted with F;

$R^a$ and $R^b$ are independently selected from H; $C_{1-6}$ alkyl; t-Boc; aryl; $C_{3-6}$cycloalkyl optionally substituted with 1 or 2 fluoro; $C_{1-6}$alkoxy-$C_{1-6}$alkyl; tetrahydropyranyl; $C_{1-6}$alkyl-OH; $C_{1-6}$alkyl-arylA; $C_{1-6}$alkyl-C(H)(OH)-arylA; $C_{1-6}$alkyl-imidazolyl optionally substituted with methyl, $C_{1-6}$alkyl-benzimidazolyl optionally substituted with methyl; $C_{1-6}$alkyl-pyrazolyl; $C_{1-6}$alkyl-dihydrotriazole optionally substituted with oxo; or $C_{1-6}$alkyl-pyrrolidinyl optionally substituted with oxo;

wherein
m is 0 or 1 to 4;
said arylA is phenyl, naphthalenyl, tetrahydronaphthalenyl, or 7-10 membered fused bicyclic ring structure wherein at least one of the rings is aromatic and is optionally substituted with 2 —OH;
said tetrahydropyranyl is optionally substituted with 1 oxo;

$R^2$ is $C_{1-6}$alkyl, $C_{2-6}$alkenyl, $C_3$-$C_6$cycloalkyl or $NR^cR^d$;
wherein
the $C_{3-6}$cycloalkyl is optionally substituted with $C_{1-6}$alkyl optionally substituted with —OH, morpholinyl, $C_{1-6}$alkoxy, $C_{1-6}$alkoxy-$C_{1-6}$alkoxy,
$C_{1-6}$alkoxy-phenyl, or $C_{2-6}$alkenyl;
$R^c$ and $R^d$ are independently H or $C_{1-6}$alkyl, or may be taken together, with the N to which they are attached, to form a 4-7-membered monocyclic ring;

$R^3$ is $C_{1-6}$alkyl, $C_{2-6}$alkenyl, $C_3$-$C_6$cycloalkyl, $CHF_2$ or $CF_3$;

$R^4$ is $C_{1-8}$ alkyl, $C_{3-8}$ cycloalkyl, $C_{1-8}$ alkyl-$C_{3-8}$ cycloalkyl, adamantyl, dihydroindenyl, or a 4-8 membered heterocycloalkyl having 1 or 2 heteroatoms selected from N, O, or S, wherein $R^4$ is optionally substituted with one or two substituents independently selected from $(C_1$-$C_6)$alkyl, halo, and $—O(C_1$-$C_6)$alkyl; or $R^3$ and $R^4$ together form heptene;

Z is C or N;

$R^5$ is H or $C_{1-6}$alkyl; or $R^5$ is absent when Z is N;

W is a bond, O or NR;

R is H or $C_{1-6}$alkyl;

X is absent or is halo, $CF_3$, $—OCHF_2$, $—OCH_2F$, $—OCD_2F$, $—OCDF_2$, $C_1$-$C_6$alkyl, $C_{1-6}$alkoxy, aryl, heteroaryl, or $—O(CH_2)_{1-6}NR^aR^b$;

A is absent, O or N;

B is $(CH_2)_m$; and n is 1-4.

2. The compound according to claim 1, or a pharmaceutically acceptable salt thereof, having a formula of
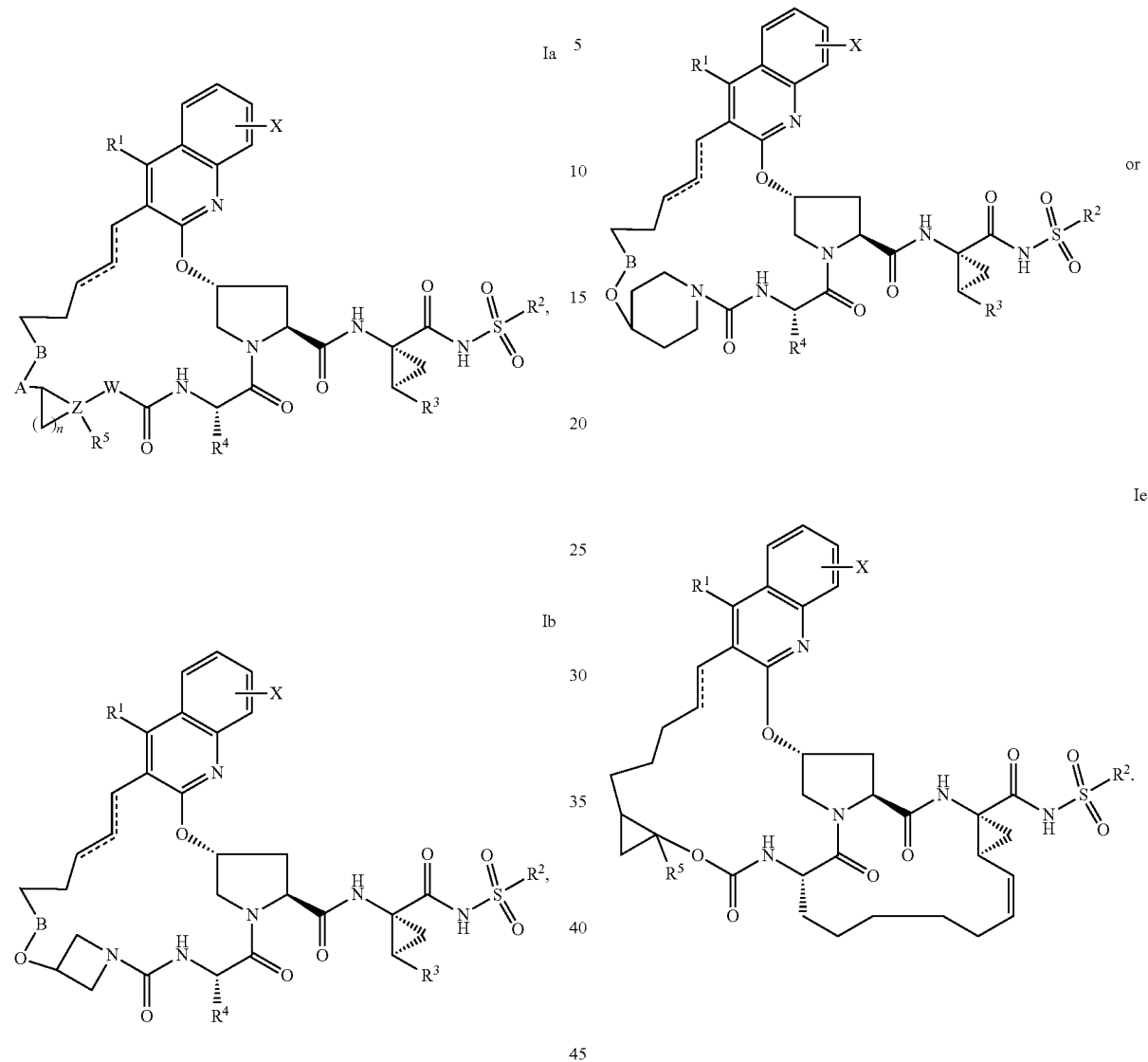
3. The compound according to claim 1, or a pharmaceutically acceptable salt thereof, having a formula of
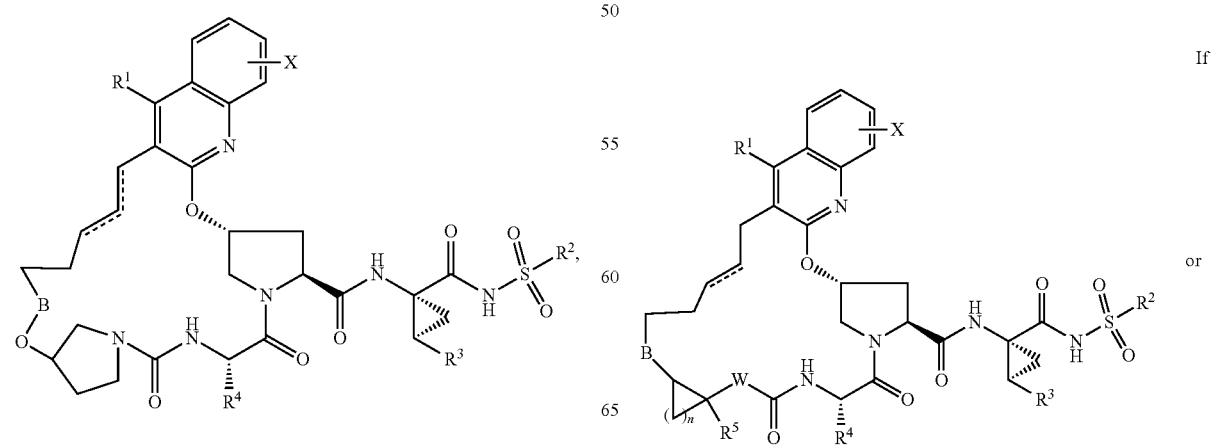

4. The compound according to claim 1, or a pharmaceutically acceptable salt thereof, having a formula of Ih

5. The compound according to claim 1, or a pharmaceutically acceptable salt thereof, wherein $R^5$ is H or $CH_3$.

6. The compound according to claim 1, or a pharmaceutically acceptable salt thereof, wherein $R^3$ is ethyl, ethylene, or cyclopropyl.

7. The compound according to claim 1, or a pharmaceutically acceptable salt thereof, wherein $R^4$ is propyl, t-butyl, cyclopentyl, cyclohexyl optionally substituted with 1 or 2 F, cyclohexylmethyl, methylcyclohexyl, methylcyclopentyl, dihydroindenyl, or tetrahydro-2H-pyranyl.

8. The compound according to claim 1, or a pharmaceutically acceptable salt thereof, wherein n is 1 to 3.

9. The compound according to claim 1, or a pharmaceutically acceptable salt thereof, wherein $R^2$ is cyclopropyl, $N(CH_3)_2$, or azetidinyl, wherein the cyclopropyl is optionally substituted with methyl, $CH(CH_3)_2$, $C(CH_3)=CH_2$, $C(CH_3)_2OH$, $CH_2CH_2$-morpholinyl, $CH_2OCH_3$, $CH_2OCH_2CH_2OCH_3$, or $CH_2OCH_2$-phenyl.

10. The compound according to claim 1, or a pharmaceutically acceptable salt thereof, wherein $R^1$ is —O—$C_{1-6}$alkyl; —$OC_{1-6}$alkyl-$het_1$; —$OC_{1-6}$alkyl-$C_{1-6}$alkoxy; —$OC_{1-6}$alkyl-$C_{1-6}$alkoxy-$C_{1-6}$alkoxy; —$OCH_2C(=O)$-$het_1$; —$O(CH_2)_{1-6}$ $OC(=O)CH_2NR^aR^b$; —$OC(O)NR^aR^b$; —$OC_{1-6}$alkyl-phosphate; —$OC_{1-6}$alkyl-S-$het_1$; —O-$het_1$; —O—$C_{1-6}$alkyl-OH optionally substituted with 1 or 2 fluoro substituents; or —$OC_{1-6}$alkyl-$NR^aR^b$ wherein $R^a$ and $R^b$ are independently

H, $C_{1-6}$ alkyl, t-Boc, $C_{3-6}$cycloalkyl optionally substituted with 1 or 2 fluoro substituents, $C_{1-6}$ alkyl-$C_{1-6}$alkoxy, $C_{1-6}$alkyl-OH, phenyl, $C_{1-6}$alkyl-phenyl, tetrahydropyranyl, $C_{1-6}$alkyl-C(H)(OH)-phenyl, naphthalenyl, $C_{1-6}$alkyl-naphthalenyl, $C_{1-6}$alkyl-oxopyrrolidinyl, $C_{1-6}$alkyl-benzimidazolyl optionally substituted with methyl, $C_{1-6}$alkyl-pyrazolyl, $C_{1-6}$alkyl-dihydrotriazole optionally substituted with oxo, or $C_{1-6}$alkyl-imidazolyl optionally substituted with methyl.

11. The compound according to claim 1, or a pharmaceutically acceptable salt thereof, wherein the $het_1$ is: oxazepanyl; oxooxazolidinyl; pyridinyl; pyrazolyl; pyrrolyl; tetrahydropyranyl; triazolyl optionally substituted with $C_{1-6}$alkyl; dioxolanyl; oxoimidazolidinyl; morpholinyl optionally substituted with dimethyl or ethyl; pyrrolidinyl optionally substituted with 1 or 2 substituents independently selected from oxo, Boc, $C_{1-6}$alkyl, OH, $C(O)NH_2$, dimethylamino, and methylsulfonyl; piperidinyl optionally substituted with 1 or 2 substituents independently selected from $C_{1-6}$alkyl, $C_{1-6}$alkoxy, $C_{1-6}$alkoxy-$C_{1-6}$alkyl optionally substituted with $CF_3$, cyclopropyl-$C_{1-6}$alkyl, cyclopropyl, —$(CH_2)_mF$, OH, —$C_{1-6}$alkyl-$SO_2C_{1-6}$alkyl, —$(CH_2)_mCF_3$, —$COOC_{1-6}$alkyl, Boc, and benzimidazolyl; imidizolyl; thiazolyl optionally substituted with methyl; azabicycloheptyl; azaspiroheptyl; azaspirononyl; oxaazabicycloheptyl; oxaazaspiroheptyl optionally substituted with methoxyethyl; azetidinyl optionally substituted with 1 or 2 substituents independently selected from $C_{1-6}$alkyl, $C_{1-6}$alkoxy, cyano, fluoro, OH, phenyl and Boc; dioxidothiomorpholinyl; piperazinyl optionally substituted with 1 or 2 substituents independently selected from $C_{1-6}$alkyl, $C_{1-6}$alkyl-cyclopropyl, $CF_3$, methylsulfonyl, Boc, and oxo; azabicyclooctyl substituted with Boc, $C_{1-6}$alkoxy-$C_{1-6}$alkyl, —$COOC_{1-6}$alkyl, or —$(CH_2)_mCF_3$; oxaazabicyclononyl optionally substituted with Boc, $C_{1-6}$alkyl, —$COOC_{1-6}$alkyl, $C_{1-6}$alkoxy-$C_{1-6}$alkyl or cyclopropyl$C_{1-6}$alkyl; or azabicyclooctanyl optionally substituted with $C_{1-6}$ alkyl.

12. The compound according to claim 1, or a pharmaceutically acceptable salt thereof, wherein X is absent or selected from —Br, —Cl, —F, methoxy, methyl, propyl and $CF_3$.

13. A compound according to claim 1 selected from:
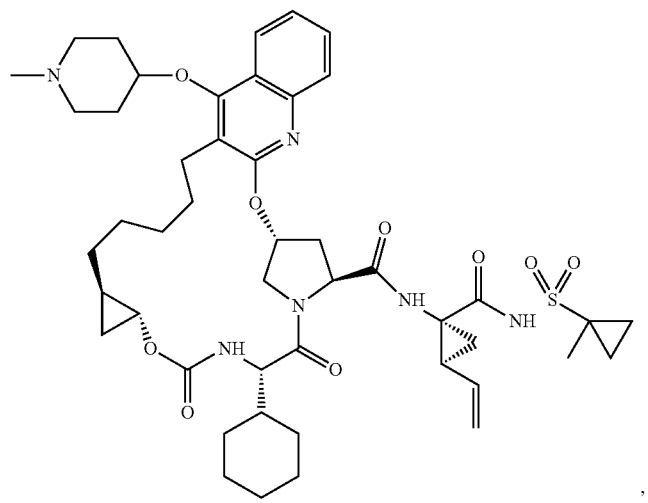
,
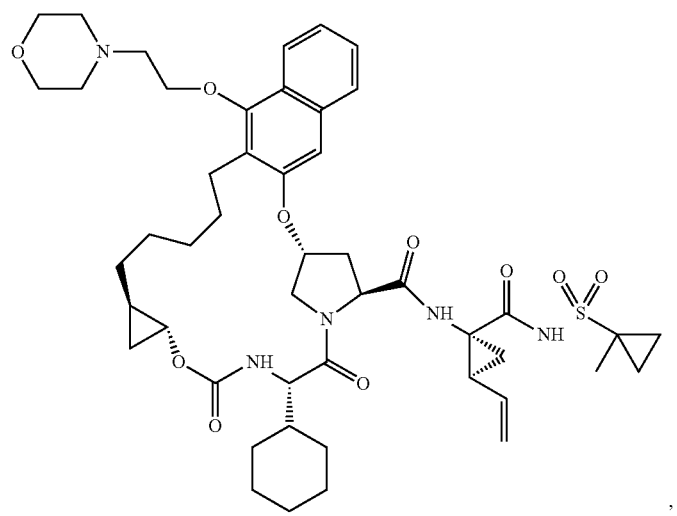
,
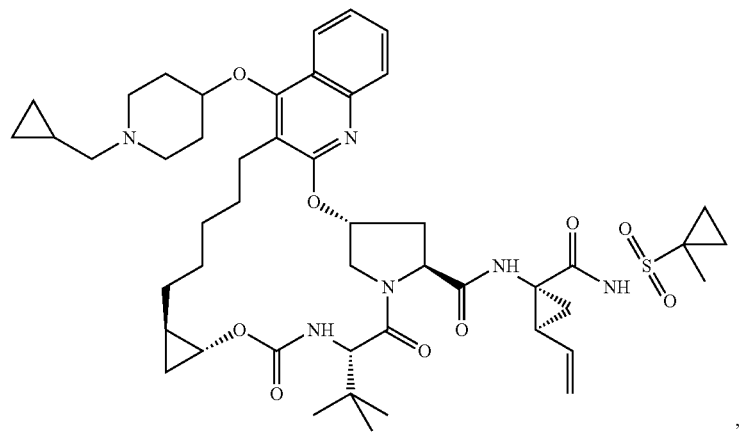
,

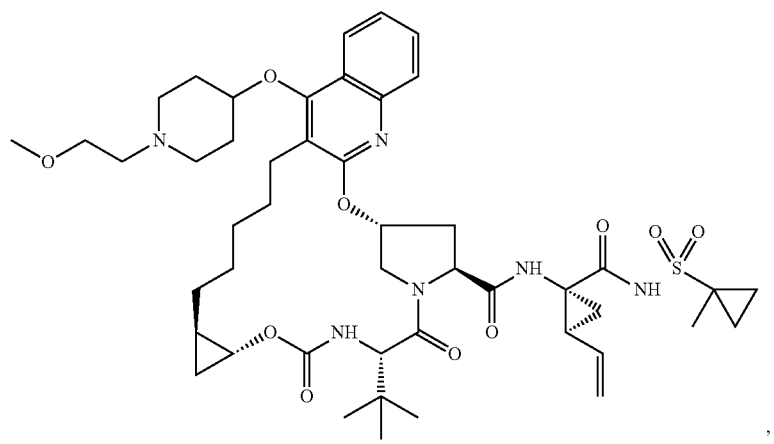
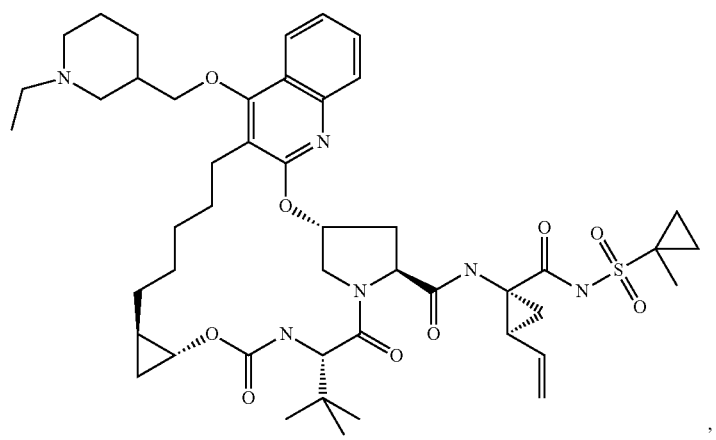
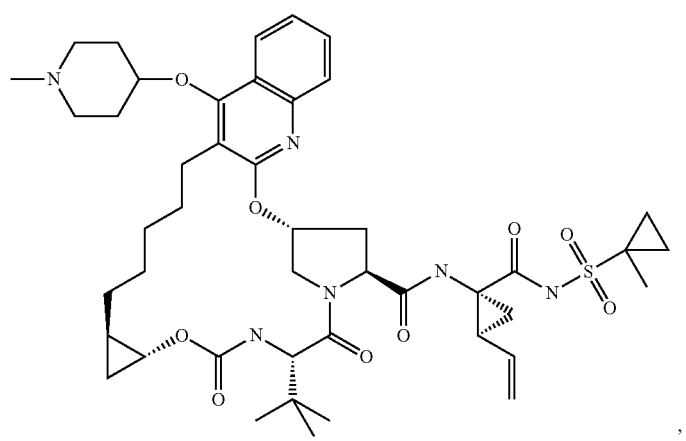

-continued
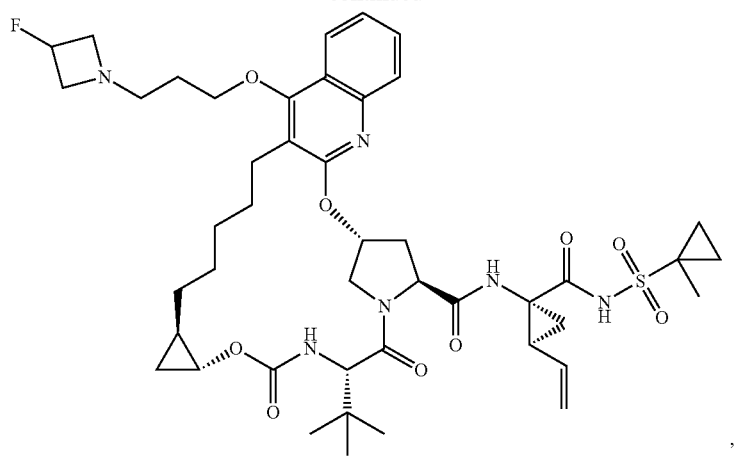
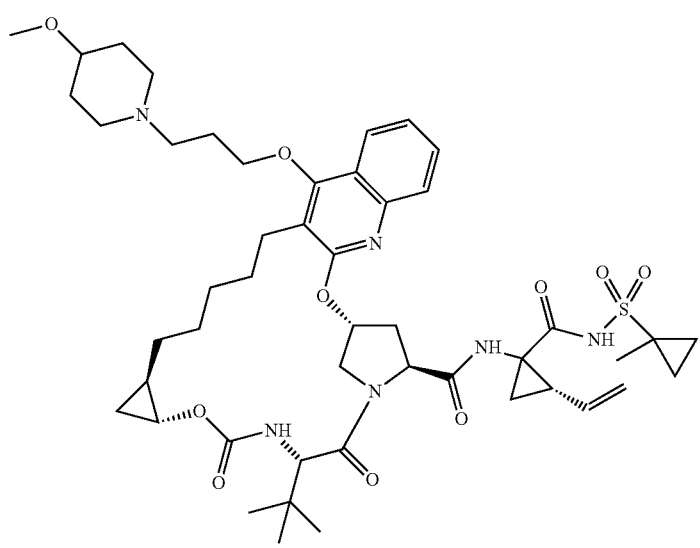
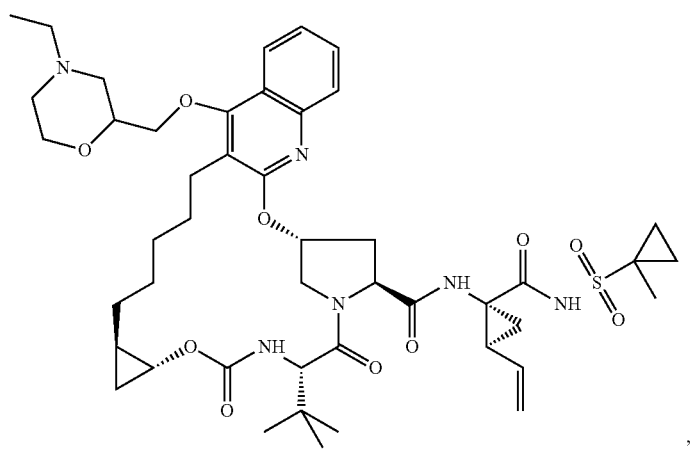

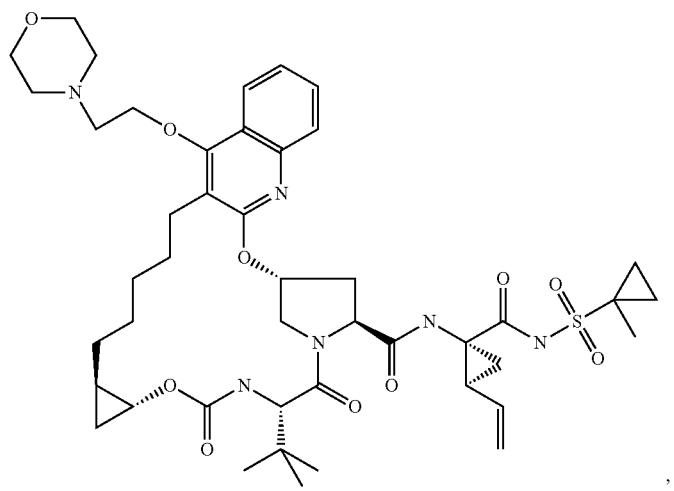
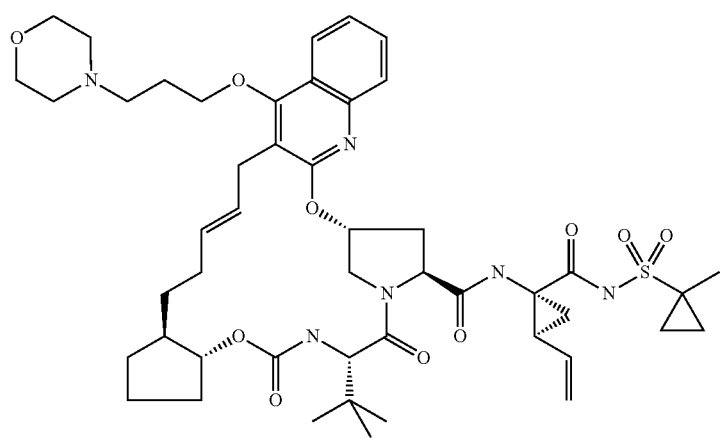
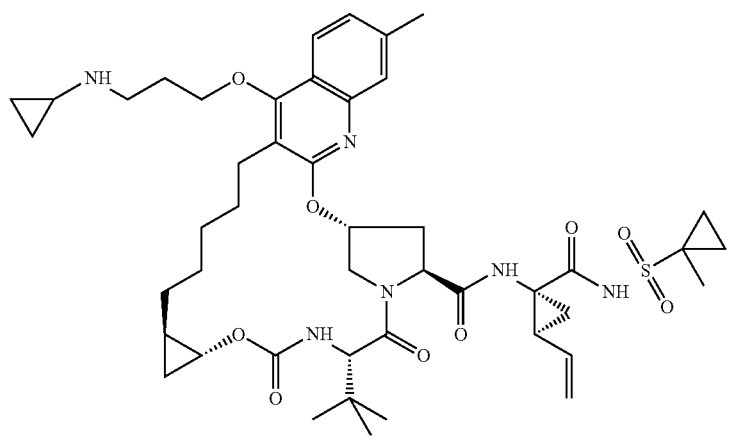

405
-continued
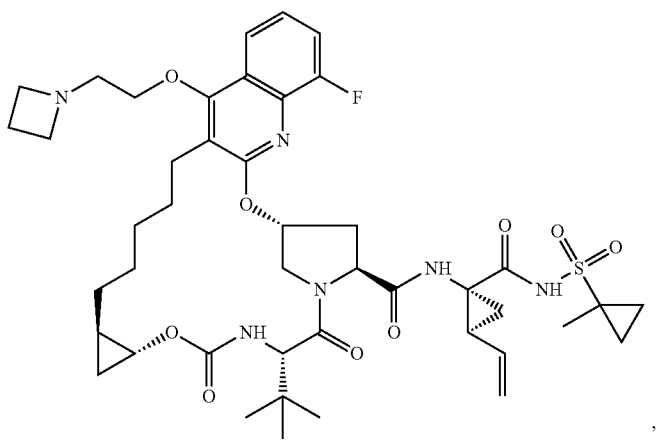
406
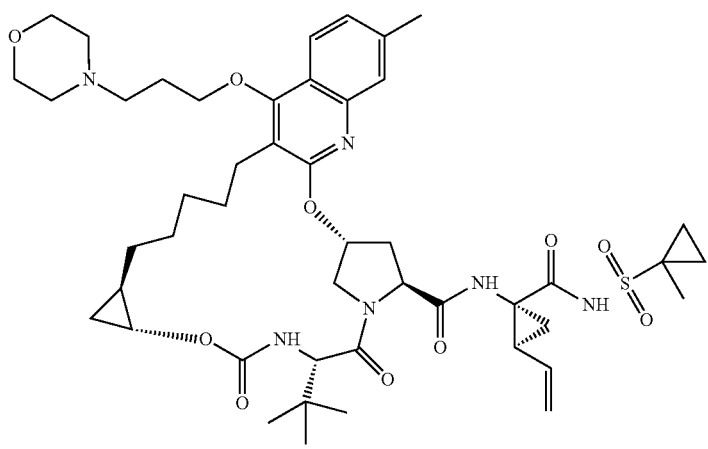
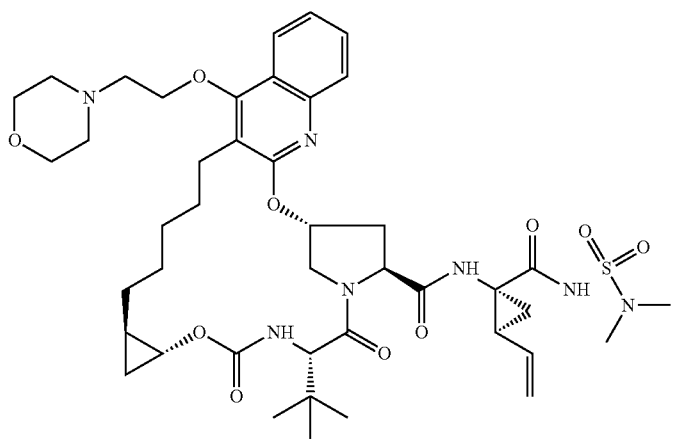

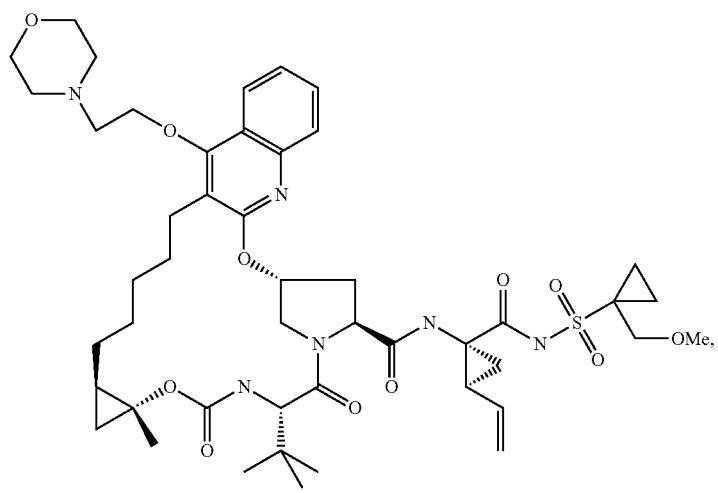
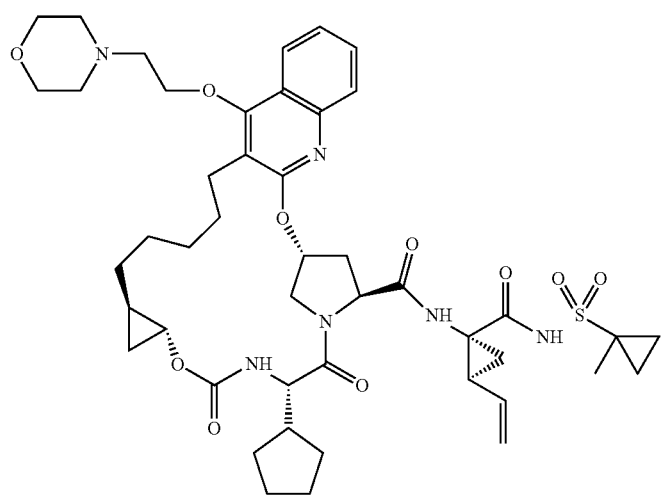
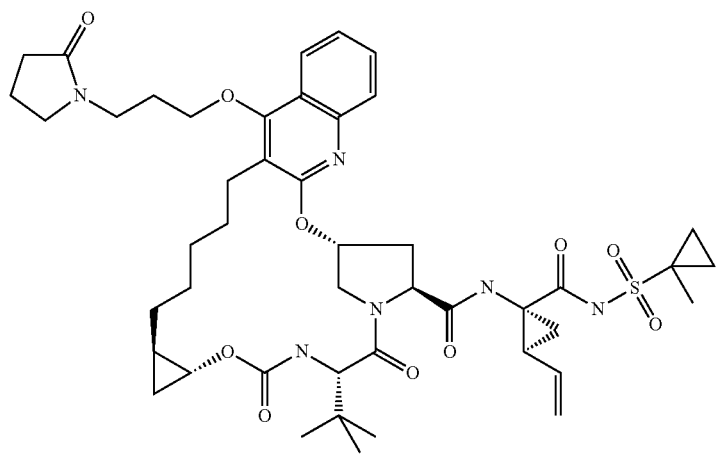

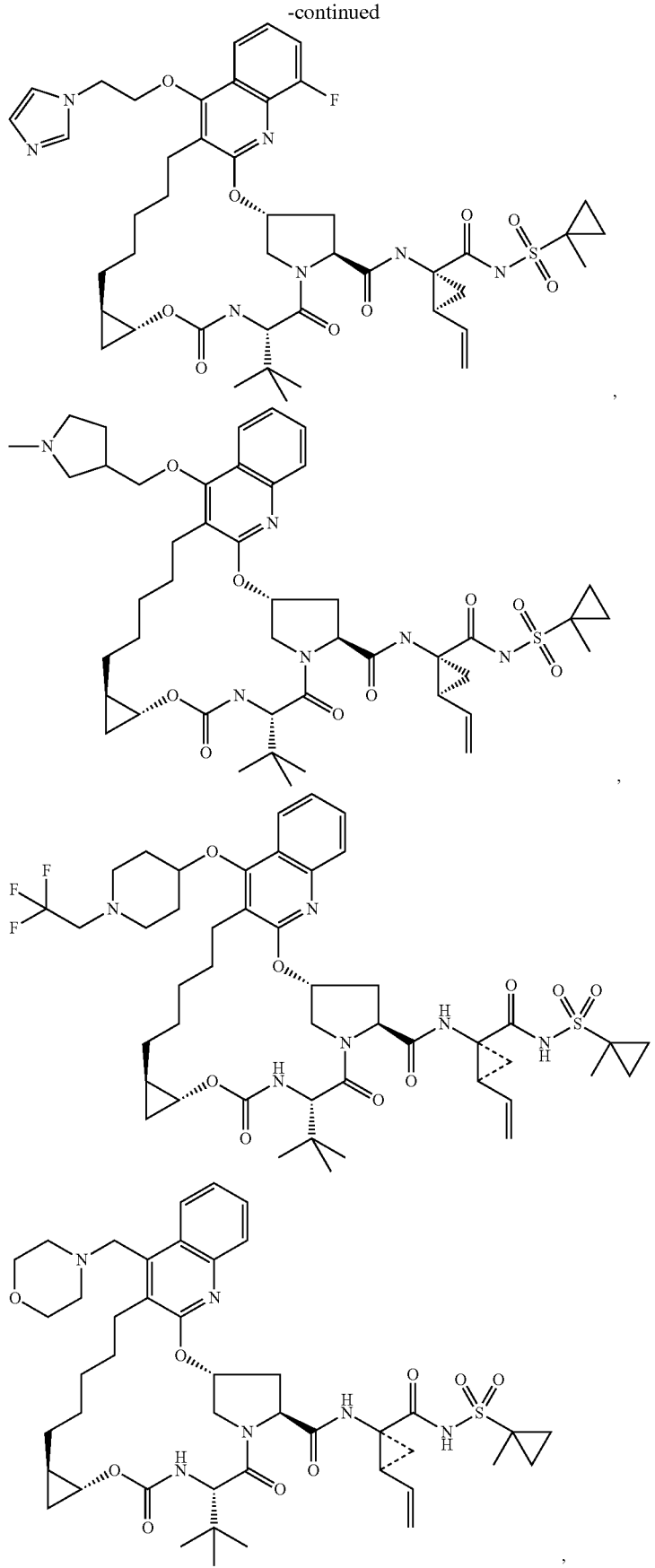

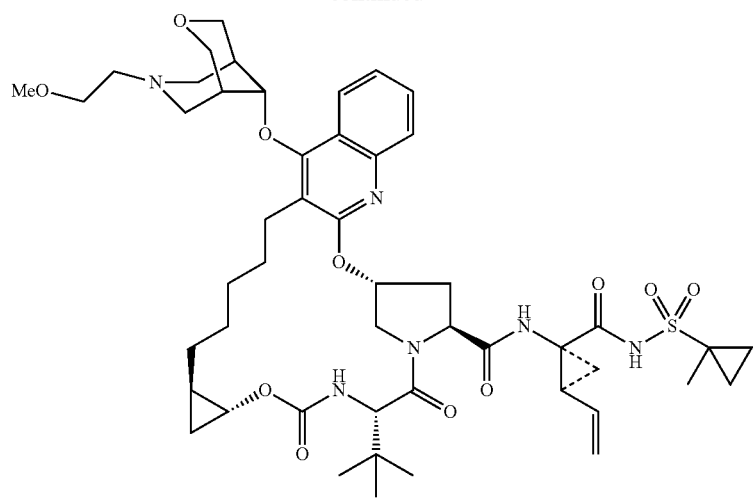
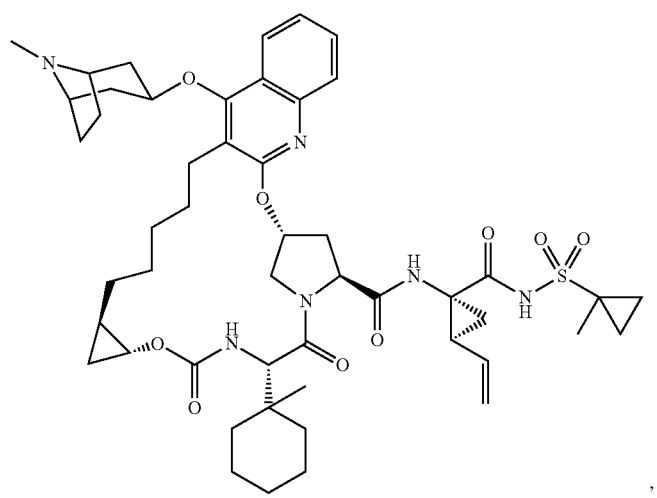
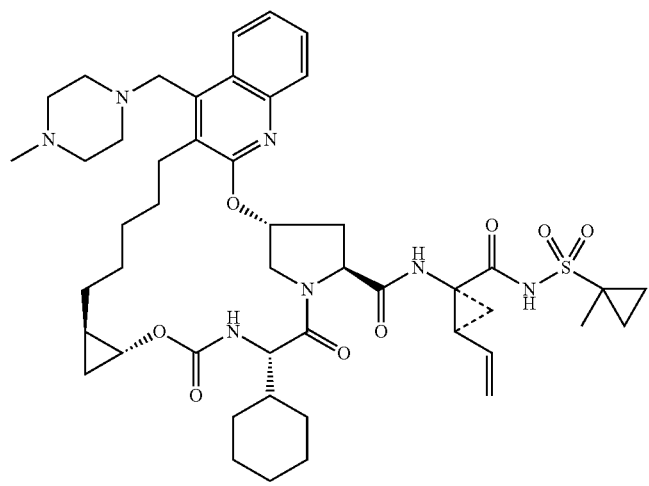

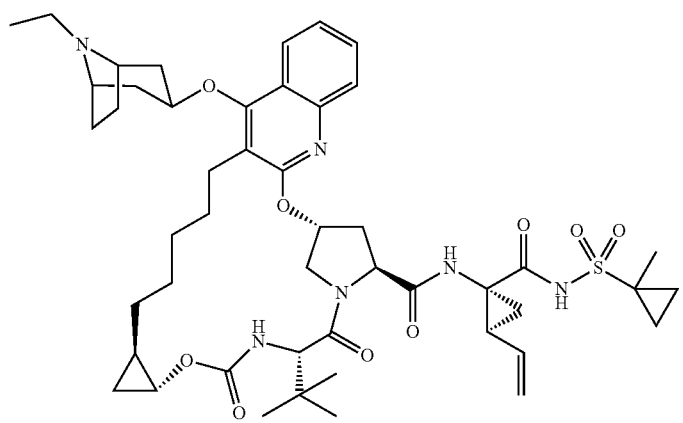
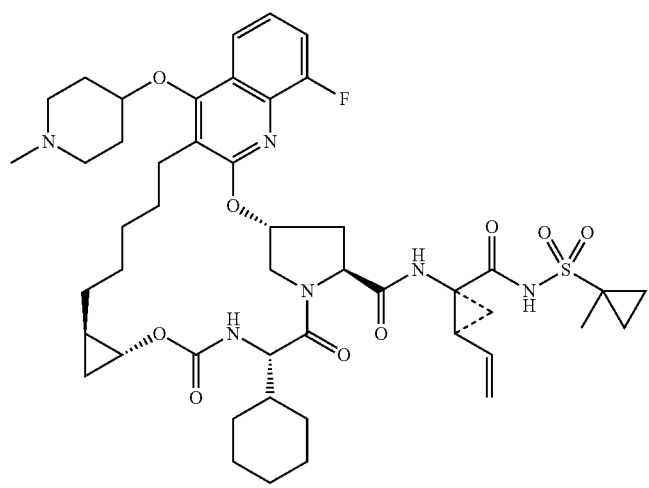
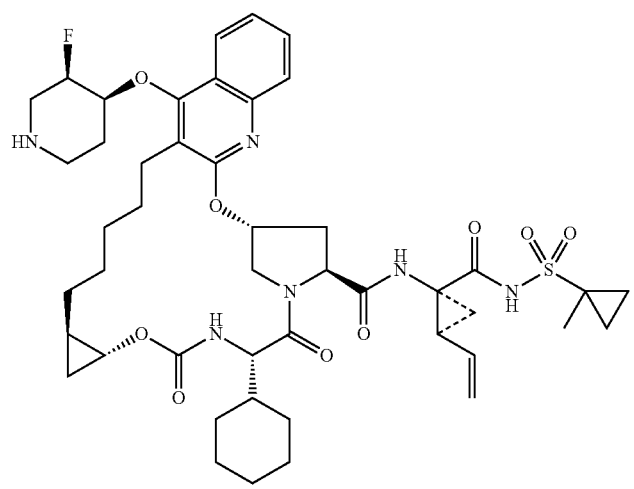

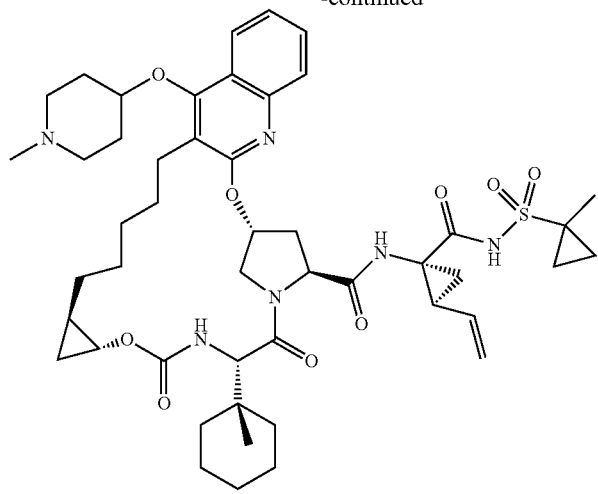
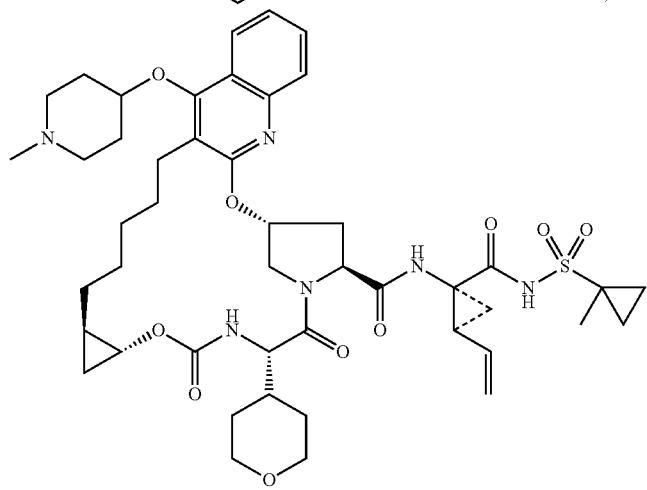, or
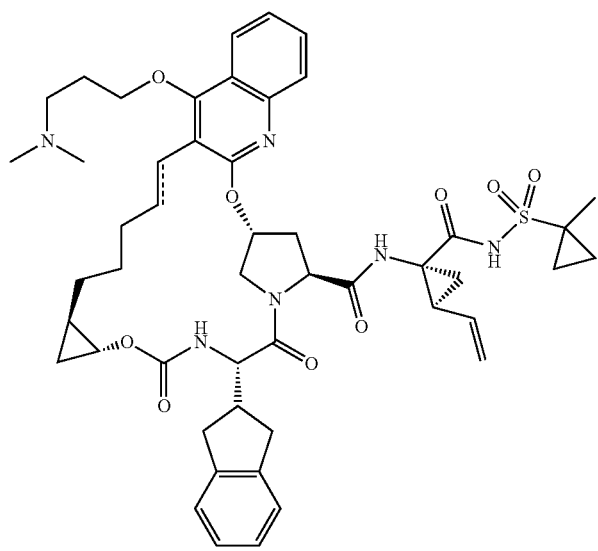,
or a pharmaceutically acceptable salt thereof.

14. A compound selected from:

(1aR,5S,11Z,12aS,13aR,16S,19R,27E,31aR)—N-[(1-methylcyclopropyl)sulfonyl]-3,15,33-trioxo-26-[2-(piperidin-1-yl)ethoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,27E,31aR)—N-[(1-methylcyclopropyl)sulfonyl]-26-[2-(morpholin-4-yl)ethoxy]-3,15,33-trioxo-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,27E,31aR)—N-[(1-methylcyclopropyl)sulfonyl]-26-[3-(morpholin-4-yl)propoxy]-3,15,33-trioxo-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,27E,31aR)—N-[(1-methylcyclopropyl)sulfonyl]-3,15,33-trioxo-26-[2-(pyrrolidin-1-yl)ethoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,27E,31aR)-26-methoxy-N-[(1-methylcyclopropyl)sulfonyl]-3,15,33-trioxo-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,31aR)—N-[(1-methylcyclopropyl)sulfonyl]-26-[2-(morpholin-4-yl)ethoxy]-3,15,33-trioxo-1,1a,3,4,5,6,7,8,9,10,12a,13,15,16,18,19,27,28,29,30,31,31a-docosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,27E,31aR)—N-[(1-methylcyclopropyl)sulfonyl]-3,15,33-trioxo-26-[3-(piperidin-1-yl)propoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide;

(1aR,5S,11Z,12aS,13aR,16S,19R,27E,31aR)—N-[(1-methylcyclopropyl)sulfonyl]-3,15,33-trioxo-26-[3-(pyrrolidin-1-yl)propoxy]-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide; or (1aR,5S,11Z,12aS,13aR,16S,19R,27E,31aR)—N-[(1-methylcyclopropyl)sulfonyl]-26-[3-(4-methylpiperazin-1-yl)propoxy]-3,15,33-trioxo-1,1a,3,4,5,6,7,8,9,10,12a,13,15,16,18,19,29,30,31,31a-icosahydro-5,17:16,19-dimethanodicyclopropa[12,13:28,29][1,20,3,14,17]dioxatriazacyclononacosino[21,22-b]quinoline-13a(14H)-carboxamide, or a pharmaceutically acceptable salt thereof.

15. A pharmaceutical composition comprising an effective amount of the compound according to claim 1, and a pharmaceutically acceptable carrier.

16. The pharmaceutical composition according to claim 15, further comprising a second therapeutic agent selected from the group consisting of HCV antiviral agents, immunomodulators, and anti-infective agents.

17. The pharmaceutical composition according to claim 16, wherein the second therapeutic agent is ribavirin.

* * * * *